(12) United States Patent
Kuwahara et al.

(10) Patent No.: US 9,974,305 B2
(45) Date of Patent: May 22, 2018

(54) FUNGICIDAL OR BACTERICIDAL COMPOSITION, AND METHOD FOR CONTROLLING DISEASES

(71) Applicant: NISSAN CHEMICAL INDUSTRIES, LTD., Chiyoda-ku (JP)

(72) Inventors: Hidehito Kuwahara, Shiraoka (JP); Nakako Hasunuma, Shiraoka (JP); Yasuhiro Fukami, Shiraoki (JP)

(73) Assignee: Nissan Chemical Industries, Ltd., Chiyoda-ku (JP)

( * ) Notice: Subject to any disclaimer, the term of this patent is extended or adjusted under 35 U.S.C. 154(b) by 0 days. days.

(21) Appl. No.: 15/117,039

(22) PCT Filed: Feb. 6, 2015

(86) PCT No.: PCT/JP2015/053385
§ 371 (c)(1),
(2) Date: Aug. 5, 2016

(87) PCT Pub. No.: WO2015/119246
PCT Pub. Date: Aug. 13, 2015

(65) Prior Publication Data
US 2017/0188580 A1    Jul. 6, 2017

(30) Foreign Application Priority Data

Feb. 7, 2014    (JP) ................. 2014-022529

(51) Int. Cl.
*A01N 43/60*    (2006.01)
*A01N 43/36*    (2006.01)
(Continued)

(52) U.S. Cl.
CPC ............ *A01N 43/60* (2013.01); *A01N 37/18* (2013.01); *A01N 43/36* (2013.01); *A01N 43/40* (2013.01);
(Continued)

(58) Field of Classification Search
None
See application file for complete search history.

(56) References Cited

FOREIGN PATENT DOCUMENTS

WO    WO 2011/151369 A1 *  12/2011  ........... C07D 231/14
WO    2014/010737 A1       1/2014

OTHER PUBLICATIONS

Izuru Yamamoto, "Trend of Agrobioregulators—Seibutsu Seigyo Kagaku eno Tenkai," CMC Publishing Co., Ltd., 2008, pp. 66-70.
(Continued)

Primary Examiner — Brian J Davis
(74) Attorney, Agent, or Firm — Oblon, McClelland, Maier & Neustadt, L.L.P.

(57) ABSTRACT

To provide a novel pesticidal composition, particularly a composition for a fungicide. A fungicidal or bactericidal composition comprising one or more compounds selected from oxime-substituted amide compounds represented by the formula (I), or their N-oxides or salts, and one or more compounds selected from known fungicidal or bactericidal compounds:

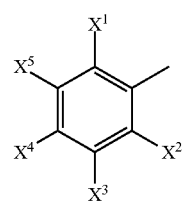

$G^1$-1

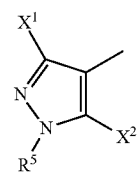

$G^1$-27

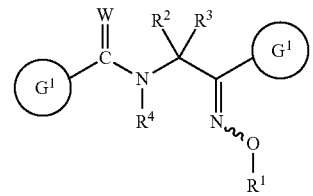

(I)

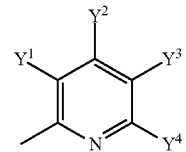

$G^2$-2 wherein $G^1$ represents a structure of $G^1$-1, $G^1$-27, etc., $G^2$ represents a structure of $G^2$-2, etc., W represents an oxygen atom, etc., $X^1$ represents difluoromethyl, trifluoromethyl, etc., $X^2$, $X^3$, $X^4$ and $X^5$ each independently represents a hydrogen atom, etc., $Y^1$ represents a halogen atom, etc., $Y^2$ represents a hydrogen atom, a halogen atom, etc., $Y^3$ represents a halogen atom, trifluoromethyl, $C_2$-$C_6$ alkynyl, etc., $Y^4$ represents a hydrogen atom, etc., $R^1$ represents $C_1$-$C_6$ alkyl, $C_1$-$C_4$ haloalkyl, etc., $R^2$ and $R^3$ each independently represents a hydrogen atom, methyl, etc., $R^4$ represents a hydrogen atom, etc., and $R^5$ represents methyl, etc.

22 Claims, No Drawings

(51) Int. Cl.
*A01N 43/78* (2006.01)
*A01N 37/18* (2006.01)
*A01N 43/74* (2006.01)
*A01N 43/56* (2006.01)
*A01N 43/40* (2006.01)

(52) U.S. Cl.
CPC ............. *A01N 43/56* (2013.01); *A01N 43/74* (2013.01); *A01N 43/78* (2013.01)

(56) References Cited

OTHER PUBLICATIONS

International Search Report dated Apr. 21, 2015 in PCT/JP2015/053385 filed Feb. 6, 2015.

\* cited by examiner

FUNGICIDAL OR BACTERICIDAL COMPOSITION, AND METHOD FOR CONTROLLING DISEASES

TECHNICAL FIELD

The present invention relates to a novel composition for controlling plant diseases, which comprises a specific oxime-substituted amide compound, or its N-oxide or salt, and an active ingredient compound of a specific fungicidal or bactericidal agent, and a method for controlling plant diseases.

BACKGROUND ART

An oxime-substituted amide compound represented by the formula (I), or its N-oxide or salt, as the first active ingredient compound in the fungicidal or bactericidal composition of the present invention, is a known compound, and its activities as a pesticidal agent have been known (see Patent Document 1).

Further, a compound being active ingredient B as the second active ingredient in the fungicidal or bactericidal composition of the present invention, is a known compound having fungicidal activities or bactericidal activities (see Non-Patent Document 1).

PRIOR ART DOCUMENTS

Patent Document

Patent Document 1: WO2014/010737

Non-Patent Document

Non-Patent Document 1: The Pesticide Manual, 16th edition, The British Crop Protection Council, 2012

DISCLOSURE OF INVENTION

Technical Problem

Plant diseases caused by infection of various pathogens on plants such as cereals, fruits, vegetables, ornamental plants, etc., will cause deterioration of the quality of agricultural crops, significant reduction in yield, and in some cases, even a serious damage such as death of plants, and thus present a significant economic loss not only to producers but also to consumers. Therefore, effective control of such plant diseases is a very important issue, in order to achieve efficient and stable production of agricultural crops. From this point of view, heretofore, developments of pest control agents for the purpose of controlling plant diseases have been made, and many effective pesticides have been put into practical use to date.

However, due to years of use of these pesticides, in recent years, there have been an increasing number of cases where pathogens have acquired resistance to such pesticides, and pest control by existing plant disease controlling agents which have been used heretofore, tends to be difficult. In addition, such a problem has become apparent that some of the existing plant disease control agents are highly toxic, or some remain for a long time in the environment to create a problem of disrupting the ecosystem. Under these circumstances, it is now consistently desired to develop a new plant disease control agent which not only has excellent controlling activities against pathogenic bacteria, but also has a high level of control characteristics such as low toxicity and low residual properties, and an effective controlling method.

It is an object of the present invention to provide a novel plant disease control agent which exhibits excellent controlling activities against pathogenic bacteria, and has characteristics such as low toxicity and low residual properties, and a plant disease control method.

Solution to Problem

As a result of extensive research with an aim to solve the above problem, the present inventors have found that a composition comprising, in combination, a specific oxime-substituted amide compound represented by the following formula (I), or its N-oxide or salt (active ingredient A), and a specific compound having fungicidal or bactericidal activities (active ingredient BA), exhibits synergistic, excellent fungicidal or bactericidal effects, which cannot be predicted from a case of using each compound alone. That is, it has been found that the above composition is extremely useful in that it shows excellent plant disease controlling activities and presents substantially no adverse effects against non-target organisms such as plants, mammals, fish, useful insects and natural enemies, and thus, the present invention has been accomplished.

That is, the present invention provides, as its gist, a composition as defined in the following [1] to [19] (hereinafter referred to also as the composition of the present invention), and a disease control method as defined in the following [20] (hereinafter referred to also as the method of the present invention).

[1] A composition for a fungicide, an insecticide, a nematicide or a bactericide, characterized by comprising one or more compounds selected from the following active ingredient A, and one or more compounds selected from the following active ingredient B, respectively in synergistically effective amounts:

(1) Active ingredient A: an oxime-substituted amide compound represented by the following formula (I), or its N-oxide or its salt,

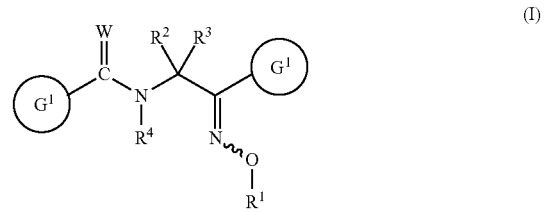

in the formula, $G^1$ represents a structure of $G^1$-1, $G^1$-2, $G^1$-3, $G^1$-7, $G^1$-8, $G^1$-9, $G^1$-11, $G^1$-12, $G^1$-13, $G^1$-16, $G^1$-27, $G^1$-32, $G^1$-33 or $G^1$-50,

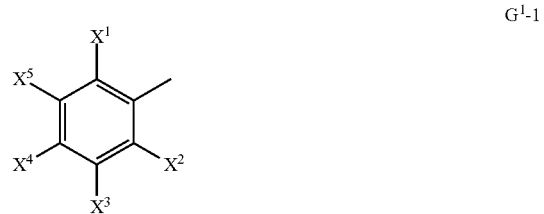

-continued
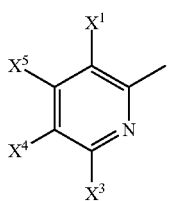
G¹-2
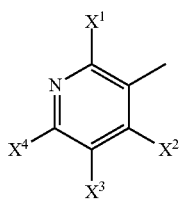
G¹-3
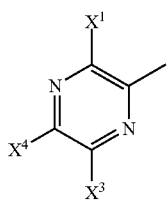
G¹-7
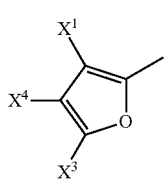
G¹-8
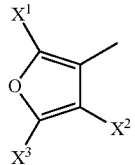
G¹-9
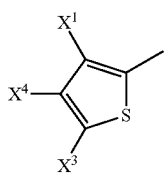
G¹-11
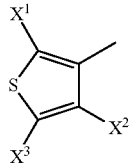
G¹-12
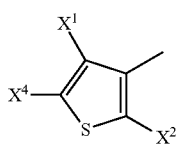
G¹-13
-continued
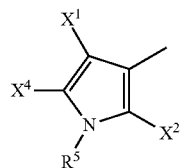
G¹-16
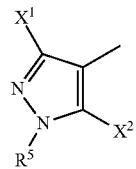
G¹-27
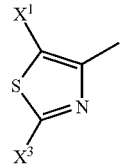
G¹-32
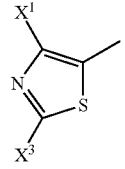
G¹-33
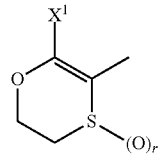
G¹-50
G² represents a structure of G²-1, G²-2, G²-6 or G²-9,
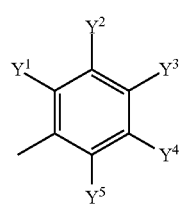
G²-1
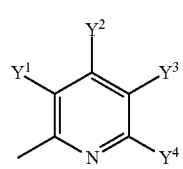
G²-2
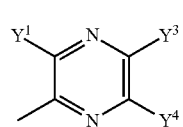
G²-6

-continued

G²-9

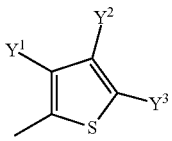

W represents an oxygen atom or a sulfur atom, $X^1$ represents a halogen atom, nitro, methyl, difluoromethyl or trifluoromethyl, $X^2$ represents a hydrogen atom, and further when $G^1$ represents a structure of $G^1$-27, and $X^1$ represents trifluoromethyl, $X^2$ may represent a halogen atom, $X^3$ represents a hydrogen atom or methyl, $X^4$ represents a hydrogen atom or a halogen atom, $X^5$ represents a hydrogen atom, $Y^1$ represents a hydrogen atom, a halogen atom, methyl, trifluoromethyl or methoxy, $Y^2$ represents a hydrogen atom, a halogen atom, cyano, methoxy, methylthio, methylsulfinyl or methylsulfonyl, $Y^3$ represents a hydrogen atom, a halogen atom, cyano, $C_1$-$C_4$ alkyl, trifluoromethyl, $C_2$-$C_4$ alkenyl, $C_2$-$C_6$ alkynyl, ($C_2$-$C_6$) alkynyl optionally substituted by $R^6$, —$OR^7$, $C_1$-$C_4$ alkylthio, —$C(R^8)$=$NOR^9$, phenyl, D-3 or D-7, $Y^4$ represents a hydrogen atom or a halogen atom, $Y^5$ represents a hydrogen atom, $R^1$ represents $C_1$-$C_6$ alkyl, $C_1$-$C_4$ haloalkyl, ($C_1$-$C_4$) alkyl substituted by $R^{10}$, $C_3$-$C_6$ cycloalkyl, $C_3$-$C_6$ alkenyl, $C_3$-$C_4$ haloalkenyl, $C_3$-$C_6$ alkynyl or phenyl, $R^2$ represents a hydrogen atom, methyl or ethyl, provided that $R^2$ represents methyl or ethyl when $G^1$ represents a structure of $G^1$-1, $X^1$ represents a chlorine atom, $X^2$, $X^3$ and $X^5$ each represents a hydrogen atom, $X^4$ represents a hydrogen atom or a chlorine atom, and $G^2$ represents a structure of $G^2$-1, $Y^3$ represents a chlorine atom, $Y^1$, $Y^2$, $Y^4$ and $Y^5$ each represents a hydrogen atom, $R^3$ represents a hydrogen atom or methyl, or $R^2$ and $R^3$ may together form a cyclopropyl ring, $R^4$ represents a hydrogen atom, $C_1$-$C_4$ haloalkylthio, $C_1$-$C_4$ alkylcarbonyl or $C_1$-$C_4$ alkoxycarbonyl, $R^5$ represents methyl, $R^6$ represents a halogen atom, $C_3$-$C_6$ cycloalkyl, hydroxy ($C_3$-$C_6$)cycloalkyl, $C_5$-$C_6$ cycloalkenyl, —OH, —$OR^7$, $C_1$-$C_4$ alkylcarbonyloxy, $C_1$-$C_4$ alkylsulfonyloxy, $C_1$-$C_4$ alkylthio, trimethylsilyl, —$C(R^8)$=$NOR^9$, phenyl, phenyl substituted by $(Z)_m$ or D-32, Z represents a halogen atom, cyano, nitro, $C_1$-$C_4$ alkyl, trifluoromethyl, methoxy, trifluoromethoxy, trifluoromethylthio or phenyl, and when m or n represents 2 or more, the respective Z's may be identical with or different from one another, and when there are two neighboring Z's, the two neighboring Z's may form —CH=CH—CH=CH— to form a 6-membered ring together with the carbon atoms attached to the two Z's, $R^7$ represents $C_1$-$C_4$ alkyl, $C_1$-$C_4$ haloalkyl, $C_1$-$C_4$ alkoxy ($C_1$-$C_2$)alkyl, E-14, $C_3$-$C_4$ alkynyl or phenyl substituted by $(Z)_m$;

$R^8$ represents a hydrogen atom or methyl, $R^9$ represents methyl or ethyl, $R^{10}$ represents cyano, $C_3$-$C_6$ cycloalkyl, E-5, E-9, $C_1$-$C_4$ alkoxy, $C_1$-$C_4$ alkylthio, trimethylsilyl, —$C(R^{11})$=$NOR^{12}$, phenyl, phenyl substituted by $(Z)_m$, D-10 or D-32, D-3, D-7, D-10 and D-32, respectively, represent aromatic heterocyclic rings of the following structural formulae,

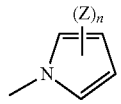
D-3

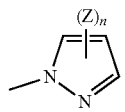
D-7

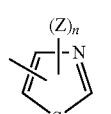
D-10

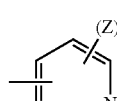
D-32

E-5, E-9 and E-14, respectively, represent saturated heterocyclic rings of the following structural formulae,

E-5

E-9

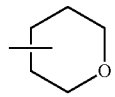
E-14

$R^{11}$ represents methyl, $R^{12}$ represents methyl or ethyl, m represents an integer of 1, 2 or 3, n represents an integer of 0, 1 or 2, (2) active ingredient B:

B-I group: benalaxyl, benalaxyl-M, furalaxyl, metalaxyl, metalaxyl-M, ofurace, oxadixyl, bupirimate, ethirimol, hymexazol, octhilinone and oxolinic acid, B-II group: benomyl, carbendazim, fuberidazole, thiabendazole, thiophanate-methyl, diethofencarb, ethaboxam, zoxamide, pencycuron, fluopicolide, diflumetorim and benodanil, B-III group: benzovindiflupyr, bixafen, boscalid, carboxin, fenfuram, fluopyram, flutolanil, fluxapyroxad, furametpyr, isofetamid, isopyrazam, mepronil, oxycarboxin, penflufen, penthiopyrad, sedaxane, thifluzamide, azoxystrobin, coumoxystrobin, dimoxystrobin, enestrobin, enoxastrobin, famoxadone, fenamidone, fenaminstrobin, flufenoxystrobin, fluoxastrobin, kresoxim-methyl, mandestrobin, metominostrobin, orysastrobin, picoxystrobin, pyraclostrobin, pyrametostrobin, pyraoxystrobin, pyribencarb-methyl, pyriminostrobin, triclopyricab, trifloxystrobin, amisulbrom, cyazofamid, dinocap, fluazinam, meptyldinocap, fentin, tributyltin oxide, silthiofam and ametoctradin, B-IV group: cyprodinil, mepanipyrim, pyrimethanil, blasticidin-S, kasugamycin, streptomycin and oxytetracycline, B-V group: proquinazid, quinoxyfen, fenpiclonil, fludioxonil and chlozolinate, B-V group: iprodione, procymidone and vinclozolin, B-VI group: edifenphos, iprobenfos, isoprothiolane, pyrazophos, biphenyl, chloroneb, dicloran, etridiazole, quintozene, tecnazene, tolclofos-methyl, propamocarb hydrochloride and *Bacillus subtilis* (Strain: D747, FZB24, GBO3, HAI0404, MBI600, QST713, Y1336, etc.), B-VII group: azaconazole, bitertanol, bromuconazole, climbazole, cyproconazole, diclobutrazol, difenoconazole, diniconazole, diniconazole-M, epoxiconazole, etaconazole, fenarimol, fenbuconazole, fluotrimazole, fluquinconazole, flusilazole, flutriafol, furconazole, hexaconazole, imazalil, imibenconazole, ipconazole, metconazole, myclobutanil, nuarimol, oxpoconazole fumarate, pefurazoate, penconazole, prochloraz, propiconazole, prothioconazole, pyrifenox, pyrisoxazole, simeconazole, tebuconazole, tetraconazole, triadimefon, triadimenol, triflumizole, triforine, triticonazole, aldimorph, dodemorph acetate, fenpropidin, fenpropimorph, piperalin, spiroxamine, tridemorph, fenhexamid and fenpyrazamine, B-VIII group: validamycin, polyoxins, polyoxorim, benthiavalicarb-isopropyl, dimethomorph, flumorph, iprovalicarb, mandipropamid, pyrimorph and valifenalate, B-IX group: phthalide, pyroquilon, tricyclazole, carpropamid, diclocymet and fenoxanil, B-X group: acibenzolar-S-methyl, probenazole, isotianil and tiadinil, B-XI group: laminarin, bordeaux mixture, cheshunt mixture, copper carbonate basic, copper hydroxide, copper naphthenate, copper oleate, copper oxychloride, copper sulfate, basic copper sulfate, oxine copper, calcium polysulfide, sulfur, amobam, ferbam, mancozeb, maneb, metiram, polycarbamate, propineb, thiram, ziram, captan, folpet, chlorothalonil, dichlofluanid, tolylfluanid, guazatine, iminoctadine-albesilate, iminoctadine-triacetate, anilazine, dithianon, chinomethionat and fluoroimide, B-XII group: cyflufenamid, cymoxanil, diclomezine, dodine, ferimzone, flusulfamide, flutianil, fosetyl-aluminium, metrafenone, oxathiapiprolin, pyriofenone, tebufloquin, tolprocarb, triazoxide, potassium hydrogen carbonate, sodium hydrogen carbonate, shiitake mycelium extract, shiitake fruiting body extract, BCF-082 (test name) and NNF-0721 (test name).

[2] The composition for a fungicide, an insecticide, a nematicide or a bactericide according to the above [1], wherein $G^1$ represents a structure of $G^1$-1, $G^1$-2, $G^1$-3, $G^1$-7, $G^1$-11, $G^1$-12, $G^1$-16, $G^1$-27 or $G^1$-33, $G^2$ represents a structure of $G^2$-1, $G^2$-2 or $G^2$-9, W represents an oxygen atom, $X^1$ represents a halogen atom, methyl, difluoromethyl or trifluoromethyl, $X^2$ represents a hydrogen atom, $X^3$ represents a hydrogen atom or methyl, $X^4$ represents a hydrogen atom, $X^5$ represents a hydrogen atom, $Y^1$ represents a halogen atom, $Y^2$ represents a hydrogen atom, a halogen atom, methoxy, methylthio or methylsulfonyl, $Y^3$ represents a halogen atom, trifluoromethyl, $C_2$-$C_4$ alkenyl, $C_2$-$C_6$ alkynyl, ($C_2$-$C_6$) alkynyl optionally substituted by $R^6$, $C_1$-$C_4$ haloalkoxy or —C($R^8$)=$NOR^9$, $Y^4$ represents a hydrogen atom or a halogen atom, $Y^5$ represents a hydrogen atom, $R^1$ represents $C_1$-$C_6$ alkyl, $C_1$-$C_4$ haloalkyl, ($C_1$-$C_4$) alkyl substituted by $R^{10}$, $C_3$-$C_6$ cycloalkyl, $C_3$-$C_6$ alkenyl, $C_3$-$C_4$ haloalkenyl or $C_3$-$C_6$ alkynyl, $R^2$ represents a hydrogen atom or methyl, provided that when $G^2$ is a structure represented by $G^2$-1, $R^2$ represents methyl, $R^3$ represents a hydrogen atom, $R^4$ represents a hydrogen atom, $R^5$ represents methyl, $R^6$ represents a halogen atom, $C_3$-$C_6$ cycloalkyl, —$OR^7$, trimethylsilyl, —C($R^8$)=$NOR^9$ or phenyl, $R^7$ represents $C_1$-$C_4$ alkyl or $C_1$-$C_4$ alkoxymethyl, $R^{10}$ represents $C_3$-$C_6$ cycloalkyl, trimethylsilyl, phenyl, phenyl substituted by $(Z)_m$, or D-32, Z represents a halogen atom or cyano, and when m represents 2 or more, the respective Z's may be identical with or different from one another, n represents an integer of 1.

[3] The composition for a fungicide, an insecticide, a nematicide or a bactericide according to the above [1] or [2], wherein $G^1$ represents a structure of $G^1$-1, $G^1$-3, $G^1$-27 or $G^1$-33, $G^2$ represents a structure of $G^2$-2, $X^1$ represents a chlorine atom, an iodine atom, difluoromethyl or trifluoromethyl, $X^2$ represents a hydrogen atom, $X^3$ represents a hydrogen atom or methyl, $X^4$ represents a hydrogen atom, $X^5$ represents a hydrogen atom, $Y^1$ represents a chlorine atom or a bromine atom, $Y^2$ represents a hydrogen atom, a chlorine atom or methoxy, $Y^3$ represents a chlorine atom, a bromine atom, trifluoromethyl, $C_2$-$C_6$ alkynyl, or ($C_2$-$C_6$) alkynyl optionally substituted by $R^6$, $Y^4$ represents a hydrogen atom, $R^1$ represents $C_1$-$C_4$ alkyl, $C_1$-$C_4$ haloalkyl or cyclopropylmethyl, $R^2$ represents a hydrogen atom or methyl, $R^3$ represents a hydrogen atom, $R^4$ represents a hydrogen atom, $R^5$ represents methyl, $R^6$ represents a halogen atom, cyclopropyl or $C_1$-$C_4$ alkoxy.

[4] The composition for a fungicide, an insecticide, a nematicide or a bactericide according to any one of the above [1] to [3], wherein $G^1$ represents a structure of $G^1$-1, $X^1$ represents an iodine atom or trifluoromethyl, $X^2$, $X^3$, $X^4$ and $X^5$ each represents a hydrogen atom.

[5] The composition for a fungicide, an insecticide, a nematicide or a bactericide according to any one of the above [1] to [3], wherein $G^1$ represents a structure of $G^1$-3, $X^1$ represents a chlorine atom or difluoromethyl, $X^2$, $X^3$ and $X^4$ each represents a hydrogen atom.

[6] The composition for a fungicide, an insecticide, a nematicide or a bactericide according to any one of the above [1] to [3], wherein $G^1$ represents a structure of $G^1$-27, $X^1$ represents difluoromethyl, $X^2$ represents a hydrogen atom, $R^5$ represents methyl.

[7] The composition for a fungicide, an insecticide, a nematicide or a bactericide according to any one of the above [1] to [3], wherein $G^1$ represents a structure of $G^1$-33, $X^1$ represents difluoromethyl, $X^3$ represents methyl.

[8] The composition for a fungicide, an insecticide, a nematicide or a bactericide according to any one of the above [1] to [7], which contains, as active ingredient B, a compound selected from the active ingredient B-I group.
[9] The composition for a fungicide, an insecticide, a nematicide or a bactericide according to any one of the above [1] to [7], which contains, as active ingredient B, a compound selected from the active ingredient B-II group.
[10] The composition for a fungicide, an insecticide, a nematicide or a bactericide according to any one of the above [1] to [7], which contains, as active ingredient B, a compound selected from the active ingredient B-III group.
[11] The composition for a fungicide, an insecticide, a nematicide or a bactericide according to any one of the above [1] to [7], which contains, as active ingredient B, a compound selected from the active ingredient B-IV group.
[12] The composition for a fungicide, an insecticide, a nematicide or a bactericide according to any one of the above [1] to [7], which contains, as active ingredient B, a compound selected from the active ingredient B-V group.
[13] The composition for a fungicide, an insecticide, a nematicide or a bactericide according to any one of the above [1] to [7], which contains, as active ingredient B, a compound selected from the active ingredient B-VI group.
[14] The composition for a fungicide, an insecticide, a nematicide or a bactericide according to any one of the above [1] to [7], which contains, as active ingredient B, a compound selected from the active ingredient B-VII group.
[15] The composition for a fungicide, an insecticide, a nematicide or a bactericide according to any one of the above [1] to [7], which contains, as active ingredient B, a compound selected from the active ingredient B-VIII group.
[16] The composition for a fungicide, an insecticide, a nematicide or a bactericide according to any one of the above [1] to [7], which contains, as active ingredient B, a compound selected from the active ingredient B-IX group.
[17] The composition for a fungicide, an insecticide, a nematicide or a bactericide according to any one of the above [1] to [7], which contains, as active ingredient B, a compound selected from the active ingredient B-X group.
[18] The composition for a fungicide, an insecticide, a nematicide or a bactericide according to any one of the above [1] to [7], which contains, as active ingredient B, a compound selected from the active ingredient B-XI group.
[19] The composition for a fungicide, an insecticide, a nematicide or a bactericide according to any one of the above [1] to [7], which contains, as active ingredient B, a compound selected from the active ingredient B-XII group.
[20] A method for controlling pests, noxious insects, nematodes or bacteria, by treatment at the same time or in close temporal proximity with one or more compounds selected from active ingredient A as defined in the above [1] and one or more compounds selected from B-I group to B-XII group of active ingredient B as defined in the above [1].
[21] The method for controlling pests, noxious insects, nematodes or bacteria according to the above [20], wherein the application rate of each of active ingredient A and active ingredient B is from 0.1 to 1,000 g a.i./ha.
[22] The method for controlling pests, noxious insects, nematodes or bacteria according to the above [20] or [21], wherein the application dosage, as the amount of active ingredients, is from 0.005 to 50 kg/ha.

Advantageous Effects of Invention

The fungicidal or bactericidal composition of the present invention, and the disease control method using the composition of the present invention, exhibit synergistic excellent controlling effects against plant diseases caused by various pathogens, and also exhibit synergistic sufficient controlling effects even against pathogens that have acquired resistance to conventional plant disease control agents.

DESCRIPTION OF EMBODIMENTS

The oxime-substituted amide compound represented by the formula (I) to be used as active ingredient A of the present invention, has geometric isomers of E-form and Z-form, and the compound to be used as active ingredient A of the present invention is one to encompass such E-form, Z-form or a mixture comprising E-form and Z-form in optional proportions.

Further, the compound represented by the formula (I) to be used as active ingredient A of the present invention, may, depending on its substituents, sometimes have optically active isomers due to the presence of one or more asymmetric carbon atoms, and the compound to be used as active ingredient A of the present invention includes all of such optically active isomers or racemic forms.

The halogen atom in the present specification includes a fluorine atom, a chlorine atom, a bromine atom and an iodine atom. Further, notation "halo" in this specification also represents these halogen atoms.

Notation "$C_a$-$C_b$ alkyl" represents a linear or branched hydrocarbon group having from a to b carbon atoms, and, for example, a methyl group, an ethyl group, a propyl group, an isopropyl group, a butyl group, an isobutyl group, a s-butyl group, a tert-butyl group, a pentyl group, a 1-ethylpropyl group, a 2,2-dimethylpropyl group, a hexyl group, etc. may be mentioned as specific examples, and it is selected within the specified range of the number of carbon atoms.

Here, sec- means secondary, tert- means tertiary, respectively, and the same applies hereinafter.

Notation "$C_a$-$C_b$ haloalkyl" represents a linear or branched hydrocarbon group having from a to b carbon atoms, wherein hydrogen atom(s) bonded to carbon atom(s) is(are) optionally substituted by halogen atom(s), and at that time, if substituted by two or more halogen atoms, such halogen atoms may be the same or different from one another. For example, a fluoromethyl group, a chloromethyl group, a bromomethyl group, an iodomethyl group, a difluoromethyl group, a dichloromethyl group, a trifluoromethyl group, a chlorodifluoromethyl group, a trichloromethyl group, a bromodifluoromethyl group, a 1-fluoroethyl group, a 2-fluoroethyl group, a 2-chloroethyl group, a 2-bromoethyl group, a 2,2-difluoroethyl group, a 2,2,2-trifluoroethyl group, a 2-chloro-2,2-difluoroethyl group, a 2,2,2-trichloroethyl group, a 2-bromo-2,2-difluoroethyl group, a 1,1,2,2-tetrafluoroethyl group, a 2-chloro-1,1,2-trifluoroethyl group, a pentafluoroethyl group, a 2,2-difluoropropyl group, a 3,3,3-trifluoropropyl group, a 3-bromo-3,3-difluoropropyl group, a 2,2,3,3-tetrafluoropropyl group, a 2,2,3,3,3-pentafluoropropyl group, a 1,1,2,3,3,3-hexafluoropropyl group, a heptafluoropropyl group, a 2,2,2-trifluoro-1-(methyl)ethyl group, a 2,2,2-trifluoro-1-(trifluoromethyl)ethyl group, a 1,2,2,2-tetrafluoro-1-(trifluoromethyl)ethyl group, a 2,2,3,4,4,4-hexafluorobutyl group, a 2,2,3,3,4,4,4-heptafluorobutyl group, a nonafluorobutyl group, etc. may be mentioned as specific examples, and it is selected within the specified range of the number of carbon atoms.

Notation "$C_a$-$C_b$ cycloalkyl" represents a cyclic hydrocarbon group having from a to b carbon atoms, which may form a monocyclic or composite ring structure of from a three-membered ring to a 10-membered ring. Further, each ring may be optionally substituted by an alkyl group within a specified range of the number of carbon atoms. For example, a cyclopropyl group, a cyclobutyl group, a 1-methylcyclopropyl group, a 2-methylcyclopropyl group, a cyclopentyl group, a 2,2-dimethylcyclopropyl group, a 1-methylcyclobutyl group, a cyclohexyl group, etc. may be mentioned as specific examples, and it is selected within the specified range of the number of carbon atoms.

Notation "$C_a$-$C_b$ alkenyl" represents a linear or branched unsaturated hydrocarbon having from a to b carbon atoms and having one or more double bonds in its molecule, and, for example, a vinyl group, a 1-propenyl group, a 2-propenyl group, a 1-methylethenyl group, a 1-butenyl group, a 2-butenyl group, a 1-methyl-1-propenyl group, a 2-methyl-1-propenyl group, a 2-methyl-2-propenyl group, a 3-methyl-3-butenyl group, etc. may be mentioned as specific examples, and it is selected within the specified range of the number of carbon atoms.

Notation "$C_a$-$C_b$ haloalkenyl" represents a linear or branched unsaturated hydrocarbon having from a to b carbon atoms and having one or more double bonds in its molecule, wherein hydrogen atom(s) bonded to carbon atom(s) is(are) optionally substituted by halogen atom(s). At that time, if substituted by two or more halogen atoms, such halogen atoms may be the same or different from one another. For example, a 2-fluoro-vinyl group, a 2-chloro-vinyl group, a 1,2-dichloro-vinyl group, a 2,2-dichloro-vinyl group, a 2,2-dibromo-vinyl group, a 2-fluoro-2-propenyl group, a 2-chloro-2-propenyl group, a 3-chloro-2-propenyl group, a 3,3-difluoro-2-propenyl group, a 2,3-dichloro-2-propenyl group, a 3,3-dichloro-2-propenyl group, a 2,3,3-trifluoro-2-propenyl group, a 2,3,3-trichloro-2-propenyl group, a 1-(trifluoromethyl)ethenyl group, a 4,4-difluoro-3-butenyl group, a 3,4,4-trifluoro-3-butenyl group, a 2,4,4,4-tetrafluoro-2-butenyl group, a 3-chloro-4,4,4-trifluoro-2-butenyl group, etc. may be mentioned as specific examples, and it is selected within the specified range of the number of carbon atoms.

Notation "$C_a$-$C_b$ alkynyl" represents a linear or branched unsaturated hydrocarbon group having from a to b carbon atoms and having one or more triple bonds in its molecule, and, for example, an ethynyl group, a 1-propynyl, a 2-propynyl, a 1-butynyl group, a 2-butynyl group, a 3-butynyl group, a 1-methyl-2-propynyl group, a 1-pentynyl group, a 2-pentynyl group, a 1-hexynyl group, a 3-hexynyl group, a 3-methyl-1-pentynyl group, a 4-methyl-1-pentynyl group, a 3,3-dimethyl-1-butynyl group, etc. may be mentioned as specific examples, and it is selected within the specified range of the number of carbon atoms.

Notation "$C_a$-$C_b$ haloalkynyl" represents a linear or branched unsaturated hydrocarbon group having from a to b carbon atoms and having one or more triple bonds in its molecule, wherein hydrogen atom(s) bonded to carbon atom(s) is(are) optionally substituted by halogen atom(s). At that time, if substituted by two or more halogen atoms, such halogen atoms may be the same or different from one another. For example, a 2-chloroethynyl group, a 2-bromoethynyl group, a 2-iodoethynyl group, a 3-fluoro-1-propynyl group, a 3-chloro-1-propynyl group, a 3-chloro-2-propynyl group, a 3-bromo-1-propynyl group, a 3-bromo-2-propynyl group, a 3-iodo-2-propynyl group, a 3,3-difluoro-1-propynyl group, a 3,3,3-trifluoro-1-propynyl group, a 3-bromo-1-butynyl group, a 3-fluoro-3-methyl-1-butynyl group, a 3-chloro-3-methyl-1-butynyl group, a 3-bromo-3-methyl-1-butynyl group, etc. may be mentioned as specific examples, and it is selected within the specified range of the number of carbon atoms.

Notation "$C_a$-$C_b$ alkoxy" represents an alkyl-O— group having from a to b carbon atoms, as defined above, and, for example, a methoxy group, an ethoxy group, a propyloxy group, an isopropyloxy group, a butyloxy group, an isobutyloxy group, a s-butyloxy group, a tert-butyloxy group, a pentyloxy group, a hexyloxy group, etc. may be mentioned as specific examples, and it is selected within the specified range of the number of carbon atoms.

Notation "$C_a$-$C_b$ haloalkoxy" represents a haloalkyl-O— group having from a to b carbon atoms, as defined above, and, for example, a difluoromethoxy group, a trifluoromethoxy group, a chlorodifluoromethoxy group, a bromodifluoromethoxy group, a 2-fluoroethoxy group, a 2-chloroethoxy group, a 2,2,2-trifluoroethoxy group, a 1,1,2,2-tetrafluoroethoxy group, a 2-chloro-1,1,2-trifluoroethoxy group, a 1,1,2,3,3,3-hexafluoro-propyloxy group, etc. may be mentioned as specific examples, and it is selected within the specified range of the number of carbon atoms.

Notation "$C_a$-$C_b$ alkylthio" represents an alkyl-S— group having from a to b carbon atoms, as defined above, and, for example, a methylthio group, an ethylthio group, a propylthio group, an isopropylthio group, a butylthio group, an isobutylthio group, a s-butylthio group, a tert-butylthio group, etc. may be mentioned as specific examples, and it is selected within the specified range of the number of carbon atoms.

Notation "$C_a$-$C_b$ haloalkylthio" represents a haloalkyl-S— group having from a to b carbon atoms, as defined above, and, for example, a difluoromethylthio group, a trifluoromethylthio group, a chlorodifluoromethylthio group, a trichloromethylthio group, a bromodifluoromethylthio group, a 2,2,2-trifluoroethylthio group, a 1,1,2,2-tetrafluoroethylthio group, a 2-chloro-1,1,2-trifluoroethylthio group, a pentafluoroethylthio group, a 1,1,2,3,3,3-hexafluoropropylthio group, a heptafluoropropylthio group, a 1,2,2,2-tetrafluoro-1-(trifluoromethyl)ethylthio group, a nonafluorobutylthio group, etc. may be mentioned as specific examples, and it is selected within the specified range of the number of carbon atoms.

Notation "$C_a$-$C_b$ alkylsulfinyl" represents an alkyl-S(O) group having from a to b carbon atoms, as defined above, and, for example, a methylsulfinyl group, an ethylsulfinyl group, a propylsulfinyl group, an isopropylsulfinyl group, a butylsulfinyl group, an iso-butylsulfinyl group, a s-butylsulfinyl group, tert-butylsulfinyl group, etc. may be mentioned as specific examples, and it is selected within the specified range of the number of carbon atoms.

Notation "$C_a$-$C_b$ alkylsulfonyl" represents an alkyl-S(O)$_2$ having from a to b carbon atoms, as defined above, and, for example, a methylsulfonyl group, an ethylsulfonyl group, a propylsulfonyl group, an isopropylsulfonyl group, a butylsulfonyl group, an iso-butylsulfonyl group, a s-butylsulfonyl group, a tert-butylsulfonyl group, etc. may be mentioned as specific examples, and it is selected within the specified range of the number of carbon atoms.

Notation "tri($C_a$-$C_b$ alkyl)silyl" represents a silyl group substituted by alkyl groups each having from a to b carbon atoms, as defined above, which may be the same or different from one another, and, for example, a trimethylsilyl group, a triethylsilyl group, a tri(propyl)silyl group, an ethyldimethylsilyl group, a propyldimethylsilyl group, a butyldimethylsilyl group, an isobutyldimethylsilyl group, a tert-butyldimethylsilyl group, etc. may be mentioned as specific examples, and it is selected within the specified range of the number of carbon atoms.

Notation "$C_a$-$C_b$ alkylcarbonyl" represents an alkyl-C(O)— group having from a to b carbon atoms, as defined above, and, for example, an acetyl group, a propionyl group, a butyryl group, an isobutyryl group, a valeryl group, an isovaleryl group, a 2-methyl butanoyl group, a pivaloyl group, etc. may be mentioned as specific examples, and it is selected within the specified range of the number of carbon atoms.

Notation "$C_a$-$C_b$ alkoxycarbonyl" represents an alkyl-O—C(O)— group having from a to b carbon atoms, as defined above, and, for example, a methoxycarbonyl group, a ethoxycarbonyl group, a propyloxycarbonyl group, an isopropyloxycarbonyl group, a butoxycarbonyl group, an isobutoxycarbonyl group, a tert-butoxycarbonyl group, etc. may be mentioned as specific examples, and it is selected within the specified range of the number of carbon atoms.

Notation "($C_a$-$C_b$) alkyl substituted by $R^{10}$" represents an alkyl group having from a to b carbon atoms, as defined above, wherein a hydrogen atom bonded to a carbon atom is substituted by optional $R^{10}$, and it is selected within the specified range of the number of carbon atoms.

Notation "hydroxy($C_d$-$C_e$)cycloalkyl" or "$C_a$-$C_b$ alkoxy ($C_d$-$C_e$)cycloalkyl" represents a cycloalkyl group as defined above, having from d to e carbon atoms, wherein a hydrogen atom bonded to a carbon atom is optionally substituted by a hydroxy group or by an optional $C_a$-$C_b$ alkoxy group as defined above, respectively, and it is selected within the specified range of the number of carbon atoms.

Notation "($C_a$-$C_b$) alkynyl substituted by $R^6$" represents an alkynyl group as defined above, having from a to b carbon atoms, wherein a hydrogen atom bonded to a carbon atom is substituted by optional $R^6$, and it is selected within the specified range of the number of carbon atoms.

Preferred ranges of the respective substituents in the oxime-substituted amide compound represented by the formula (I) to be used as active ingredient A of the present invention, may be optionally combined, and they respectively represent the preferred ranges of compounds to be used as active ingredient A of the present invention.

The oxime-substituted amide compound represented by the formula (I) to be used as active ingredient A in the pesticidal composition of the present invention, is a known compound as disclosed in International Patent Application Publication (WO2014/010737), and specifically, compounds listed in Table 1 may be mentioned. However, the compounds in Table 1 are exemplary, and the oxime-substituted amide compound to be used as active ingredient A of the present invention is not limited thereto.

In the Table, a substituent identified by Et represents an ethyl group, and hereinafter, n-Pr and Pr-n represent an n-propyl group, i-Pr and Pr-i represent an isopropyl group, c-Pr and Pr-c represent a cyclopropyl group, n-Bu and Bu-n represent a normal butyl group, s-Bu and Bu-s represent a secondary butyl group, t-Bu and Bu-t represent a tertiary butyl group, Pen-c represents a cyclopentyl group, and Ph represents a phenyl group.

In the Table, notation "-" in the column for the substituent $Y^5$ indicates that the corresponding substituent is not present.

In the Table, notation (R) or (S) in the column for the substituent $R^2$ indicates that in the mixing ratio of the optical isomers of the carbon atom to which $R^2$ is bonded, (R)-form or (S)-form is at least 90%, respectively.

Further, notation (E) or (Z) in the column for the substituent $R^1$ indicates that in the mixing ratio of oxime geometric isomers to which the substituent $R^1$ is bonded, (E)-form or (Z)-form is at least 90%, respectively.

These definitions will apply also to the Tables given hereinafter.

TABLE 1

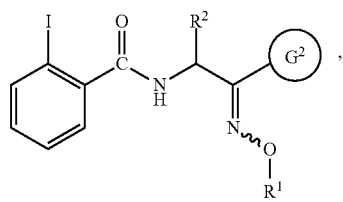
[I]-1

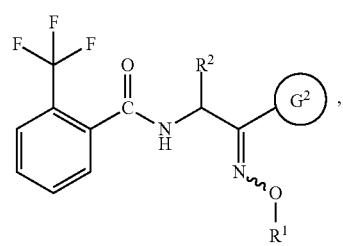
[I]-2

TABLE 1-continued

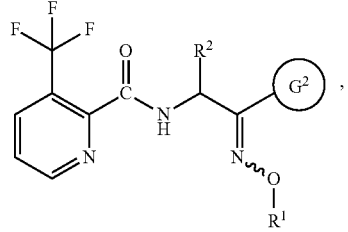
[I]-3

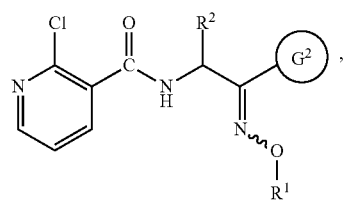
[I]-4

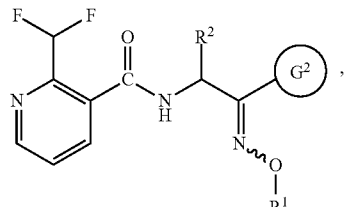
[I]-5

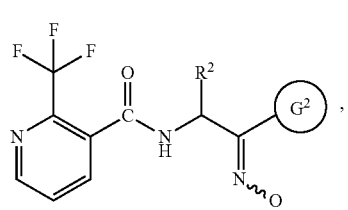
[I]-6

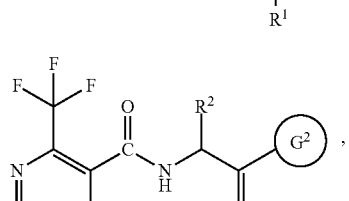
[I]-7

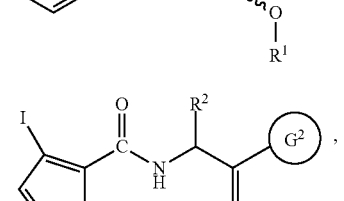
[I]-8

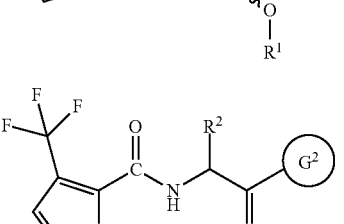
[I]-9

TABLE 1-continued

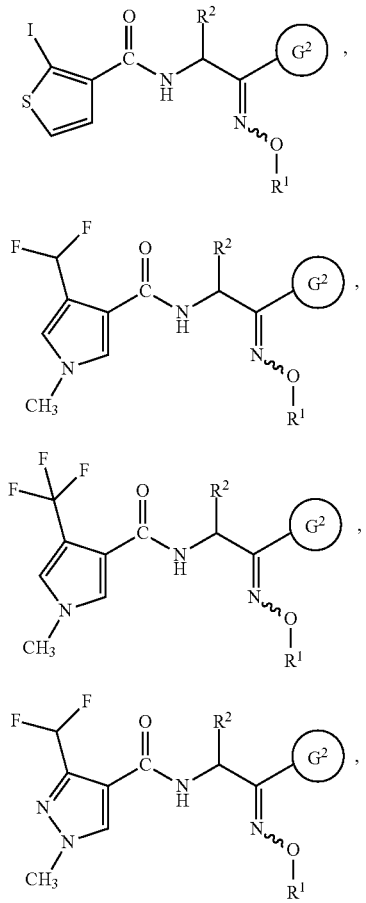

[I]-10, [I]-11, [I]-12, [I]-13

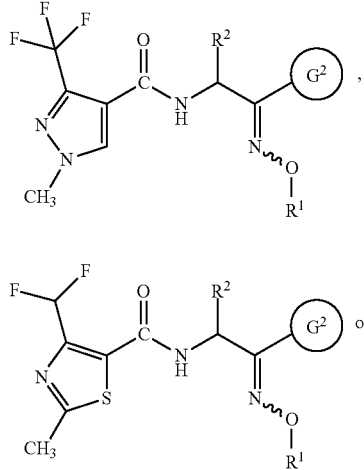

[I]-14, [I]-15

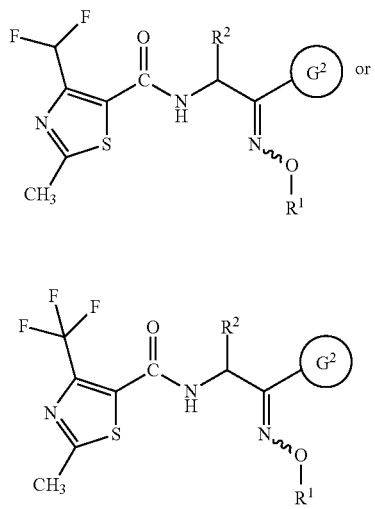

[I]-16

In the above structural formulae, substituent $G^2$ represents the following $G^2$-1 or $G^2$-2.

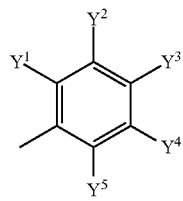

$G^2$-1

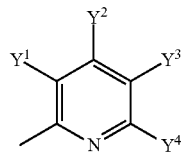

$G^2$-2

| $R^2$ | $G^2$ | $Y^1$ | $Y^2$ | $Y^3$ | $Y^4$ | $Y^5$ | $R^1$ |
|---|---|---|---|---|---|---|---|
| $CH_3$ | $G^2$-1 | Cl | H | Cl | H | H | $CH_3$ |
| $CH_3$ | $G^2$-1 | Cl | H | Cl | H | H | $CH_3$(E) |
| $CH_3$(S) | $G^2$-1 | Cl | H | Cl | H | H | $CH_3$ |
| $CH_3$(S) | $G^2$-1 | Cl | H | Cl | H | H | $CH_3$(E) |
| $CH_3$ | $G^2$-1 | Cl | H | Cl | H | H | Et(E) |
| $CH_3$(S) | $G^2$-1 | Cl | H | Cl | H | H | Et(E) |
| $CH_3$ | $G^2$-1 | Cl | H | C≡CCH$_3$ | H | H | $CH_3$(E) |
| $CH_3$(S) | $G^2$-1 | Cl | H | C≡CCH$_3$ | H | H | $CH_3$(E) |
| $CH_3$ | $G^2$-1 | Cl | H | C≡CCH$_3$ | H | H | Et(E) |
| $CH_3$(S) | $G^2$-1 | Cl | H | C≡CCH$_3$ | H | H | Et(E) |
| $CH_3$ | $G^2$-1 | Cl | H | C≡CPr-c | H | H | $CH_3$(E) |
| $CH_3$(S) | $G^2$-1 | Cl | H | C≡CPr-c | H | H | $CH_3$(E) |

-continued

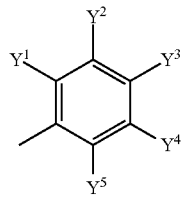

G²-1

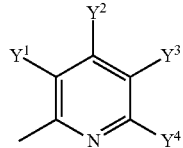

G²-2

| R² | G² | Y¹ | Y² | Y³ | Y⁴ | Y⁵ | R¹ |
|---|---|---|---|---|---|---|---|
| H | G²-2 | Cl | H | Cl | H | — | CH₃ |
| H | G²-2 | Cl | H | Cl | H | — | CH₃(Z) |
| CH₃ | G²-2 | Cl | H | Cl | H | — | CH₃(Z) |
| CH₃(S) | G²-2 | Cl | H | Cl | H | — | CH₃(Z) |
| H | G²-2 | Cl | H | Cl | H | — | Et |
| H | G²-2 | Cl | H | Cl | H | — | Et(Z) |
| CH₃ | G²-2 | Cl | H | Cl | H | — | Et(Z) |
| CH₃(S) | G²-2 | Cl | H | Cl | H | — | Et(Z) |
| H | G²-2 | Cl | H | Cl | H | — | n-Pr |
| H | G²-2 | Cl | H | Cl | H | — | n-Pr(Z) |
| H | G²-2 | Cl | H | Cl | H | — | i-Pr |
| H | G²-2 | Cl | H | Cl | H | — | i-Pr(Z) |
| CH₃ | G²-2 | Cl | H | Cl | H | — | i-Pr |
| CH₃ | G²-2 | Cl | H | Cl | H | — | i-Pr(Z) |
| CH₃(S) | G²-2 | Cl | H | Cl | H | — | i-Pr |
| CH₃(S) | G²-2 | Cl | H | Cl | H | — | i-Pr(Z) |
| H | G²-2 | Cl | H | Cl | H | — | s-Bu |
| H | G²-2 | Cl | H | Cl | H | — | s-Bu(Z) |
| H | G²-2 | Cl | H | Cl | H | — | t-Bu |
| H | G²-2 | Cl | H | Cl | H | — | t-Bu(Z) |
| H | G²-2 | Cl | H | Cl | H | — | CH₂CF₃ |
| H | G²-2 | Cl | H | Cl | H | — | CH₂CF₃(Z) |
| H | G²-2 | Cl | H | Cl | H | — | CH₂CH=CH₂ |
| H | G²-2 | Cl | H | Cl | H | — | CH₂CH=CH₂(Z) |
| H | G²-2 | Cl | H | Cl | H | — | CH₂Ph |
| H | G²-2 | Cl | H | Cl | H | — | CH₂Ph(Z) |
| H | G²-2 | Cl | H | Cl | F | — | CH₃(Z) |
| H | G²-2 | Cl | H | Cl | F | — | Et(Z) |
| H | G²-2 | Cl | H | Cl | F | — | i-Pr(Z) |
| H | G²-2 | Cl | H | Br | H | — | CH₃ |
| H | G²-2 | Cl | H | Br | H | — | CH₃(Z) |
| H | G²-2 | Cl | H | Br | H | — | Et |
| H | G²-2 | Cl | H | Br | H | — | Et(Z) |
| H | G²-2 | Cl | H | Br | H | — | i-Pr |
| H | G²-2 | Cl | H | Br | H | — | i-Pr(Z) |
| H | G²-2 | Cl | H | CF₃ | H | — | CH₃ |
| H | G²-2 | Cl | H | CF₃ | H | — | CH₃(Z) |
| H | G²-2 | Cl | H | CF₃ | H | — | Et |
| H | G²-2 | Cl | H | CF₃ | H | — | Et(Z) |
| H | G²-2 | Cl | H | CF₃ | H | — | n-Pr(Z) |
| H | G²-2 | Cl | H | CF₃ | H | — | i-Pr |
| H | G²-2 | Cl | H | CF₃ | H | — | i-Pr(Z) |
| H | G²-2 | Cl | H | CF₃ | H | — | CH₂Pr-c(Z) |
| H | G²-2 | Cl | H | CF₃ | H | — | s-Bu |
| H | G²-2 | Cl | H | CF₃ | H | — | s-Bu(Z) |
| H | G²-2 | Cl | H | CF₃ | H | — | CH(CH₃)CH=CH₂ |
| H | G²-2 | Cl | H | CF₃ | H | — | CH(CH₃)CH=CH₂(Z) |
| H | G²-2 | Cl | H | C≡CCH₃ | H | — | CH₃ |
| H | G²-2 | Cl | H | C≡CCH₃ | H | — | CH₃(Z) |
| H | G²-2 | Cl | H | C≡CCH₃ | H | — | Et |
| H | G²-2 | Cl | H | C≡CCH₃ | H | — | Et(Z) |
| H | G²-2 | Cl | H | C≡CCH₃ | H | — | n-Pr |
| H | G²-2 | Cl | H | C≡CCH₃ | H | — | n-Pr(Z) |
| H | G²-2 | Cl | H | C≡CCH₃ | H | — | i-Pr |
| H | G²-2 | Cl | H | C≡CCH₃ | H | — | i-Pr(Z) |
| H | G²-2 | Cl | H | C≡CCH₃ | H | — | s-Bu |
| H | G²-2 | Cl | H | C≡CCH₃ | H | — | s-Bu(Z) |

-continued

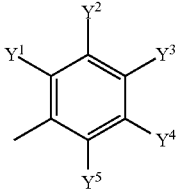

G²-1

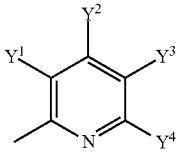

G²-2

| R² | G² | Y¹ | Y² | Y³ | Y⁴ | Y⁵ | R¹ |
|---|---|---|---|---|---|---|---|
| H | G²-2 | Cl | H | C≡CCH₃ | H | — | t-Bu |
| H | G²-2 | Cl | H | C≡CCH₃ | H | — | t-Bu(Z) |
| H | G²-2 | Cl | H | C≡CPr-c | H | — | CH₃ |
| H | G²-2 | Cl | H | C≡CPr-c | H | — | CH₃(Z) |
| H | G²-2 | Cl | H | C≡CPr-c | H | — | Et |
| H | G²-2 | Cl | H | C≡CPr-c | H | — | Et(Z) |
| H | G²-2 | Cl | H | C≡CPr-c | H | — | n-Pr |
| H | G²-2 | Cl | H | C≡CPr-c | H | — | n-Pr(Z) |
| H | G²-2 | Cl | H | C≡CPr-c | H | — | i-Pr |
| H | G²-2 | Cl | H | C≡CPr-c | H | — | i-Pr(Z) |
| H | G²-2 | Cl | H | C≡CPr-c | H | — | s-Bu |
| H | G²-2 | Cl | H | C≡CPr-c | H | — | s-Bu(Z) |
| H | G²-2 | Cl | H | C≡CPr-c | H | — | t-Bu |
| H | G²-2 | Cl | H | C≡CPr-c | H | — | t-Bu(Z) |
| H | G²-2 | Cl | H | C≡CBu-t | H | — | CH₃ |
| H | G²-2 | Cl | H | C≡CBu-t | H | — | CH₃(Z) |
| H | G²-2 | Cl | H | C≡CBu-t | H | — | Et |
| H | G²-2 | Cl | H | C≡CBu-t | H | — | Et(Z) |
| H | G²-2 | Cl | H | C≡CBu-t | H | — | i-Pr |
| H | G²-2 | Cl | H | C≡CBu-t | H | — | i-Pr(Z) |
| H | G²-2 | Cl | H | C≡CBu-t | H | — | t-Bu(Z) |
| H | G²-2 | Cl | H | C≡CSi(CH₃)₃ | H | — | i-Pr |
| H | G²-2 | Cl | H | C≡CSi(CH₃)₃ | H | — | i-Pr(Z) |
| H | G²-2 | Cl | H | C≡CPh | H | — | i-Pr |
| H | G²-2 | Cl | H | C≡CPh | H | — | i-Pr(Z) |
| H | G²-2 | Cl | OCH₃ | Cl | H | — | CH₃ |
| H | G²-2 | Cl | OCH₃ | Cl | H | — | CH₃(Z) |
| H | G²-2 | Cl | OCH₃ | Cl | H | — | Et |
| H | G²-2 | Cl | OCH₃ | Cl | H | — | Et(Z) |
| H | G²-2 | Cl | OCH₃ | Cl | H | — | i-Pr |
| H | G²-2 | Cl | OCH₃ | Cl | H | — | i-Pr(Z) |
| H | G²-2 | Cl | OEt | Cl | H | — | CH₃(Z) |
| H | G²-2 | Cl | OEt | Cl | H | — | Et(Z) |
| H | G²-2 | Cl | OEt | Cl | H | — | i-Pr(Z) |
| H | G²-2 | Cl | SCH₃ | Cl | H | — | i-Pr |
| H | G²-2 | Cl | S(O)CH₃ | Cl | H | — | i-Pr |
| H | G²-2 | Cl | SO₂CH₃ | Cl | H | — | i-Pr |
| H | G²-2 | Br | H | Br | H | — | CH₃ |
| H | G²-2 | Br | H | Br | H | — | CH₃(Z) |
| CH₃ | G²-2 | Br | H | Br | H | — | CH₃(Z) |
| H | G²-2 | Br | H | Br | H | — | Et |
| H | G²-2 | Br | H | Br | H | — | Et(Z) |
| H | G²-2 | Br | H | Br | H | — | i-Pr |
| H | G²-2 | Br | H | Br | H | — | i-Pr(Z) |

Now, specific Synthesis Examples for oxime-substituted amide compounds represented by the formula (I), as active ingredient A of the present invention, will be described, but it should be understood that the synthetic methods are not limited to these Examples.

Here, the chemical shift value of the proton nuclear magnetic resonance ($^1$HNMR) used for the identification of compounds, was measured by using Me$_4$Si (tetramethylsilane) as the reference substance, at 300 MHz (model: ECX300 or ECP300, manufactured by JEOL Ltd.).

Symbols in the proton nuclear magnetic resonance chemical shift values have the following meanings.

s: singlet, d: doublet, t: triplet, q: quartet, m: multiplet, br: broad.

Here, the name of the solvent used in NMR measurements, is shown in parentheses ( ) in the data of chemical shift values.

Synthesis Example 1

(Z)—N-[2-[3-chloro-5-(cyclopropylethynyl)pyridin-2-yl]-2-(isopropoxyimino)ethyl]-3-difluoromethyl-1-methyl-1H-pyrazole-4-carboxamide (Compound No. 25)

Step 1: Production of 3-chloro-5-(cyclopropylethynyl)pyridine-2-carbonitrile

To a 200 ml solution of 17.37 g of 3,5-dichloropyridine-2-carbonitrile in N,N-dimethylformamide, 50.60 g of triethylamine, 7.90 g of cyclopropyl acetylene, 2.20 g of copper(I) iodide and 2.10 g of dichlorobis(triphenylphosphine)palladium(II), were added. After completion of the addition, the mixture was stirred under a nitrogen atmosphere overnight at room temperature. After completion of the reaction, 500 ml of water was added to the reaction mixture, followed by extraction with ethyl acetate (250 ml×2). The obtained organic layers were put together and washed with water (500 ml×1). Thereafter, using in the order of saturated aqueous sodium chloride and then anhydrous sodium sulfate, dehydration and drying were carried out, and the solvent was distilled off under reduced pressure. The obtained residue was purified by silica gel column chromatography by eluting it with ethyl acetate-hexane [1:9 (volume ratio, the same applies hereinafter)], to obtain 18.40 g of the desired product as a brown solid.

$^1$H NMR (CDCl$_3$, Me$_4$Si, 300 MHz) δ 8.50 (d, J=1.7 Hz, 1H), 7.77 (d, J=1.7 Hz, 1H), 1.45-1.55 (m, 1H), 0.8-1.05 (m, 4H).

Step 2: Production of 1-[3-chloro-5-(cyclopropylethynyl)pyridin-2-yl]ethanone

To a 90 ml solution of 9.0 g of 3-chloro-5-(cyclopropylethynyl) pyridine-2-carbonitrile in tetrahydrofuran, 22 ml of a 3 M diethyl ether solution of methylmagnesium bromide was added dropwisely with stirring under cooling with ice. After completion of the dropwise addition, the reaction mixture was stirred at the same temperature for 40 minutes. After completion of the reaction, the reaction mixture was added dropwisely to 200 ml of a 1N aqueous hydrochloric acid solution, and the mixture was extracted with ethyl acetate (125 ml×2). The obtained organic layers were put together and washed with water (100 ml×1). Then, using in the order of saturated aqueous sodium chloride and then anhydrous sodium sulfate, dehydration and drying were carried out, and the solvent was distilled off under reduced pressure. The obtained residue was purified by silica gel column chromatography by eluting it with ethyl acetate-hexane (1:9), to obtain 9.6 g of the desired product as a brown solid.

$^1$H NMR (CDCl$_3$, Me$_4$Si, 300 MHz) δ 8.45 (d, J=1.7 Hz, 1H), 7.72 (d, J=1.7 Hz, 1H), 2.67 (s, 3H), 1.4-1.6 (m, 1H), 0.8-1.05 (m, 4H).

Step 3: Production of 2-bromo-1-[3-chloro-5-(cyclopropylethynyl)pyridin-2-yl]ethanone To a 145 ml solution of 9.6 g of 1-[3-chloro-5-(cyclopropylethynyl)pyridin-2-yl]ethanone in tetrahydrofuran, 16.3 g of trimethylphenylammonium tribromide was added. After completion of the addition, the reaction mixture was stirred at room temperature for 2 hours. After completion of the reaction, precipitated solid was removed by filtering by means of Celite. The obtained filtrate was washed with 100 ml of ethyl acetate, and the filtrates were put together, and the solvent was distilled off under reduced pressure. The obtained residue was purified by silica gel column chromatography by eluting it with ethyl acetate-hexane (1:9), to obtain 12.0 g of the desired compound as a pale brown solid.

$^1$H NMR (CDCl$_3$, Me$_4$Si, 300 MHz) δ 8.46 (d, J=1.7 Hz, 1H), 7.76 (d, J=1.7 Hz, 1H), 4.71 (s, 2H), 1.4-1.6 (m, 1H), 0.8-1.05 (m, 4H).

Step 4: Production of 2-bromo-1-[3-chloro-5-(cyclopropylethynyl)pyridin-2-yl]ethanone-O-isopropyl oxime To a 10 ml solution of 1.50 g of 2-bromo-1-[3-chloro-5-(cyclopropylethynyl)pyridin-2-yl]ethanone and 2.28 g of trifluoroacetic acid in dichloromethane, a 3 ml solution of 1.44 g of N-(isopropoxy)carbamide acid-tert-butyl in dichloromethane was added dropwisely with stirring under cooling with ice. After completion of the dropwise addition, the reaction mixture was stirred at room temperature overnight. After completion of the reaction, the solvent was distilled off under reduced pressure. Thereafter, 20 ml of water was added to the obtained residue, and the mixture was extracted with ethyl acetate (15 ml×2). The obtained organic layers were put together and washed with water (20 ml×1). Then, using in the order of saturated aqueous sodium chloride and then anhydrous sodium sulfate, dehydration and drying were carried out, and the solvent was distilled off under reduced pressure. The obtained residue was purified by silica gel column chromatography by eluting it with ethyl acetate-hexane (1:4), to obtain 1.57 g of the desired product as a pale yellow oily substance (E/Z=3/1).

$^1$H NMR (CDCl$_3$, Me$_4$Si, 300 MHz) δ 8.49 and 8.47 (d, J=1.7 Hz, 1H), 7.73 and 7.71 (d, J=1.7 Hz, 1H), 4.53 and 4.41 (s, 2H), 4.55 and 4.39 (sep, J=6.1 Hz, 1H), 1.4-1.55 (m, 1H), 1.36 and 1.21 (d, J=6.1 Hz, 6H), 0.8-1.0 (m, 4H).

Step 5: Production of N-[2-[3-chloro-5-(cyclopropylethynyl)pyridin-2-yl]-2-(isopropoxyimino)ethyl]phthalimide To a 20 ml solution of 1.57 g of 2-bromo-1-[3-chloro-5-(cyclopropylethynyl)pyridin-2-yl]ethanone-O-isopropyl oxime in N,N-dimethylformamide, 0.88 g of potassium phthalimide was added. After completion of the addition, the reaction mixture was stirred at room temperature overnight. After completion of the reaction, 30 ml of water was added to the reaction mixture, followed by extraction with ethyl acetate (30 ml×2). The obtained organic layer was washed with water (30 ml×1), then dehydrated and dried by using saturated aqueous sodium chloride and then anhydrous sodium sulfate, and the solvent was distilled off under reduced pressure. The obtained residue was purified by silica gel column chromatography by eluting it with ethyl acetate-hexane (3:7), to obtain 1.50 g of the desired product as a pale yellow solid (E/Z=3/1).

$^1$H NMR (CDCl$_3$, Me$_4$Si, 300 MHz) δ 8.44 and 8.31 (d, J=1.8 Hz, 1H), 7.55-7.9 (m, 5H), 4.99 and 4.77 (s, 2H), 4.47 and 4.33 (sep, J=6.3 Hz, 1H), 1.35-1.55 (m, 1H), 1.26 and 1.13 (d, J=6.3 Hz, 6H), 0.75-1.0 (m, 4H).

Step 6: Production of 2-amino-1-[3-chloro-5-(cyclopropylethynyl)pyridin-2-yl]ethanone-O-isopropyl oxime To a 20 ml solution of 1.50 g of N-[2-[3-chloro-5-(cyclopropylethynyl)pyridin-2-yl]-2-(isopropoxyimino)ethyl]phthalimide in ethanol, 533 mg of hydrazine monohydrate was added. After completion of the addition, the reaction mixture was stirred for 2 hours under heating and refluxing. After completion of the reaction, the reaction mixture was left to cool to room temperature, and the solvent was distilled off under reduced pressure. Then, 30 ml of water was added, and the mixture was extracted with dichloromethane (20 ml×2). The obtained organic layers were put together, washed with water (20 ml×1), then dehydrated and dried by using saturated aqueous sodium chloride and then anhydrous sodium sulfate, and the solvent was distilled off under reduced pressure to obtain 1.04 g of a crude desired product as a pale yellow oily substance (E/Z=2/1). This product was used, without further purification, directly in the next step.

$^1$H NMR (CDCl$_3$, Me$_4$Si, 300 MHz) δ 8.49 and 8.47 (d, J=1.7 Hz, 1H), 7.71 and 7.68 (d, J=1.7 Hz, 1H), 4.48 and 4.34 (sep, J=6.3 Hz, 1H), 3.87 and 3.73 (s, 2H), 1.55 (bs, 2H), 1.4-1.55 (m, 1H), 1.33 and 1.18 (d, J=6.3 Hz, 6H), 0.8-1.0 (m, 4H).

Step 7: Production of N-[2-[3-chloro-5-(cyclopropylethynyl)pyridin-2-yl]-2-(isopropoxyimino)ethyl]-3-difluoromethyl-1-methyl-1H-pyrazole-4-carboxamide To a 1 ml solution of 68 mg of 3-difluoromethyl-1-methyl-1H-pyrazole-4-carboxylic acid in dichloromethane, 10 mg of N,N-dimethylformamide and 66 mg of oxalyl chloride were added. After completion of the addition, the reaction mixture was stirred at room temperature for 1 hour. After completion of the reaction, the solvent was distilled off from the reaction mixture under reduced pressure. The obtained residue was dissolved in 1 ml of dichloromethane and, with stirring under cooling with ice, added dropwisely to a mixed solution of 100 mg of 2-amino-1-[3-chloro-5-(cyclopropylethynyl)pyridin-2-yl]ethanone-O-isopropyl oxime and 200 mg of potassium carbonate in 2 ml of dichloromethane and 2 ml of water. After completion of the dropwise addition, stirring was further continued for 1 hour at room temperature. After completion of the reaction, 10 ml of water was added to the reaction mixture, followed by extraction with dichloromethane (10 ml×1). The obtained organic layer was washed with water (10 ml×1), and then dehydrated and dried by using saturated aqueous sodium chloride and then anhydrous sodium sulfate, and the solvent was distilled off under reduced pressure. The obtained residue was purified by silica gel column chromatography by eluting it with ethyl acetate-hexane (2:3), to obtain 150 mg of the desired product as a pale yellow resinous substance (E/Z=2/1).

$^1$H NMR (CDCl$_3$, Me$_4$Si, 300 MHz) b 8.45 and 8.43 (d, J=1.8 Hz, 1H), 7.88 and 7.82 (s, 1H), 7.68 and 7.66 (d, J=1.8 Hz, 1H), 7.12 (bs, 1H), 6.85 and 6.75 (t, J=54.2 Hz, 1H), 4.70 and 4.46 (d, J=6.1, 4.9 Hz, 2H), 4.47 and 4.36 (sep, J=6.3 Hz, 1H), 3.90 and 3.87 (s, 3H), 1.4-1.55 (m, 1H), 1.32 and 1.18 (d, J=6.3 Hz, 6H), 0.8-1.0 (m, 4H).

Step 8: Production of (Z)—N-[2-[3-chloro-5-(cyclopropylethynyl)pyridin-2-yl]-2-(isopropoxyimino)ethyl]-3-difluoromethyl-1-methyl-1H-pyrazole-4-carboxamide 150 mg of N-[2-[3-chloro-5-(cyclopropylethynyl)pyridin-2-yl]-2-(isopropoxyimino)ethyl]-3-difluoromethyl-1-methyl-1H-pyrazole-4-carboxamide (E/Z=2/1) was dissolved in 4 ml of ethyl acetate and irradiated with light for 8 hours by using a high-pressure mercury lamp (manufactured by USHIO INC., lamp UM-102, lighting device UM-103B-B) in a quartz cell (manufactured by Fine, entirely transparent for spectroscopic analysis). After completion of the reaction, the solvent was distilled off from the reaction mixture under reduced pressure. The obtained residue was purified by silica gel column chromatography by eluting it with ethyl acetate-hexane (2:3), to obtain 53 mg of the desired product as white crystals.

Melting point: 105.0 to 107.0° C.

$^1$H NMR (CDCl$_3$, Me$_4$Si, 300 MHz) δ 8.45 (d, J=1.8 Hz, 1H), 7.88 (s, 1H), 7.66 (d, J=1.8 Hz, 1H), 7.12 (bs, 1H), 6.85 (t, J=54.2 Hz, 1H), 4.46 (d, J=4.9 Hz, 2H), 4.35 (sep, J=6.3 Hz, 1H), 3.90 (s, 3H), 1.4-1.5 (m, 1H), 1.17 (d, J=6.3 Hz, 6H), 0.85-0.95 (m, 2H), 0.8-0.85 (m, 2H).

Synthesis Example 2

(Z)—N-[2-[3-chloro-5-(1-propynyl)pyridin-2-yl]-2-(isopropoxyimino)ethyl]-3-difluoromethyl-1-methyl-1H-pyrazole-4-carboxamide (Compound No. 20)

Step 1: Production of 3-chloro-5-(1-propynyl)pyridine-2-carbonitrile

Under a nitrogen atmosphere, 92 ml of a 0.5 M tetrahydrofuran solution of 1-propynyl magnesium bromide was added dropwisely to a 120 ml solution of 10.87 g of zinc(II) bromide in tetrahydrofuran, with stirring under cooling with ice. After completion of the dropwise addition, the reaction mixture was stirred at the same temperature for 10 minutes. After completion of the stirring, to the reaction mixture, 5.00 g of 3,5-dichloropyridine-2-carbonitrile and 0.94 g of dichloro[1,1'-bis(diphenylphosphino)ferrocene]palladium (II) were added. After completion of the addition, the reaction mixture was continuously stirred at 50° C. for 2 hours. After completion of the reaction, the reaction mixture was left to cool to room temperature, then, 40 ml of water was added, followed by extraction with ethyl acetate (20 ml×2). The obtained organic layers were put together, washed with water (40 ml×1) and then dehydrated and dried by using saturated aqueous sodium chloride and then anhydrous sodium sulfate, and the solvent was distilled off under reduced pressure. The obtained residue was purified by silica gel column chromatography by eluting it with hexane, to obtain 5.50 g of the desired product as a pale yellow solid.

¹H NMR (CDCl₃, Me₄Si, 300 MHz) δ 8.54 (d, J=1.8 Hz, 1H), 7.80 (d, J=1.8 Hz, 1H), 2.13 (s, 3H).

Step 2: Production of 1-[3-chloro-5-(1-propynyl) pyridin-2-yl]ethanone

To a 40 ml solution of 4.58 g of 3-chloro-5-(1-propynyl)pyridine-2-carbonitrile in tetrahydrofuran, 17 ml of a 3 M diethyl ether solution of methylmagnesium bromide was added dropwisely with stirring under cooling with ice. After completion of the dropwise addition, the reaction mixture was stirred at the same temperature for 2 hours. After completion of the reaction, the reaction mixture was added dropwisely to 30 ml of water, and the mixture was extracted with ethyl acetate (15 ml×2). The obtained organic layers were put together, washed with water (30 ml×1) and then dehydrated and dried by using saturated aqueous sodium chloride and then anhydrous sodium sulfate, and the solvent was distilled off under reduced pressure, to obtain 4.76 g of a crude desired product as a black solid. This product was used, without further purification, directly in the next step.

¹H NMR (CDCl₃, Me₄Si, 300 MHz) δ 8.49 (d, J=1.7 Hz, 1H), 7.75 (d, J=1.7 Hz, 1H), 2.69 (s, 3H), 2.12 (s, 3H).

Step 3: Production of 2-bromo-1-[3-chloro-5-(1-propynyl)pyridin-2-yl]ethanone

To a 30 ml solution of 4.76 g of 1-[3-chloro-5-(1-propynyl)pyridin-2-yl]ethanone in acetonitrile, 9.27 g of trimethylphenylammonium tribromide was added. After completion of the addition, the reaction mixture was stirred at 50° C. for 1 hour. After completion of the reaction, the reaction mixture was left to cool to room temperature, then 50 ml of water was added, and the mixture was extracted with ethyl acetate (30 ml×2). The obtained organic layers were put together, washed with water (30 ml×1) and then dehydrated and dried by using saturated aqueous sodium chloride and then anhydrous sodium sulfate, and the solvent was distilled off under reduced pressure. The obtained residue was purified by silica gel column chromatography by eluting it with hexane, to obtain 3.20 g of the desired product as a black solid.

¹H NMR (CDCl₃, Me₄Si, 300 MHz) δ 8.50 (d, J=1.7 Hz, 1H), 7.80 (d, J=1.7 Hz, 1H), 4.73 (s, 2H), 2.14 (s, 3H).

Step 4: Production of 2-bromo-1-[3-chloro-5-(1-propynyl)pyridin-2-yl]ethanone-O-isopropyl oxime To a 10 ml solution of 2.00 g of 2-bromo-1-[3-chloro-5-(1-propynyl)pyridin-2-yl]ethanone and 3.35 g of trifluoroacetic acid in dichloromethane, a 3 ml solution of 1.41 g of N-(isopropoxy)carbamide acid-tert-butyl in dichloromethane was added dropwisely with stirring under cooling with ice. After completion of the dropwise addition, the reaction mixture was stirred at room temperature overnight. After completion of the reaction, the solvent was distilled off from the reaction mixture under reduced pressure. To the obtained residue, 30 ml of water was added, and the mixture was extracted with ethyl acetate (15 ml×2). The obtained organic layers were put together, washed with water (30 ml×1) and then dehydrated and dried by using saturated aqueous sodium chloride and then anhydrous sodium sulfate, and the solvent was distilled off under reduced pressure. The obtained residue was purified by silica gel column chromatography by eluting it with ethyl acetate-hexane (1:9), to obtain 1.90 g of the desired product as a pale yellow oily substance (E/Z=3/1).

¹H NMR (CDCl₃, Me₄Si, 300 MHz) δ 8.51 and 8.49 (d, J=1.7 Hz, 1H), 7.75 and 7.72 (d, J=1.7 Hz, 1H), 4.54 and 4.41 (s, 2H), 4.56 and 4.40 (sep, J=6.5 Hz, 1H), 2.10 (s, 3H), 1.37 and 1.22 (d, J=6.5 Hz, 6H).

Step 5: Production of N-[2-[3-chloro-5-(1-propynyl) pyridin-2-yl]-2-(isopropoxyimino)ethyl]phthalimide To a 20 ml solution of 1.90 g of 2-bromo-1-[3-chloro-5-(1-propynyl)pyridin-2-yl]ethanone-O-isopropyl oxime in N,N-dimethylformamide, 0.96 g of potassium phthalimide was added. After completion of the addition, the reaction mixture was stirred at room temperature overnight. After completion of the reaction, 30 ml of water was added to the reaction mixture, followed by extraction with ethyl acetate (20 ml×2). The obtained organic layer was washed with water (30 ml×1) and then dehydrated and dried by using saturated aqueous sodium chloride and then anhydrous sodium sulfate, and the solvent was distilled off under reduced pressure. The obtained residue was purified by silica gel column chromatography by eluting it with ethyl acetate-hexane (3:7), to obtain 1.49 g of the desired product as a pale yellow solid (E/Z=3/1).

Melting point: 110.0 to 113.0° C.

¹H NMR (CDCl₃, Me₄Si, 300 MHz) b 8.44 and 8.31 (d, J=1.8 Hz, 1H), 7.6-7.9 (m, 5H), 4.98 and 4.77 (s, 2H), 4.46 and 4.32 (sep, J=6.4 Hz, 1H), 2.07 and 2.05 (s, 3H), 1.25 and 1.12 (d, J=6.4 Hz, 6H).

Step 6: Production of 2-amino-1-[3-chloro-5-(1-propynyl)pyridin-2-yl]ethanone-O-isopropyl oxime To a 20 ml solution of 1.49 g of N-[2-[3-chloro-5-(1-propynyl)pyridin-2-yl]-2-(isopropoxyimino)ethyl]phthalimide in ethanol, 565 mg of hydrazine monohydrate was added. After completion of the addition, the reaction mixture was stirred for 3 hours under heating and refluxing. After completion of the reaction, the reaction mixture was left to cool to room temperature, and the solvent was distilled off under reduced pressure. Then, 20 ml of water was added, and the mixture was extracted with chloroform (20 ml×2). The obtained organic layers were put together, washed with water (20 ml×1) and then dehydrated and dried by using saturated aqueous sodium chloride and then anhydrous sodium sulfate, and the solvent was distilled off under reduced pressure to obtain 1.04 g of a crude desired product as a pale yellow oily substance (E/Z=5/2). This product was used, without further purification, directly in the next step.

¹H NMR (CDCl₃, Me₄Si, 300 MHz) δ 8.51 and 8.49 (d, J=2.0 Hz, 1H), 7.73 and 7.70 (d, J=2.0 Hz, 1H), 4.48 and 4.35 (sep, J=6.3 Hz, 1H), 3.88 and 3.73 (s, 2H), 2.10 (s, 3H), 1.56 (bs, 2H), 1.33 and 1.19 (d, J=6.3 Hz, 6H).

Step 7: Production of N-[2-[3-chloro-5-(1-propynyl) pyridin-2-yl]-2-(isopropoxyimino)ethyl]-3-difluoromethyl-1-methyl-1H-pyrazole-4-carboxamide To a 1 ml solution of 88 mg of 3-difluoromethyl-1-methyl-1H-pyrazole-4-carboxylic acid in dichloromethane, 10 mg of N,N-dimethylformamide and 57 mg of oxalyl chloride were added. After completion of the addition, the reaction mixture was stirred at room temperature for 1 hour. After completion of the reaction, the solvent was distilled off under reduced pressure. Thereafter, the obtained residue was dissolved in 1 ml of dichloromethane and added dropwisely, with stirring under cooling with ice, to a mixed solution of 80 mg of 2-amino-1-[3-chloro-5-(1-propynyl)pyridin-2-yl]

ethanone-O-isopropyl oxime and 124 mg of potassium carbonate in 2 ml of dichloromethane and 2 ml of water. After completion of the dropwise addition, the reaction mixture was further stirred at room temperature for 1 hour. After completion of the reaction, 10 ml of water was added to the reaction mixture, followed by extraction with dichloromethane (10 ml×1). The organic layer was washed with water (10 ml×1) and then dehydrated and dried by using saturated aqueous sodium chloride and then anhydrous sodium sulfate, and the solvent was distilled off under reduced pressure. The obtained residue was purified by silica gel column chromatography by eluting it with ethyl acetate-hexane (3:5), to obtain 185 mg of the desired product as a pale yellow resinous substance (E/Z=2/1).

$^1$H NMR (CDCl$_3$, Me$_4$Si, 300 MHz) δ 8.51 and 8.47 (d, J=1.7 Hz, 1H), 7.91 and 7.85 (s, 1H), 7.71 and 7.70 (d, J=1.7 Hz, 1H), 7.14 (bs, 1H), 6.88 and 6.77 (t, J=54.0 Hz, 1H), 4.73 and 4.49 (d, J=5.8, 4.9 Hz, 2H), 4.50 and 4.39 (sep, J=6.3 Hz, 1H), 3.93 and 3.89 (s, 3H), 2.09 and 2.05 (s, 3H), 1.35 and 1.21 (d, J=6.3 Hz, 6H).

Step 8: Production of (Z)—N-[2-[3-chloro-5-(1-propynyl)pyridin-2-yl]-2-(isopropoxyimino)ethyl]-3-difluoromethyl-1-methyl-1H-pyrazole-4-carboxamide 185 mg of N-[2-[3-chloro-5-(1-propynyl)pyridin-2-yl]-2-(isopropoxyimino)ethyl]-3-difluoromethyl-1-methyl-1H-pyrazole-4-carboxamide (E/Z=2/1) was dissolved in 4 ml of ethyl acetate and irradiated with light for 8 hours by using a 100 W high-pressure mercury lamp (manufactured by USHIO INC., Lamp UM-102, lighting device UM-103B-B) in a quartz cell (manufactured by Fine, entirely transparent for spectroscopic analysis). After completion of the reaction, the solvent was distilled off under reduced pressure, and then, the obtained residue was purified by silica gel column chromatography by eluting it with ethyl acetate-hexane (3:5), to obtain 71 mg of the desired product as white crystals.

Melting point: 102.0 to 103.0° C.
$^1$H NMR (CDCl$_3$, Me$_4$Si, 300 MHz) δ 8.51 (d, J=1.7 Hz, 1H), 7.91 (s, 1H), 7.70 (d, J=1.7 Hz, 1H), 7.14 (bs, 1H), 6.88 (t, J=54.0 Hz, 1H), 4.49 (d, J=4.9 Hz, 2H), 4.39 (sep, J=6.3 Hz, 1H), 3.93 (s, 3H), 2.09 (s, 3H), 1.21 (d, J=6.3 Hz, 6H).

Synthesis Example 3

(Z)—N-[2-[3,5-dichloro-4-(methoxy)pyridin-2-yl]-2-(methoxyimino)ethyl]-2-(trifluoromethyl)benzamide (Compound No. 8)

Step 1: Production of N-[2-[3,5-dichloro-4-(methoxy)pyridin-2-yl]-2-oxoethyl]carbamide acid-tert-butyl To 52.7 ml of a 1.0 M tetrahydrofuran-toluene solution of a 2,2,6,6-tetramethylpiperidinyl magnesium chloride-lithium chloride complex under a nitrogen atmosphere, a 15 ml solution of 8.9 g of 3,5-dichloro-4-(methoxy)pyridine in tetrahydrofuran was added dropwisely with stirring at −20° C. After completion of the dropwise addition, the reaction mixture was stirred at −15° C. for 45 minutes. After completion of the stirring, to the reaction mixture, a 15 ml solution of 5.0 g of N-methoxy-N-methyl-2-(tert-butoxycarbonylamino)acetamide in tetrahydrofuran was added dropwisely. After completion of the dropwise addition, the reaction mixture was further stirred at 0° C. for 2.5 hours.

After completion of the reaction, 30 ml of a saturated aqueous ammonium chloride solution and 20 ml of water were added to the reaction mixture, followed by extraction with ethyl acetate (100 ml×2). The obtained organic layers were put together, washed with water (50 ml×1) and then dehydrated and dried by using saturated aqueous sodium chloride and then anhydrous sodium sulfate, and the solvent was distilled off under reduced pressure. The obtained residue was purified by silica gel column chromatography by eluting it with ethyl acetate-hexane (gradient from 5:95 to 50:50) to obtain 2.8 g of the desired product as pale yellow crystals.

Melting point: 59.0 to 60.0° C.
$^1$H NMR (CDCl$_3$, Me$_4$Si, 300 MHz) δ 8.48 (s, 1H), 5.30 (bs, 1H), 4.73 (d, J=4.8 Hz, 2H), 4.04 (s, 3H), 1.47 (s, 9H).

Step 2: Production of tert-butyl N-[2-[3,5-dichloro-4-(methoxy)pyridin-2-yl]-2-(methoxyimino)ethyl]carbamate To a 10.4 ml solution of 1.4 g of tert-butyl N-[2-[3,5-dichloro-4-(methoxy)pyridin-2-yl]-2-oxoethyl]carbamate and 698 mg of methoxyamine hydrochloride in ethanol, 825 mg of pyridine was added. After completion of the addition, the reaction mixture was stirred at room temperature for 18 hours. After completion of the reaction, the solvent was distilled off from the reaction mixture under reduced pressure. Thereafter, to the obtained residue, 5 ml of water was added, followed by extraction with ethyl acetate (5 ml×2). The obtained organic layers were put together, and dehydrated and dried by using saturated aqueous sodium chloride and then anhydrous sodium sulfate, and the solvent was distilled off under reduced pressure. The obtained residue was purified by silica gel column chromatography by eluting it with ethyl acetate-hexane (gradient from 5:95 to 50:50) to obtain 1.4 g of the desired product as a pale yellow oily substance.

$^1$H NMR (CDCl$_3$, Me$_4$Si, 300 MHz) b 8.46 and 8.44 (s, 1H), 5.04 and 4.97 (bs, 1H), 3.8-4.45 (m, 8H), 1.38 and 1.33 (s, 9H).

Step 3: Production of 2-amino-1-[3,5-dichloro-4-(methoxy)pyridin-2-yl]ethanone-O-methyloxime trifluoroacetate To 1.4 g of tert-butyl N-[2-[3,5-dichloro-4-(methoxy)pyridin-2-yl]-2-(methoxyimino)ethyl]carbamate, 15 ml of trifluoroacetic acid was added. After completion of the addition, the reaction mixture was stirred at room temperature for 1 hour. After completion of the reaction, the solvent was distilled off from the reaction mixture under reduced pressure, to obtain 2.8 g of a crude desired product (approximately 40% trifluoroacetic acid solution) as a brown oily substance.

$^1$H NMR (CDCl$_3$, Me$_4$Si, 300 MHz) δ 8.48 and 8.45 (s, 1H), 7.86 (bs, 2H), 3.9-4.35 (m, 8H).

Step 4: Production of N-[2-[3,5-dichloro-4-(methoxy)pyridin-2-yl]-2-(methoxyimino)ethyl]-2-(trifluoromethyl)benzamide To a solution of 330 mg of 2-amino-1-[3,5-dichloro-4-(methoxy)pyridin-2-yl]ethanone-O-methyloxime trifluoroacetate in 1 ml of water and 1 ml of dichloromethane, with stirring at room temperature, 125 mg of 2-(trifluoromethyl) benzoyl chloride and 276 mg of potassium carbonate were added. After completion of the addition, the reaction mixture was stirred at room temperature for 1 hour. After completion of the reaction, the organic layer was separated and dried over anhydrous sodium sulfate, and the solvent was distilled off under reduced pressure. The obtained residue was purified by silica gel column chromatography by eluting it with ethyl acetate-hexane (gradient from 5:95 to 50:50) to obtain 140 mg of the desired product as a colorless resinous substance.

$^1$H NMR (CDCl$_3$, Me$_4$Si, 300 MHz) δ 8.47 and 8.43 (s, 1H), 7.35-7.75 (m, 4H), 6.49 and 6.41 (bs, 1H), 4.74 and 4.53 (d, J=5.4 Hz, 2H), 3.85-4.1 (m, 6H).

Step 5: Production of (Z)—N-[2-[3,5-dichloro-4-(methoxy)pyridin-2-yl]-2-(methoxyimino)ethyl]-2-(trifluoromethyl)benzamide 140 mg of N-[2-[3,5-dichloro-4-(methoxy)pyridin-2-yl]-2-(methoxyimino)ethyl]-2-(trifluoromethyl)benzamide was dissolved in 3.5 ml of ethyl acetate and irradiated with light for 18 hours by using a 100 W high-pressure mercury lamp (manufactured by USHIO INC., Lamp UM-102, lighting device UM-103B-B) in a quartz cell (manufactured by Fine, entirely transparent for spectroscopic analysis). After completion of the reaction, the solvent was distilled off under reduced pressure to obtain 140 mg of the desired product as white crystals.

Melting point: 74.0 to 76.0° C.

$^1$H NMR (CDCl$_3$, Me$_4$Si, 300 MHz) δ 8.47 (s, 1H), 7.5-7.75 (m, 4H), 6.47 (bs, 1H), 4.53 (d, J=5.1 Hz, 2H), 4.06 (s, 3H), 3.88 (s, 3H).

In Table 2, more specific examples of the oxime-substituted amide compound represented by the formula (I) to be used as active ingredient A of the present invention, which can be prepared in the same manner as in Synthesis Examples 1 to 3, will be shown, but the oxime-substituted amide compound to be used as active ingredient A of the present invention is not limited thereto.

In the Table, "*1" in the column for the melting point means that the property of the compound was oily or resinous.

TABLE 2

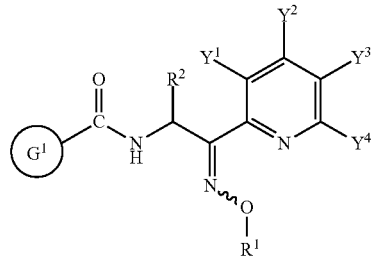

Substituent G$^1$ represents the following G$^1$-1a, G$^1$-3a, G$^1$-3b, G$^1$-27a or G$^1$-33a.

G$^1$-1a

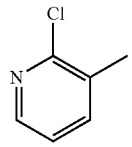

G$^1$-3a

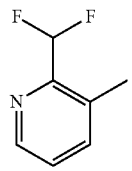

G$^1$-3b

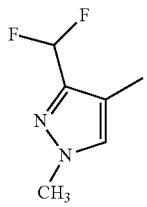

G$^1$-27a

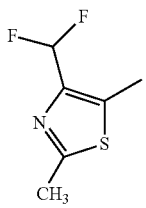

G¹-33a

| No. | G¹ | R² | Y¹ | Y² | Y³ | Y⁴ | R¹ | m.p. (° C.) |
|---|---|---|---|---|---|---|---|---|
| 1 | G¹-1a | H | Cl | H | Cl | H | CH₃ | *1 |
| 2 | G¹-1a | H | Cl | H | Cl | H | CH₃(Z) | 88.0-89.0 |
| 3 | G¹-1a | H | Cl | H | Cl | H | n-Pr | *1 |
| 4 | G¹-1a | H | Cl | H | Cl | H | i-Pr(Z) | 109.0-111.0 |
| 5 | G¹-3b | H | Cl | H | Cl | H | i-Pr(Z) | *1 |
| 6 | G¹-1a | CH₃(S) | Cl | H | Cl | H | i-Pr(Z) | *1 |
| 7 | G¹-1a | H | Cl | H | Cl | F | Et(Z) | *1 |
| 8 | G¹-1a | H | Cl | OCH₃ | Cl | H | CH₃(Z) | 74.0-76.0 |
| 9 | G¹-1a | H | Cl | OCH₃ | Cl | H | i-Pr(Z) | 70.0-71.0 |
| 10 | G¹-27a | H | Cl | OCH₃ | Cl | H | i-Pr(Z) | *1 |
| 11 | G¹-1a | H | Cl | OEt | Cl | H | CH₃(Z) | 90.0-92.0 |
| 12 | G¹-1a | H | Cl | H | Br | H | CH₃(Z) | 85.0-86.0 |
| 13 | G¹-1a | H | Cl | H | Br | H | Et(Z) | 101.0-102.0 |
| 14 | G¹-1a | H | Cl | H | CF₃ | H | i-Pr(Z) | 97.0-98.0 |
| 15 | G¹-1a | H | Cl | H | CF₃ | H | CH₂Pr-c(Z) | 73.0-74.0 |
| 16 | G¹-3b | H | Cl | H | C≡CCH₃ | H | Et(Z) | 128.0-131.0 |
| 17 | G¹-3b | H | Cl | H | C≡CCH₃ | H | n-Pr(Z) | *1 |
| 18 | G¹-1a | H | Cl | H | C≡CCH₃ | H | i-Pr(Z) | 106.0-108.0 |
| 19 | G¹-3b | H | Cl | H | C≡CCH₃ | H | i-Pr(Z) | *1 |
| 20 | G¹-27a | H | Cl | H | C≡CCH₃ | H | i-Pr(Z) | 102.0-103.0 |
| 21 | G¹-33a | H | Cl | H | C≡CCH₃ | H | i-Pr(Z) | *1 |
| 22 | G¹-27a | H | Cl | H | C≡CPr-c | H | CH₃ | *1 |
| 23 | G¹-27a | H | Cl | H | C≡CPr-c | H | CH₃(Z) | 96.0-98.0 |
| 24 | G¹-27a | H | Cl | H | C≡CPr-c | H | Et(Z) | 96.0-98.0 |
| 25 | G¹-27a | H | Cl | H | C≡CPr-c | H | i-Pr(Z) | 105.0-107.0 |
| 26 | G¹-1a | H | Cl | H | C≡CPr-c | H | s-Bu | *1 |
| 27 | G¹-27a | H | Cl | H | C≡CPr-c | H | s-Bu(Z) | *1 |
| 28 | G¹-27a | H | Cl | H | C≡CBu-t | H | CH₃(Z) | 132.0-135.0 |
| 29 | G¹-1a | H | Cl | H | C≡CPh | H | i-Pr | *1 |
| 30 | G¹-3b | H | Br | H | Br | H | i-Pr(Z) | *1 |
| 31 | G¹-27a | H | Br | H | Br | H | i-Pr(Z) | *1 |
| 32 | G¹-1a | H | Cl | SO₂CH₃ | Cl | H | i-Pr(Z) | *1 |
| 33 | G¹-1a | H | Cl | H | Cl | H | CH₂CF₃(Z) | 101.0-103.0 |
| 34 | G¹-27a | H | Cl | H | C≡CCH₃ | H | t-Bu(Z) | 134.0-140.0 |
| 35 | G¹-3a | H | Cl | H | C≡CBu-t | H | CH₃(Z) | 45.0-47.0 |
| 36 | G¹-1a | H | Cl | H | C≡CPr-c | H | CH₃(Z) | *1 |
| 37 | G¹-27a | H | Cl | H | C≡CBu-t | H | i-Pr(Z) | *1 |

Among oxime-substituted amide compounds of the formula (I) shown in Table 2, ¹H NMR data of compounds, of which the properties were resinous, will be shown in Table 3.

TABLE 3

| No. | ¹H NMR (CDCl₃, Me₄Si, 300 MHz) |
|---|---|
| 1 | δ8.50 and 8.45 (d, J = 2.1 Hz, 1H), 7.80 and 7.78 (d, J = 2.1 Hz, 1H), 7.35-7.75 (m, 4H), 6.48 and 6.43 (bs, 1H), 4.73 and 4.53 (d, J = 6.3 Hz, 2H), 4.06 and 4.02 (s, 3H). |
| 3 | 8.49 and 8.44 (d, J = 2.1 Hz, 1H), 7.80 and 7.78 (d, J = 2.1 Hz, 1H), 7.35-7.7 (m, 4H), 6.53 and 6.49 (bs, 1H), 4.75 and 4.52 (d, J = 6.3 Hz, 2H), 4.21 and 4.03 (t, J = 6.9 Hz, 2H), 1.7-1.8 and 1.55-4.65 (m, 2H), 0.96 and 0.86 (t, J = 7.5 Hz, 3H). |
| 5 | δ8.7-8.8 (m, 1H), 8.49 (d, J = 2.1 Hz, 1H), 7.9-8.0 (m, 1H), 7.78 (d, J = 2.1 Hz, 1H), 7.45-7.55 (m, 1H), 6.8-7.2 (m, 2H), 4.52 (d, J = 5.7 Hz, 2H), 4.3-4.45 (m, 1H), 1.19 (d, J = 6.0 Hz, 6H). |
| 6 | δ8.48 (d, J = 2.1 Hz, 1H), 7.78 (d, J = 2.1 Hz, 1H), 7.45-7.75 (m, 4H), 6.84 (bs, 1H), 5.15-5.3 (m, 1H), 4.25-4.45 (m, 1H), 1.44 (d, J = 6.6 Hz, 3H), 1.18 (d, J = 6.0 Hz, 6H). |
| 7 | δ7.90 (d, J = 7.8 Hz, 1H), 7.45-7.75 (m, 4H), 6.3-6.45 (m, 1H), 4.52 (d, J = 4.9 Hz, 2H), 4.14 (q, J = 7.1 Hz, 2H), 1.22 (t, J = 7.1 Hz, 3H). |

TABLE 3-continued

| No. | $^1$H NMR (CDCl$_3$, Me$_4$Si, 300 MHz) |
|---|---|
| 10 | δ8.46 (s, 1H), 7.90 (s, 1H), 7.06 (bs, 1H), 6.84 (t, J = 54.6 Hz, 1H), 4.48 (d, J = 4.8 Hz, 2H), 4.3-4.45 (m, 1H), 4.03 (s, 3H), 3.93 (s, 3H), 1.21 (d, J = 6.3 Hz, 6H). |
| 17 | δ8.78 (d, J = 4.9 Hz, 1H), 8.51 (d, J = 1.7 Hz, 1H), 7.94 (d, J = 7.8 Hz, 1H), 7.74 (d, J = 1.7 Hz, 1H), 7.49 (dd, J = 7.8, 4.9 Hz, 1H), 7.03 (t, J = 54.5 Hz, 1H), 6.85 (bs, 1H), 4.54 (d, J = 5.1 Hz, 2H), 4.05 (t, J = 6.6 Hz, 2H), 2.10 (s, 3H), 1.55-1.75 (m, 2H), 0.87 (t, J = 7.3 Hz, 3H). |
| 19 | δ8.77 (dd, J = 4.8, 1.0 Hz, 1H), 8.50 (d, J = 1.7 Hz, 1H), 7.94 (d, J = 7.8 Hz, 1H), 7.73 (d, J = 1.7 Hz, 1H), 7.48 (dd, J = 7.8, 4.8 Hz, 1H), 7.03 (t, J = 54.1 Hz, 1H), 6.93 (bs, 1H), 4.53 (d, J = 5.1 Hz, 2H), 4.37 (sep, J = 6.1 Hz, 1H), 2.10 (s, 3H), 1.20 (d, J = 6.1 Hz, 6H). |
| 21 | δ8.50 (d, J = 1.7 Hz, 1H), 7.72 (d, J = 1.4 Hz, 1H), 7.21 (t, J = 54.0 Hz, 1H), 7.03 (bs, 1H), 4.48 (d, J = 4.8 Hz, 2H), 4.40 (sep, J = 6.5 Hz, 1H), 2.77 (s, 3H), 2.10 (s, 3H), 1.22 (d, J = 6.5 Hz, 6H). |
| 22 | δ8.47 and 8.45 (s, 1H), 7.88 and 7.85 (s, 1H), 7.65-7.7 (m, 1H), 6.99 (bs, 1H), 6.87 and 6.75 (t, J = 54.0 Hz, 1H), 4.71 and 4.49 (d, J = 5.1 Hz, 2H), 3.85-4.1 (m, 6H), 1.4-1.55 (m, 1H), 0.8-1.0 (m, 4H). |
| 26 | δ8.48 and 8.42 (d, J = 1.7 Hz, 1H), 7.74 and 7.70 (d, J = 1.7 Hz, 1H), 7.3-7.75 (m, 4H), 6.60 (bs, 1H), 4.78 and 4.52 (d, J = 4.8 Hz, 2H), 4.1-4.35 (m, 1H), 1.25-1.7 (m, 3H), 1.17 (d, J = 6.5 Hz, 3H), 0.75-1.0 (m, 4H), 0.83 (t, J = 7.5 Hz, 3H). |
| 27 | δ8.47 (d, J = 1.7 Hz, 1H), 7.90 (s, 1H), 7.68 (d, J = 1.7 Hz, 1H), 7.12 (bs, 1H), 6.88 (t, J = 54.1 Hz, 1H), 4.48 (d, J = 4.8 Hz, 2H), 4.1-4.25 (m, 1H), 3.93 (s, 3H), 1.35-1.7 (m, 3H), 1.19 (d, J = 6.5 Hz, 3H), 0.8-1.0 (m, 4H), 0.84 (t, J = 7.3 Hz, 3H). |
| 29 | δ8.65 and 8.59 (d, J = 1.7 Hz, 1H), 7.91 and 7.87 (d, J = 1.7 Hz, 1H), 7.35-7.75 (m, 9H), 6.59 (bs, 1H), 4.80 and 4.56 (d, J = 5.8 and 5.1 Hz, 2H), 4.54 and 4.38 (sep, J = 6.3 Hz, 1H), 1.34 and 1.19 (d, J = 6.3 Hz, 6H). |
| 30 | δ8.7-8.8 (m, 1H), 8.61 (d, J = 1.8 Hz, 1H), 8.05-8.1 (m, 1H), 7.9-8.0 (m, 1H), 7.4-7.5 (m, 1H), 6.8-7.3 (m, 2H), 4.51 (d, J = 5.4 Hz, 2H), 4.3-4.45 (m, 1H), 1.20 (d, J = 6.3 Hz, 6H). |
| 31 | δ8.61 (d, J = 2.1 Hz, 1H), 8.06 (d, J = 2.1 Hz, 1H), 7.90 (s, 1H), 7.09 (bs, 1H), 6.85 (t, J = 54.0 Hz, 1H), 4.3-4.5 (m, 3H), 3.92 (s, 3H), 1.21 (d, J = 6.6 Hz, 6H). |
| 32 | δ8.70 and 8.65 (s, 1H), 7.35-7.75 (m, 4H), 6.48 and 6.39 (bs, 1H), 4.3-4.75 (m, 3H), 3.3-3.4 (m, 3H), 1.1-1.35 (m, 6H). |
| 36 | δ8.46 and 8.42 (d, J = 1.8 Hz, 1H), 7.45-7.75 (m, 5H), 6.45-6.65 (m, 1H), 4.74 and 4.52 (d, J = 5.1 Hz, 2H), 4.06 and 3.86 (s, 3H), 1.4-1.55 (m, 1H), 0.8-1.0 (m, 4H). |
| 37 | δ8.50 (d, J = 2.1 Hz, 1H), 7.91 (s, 1H), 7.72 (d, J = 2.1 Hz, 1H), 7.14 (bs, 1H), 6.88 (t, J = 54.0 Hz, 1H), 4.49 (d, J = 4.5 Hz, 2H), 4.39 (sep, J = 6.3 Hz, 1H), 3.94 (s, 3H), 1.33 (s, 9H), 1.20 (d, J = 6.3 Hz, 6H). |

As the known fungicidal or bactericidal active compound to be used as active ingredient B of the present invention, for example, compound(s) selected from each of the following groups may be mentioned.

Active Ingredient B-I Group:

TABLE 4

| NO. | Compound name (common name) |
|---|---|
| A01 | benalaxyl (benalaxyl) |
| A02 | benalaxyl-M (benalaxyl-M) |
| A03 | furalaxyl (furalaxyl) |
| A04 | metalaxyl (metalaxyl) |
| A05 | metalaxyl-M (metalaxyl-M) |
| A06 | ofurace (ofurace) |
| A07 | oxadixyl (oxadixyl) |
| A08 | bupirimate (bupirimate) |
| A09 | ethirimol (ethirimol) |
| A10 | hymexazol (hymexazol) |
| A11 | octhilinone (octhilinone) |
| A12 | oxolinic acid (oxolinic acid) |

Active Ingredient B-II Group;

TABLE 5

| NO. | Compound name (common name) |
|---|---|
| B01 | benomyl (benomyl) |
| B02 | carbendazim (carbendazim) |
| B03 | fuberidazole (fuberidazole) |
| B04 | thiabendazole (thiabendazole) |
| B05 | thiophanate-methyl (thiophanate-methyl) |
| B06 | diethofencarb (diethofencarb) |
| B07 | ethaboxam (ethaboxam) |
| B08 | zoxamide (zoxamide) |
| B09 | pencycuron (pencycuron) |
| B10 | fluopicolide (fluopicolide) |
| B11 | diflumetorim (diflumetorim) |
| B12 | benodanil (benodanil) |

Active Ingredient B-III Group;

TABLE 6

| NO. | Compound name (common name) |
|---|---|
| C01 | benzovindiflupyr (benzovindiflupyr) |
| C02 | bixafen (bixafen) |

TABLE 6-continued

| NO. | Compound name (common name) |
|---|---|
| C03 | boscalid (boscalid) |
| C04 | carboxin (carboxin) |
| C05 | fenfuram (fenfuram) |
| C06 | fluopyram (fluopyram) |
| C07 | flutolanil (flutolanil) |
| C08 | fluxapyroxad (fluxapyroxad) |
| C09 | furametpyr (furametpyr) |
| C10 | isofetamid (isofetamid) |
| C11 | isopyrazam (isopyrazam) |
| C12 | mepronil (mepronil) |
| C13 | oxycarboxin (oxycarboxin) |
| C14 | penflufen (penflufen) |
| C15 | penthiopyrad (penthiopyrad) |
| C16 | sedaxane (sedaxane) |
| C17 | thifluzamide (thifluzamide) |
| C18 | azoxystrobin (azoxystrobin) |
| C19 | coumoxystrobin (coumoxystrobin) |
| C20 | dimoxystrobin (dimoxystrobin) |
| C21 | enestrobin (enestrobin) |
| C22 | enoxastrobin (enoxastrobin) |
| C23 | famoxadone (famoxadone) |
| C24 | fenamidone (fenamidone) |
| C25 | fenaminstrobin (fenaminstrobin) |
| C26 | flufenoxystrobin (flufenoxystrobin) |
| C27 | fluoxastrobin (fluoxastrobin) |
| C28 | kresoxim-methyl (kresoxim-methyl) |
| C29 | mandestrobin (mandestrobin) |
| C30 | metominostrobin (metominostrobin) |
| C31 | orysastrobin (orysastrobin) |
| C32 | picoxystrobin (picoxystrobin) |
| C33 | pyraclostrobin (pyraclostrobin) |
| C34 | pyrametostrobin (pyrametostrobin) |
| C35 | pyraoxystrobin (pyraoxystrobin) |
| C36 | pyribencarb-methyl (pyribencarb-methyl) |
| C37 | pyriminostrobin (pyriminostrobin) |
| C38 | triclopyricab (triclopyricab) |
| C39 | trifloxystrobin (trifloxystrobin) |
| C40 | amisulbrom (amisulbrom) |
| C41 | cyazofamid (cyazofamid) |
| C42 | dinocap (dinocap) |
| C43 | fluazinam (fluazinam) |
| C44 | meptyldinocap (meptyldinocap) |
| C45 | fentin (fentin) |
| C46 | tributyltin oxide (tributyltin oxide) |
| C47 | silthiofam (silthiofam) |
| C48 | ametoctradin (ametoctradin) |

Active Ingredient B-IV Group;

TABLE 7

| NO. | Compound name (common name) |
|---|---|
| D1 | cyprodinil (cyprodinil) |
| D2 | mepanipyrim (mepanipyrim) |
| D3 | pyrimethanil (pyrimethanil) |
| D4 | blasticidin-S (blasticidin-S) |
| D5 | kasugamycin (kasugamycin) |
| D6 | streptomycin (streptomycin) |
| D7 | oxytetracycline (oxytetracycline) |

Active Ingredient B-V Group;

TABLE 8

| NO. | Compound name (common name) |
|---|---|
| E01 | proquinazid (proquinazid) |
| E02 | quinoxyfen (quinoxyfen) |
| E03 | fenpiclonil (fenpiclonil) |
| E04 | fludioxonil (fludioxonil) |
| E05 | chlozolinate (chlozolinate) |

Active Ingredient B-V Group;

TABLE 9

| NO. | Compound name (common name) |
|---|---|
| F01 | iprodione (iprodione) |
| F02 | procymidone (procymidone) |
| F03 | vinclozolin (vinclozolin) |

Active Ingredient B-VI Group;

TABLE 10

| NO. | Compound name (common name) |
|---|---|
| G01 | edifenphos (edifenphos) |
| G02 | iprobenfos (iprobenfos) |
| G03 | isoprothiolane (isoprothiolane) |
| G04 | pyrazophos (pyrazophos) |
| G05 | biphenyl (biphenyl) |
| G06 | chloroneb (chloroneb) |
| G07 | dichloran (dicloran) |
| G08 | etridiazole (etridiazole) |
| G09 | quintozene (quintozene) |
| G10 | tecnazene (tecnazene) |
| G11 | tolclofos-methyl (tolclofos-methyl) |
| G12 | propamocarb hydrochloride (propamocarb hydrochloride) |
| G13 | *Bacillus subtilis* (*Bacillus subtilis*, Strain: D747, FZB24, GB03, HAI0404, MBI600, QST713, Y1336, etc.) |

Active Ingredient B-VII Group;

TABLE 11

| NO. | Compound name (common name) |
|---|---|
| H01 | azaconazole (azaconazole) |
| H02 | bitertanol (bitertanol) |
| H03 | bromuconazole (bromuconazole) |
| H04 | climbazole (climbazole) |
| H05 | cyproconazole (cyproconazole) |
| H06 | diclobutrazol (diclobutrazol) |
| H07 | difenoconazole (difenoconazole) |
| H08 | diniconazole (diniconazole) |
| H09 | diniconazole-M (diniconazole-M) |
| H10 | epoxiconazole (epoxiconazole) |
| H11 | etaconazole (etaconazole) |
| H12 | fenarimol (fenarimol) |
| H13 | fenbuconazole (fenbuconazole) |
| H14 | fluotrimazole (fluotrimazole) |
| H15 | fluquinconazole (fluquinconazole) |
| H16 | flusilazole (flusilazole) |
| H17 | flutriafol (flutriafol) |
| H18 | furconazole (furconazole) |
| H19 | hexaconazole (hexaconazole) |
| H20 | imazalil (imazalil) |
| H21 | imibenconazole (imibenconazole) |
| H22 | ipconazole (ipconazole) |
| H23 | metconazole (metconazole) |
| H24 | myclobutanil (myclobutanil) |
| H25 | nuarimol (nuarimol) |
| H26 | oxpoconazole fumarate (oxpoconazole fumarate) |
| H27 | pefurazoate (pefurazoate) |
| H28 | penconazole (penconazole) |
| H29 | prochloraz (prochloraz) |
| H30 | propiconazole (propiconazole) |
| H31 | prothioconazole (prothioconazole) |
| H32 | pyrifenox (pyrifenox) |
| H33 | pyrisoxazole (pyrisoxazole) |
| H34 | simeconazole (simeconazole) |
| H35 | tebuconazole (tebuconazole) |
| H36 | tetraconazole (tetraconazole) |
| H37 | triadimefon (triadimefon) |
| H38 | triadimenol (triadimenol) |
| H39 | triflumizole (triflumizole) |
| H40 | triforine (triforine) |
| H41 | triticonazole (triticonazole) |

TABLE 11-continued

| NO. | Compound name (common name) |
|---|---|
| H42 | aldimorph (aldimorph) |
| H43 | dodemorph acetate (dodemorph-acetate) |
| H44 | fenpropidin (fenpropidin) |
| H45 | fenpropimorph (fenpropimorph) |
| H46 | piperalin (piperalin) |
| H47 | spiroxamine (spiroxamine) |
| H48 | tridemorph (tridemorph) |
| H49 | fenhexamid (fenhexamid) |
| H50 | fenpyrazamine (fenpyrazamine) |

Active Ingredient B-VIII Group;

TABLE 12

| NO. | Compound name (common name) |
|---|---|
| I01 | validamycin (validamycin) |
| I02 | polyoxins (polyoxins) |
| I03 | polyoxin-D (polyoxorim) |
| I04 | benthiavalicarb-isopropyl (benthiavalicarb-isopropyl) |
| I05 | dimethomorph (dimethomorph) |
| I06 | flumorph (flumorph) |
| I07 | iprovalicarb (iprovalicarb) |
| I08 | mandipropamid (mandipropamid) |
| I09 | pyrimorph (pyrimorph) |
| I10 | valifenalate (valifenalate) |

Active Ingredient B-IX Group;

TABLE 13

| NO. | Compound name (common name) |
|---|---|
| J01 | phthalide (phthalide) |
| J02 | pyroquilon (pyroquilon) |
| J03 | tricyclazole (tricyclazole) |
| J04 | carpropamid (carpropamid) |
| J05 | diclocymet (diclocymet) |
| J06 | fenoxanil (fenoxanil) |

Active Ingredient B-X Group;

TABLE 14

| NO. | Compound name (common name) |
|---|---|
| K01 | acibenzolar-S-methyl (acibenzolar-S-methyl) |
| K02 | probenazole (probenazole) |
| K03 | isotianil (isotianil) |
| K04 | tiadinil (tiadinil) |

Active Ingredient B-XI Group;

TABLE 15

| NO. | Compound name (common name) |
|---|---|
| L01 | laminarin (laminarin) |
| L02 | bordeaux mixture (bordeaux mixture) |
| L03 | cheshunt mixture (cheshunt mixture) |
| L04 | copper carbonate, basic (copper carbonate, basic) |
| L05 | copper hydroxide (copper hydroxide) |
| L06 | copper naphthenate (copper naphthenate) |
| L07 | copper oleate (copper oleate) |
| L08 | copper oxychloride (copper oxychloride) |
| L09 | copper sulfate (copper sulfate) |
| L10 | copper sulfate, basic (copper sulfate, basic) |
| L11 | oxine copper (oxine copper) |
| L12 | calcium polysulfide (calcium polysulfide) |
| L13 | sulfur (sulfur) |
| L14 | amobam (amobam) |
| L15 | ferbam (ferbam) |

TABLE 15-continued

| NO. | Compound name (common name) |
|---|---|
| L16 | mancozeb (mancozeb) |
| L17 | maneb (maneb) |
| L18 | metiram (metiram) |
| L19 | polycarbamate (polycarbamate) |
| L20 | propineb (propineb) |
| L21 | thiram (thiram) |
| L22 | ziram (ziram) |
| L23 | captan (captan) |
| L24 | folpet (folpet) |
| L25 | chlorothalonil (chlorothalonil) |
| L26 | dichlofluanid (dichlofluanid) |
| L27 | tolylfluanid (tolylfluanid) |
| L28 | guazatine (guazatine) |
| L29 | iminoctadine-albesilate (iminoctadine-albesilate) |
| L30 | iminoctadine-triacetate (iminoctadine-triacetate) |
| L31 | anilazine (anilazine) |
| L32 | dithianon (dithianon) |
| L33 | chinomethionat (chinomethionat) |
| L34 | fluoroimide (fluoroimide) |

Active Ingredient B-XII Group;

TABLE 16

| NO. | Compound name (common name) |
|---|---|
| M01 | cyflufenamid (cyflufenamid) |
| M02 | cymoxanil (cymoxanil) |
| M03 | diclomezine (diclomezine) |
| M04 | dodine (dodine) |
| M05 | ferimzone (ferimzone) |
| M06 | flusulfamide (flusulfamide) |
| M07 | flutianil (flutianil) |
| M08 | fosetyl-aluminium (fosetyl-aluminium) |
| M09 | metrafenone (metrafenone) |
| M10 | oxathiapiprolin (oxathiapiprolin) |
| M11 | pyriofenone (pyriofenone) |
| M12 | tebufloquin (tebufloquin) |
| M13 | tolprocarb (tolprocarb) |
| M14 | triazoxide (triazoxide) |
| M15 | potassium hydrogen carbonate (potassium hydrogen carbonate) |
| M16 | sodium hydrogen carbonate (sodium hydrogen carbonate) |
| M17 | shiitake mycelium extract |
| M18 | shiitake fruiting body extract |
| M19 | BCF-082 (test name) |
| M20 | NNF-0721 (test name) |
| M21 | MIF-1002 (test name) |
| M22 | NF-180 (test name) |
| M23 | picarbutrazox (picarbutrazox) |

Now, examples of the combination of [active ingredient A] selected from an oxime-substituted amide compounds represented by the formula (I) and [active ingredient B] selected from known fungicidal or bactericidal compounds, which exhibits a synergistic disease controlling effect, will be given below.

In the following notations, for example, notation "1+(A01)" represents a combination of active ingredient A being the compound of No. 1 in Table 2, and active ingredient B being benalaxyl of No. A01 in Table 4.

Examples of the combination of compounds: "1+(A01)", "1+(A02)", "1+(A03)", "1+(A04)", "1+(A05)", "1+(A06)", "1+(A07)", "1+(A08)", "1+(A09)", "1+(A10)", "1+(A11)", "1+(A12)", "1+(B01)", "1+(B02)", "1+(B03)", "1+(B04)", "1+(B05)", "1+(B06)", "1+(B07)", "1+(B08)", "1+(B09)", "1+(B10)", "1+(B11)", "1+(B12)", "1+(C01)", "1+(C02)", "1+(C03)", "1+(C04)", "1+(C05)", "1+(C006)", "1+(C07)", "1+(C08)", "1+(C09)", "1+(C10)", "1+(C11)", "1+(C12)", "1+(C13)", "1+(C14)", "1+(C15)", "1+(C16)", "1+(C17)", "1+(C18)", "1+(C19)", "1+(C20)", "1+(C21)", "1+(C22)", "1+(C23)", "1+(C24)", "1+(C25)", "1+(C26)", "1+(C27)", "1+(C28)", "1+(C29)", "1+(C30)", "1+(C31)", "1+(C32)", "1+(C33)", "1+(C34)", "1+(C35)", "1+(C36)", "1+(C37)", "1+(C38)", "1+(C39)", "1+(C40)", "1+(C41)", "1+(C42)", "1+(C43)", "1+(C44)", "1+(C45)", "1+(C46)", "1+(C47)", "1+(C48)", "1+(D01)", "1+(D02)", "1+(D03)", "1+(D04)", "1+(D05)", "1+(E01)", "1+(E02)", "1+(E03)", "1+(E04)", "1+(E05)", "1+(F01)", "1+(F02)", "1+(F03)", "1+(G01)", "1+(G02)", "1+(G03)", "1+(G04)", "1+(G05)", "1+(G06)", "1+(G07)", "1+(G08)", "1+(G09)", "1+(G10)", "1+(G11)", "1+(G12)", "1+(G13)", "1+(H01)", "1+(H02)", "1+(H03)", "1+(H04)", "1+(H05)", "1+(H06)", "1+(H07)", "1+(H08)", "1+(H09)", "1+(H10)", "1+(H11)", "1+(H12)", "1+(H13)", "1+(H14)", "1+(H15)", "1+(H16)", "1+(H17)", "1+(H18)", "1+(H19)", "1+(H20)", "1+(H21)", "1+(H22)", "1+(H23)", "1+(H24)", "1+(H25)", "1+(H26)", "1+(H27)", "1+(H28)", "1+(H29)", "1+(H30)", "1+(H31)", "1+(H32)", "1+(H33)", "1+(H34)", "1+(H35)", "1+(H36)", "1+(H37)", "1+(H38)", "1+(H39)", "1+(H40)", "1+(H41)", "1+(H42)", "1+(H43)", "1+(H44)", "1+(H45)", "1+(H46)", "1+(H47)", "1+(H48)", "1+(H49)", "1+(H50)", "1+(I01)", "1+(I02)", "1+(I03)", "1+(I04)", "1+(I05)", "1+(I06)", "1+(I07)", "1+(I08)", "1+(I09)", "1+(I10)", "1+(J01)", "1+(J02)", "1+(J03)", "1+(J04)", "1+(J05)", "1+(J06)", "1+(K01)", "1+(K02)", "1+(K03)", "1+(K04)", "1+(K05)", "1+(K06)", "1+(K07)", "1+(K08)", "1+(K09)", "1+(K10)", "1+(K11)", "1+(K12)", "1+(K13)", "1+(K14)", "1+(L01)", "1+(L02)", "1+(L03)", "1+(L04)", "1+(L05)", "1+(L06)", "1+(L07)", "1+(L08)", "1+(L09)", "1+(L10)", "1+(L11)", "1+(L12)", "1+(L13)", "1+(L14)", "1+(L15)", "1+(L16)", "1+(L17)", "1+(L18)", "1+(L19)", "1+(L20)", "1+(L21)", "1+(L22)", "1+(L23)", "1+(L24)", "1+(L25)", "1+(L26)", "1+(L27)", "1+(L28)", "1+(L29)", "1+(L30)", "1+(L31)", "1+(L32)", "1+(L33)", "1+(L34)", "1+(M01)", "1+(M02)", "1+(M03)", "1+(M04)", "1+(M05)", "1+(M06)", "1+(M07)", "1+(M08)", "1+(M09)", "1+(M10)", "1+(M11)", "1+(M12)", "1+(M13)", "1+(M14)", "1+(M15)", "1+(M16)", "1+(M17)", "1+(M18)", "1+(M19)", "1+(M20)", "1+(M21)", "1+(M22)", "1+(M23)"

"2+(A01)", "2+(A02)", "2+(A03)", "2+(A04)", "2+(A05)", "2+(A06)", "2+(A07)", "2+(A08)", "2+(A09)", "2+(A10)", "2+(A11)", "2+(A12)", "2+(B01)", "2+(B02)", "2+(B03)", "2+(B04)", "2+(B05)", "2+(B06)", "2+(B07)", "2+(B08)", "2+(B09)", "2+(B10)", "2+(B11)", "2+(B12)", "2+(C01)", "2+(C02)", "2+(03)", "2+(C04)", "2+(C05)", "2+(C06)", "2+(C07)", "2+(C08)", "2+(C09)", "2+(C10)", "2+(C11)", "2+(C12)", "2+(C13)", "2+(C14)", "2+(C15)", "2+(C16)", "2+(C17)", "2+(C18)", "2+(C19)", "2+(C20)", "2+(C21)", "2+(C22)", "2+(C23)", "2+(C24)", "2+(C25)", "2+(C26)", "2+(C27)", "2+(C28)", "2+(C29)", "2+(C30)", "2+(C31)", "2+(C32)", "2+(C33)", "2+(C34)", "2+(C35)", "2+(C36)", "2+(C37)", "2+(C38)", "2+(C39)", "2+(C40)", "2+(C41)", "2+(C42)", "2+(C43)", "2+(C44)", "2+(C45)", "2+(C46)", "2+(C47)", "2+(C48)", "2+(D01)", "2+(D02)", "2+(D03)", "2+(D04)", "2+(D05)", "2+(E01)", "2+(E02)", "2+(E03)", "2+(E04)", "2+(E05)", "2+(F01)", "2+(F02)", "2+(F03)", "2+(G01)", "2+(G02)", "2+(G03)", "2+(G04)", "2+(G05)", "2+(G06)", "2+(G07)", "2+(G08)", "2+(G09)", "2+(G10)", "2+(G11)", "2+(G12)", "2+(G13)", "2+(H01)", "2+(H02)", "2+(H03)", "2+(H04)", "2+(H05)", "2+(H06)", "2+(H07)", "2+(H08)", "2+(H09)", "2+(H10)", "2+(H11)", "2+(H12)", "2+(H13)", "2+(H14)", "2+(H15)", "2+(H16)", "2+(H17)", "2+(H18)", "2+(H19)", "2+(H20)", "2+(H21)", "2+(H22)", "2+(H23)", "2+(H24)", "2+(H25)", "2+(H26)", "2+(H27)", "2+(H28)", "2+(H29)", "2+(H30)", "2+(H31)", "2+(H32)", "2+(H33)", "2+(H34)", "2+(H35)", "2+(H36)", "2+(H37)", "2+(H38)", "2+(H39)", "2+(H40)", "2+(H41)", "2+(H42)", "2+(H43)", "2+(H44)", "2+(H45)", "2+(H46)", "2+(H47)", "2+(H48)", "2+(H49)", "2+(H50)", "2+(I01)", "2+(I02)", "2+(I03)", "2+(I04)", "2+(I05)", "2+(I06)", "2+(I07)", "2+(I08)", "2+(I09)", "2+(I10)", "2+(J01)", "2+(J02)", "2+(J03)", "2+(J04)", "2+(J05)", "2+(J06)", "2+(K01)", "2+(K02)", "2+(K03)", "2+(K04)", "2+(K05)", "2+(K06)", "2+(K07)", "2+(K08)", "2+(K09)", "2+(K10)", "2+(K11)", "2+(K12)", "2+(K13)", "2+(K14)", "2+(L01)", "2+(L02)", "2+(L03)", "2+(L04)", "2+(L05)", "2+(L06)", "2+(L07)", "2+(L08)", "2+(L09)", "2+(L10)", "2+(L11)", "2+(L12)", "2+(L13)", "2+(L14)", "2+(L15)", "2+(L16)", "2+(L17)", "2+(L18)", "2+(L19)", "2+(L20)", "2+(L21)", "2+(L22)", "2+(L23)", "2+(L24)", "2+(L25)", "2+(L26)", "2+(L27)", "2+(L28)", "2+(L29)", "2+(L30)", "2+(L31)", "2+(L32)", "2+(L33)", "2+(L34)", "2+(M01)", "2+(M02)", "2+(M03)", "2+(M04)", "2+(M05)", "2+(M06)", "2+(M07)", "2+(M08)", "2+(M09)", "2+(M10)", "2+(M11)", "2+(M12)", "2+(M13)", "2+(M14)", "2+(M15)", "2+(M16)", "2+(M17)", "2+(M18)", "2+(M19)", "2+(M20)", "2+(M21)", "2+(M22)", "2+(M23)"

"3+(A01)", "3+(A02)", "3+(A03)", "3+(A04)", "3+(A05)", "3+(A06)", "3+(A07)", "3+(A08)", "3+(A09)", "3+(A10)", "3+(A11)", "3+(A12)", "3+(B01)", "3+(B02)", "3+(B03)", "3+(B04)", "3+(B05)", "3+(B06)", "3+(B07)", "3+(B08)", "3+(B09)", "3+(B10)", "3+(B11)", "3+(B12)", "3+(C01)", "3+(C02)", "3+(C03)", "3+(C04)", "3+(C05)", "3+(C06)", "3+(C07)", "3+(C08)", "3+(C09)", "3+(C10)", "3+(C11)", "3+(C12)", "3+(C13)", "3+(C14)", "3+(C15)", "3+(C16)", "3+(C17)", "3+(C18)", "3+(C19)", "3+(C20)", "3+(C21)", "3+(C22)", "3+(C23)", "3+(C24)", "3+(C25)", "3+(C26)", "3+(C27)", "3+(C28)", "3+(C29)", "3+(C30)", "3+(C31)", "3+(C32)", "3+(C33)", "3+(C34)", "3+(C35)", "3+(C36)", "3+(C37)", "3+(C38)", "3+(C39)", "3+(C40)", "3+(C41)", "3+(C42)", "3+(C43)", "3+(C44)", "3+(C45)", "3+(C46)", "3+(C47)", "3+(C48)", "3+(D01)", "3+(D02)", "3+(D03)", "3+(D04)", "3+(D05)", "3+(E01)", "3+(E02)", "3+(E03)", "3+(E04)", "3+(E05)", "3+(F01)", "3+(F02)", "3+(F03)", "3+(G01)", "3+(G02)", "3+(G03)", "3+(G04)", "3+(G05)", "3+(G06)", "3+(G07)", "3+(G08)", "3+(G09)", "3+(G10)", "3+(G11)", "3+(G12)", "3+(G13)", "3+(H01)", "3+(H02)", "3+(H03)", "3+(H04)", "3+(H05)", "3+(H06)", "3+(H07)", "3+(H08)", "3+(H09)", "3+(H10)", "3+(H11)", "3+(H12)", "3+(H13)", "3+(H14)", "3+(H15)", "3+(H16)", "3+(H17)", "3+(H18)", "3+(H19)", "3+(H20)", "3+(H21)", "3+(H22)", "3+(H23)", "3+(H24)", "3+(H25)", "3+(H26)", "3+(H27)", "3+(H28)", "3+(H29)", "3+(H30)", "3+(H31)", "3+(H32)", "3+(H33)", "3+(H34)", "3+(H35)", "3+(H36)", "3+(H37)", "3+(H38)", "3+(H39)", "3+(H40)", "3+(H41)", "3+(H42)", "3+(H43)", "3+(H44)", "3+(H45)", "3+(H46)", "3+(H47)", "3+(H48)", "3+(H49)", "3+(H50)", "3+(I01)", "3+(I02)", "3+(I03)", "3+(I04)", "3+(I05)", "3+(I06)", "3+(I07)", "3+(I08)", "3+(I09)", "3+(I10)", "3+(J01)", "3+(J02)", "3+(J03)", "3+(J04)", "3+(J05)", "3+(J06)", "3+(K01)", "3+(K02)", "3+(K03)", "3+(K04)", "3+(K05)", "3+(K06)", "3+(K07)", "3+(K08)", "3+(K09)", "3+(K10)", "3+(K11)", "3+(K12)", "3+(K13)", "3+(K14)", "3+(L01)", "3+(L02)", "3+(L03)", "3+(L04)", "3+(L05)", "3+(L06)", "3+(L07)", "3+(L08)", "3+(L09)", "3+(L10)", "3+(L11)", "3+(L12)", "3+(L13)", "3+(L14)", "3+(L15)", "3+(L16)", "3+(L17)", "3+(L18)", "3+(L19)", "3+(L20)", "3+(L21)", "3+(L22)", "3+(L23)", "3+(L24)", "3+(L25)", "3+(L26)", "3+(L27)", "3+(L28)", "3+(L29)", "3+(L30)", "3+(L31)", "3+(L32)", "3+(L33)", "3+(L34)", "3+(M01)", "3+(M02)", "3+(M03)", "3+(M04)", "3+(M05)", "3+(M06)", "3+(M07)", "3+(M08)", "3+(M09)", "3+(M10)", "3+(M11)", "3+(M12)", "3+(M13)", "3+(M14)", "3+(M15)", "3+(M16)", "3+(M17)", "3+(M18)", "3+(M19)", "3+(M20)", "3+(M21)", "3+(M22)", "3+(M23)",

"4+(A01)", "4+(A02)", "4+(A03)", "4+(A04)", "4+(A05)", "4+(A06)", "4+(A07)", "4+(A08)", "4+(A09)", "4+(A10)", "4+(A11)", "4+(A12)", "4+(B01)", "4+(B02)", "4+(B03)", "4+(B04)", "4+(B05)", "4+(B06)", "4+(B07)", "4+(B08)", "4+(B09)", "4+(B10)", "4+(B11)", "4+(B12)", "4+(C01)", "4+(C02)", "4+(C03)", "4+(C04)", "4+(C05)", "4+(C06)", "4+(C07)", "4+(C08)", "4+(C09)", "4+(C10)", "4+(C11)", "4+(C12)", "4+(C13)", "4+(C14)", "4+(C15)", "4+(C16)", "4+(C17)", "4+(C18)", "4+(C19)", "4+(C20)", "4+(C21)", "4+(C22)", "4+(C23)", "4+(C24)", "4+(C25)", "4+(C26)", "4+(C27)", "4+(C28)", "4+(C29)", "4+(C30)", "4+(C31)", "4+(C32)", "4+(C33)", "4+(C34)", "4+(C35)", "4+(C36)", "4+(C37)", "4+(C38)", "4+(C39)", "4+(C40)", "4+(C41)", "4+(C42)", "4+(C43)", "4+(C44)", "4+(C45)", "4+(C46)", "4+(C47)", "4+(C48)", "4+(D01)", "4+(D02)", "4+(D03)", "4+(D04)", "4+(D05)", "4+(E01)", "4+(E02)", "4+(E03)", "4+(E04)", "4+(E05)", "4+(F01)", "4+(F02)", "4+(F03)", "4+(G01)", "4+(G02)", "4+(G03)", "4+(G04)", "4+(G05)", "4+(G06)", "4+(G07)", "4+(G08)", "4+(G09)", "4+(G10)", "4+(G11)", "4+(G12)", "4+(G13)", "4+(H01)", "4+(H02)", "4+(H03)", "4+(H04)", "4+(H05)", "4+(H06)", "4+(H07)", "4+(H08)", "4+(H09)", "4+(H10)", "4+(H11)", "4+(H12)", "4+(H13)", "4+(H14)", "4+(H15)", "4+(H16)", "4+(H17)", "4+(H18)", "4+(H19)", "4+(H20)", "4+(H21)", "4+(H22)", "4+(H23)", "4+(H24)", "4+(H25)", "4+(H26)", "4+(H27)", "4+(H28)", "4+(H29)", "4+(H30)", "4+(H31)", "4+(H32)", "4+(H33)", "4+(H34)", "4+(H35)", "4+(H36)", "4+(H37)", "4+(H38)", "4+(H39)", "4+(H40)", "4+(H41)", "4+(H42)", "4+(H43)", "4+(H44)", "4+(H45)", "4+(H46)", "4+(H47)", "4+(H48)", "4+(H49)", "4+(H50)", "4+(I01)", "4+(I02)", "4+(I03)", "4+(I04)", "4+(I05)", "4+(I06)", "4+(I07)", "4+(I08)", "4+(I09)", "4+(I10)", "4+(J01)", "4+(J02)", "4+(J03)", "4+(J04)", "4+(J05)", "4+(J06)", "4+(K01)", "4+(K02)", "4+(K03)", "4+(K04)", "4+(K05)", "4+(K06)", "4+(K07)", "4+(K08)", "4+(K09)", "4+(K10)", "4+(K11)", "4+(K12)", "4+(K13)", "4+(K14)", "4+(L01)", "4+(L02)", "4+(L03)", "4+(L04)", "4+(L05)", "4+(L06)", "4+(L07)", "4+(L08)", "4+(L09)", "4+(L10)", "4+(L11)", "4+(L12)", "4+(L13)", "4+(L14)", "4+(L15)", "4+(L16)", "4+(L17)", "4+(L18)", "4+(L19)", "4+(L20)", "4+(L21)", "4+(L22)", "4+(L23)", "4+(L24)", "4+(L25)", "4+(L26)", "4+(L27)", "4+(L28)", "4+(L29)", "4+(L30)", "4+(L31)", "4+(L32)", "4+(L33)", "4+(L34)", "4+(M01)", "4+(M02)", "4+(M03)", "4+(M04)", "4+(M05)", "4+(M06)", "4+(M07)", "4+(M08)", "4+(M09)", "4+(M10)", "4+(M11)", "4+(M12)", "4+(M13)", "4+(M14)", "4+(M15)", "4+(M16)", "4+(M17)", "4+(M18)", "4+(M19)", "4+(M20)", "4+(M21)", "4+(M22)", "4+(M23)",

"5+(A01)", "5+(A02)", "5+(A03)", "5+(A04)", "5+(A05)", "5+(A06)", "5+(A07)", "5+(A08)", "5+(A09)", "5+(A10)", "5+(A11)", "5+(A12)", "5+(B01)", "5+(B02)", "5+(B03)", "5+(B04)", "5+(B05)", "5+(B06)", "5+(B07)", "5+(B08)", "5+(B09)", "5+(B10)", "5+(B11)", "5+(B12)", "5+(C01)", "5+(C02)", "5+(C03)", "5+(C04)", "5+(C05)", "5+(C06)", "5+(C07)", "5+(C08)", "5+(C09)", "5+(C10)", "5+(C11)", "5+(C12)", "5+(C13)", "5+(C14)", "5+(C15)", "5+(C16)", "5+(C17)", "5+(C18)", "5+(C19)", "5+(C20)", "5+(C21)", "5+(C22)", "5+(C23)", "5+(C24)", "5+(C25)", "5+(C26)", "5+(C27)", "5+(C28)", "5+(C29)", "5+(C30)", "5+(C31)", "5+(C32)", "5+(C33)", "5+(C34)", "5+(C35)", "5+(C36)", "5+(C37)", "5+(C38)", "5+(C39)", "5+(C40)", "5+(C41)", "5+(C42)", "5+(C43)", "5+(C44)", "5+(C45)", "5+(C46)", "5+(C47)", "5+(C48)", "5+(D01)", "5+(D02)", "5+(D03)", "5+(D04)", "5+(D05)", "5+(E01)", "5+(E02)", "5+(E03)", "5+(E04)", "5+(E05)", "5+(F01)", "5+(F02)", "5+(F03)", "5+(G01)", "5+(G02)", "5+(G03)", "5+(G04)", "5+(G05)", "5+(G06)", "5+(G07)", "5+(G08)", "5+(G09)", "5+(G10)", "5+(G11)", "5+(G12)", "5+(G13)", "5+(H01)", "5+(H02)", "5+(H03)", "5+(H04)", "5+(H05)", "5+(H06)", "5+(H07)", "5+(H08)", "5+(H09)", "5+(H10)", "5+(H11)", "5+(H12)", "5+(H13)", "5+(H14)", "5+(H15)", "5+(H16)", "5+(H17)", "5+(H18)", "5+(H19)", "5+(H20)", "5+(H21)", "5+(H22)", "5+(H23)", "5+(H24)", "5+(H25)", "5+(H26)", "5+(H27)", "5+(H28)", "5+(H29)", "5+(H30)", "5+(H31)", "5+(H32)", "5+(H33)", "5+(H34)", "5+(H35)", "5+(H36)", "5+(H37)", "5+(H38)", "5+(H39)", "5+(H40)", "5+(H41)", "5+(H42)", "5+(H43)", "5+(H44)", "5+(H45)", "5+(H46)", "5+(H47)", "5+(H48)", "5+(H49)", "5+(H50)", "5+(I01)", "5+(I02)", "5+(I03)", "5+(I04)", "5+(I05)", "5+(I06)", "5+(I07)", "5+(I08)", "5+(I09)", "5+(I10)", "5+(J01)", "5+(J02)", "5+(J03)", "5+(J04)", "5+(J05)", "5+(J06)", "5+(K01)", "5+(K02)", "5+(K03)", "5+(K04)", "5+(K05)", "5+(K06)", "5+(K07)", "5+(K08)", "5+(K09)", "5+(K10)", "5+(K11)", "5+(K12)", "5+(K13)", "5+(K14)", "5+(L01)", "5+(L02)", "5+(L03)", "5+(L04)", "5+(L05)", "5+(L06)", "5+(L07)", "5+(L08)", "5+(L09)", "5+(L10)", "5+(L11)", "5+(L12)", "5+(L13)", "5+(L14)", "5+(L15)", "5+(L16)", "5+(L17)", "5+(L18)", "5+(L19)", "5+(L20)", "5+(L21)", "5+(L22)", "5+(L23)", "5+(L24)", "5+(L25)", "5+(L26)", "5+(L27)", "5+(L28)", "5+(L29)", "5+(L30)", "5+(L31)", "5+(L32)", "5+(L33)", "5+(L34)", "5+(M01)", "5+(M02)", "5+(M03)", "5+(M04)", "5+(M05)", "5+(M06)", "5+(M07)", "5+(M08)", "5+(M09)", "5+(M10)", "5+(M11)", "5+(M12)", "5+(M13)", "5+(M13)", "5+(M14)", "5+(M15)", "5+(M16)", "5+(M17)", "5+(M18)", "5+(M19)", "5+(M20)", "5+(M21)", "5+(M22)", "5+(M23)",

"6+(A01)", "6+(A02)", "6+(A03)", "6+(A04)", "6+(A05)", "6+(A06)", "6+(A07)", "6+(A08)", "6+(A09)", "6+(A10)", "6+(A11)", "6+(A12)", "6+(B01)", "6+(B02)", "6+(B03)", "6+(B04)", "6+(B05)", "6+(B06)", "6+(B07)", "6+(B08)", "6+(B09)", "6+(B10)", "6+(B11)", "6+(B12)", "6+(C01)", "6+(C02)", "6+(C03)", "6+(C04)", "6+(C05)", "6+(C06)", "6+(C07)", "6+(C08)", "6+(C09)", "6+(C10)", "6+(C11)", "6+(C12)", "6+(C13)", "6+(C14)", "6+(C15)", "6+(C16)", "6+(C17)", "6+(C18)", "6+(C19)", "6+(C20)", "6+(C21)", "6+(C22)", "6+(C23)", "6+(C24)", "6+(C25)", "6+(C26)", "6+(C27)", "6+(C28)", "6+(C29)", "6+(C30)", "6+(C31)", "6+(C32)", "6+(C33)", "6+(C34)", "6+(C35)", "6+(C36)", "6+(C37)", "6+(C38)", "6+(C39)", "6+(C40)", "6+(C41)", "6+(C42)", "6+(C43)", "6+(C44)", "6+(C45)", "6+(C46)", "6+(C47)", "6+(C48)", "6+(D01)", "6+(D02)", "6+(D03)", "6+(D04)", "6+(D05)", "6+(E01)", "6+(E02)", "6+(E03)", "6+(E04)", "6+(E05)", "6+(F01)", "6+(F02)", "6+(F03)", "6+(G01)", "6+(G02)", "6+(G03)", "6+(G04)", "6+(G05)", "6+(G06)", "6+(G07)", "6+(G08)", "6+(G09)", "6+(G10)", "6+(G11)", "6+(G12)", "6+(G13)", "6+(H01)", "6+(H02)", "6+(H03)", "6+(H04)", "6+(H05)", "6+(H06)", "6+(H07)", "6+(H08)", "6+(H09)", "6+(H10)", "6+(H11)", "6+(H12)", "6+(H13)", "6+(H14)", "6+(H15)", "6+(H16)", "6+(H17)", "6+(H18)", "6+(H19)", "6+(H20)", "6+(H21)", "6+(H22)", "6+(H23)", "6+(H24)", "6+(H25)", "6+(H26)", "6+(H27)", "6+(H28)", "6+(H29)", "6+(H30)", "6+(H31)", "6+(H32)", "6+(H33)", "6+(H34)", "6+(H35)", "6+(H36)", "6+(H37)", "6+(H38)", "6+(H39)", "6+(H40)", "6+(H41)", "6+(H42)", "6+(H43)", "6+(H44)", "6+(H45)", "6+(H46)", "6+(H47)", "6+(H48)", "6+(H49)", "6+(H50)", "6+(I01)", "6+(I02)", "6+(I03)", "6+(I04)", "6+(I05)", "6+(I06)", "6+(I07)", "6+(I08)", "6+(I09)", "6+(I10)", "6+(J01)", "6+(J02)", "6+(J03)", "6+(J04)", "6+(J05)", "6+(J06)", "6+(K01)", "6+(K02)", "6+(K03)", "6+(K04)", "6+(K05)", "6+(K06)", "6+(K07)", "6+(K08)", "6+(K09)", "6+(K10)", "6+(K11)", "6+(K12)", "6+(K13)", "6+(K14)", "6+(L01)", "6+(L02)", "6+(L03)", "6+(L04)", "6+(L05)", "6+(L06)", "6+(L07)", "6+(L08)", "6+(L09)", "6+(L10)", "6+(L11)", "6+

"(L12)", "6+(L13)", "6+(L14)", "6+(L15)", "6+(L16)", "6+(L17)", "6+(L18)", "6+(L19)", "6+(L20)", "6+(L21)", "6+(L22)", "6+(L23)", "6+(L24)", "6+(L25)", "6+(L26)", "6+(L27)", "6+(L28)", "6+(L29)", "6+(L30)", "6+(L31)", "6+(L32)", "6+(L33)", "6+(L34)", "6+(M01)", "6+(M02)", "6+(M03)", "6+(M04)", "6+(M05)", "6+(M06)", "6+(M07)", "6+(M08)", "6+(M09)", "6+(M10)", "6+(M11)", "6+(M12)", "6+(M13)", "6+(M14)", "6+(M15)", "6+(M16)", "6+(M17)", "6+(M18)", "6+(M19)", "6+(M20)", "6+(M21)", "6+(M22)", "6+(M23)",

"7+(A01)", "7+(A02)", "7+(A03)", "7+(A04)", "7+(A05)", "7+(A06)", "7+(A07)", "7+(A08)", "7+(A09)", "7+(A10)", "7+(A11)", "7+(A12)", "7+(B01)", "7+(B02)", "7+(B03)", "7+(B04)", "7+(B05)", "7+(B06)", "7+(B07)", "7+(B08)", "7+(B09)", "7+(B10)", "7+(B11)", "7+(B12)", "7+(C01)", "7+(C02)", "7+(C03)", "7+(C04)", "7+(C05)", "7+(C06)", "7+(C07)", "7+(C08)", "7+(C09)", "7+(C10)", "7+(C11)", "7+(C12)", "7+(C13)", "7+(C14)", "7+(C15)", "7+(C16)", "7+(C17)", "7+(C18)", "7+(C19)", "7+(C20)", "7+(C21)", "7+(C22)", "7+(C23)", "7+(C24)", "7+(C25)", "7+(C26)", "7+(C27)", "7+(C28)", "7+(C29)", "7+(C30)", "7+(C31)", "7+(C32)", "7+(C33)", "7+(C34)", "7+(C35)", "7+(C36)", "7+(C37)", "7+(C38)", "7+(C39)", "7+(C40)", "7+(C41)", "7+(C42)", "7+(C43)", "7+(C44)", "7+(C45)", "7+(C46)", "7+(C47)", "7+(C48)", "7+(D01)", "7+(D02)", "7+(D03)", "7+(D04)", "7+(D05)", "7+(E01)", "7+(E02)", "7+(E03)", "7+(E04)", "7+(E05)", "7+(F01)", "7+(F02)", "7+(F03)", "7+(G01)", "7+(G02)", "7+(G03)", "7+(G04)", "7+(G05)", "7+(G06)", "7+(G07)", "7+(G08)", "7+(G09)", "7+(G10)", "7+(G11)", "7+(G12)", "7+(G13)", "7+(H01)", "7+(H02)", "7+(H03)", "7+(H04)", "7+(H05)", "7+(H06)", "7+(H07)", "7+(H08)", "7+(H09)", "7+(H10)", "7+(H11)", "7+(H12)", "7+(H13)", "7+(H14)", "7+(H15)", "7+(H16)", "7+(H17)", "7+(H18)", "7+(H19)", "7+(H20)", "7+(H21)", "7+(H22)", "7+(H23)", "7+(H24)", "7+(H25)", "7+(H26)", "7+(H27)", "7+(H28)", "7+(H29)", "7+(H30)", "7+(H31)", "7+(H32)", "7+(H33)", "7+(H34)", "7+(H35)", "7+(H36)", "7+(H37)", "7+(H38)", "7+(H39)", "7+(H40)", "7+(H41)", "7+(H42)", "7+(H43)", "7+(H44)", "7+(H45)", "7+(H46)", "7+(H47)", "7+(H48)", "7+(H49)", "7+(H50)", "7+(I01)", "7+(I02)", "7+(I03)", "7+(I04)", "7+(I05)", "7+(I06)", "7+(I07)", "7+(I08)", "7+(I09)", "7+(I10)", "7+(J01)", "7+(J02)", "7+(J03)", "7+(J04)", "7+(J05)", "7+(J06)", "7+(K01)", "7+(K02)", "7+(K03)", "7+(K04)", "7+(K05)", "7+(K06)", "7+(K07)", "7+(K08)", "7+(K09)", "7+(K10)", "7+(K11)", "7+(K12)", "7+(K13)", "7+(K14)", "7+(L01)", "7+(L02)", "7+(L03)", "7+(L04)", "7+(L05)", "7+(L06)", "7+(L07)", "7+(L08)", "7+(L09)", "7+(L10)", "7+(L11)", "7+(L12)", "7+(L13)", "7+(L14)", "7+(L15)", "7+(L16)", "7+(L17)", "7+(L18)", "7+(L19)", "7+(L20)", "7+(L21)", "7+(L22)", "7+(L23)", "7+(L24)", "7+(L25)", "7+(L26)", "7+(L27)", "7+(L28)", "7+(L29)", "7+(L30)", "7+(L31)", "7+(L32)", "7+(L33)", "7+(L34)", "7+(M01)", "7+(M02)", "7+(M03)", "7+(M04)", "7+(M05)", "7+(M06)", "7+(M07)", "7+(M08)", "7+(M09)", "7+(M10)", "7+(M11)", "7+(M12)", "7+(M13)", "7+(M14)", "7+(M15)", "7+(M16)", "7+(M17)", "7+(M18)", "7+(M19)", "7+(M20)", "7+(M21)", "7+(M22)", "7+(M23)",

"8+(A01)", "8+(A02)", "8+(A03)", "8+(A04)", "8+(A05)", "8+(A06)", "8+(A07)", "8+(A08)", "8+(A09)", "8+(A10)", "8+(A11)", "8+(A12)", "8+(B01)", "8+(B02)", "8+(B03)", "8+(B04)", "8+(B05)", "8+(B06)", "8+(B07)", "8+(B08)", "8+(B09)", "8+(B10)", "8+(B11)", "8+(B12)", "8+(C01)", "8+(C02)", "8+(C03)", "8+(C04)", "8+(C05)", "8+(C06)", "8+(C07)", "8+(C08)", "8+(C09)", "8+(C10)", "8+(C11)", "8+(C12)", "8+(C13)", "8+(C14)", "8+(C15)", "8+(C16)", "8+(C17)", "8+(C18)", "8+(C19)", "8+(C20)", "8+(C21)", "8+(C22)", "8+(C23)", "8+(C24)", "8+(C25)", "8+(C26)", "8+(C27)", "8+(C28)", "8+(C29)", "8+(C30)", "8+(C31)", "8+(C32)", "8+(C33)", "8+(C34)", "8+(C35)", "8+(C36)", "8+(C37)", "8+(C38)", "8+(C39)", "8+(C40)", "8+(C41)", "8+(C42)", "8+(C43)", "8+(C44)", "8+(C45)", "8+(C46)", "8+(C47)", "8+(C48)", "8+(D01)", "8+(D02)", "8+(D03)", "8+(D04)", "8+(D05)", "8+(E01)", "8+(E02)", "8+(E03)", "8+(E04)", "8+(E05)", "8+(F01)", "8+(F02)", "8+(F03)", "8+(G01)", "8+(G02)", "8+(G03)", "8+(G04)", "8+(G05)", "8+(G06)", "8+(G07)", "8+(G08)", "8+(G09)", "8+(G10)", "8+(G11)", "8+(G12)", "8+(G13)", "8+(H01)", "8+(H02)", "8+(H03)", "8+(H04)", "8+(H05)", "8+(H06)", "8+(H07)", "8+(H08)", "8+(H09)", "8+(H10)", "8+(H11)", "8+(H12)", "8+(H13)", "8+(H14)", "8+(H15)", "8+(H16)", "8+(H17)", "8+(H18)", "8+(H19)", "8+(H20)", "8+(H21)", "8+(H22)", "8+(H23)", "8+(H24)", "8+(H25)", "8+(H26)", "8+(H27)", "8+(H28)", "8+(H29)", "8+(H30)", "8+(H31)", "8+(H32)", "8+(H33)", "8+(H34)", "8+(H35)", "8+(H36)", "8+(H37)", "8+(H38)", "8+(H39)", "8+(H40)", "8+(H41)", "8+(H42)", "8+(H43)", "8+(H44)", "8+(H45)", "8+(H46)", "8+(H47)", "8+(H48)", "8+(H49)", "8+(H50)", "8+(I01)", "8+(I02)", "8+(I03)", "8+(I04)", "8+(I05)", "8+(I06)", "8+(I07)", "8+(I08)", "8+(I09)", "8+(I10)", "8+(J01)", "8+(J02)", "8+(J03)", "8+(J04)", "8+(J05)", "8+(J06)", "8+(K01)", "8+(K02)", "8+(K03)", "8+(K04)", "8+(K05)", "8+(K06)", "8+(K07)", "8+(K08)", "8+(K09)", "8+(K10)", "8+(K11)", "8+(K12)", "8+(K13)", "8+(K14)", "8+(L01)", "8+(L02)", "8+(L03)", "8+(L04)", "8+(L05)", "8+(L06)", "8+(L07)", "8+(L08)", "8+(L09)", "8+(L10)", "8+(L11)", "8+(L12)", "8+(L13)", "8+(L14)", "8+(L15)", "8+(L16)", "8+(L17)", "8+(L18)", "8+(L19)", "8+(L20)", "8+(L21)", "8+(L22)", "8+(L23)", "8+(L24)", "8+(L25)", "8+(L26)", "8+(L27)", "8+(L28)", "8+(L29)", "8+(L30)", "8+(L31)", "8+(L32)", "8+(L33)", "8+(L34)", "8+(M01)", "8+(M02)", "8+(M03)", "8+(M04)", "8+(M05)", "8+(M06)", "8+(M07)", "8+(M08)", "8+(M23)",

"9+(A01)", "9+(A02)", "9+(A03)", "9+(A04)", "9+(A05)", "9+(A06)", "9+(A07)", "9+(A08)", "9+(A09)", "9+(A10)", "9+(A11)", "9+(A12)", "9+(B01)", "9+(B02)", "9+(B03)", "9+(B04)", "9+(B05)", "9+(B06)", "9+(B07)", "9+(B08)", "9+(B09)", "9+(B10)", "9+(B11)", "9+(B12)", "9+(C01)", "9+(C02)", "9+(C03)", "9+(C04)", "9+(C05)", "9+(C06)", "9+(C07)", "9+(C08)", "9+(C09)", "9+(C10)", "9+(C11)", "9+(C12)", "9+(C13)", "9+(C14)", "9+(C15)", "9+(C16)", "9+(C17)", "9+(C18)", "9+(C19)", "9+(C20)", "9+(C21)", "9+(C22)", "9+(C23)", "9+(C24)", "9+(C25)", "9+(C26)", "9+(C27)", "9+(C28)", "9+(C29)", "9+(C30)", "9+(C31)", "9+(C32)", "9+(C33)", "9+(C34)", "9+(C35)", "9+(C36)", "9+(C37)", "9+(C38)", "9+(C39)", "9+(G40)", "9+(C41)", "9+(C42)", "9+(C43)", "9+(C44)", "9+(C45)", "9+(C46)", "9+(C47)", "9+(C48)", "9+(D01)", "9+(D02)", "9+(D03)", "9+(D04)", "9+(D05)", "9+(E01)", "9+(E02)", "9+(E03)", "9+(E04)", "9+(E05)", "9+(F01)", "9+(F02)", "9+(F03)", "9+(G01)", "9+(G02)", "9+(G03)", "9+(G04)", "9+(G05)", "9+(G06)", "9+(G07)", "9+(G08)", "9+(G09)", "9+(G10)", "9+(G11)", "9+(G12)", "9+(G13)", "9+(H01)", "9+(H02)", "9+(H03)", "9+(H04)", "9+(H05)", "9+(H06)", "9+(H07)", "9+(H08)", "9+(H09)", "9+(H10)", "9+(H11)", "9+(H12)", "9+(H13)", "9+(H14)", "9+(H15)", "9+(H16)", "9+(H17)", "9+(H18)", "9+(H19)", "9+(H20)", "9+(H21)", "9+(H22)", "9+(H23)", "9+(H24)", "9+(H25)", "9+(H26)", "9+(H27)", "9+(H28)", "9+(H29)", "9+(H30)", "9+(H31)", "9+(H32)", "9+(H33)", "9+(H34)", "9+(H35)", "9+(H36)", "9+(H37)", "9+(H38)", "9+(H39)", "9+(H40)", "9+(H41)", "9+(H42)", "9+(H43)", "9+(H44)", "9+(H45)", "9+(H46)", "9+(H47)", "9+(H48)", "9+(H49)", "9+(H50)", "9+(I01)", "9+(I02)", "9+(I03)", "9+(I04)", "9+(I05)", "9+(I07)", "9+

"9+(I08)", "9+(I09)", "9+(I10)", "9+(J01)", "9+(J02)", "9+(J03)", "9+(J04)", "9+(J05)", "9+(J06)", "9+(K01)", "9+(K02)", "9+(K03)", "9+(K04)", "9+(K05)", "9+(K06)", "9+(K07)", "9+(K08)", "9+(K09)", "9+(K10)", "9+(K11)", "9+(K12)", "9+(K13)", "9+(K14)", "9+(L01)", "9+(L02)", "9+(L03)", "9+(L04)", "9+(L05)", "9+(L06)", "9+(L07)", "9+(L08)", "9+(L09)", "9+(L10)", "9+(L11)", "9+(L12)", "9+(L13)", "9+(L14)", "9+(L15)", "9+(L16)", "9+(L17)", "9+(L18)", "9+(L19)", "9+(L20)", "9+(L21)", "9+(L22)", "9+(L23)", "9+(L24)", "9+(L25)", "9+(L26)", "9+(L27)", "9+(L28)", "9+(L29)", "9+(L30)", "9+(L31)", "9+(L32)", "9+(L33)", "9+(L34)", "9+(M01)", "9+(M02)", "9+(M03)", "9+(M04)", "9+(M05)", "9+(M06)", "9+(M07)", "9+(M08)", "9+(M09)", "9+(M10)", "9+(M11)", "9+(M12)", "9+(M13)", "9+(M14)", "9+(M15)", "9+(M16)", "9+(M17)", "9+(M18)", "9+(M19)", "9+(M20)", "9+(M21)", "9+(M22)", "9+(M23)",

"10+(A01)", "10+(A02)", "10+(A03)", "10+(A04)", "10+(A05)", "10+(A06)", "10+(A07)", "10+(A08)", "10+(A09)", "10+(A10)", "10+(A11)", "10+(A12)", "10+(B01)", "10+(B02)", "10+(B03)", "10+(B04)", "10+(B05)", "10+(B06)", "10+(B07)", "10+(B08)", "10+(B09)", "10+(B10)", "10+(B11)", "10+(B12)", "10+(C01)", "10+(C02)", "10+(C03)", "10+(C04)", "10+(C05)", "10+(C06)", "10+(C07)", "10+(C08)", "10+(C09)", "10+(I0)", "10+(C11)", "10+(C12)", "10+(C13)", "10+(C14)", "10+(C15)", "10+(C16)", "10+(C17)", "10+(C18)", "10+(C19)", "10+(C20)", "10+(C21)", "10+(C22)", "10+(C23)", "10+(C24)", "10+(C25)", "10+(C26)", "10+(C27)", "10+(C28)", "10+(C29)", "10+(C30)", "10+(C31)", "10+(C32)", "10+(C33)", "10+(C34)", "10+(C35)", "10+(C36)", "10+(C37)", "10+(C38)", "10+(C39)", "10+(C40)", "10+(C41)", "10+(C42)", "10+(C43)", "10+(C44)", "10+(C45)", "10+(C46)", "10+(C47)", "10+(C48)", "10+(D01)", "10+(D02)", "10+(D03)", "10+(D04)", "10+(D05)", "10+(E01)", "10+(E02)", "10+(E03)", "10+(E04)", "10+(E05)", "10+(F01)", "10+(F02)", "10+(F03)", "10+(G01)", "10+(G02)", "10+(G03)", "10+(G04)", "10+(G05)", "10+(G06)", "10+(G07)", "10+(G08)", "10+(G09)", "10+(G10)", "10+(G11)", "10+(G12)", "10+(G13)", "10+(H01)", "10+(H02)", "10+(H03)", "10+(H04)", "10+(H05)", "10+(H06)", "10+(H07)", "10+(H08)", "10+(H09)", "10+(H10)", "10+(H11)", "10+(H12)", "10+(H13)", "10+(H14)", "10+(H15)", "10+(H16)", "10+(H17)", "10+(H18)", "10+(H19)", "10+(H20)", "10+(H21)", "10+(H22)", "10+(H23)", "10+(H24)", "10+(H25)", "10+(H26)", "10+(H27)", "10+(H28)", "10+(H29)", "10+(H30)", "10+(H31)", "10+(H32)", "10+(H33)", "10+(H34)", "10+(H35)", "10+(H36)", "10+(H37)", "10+(H38)", "10+(H39)", "10+(H40)", "10+(H41)", "10+(H42)", "10+(H43)", "10+(H44)", "10+(H45)", "10+(H46)", "10+(H47)", "10+(H48)", "10+(H49)", "10+(H50)", "10+(I01)", "10+(I02)", "10+(I03)", "10+(I04)", "10+(I05)", "10+(I06)", "10+(I07)", "10+(I08)", "10+(I09)", "10+(I10)", "10+(J01)", "10+(J02)", "10+(J03)", "10+(J04)", "10+(J05)", "10+(J06)", "10+(K01)", "10+(K02)", "10+(K03)", "10+(K04)", "10+(K05)", "10+(K06)", "10+(K07)", "10+(K08)", "10+(K09)", "10+(K10)", "10+(K11)", "10+(K12)", "10+(K13)", "10+(K14)", "10+(L01)", "10+(L02)", "10+(L03)", "10+(L04)", "10+(L05)", "10+(L06)", "10+(L07)", "10+(L08)", "10+(L09)", "10+(L10)", "10+(L11)", "10+(L12)", "10+(L13)", "10+(L14)", "10+(L15)", "10+(L16)", "10+(L17)", "10+(L18)", "10+(L19)", "10+(L20)", "10+(L21)", "10+(L22)", "10+(L23)", "10+(L24)", "10+(L25)", "10+(L26)", "10+(L27)", "10+(L28)", "10+(L29)", "10+(L30)", "10+(L31)", "10+(L32)", "10+(L33)", "10+(L34)", "10+(M01)", "10+(M02)", "10+(M03)", "10+(M04)", "10+(M05)", "10+(M06)", "10+(M07)", "10+(M08)", "10+(M09)", "10+(M10)", "10+(M11)", "10+(M12)", "10+(M13)", "10+(M14)", "10+(M15)", "10+(M16)", "10+(M17)", "10+(M18)", "10+(M19)", "10+(M20)", "10+(M21)", "10+(M22)", "10+(M23)",

"11+(A01)", "11+(A02)", "11+(A03)", "11+(A04)", "11+(A05)", "11+(A06)", "11+(A07)", "11+(A08)", "11+(A09)", "11+(A10)", "11+(A11)", "11+(A12)", "11+(B01)", "11+(B02)", "11+(B03)", "11+(B04)", "11+(B05)", "11+(B06)", "11+(B07)", "11+(B08)", "11+(B09)", "11+(B10)", "11+(B11)", "11+(B12)", "11+(C01)", "11+(C02)", "11+(C03)", "11+(C04)", "11+(C05)", "11+(C06)", "11+(C07)", "11+(C08)", "11+(C09)", "11+(C10)", "11+(C11)", "11+(C12)", "11+(C13)", "11+(C14)", "11+(C15)", "11+(C16)", "11+(C17)", "11+(C18)", "11+(C19)", "11+(C20)", "11+(C21)", "11+(C22)", "11+(C23)", "11+(C24)", "11+(C25)", "11+(C26)", "11+(C27)", "11+(C28)", "11+(C29)", "11+(C30)", "11+(C31)", "11+(C32)", "11+(C33)", "11+(C34)", "11+(C35)", "11+(C36)", "11+(C37)", "11+(C38)", "11+(C39)", "11+(C40)", "11+(C41)", "11+(C42)", "11+(C43)", "11+(C44)", "11+(C45)", "11+(C46)", "11+(C47)", "11+(C48)", "11+(D01)", "11+(D02)", "11+(D03)", "11+(D04)", "11+(D05)", "11+(E01)", "11+(E02)", "11+(E03)", "11+(E04)", "11+(E05)", "11+(F01)", "11+(F02)", "11+(F03)", "11+(G01)", "11+(G02)", "11+(G03)", "11+(G04)", "11+(G05)", "11+(G06)", "11+(G07)", "11+(G08)", "11+(G09)", "11+(G10)", "11+(G11)", "11+(G12)", "11+(G13)", "11+(H01)", "11+(H02)", "11+(H03)", "11+(H04)", "11+(H05)", "11+(H06)", "11+(H07)", "11+(H08)", "11+(H09)", "11+(H10)", "11+(H11)", "11+(H12)", "11+(H13)", "11+(H14)", "11+(H15)", "11+(H16)", "11+(H17)", "11+(H18)", "11+(H19)", "11+(H20)", "11+(H21)", "11+(H22)", "11+(H23)", "11+(H24)", "11+(H25)", "11+(H26)", "11+(H27)", "11+(H28)", "11+(H29)", "11+(H30)", "11+(H31)", "11+(H32)", "11+(H33)", "11+(H34)", "11+(H35)", "11+(H36)", "11+(H37)", "11+(H38)", "11+(H39)", "11+(H40)", "11+(H41)", "11+(H42)", "11+(H43)", "11+(H44)", "11+(H45)", "11+(H46)", "11+(H47)", "11+(H48)", "11+(H49)", "11+(H50)", "11+(I01)", "11+(I02)", "11+(I03)", "11+(I04)", "11+(I05)", "11+(I06)", "11+(I07)", "11+(I08)", "11+(I09)", "11+(I10)", "11+(J01)", "11+(J02)", "11+(J03)", "11+(J04)", "11+(J05)", "11+(J06)", "11+(K01)", "11+(K02)", "11+(K03)", "11+(K04)", "11+(K05)", "11+(K06)", "11+(K07)", "11+(K08)", "11+(K09)", "11+(K10)", "11+(K11)", "11+(K12)", "11+(K13)", "11+(K14)", "11+(L01)", "11+(L02)", "11+(L03)", "11+(L04)", "11+(L05)", "11+(L06)", "11+(L07)", "11+(L08)", "11+(L09)", "11+(L10)", "11+(L11)", "11+(L12)", "11+(L13)", "11+(L14)", "11+(L15)", "11+(L16)", "11+(L17)", "11+(L18)", "11+(L19)", "11+(L20)", "11+(L21)", "11+(L22)", "11+(L23)", "11+(L24)", "11+(L25)", "11+(L26)", "11+(L27)", "11+(L28)", "11+(L29)", "11+(L30)", "11+(L31)", "11+(L32)", "11+(L33)", "11+(L34)", "11+(M01)", "11+(M02)", "11+(M03)", "11+(M04)", "11+(M05)", "11+(M06)", "11+(M07)", "11+(M08)", "11+(M09)", "11+(M10)", "11+(M11)", "11+(M12)", "11+(M+(M143)", "11+(M+(4)", "11+(M5)", "11+(M16)", "11+(M17)", "11+(M18)", "11+(M19)", "11+(M20)", "11+(M21)", "11+(M22)", "11+(M23)",

"12+(A01)", "12+(A02)", "12+(A03)", "12+(A04)", "12+(A05)", "12+(A06)", "12+(A07)", "12+(A08)", "12+(A09)", "12+(A10)", "12+(A11)", "12+(A12)", "12+(B01)", "12+(B02)", "12+(B03)", "12+(B04)", "12+(B05)", "12+(B06)", "12+(B07)", "12+(B08)", "12+(B09)", "12+(B10)", "12+(B11)", "12+(B12)", "12+(C01)", "12+

"12+(C02)", "12+(C03)", "12+(C04)", "12+(C05)", "12+(C06)", "12+(C07)", "12+(C08)", "12+(C09)", "12+(C10)", "12+(C11)", "12+(C12)", "12+(C13)", "12+(C14)", "12+(C15)", "12+(C16)", "12+(C17)", "12+(C18)", "12+(C19)", "12+(C20)", "12+(C21)", "12+(C22)", "12+(C23)", "12+(C24)", "12+(C25)", "12+(C26)", "12+(C27)", "12+(C28)", "12+(C29)", "12+(C30)", "12+(C31)", "12+(C32)", "12+(C33)", "12+(C34)", "12+(C35)", "12+(C36)", "12+(C37)", "12+(C38)", "12+(C39)", "12+(C40)", "12+(C41)", "12+(C42)", "12+(C43)", "12+(C44)", "12+(C45)", "12+(C46)", "12+(C47)", "12+(C48)", "12+(D01)", "12+(D02)", "12+(D03)", "12+(D04)", "12+(D05)", "12+(E01)", "12+(E02)", "12+(E03)", "12+(E04)", "12+(E05)", "12+(F01)", "12+(F02)", "12+(F03)", "12+(G01)", "12+(G02)", "12+(G03)", "12+(G04)", "12+(G05)", "12+(G06)", "12+(G07)", "12+(G08)", "12+(G09)", "12+(G10)", "12+(G11)", "12+(G12)", "12+(G13)", "12+(H01)", "12+(H02)", "12+(H03)", "12+(H04)", "12+(H05)", "12+(H06)", "12+(H07)", "12+(H08)", "12+(H09)", "12+(H10)", "12+(H11)", "12+(H12)", "12+(H13)", "12+(H14)", "12+(H15)", "12+(H16)", "12+(H17)", "12+(H18)", "12+(H19)", "12+(H20)", "12+(H21)", "12+(H22)", "12+(H23)", "12+(H24)", "12+(H25)", "12+(H26)", "12+(H27)", "12+(H28)", "12+(H29)", "12+(H30)", "12+(H31)", "12+(H32)", "12+(H33)", "12+(H34)", "12+(H35)", "12+(H36)", "12+(H37)", "12+(H38)", "12+(H39)", "12+(H40)", "12+(H41)", "12+(H42)", "12+(H43)", "12+(H44)", "12+(H45)", "12+(H46)", "12+(H47)", "12+(H48)", "12+(H49)", "12+(H50)", "12+(I01)", "12+(I02)", "12+(I03)", "12+(I04)", "12+(I05)", "12+(I06)", "12+(I07)", "12+(I08)", "12+(I09)", "12+(I10)", "12+(J01)", "12+(J02)", "12+(J03)", "12+(J04)", "12+(J05)", "12+(J06)", "12+(K01)", "12+(K02)", "12+(K03)", "12+(K04)", "12+(K05)", "12+(K06)", "12+(K07)", "12+(K08)", "12+(K09)", "12+(K10)", "12+(K11)", "12+(K12)", "12+(K13)", "12+(K14)", "12+(L01)", "12+(L02)", "12+(L03)", "12+(L04)", "12+(L05)", "12+(L06)", "12+(L07)", "12+(L08)", "12+(L09)", "12+(L10)", "12+(L11)", "12+(L12)", "12+(L13)", "12+(L14)", "12+(L15)", "12+(L16)", "12+(L17)", "12+(L18)", "12+(L19)", "12+(L20)", "12+(L21)", "12+(L22)", "12+(L23)", "12+(L24)", "12+(L25)", "12+(L26)", "12+(L27)", "12+(L28)", "12+(L29)", "12+(L30)", "12+(L31)", "12+(L32)", "12+(L33)", "12+(L34)", "12+(M01)", "12+(M02)", "12+(M03)", "12+(M04)", "12+(M05)", "12+(M06)", "12+(M07)", "12+(M08)", "12+(M09)", "12+(M10)", "12+(M11)", "12+(M12)", "12+(M13)", "12+(M14)", "12+(M15)", "12+(M16)", "12+(M17)", "12+(M18)", "12+(M19)", "12+(M20)", "12+(M23)",

"13+(A01)", "13+(A02)", "13+(A03)", "13+(A04)", "13+(A05)", "13+(A06)", "13+(A07)", "13+(A08)", "13+(A09)", "13+(A10)", "13+(A11)", "13+(A12)", "13+(B01)", "13+(B02)", "13+(B03)", "13+(B04)", "13+(B05)", "13+(B06)", "13+(B07)", "13+(B08)", "13+(B09)", "13+(B10)", "13+(B11)", "13+(B12)", "13+(C01)", "13+(C02)", "13+(C03)", "13+(C04)", "13+(C05)", "13+(C06)", "13+(C07)", "13+(C08)", "13+(C09)", "13+(C10)", "13+(C11)", "13+(C12)", "13+(C13)", "13+(C14)", "13+(C15)", "13+(C16)", "13+(C17)", "13+(C18)", "13+(C19)", "13+(C20)", "13+(C21)", "13+(C22)", "13+(C23)", "13+(C24)", "13+(C25)", "13+(C26)", "13+(C27)", "13+(C28)", "13+(C29)", "13+(C30)", "13+(C31)", "13+(C32)", "13+(C33)", "13+(C34)", "13+(C35)", "13+(C36)", "13+(C37)", "13+(C38)", "13+(C39)", "13+(C40)", "13+(C41)", "13+(C42)", "13+(C43)", "13+(C44)", "13+(C45)", "13+(C46)", "13+(C47)", "13+(C48)", "13+(D01)", "13+(D02)", "13+(D03)", "13+(D04)", "13+(D05)", "13+(E01)", "13+(E02)", "13+(E03)", "13+(E04)", "13+(E05)", "13+(F01)", "13+(F02)", "13+(F03)", "13+(G01)", "13+(G02)", "13+(G03)", "13+(G04)", "13+(G05)", "13+(G06)", "13+(G07)", "13+(G08)", "13+(G09)", "13+(G10)", "13+(G11)", "13+(G12)", "13+(G13)", "13+(H01)", "13+(H02)", "13+(H03)", "13+(H04)", "13+(H05)", "13+(H06)", "13+(H07)", "13+(H08)", "13+(H09)", "13+(H10)", "13+(H11)", "13+(H12)", "13+(H13)", "13+(H14)", "13+(H15)", "13+(H16)", "13+(H17)", "13+(H18)", "13+(H19)", "13+(H20)", "13+(H21)", "13+(H22)", "13+(H23)", "13+(H24)", "13+(H25)", "13+(H26)", "13+(H27)", "13+(H28)", "13+(H29)", "13+(H30)", "13+(H31)", "13+(H32)", "13+(H33)", "13+(H34)", "13+(H35)", "13+(H36)", "13+(H37)", "13+(H38)", "13+(H39)", "13+(H40)", "13+(H41)", "13+(H42)", "13+(H43)", "13+(H44)", "13+(H45)", "13+(H46)", "13+(H47)", "13+(H48)", "13+(H49)", "13+(H50)", "13+(I01)", "13+(I02)", "13+(I03)", "13+(I04)", "13+(I05)", "13+(I06)", "13+(I07)", "13+(I08)", "13+(I09)", "13+(I10)", "13+(J01)", "13+(J02)", "13+(J03)", "13+(J04)", "13+(J05)", "13+(J06)", "13+(K01)", "13+(K02)", "13+(K03)", "13+(K04)", "13+(K05)", "13+(K06)", "13+(K07)", "13+(K08)", "13+(K09)", "13+(K10)", "13+(K11)", "13+(K12)", "13+(K13)", "13+(K14)", "13+(L01)", "13+(L02)", "13+(L03)", "13+(L04)", "13+(L05)", "13+(L06)", "13+(L07)", "13+(L08)", "13+(L09)", "13+(L10)", "13+(L11)", "13+(L12)", "13+(L13)", "13+(L14)", "13+(L15)", "13+(L16)", "13+(L17)", "13+(L18)", "13+(L19)", "13+(L20)", "13+(L21)", "13+(L22)", "13+(L23)", "13+(L24)", "13+(L25)", "13+(L26)", "13+(L27)", "13+(L28)", "13+(L29)", "13+(L30)", "13+(L31)", "13+(L32)", "13+(L33)", "13+(L34)", "13+(M01)", "13+(M02)", "13+(M03)", "13+(M04)", "13+(M05)", "13+(M06)", "13+(M07)", "13+(M08)", "13+(M09)", "13+(M10)", "13+(M11)", "13+(M12)", "13+(M13)", "13+(M14)", "13+(M15)", "13+(M16)", "13+(M17)", "13+(M18)", "13+(M19)", "13+(M20)", "13+(M21)", "13+(M22)", "13+(M23)",

"14+(A01)", "14+(A02)", "14+(A03)", "14+(A04)", "14+(A05)", "14+(A06)", "14+(A07)", "14+(A08)", "14+(A09)", "14+(A10)", "14+(A11)", "14+(A12)", "14+(B01)", "14+(B02)", "14+(B03)", "14+(B04)", "14+(B05)", "14+(B06)", "14+(B07)", "14+(B08)", "14+(B09)", "14+(B10)", "14+(B11)", "14+(B12)", "14+(C01)", "14+(C02)", "14+(C03)", "14+(C04)", "14+(C05)", "14+(C06)", "14+(C07)", "14+(C08)", "14+(C09)", "14+(C10)", "14+(C11)", "14+(C12)", "14+(C13)", "14+(C14)", "14+(C15)", "14+(C16)", "14+(C17)", "14+(C18)", "14+(C19)", "14+(C20)", "14+(C21)", "14+(C22)", "14+(C23)", "14+(C24)", "14+(C25)", "14+(C26)", "14+(C27)", "14+(C28)", "14+(C29)", "14+(C30)", "14+(C31)", "14+(C32)", "14+(C33)", "14+(C34)", "14+(C35)", "14+(C36)", "14+(C37)", "14+(C38)", "14+(C39)", "14+(C40)", "14+(C41)", "14+(C42)", "14+(C43)", "14+(C44)", "14+(C45)", "14+(C46)", "14+(C47)", "14+(C48)", "14+(D01)", "14+(D02)", "14+(D03)", "14+(D04)", "14+(D05)", "14+(E01)", "14+(E02)", "14+(E03)", "14+(E04)", "14+(E05)", "14+(F01)", "14+(F02)", "14+(F03)", "14+(G01)", "14+(G02)", "14+(G03)", "14+(G04)", "14+(G05)", "14+(G06)", "14+(G07)", "14+(G08)", "14+(G09)", "14+(G10)", "14+(G11)", "14+(G12)", "14+(G13)", "14+(H01)", "14+(H02)", "14+(H03)", "14+(H04)", "14+(H05)", "14+(H06)", "14+(H07)", "14+(H08)", "14+(H09)", "14+(H10)", "14+(H11)", "14+(H12)", "14+(H13)", "14+(H14)", "14+(H15)", "14+(H16)", "14+(H17)", "14+(H18)", "14+(H19)", "14+(H20)", "14+(H21)", "14+(H22)", "14+

"(H23)", "14+(H24)", "14+(H25)", "14+(H26)", "14+(H27)", "14+(H28)", "14+(H29)", "14+(H30)", "14+(H31)", "14+(H32)", "14+(H33)", "14+(H34)", "14+(H35)", "14+(H36)", "14+(H37)", "14+(H38)", "14+(H39)", "14+(H40)", "14+(H41)", "14+(H42)", "14+(H43)", "14+(H44)", "14+(H45)", "14+(H46)", "14+(H47)", "14+(H48)", "14+(H49)", "14+(H50)", "14+(I01)", "14+(I02)", "14+(I03)", "14+(I04)", "14+(I05)", "14+(I06)", "14+(I07)", "14+(I08)", "14+(I09)", "14+(I10)", "14+(J01)", "14+(J02)", "14+(J03)", "14+(J04)", "14+(J05)", "14+(J06)", "14+(K01)", "14+(K02)", "14+(K03)", "14+(K04)", "14+(K05)", "14+(K06)", "14+(K07)", "14+(K08)", "14+(K09)", "14+(K10)", "14+(K11)", "14+(K12)", "14+(K13)", "14+(K14)", "14+(L01)", "14+(L02)", "14+(L03)", "14+(L04)", "14+(L05)", "14+(L06)", "14+(L07)", "14+(L08)", "14+(L09)", "14+(L10)", "14+(L11)", "14+(L12)", "14+(L13)", "14+(L14)", "14+(L15)", "14+(L16)", "14+(L17)", "14+(L18)", "14+(L19)", "14+(L20)", "14+(L21)", "14+(L22)", "14+(L23)", "14+(L24)", "14+(L25)", "14+(L26)", "14+(L27)", "14+(L28)", "14+(L29)", "14+(L30)", "14+(L31)", "14+(L32)", "14+(L33)", "14+(L34)", "14+(M01)", "14+(M02)", "14+(M03)", "14+(M04)", "14+(M05)", "14+(M06)", "14+(M07)", "14+(M08)", "14+(M09)", "14+(M10)", "14+(M11)", "14+(M12)", "14+(M13)", "14+(M14)", "14+(M15)", "14+(M16)", "14+(M17)", "14+(M18)", "14+(M19)", "14+(M20)", "14+(M21)", "14+(M22)", "14+(M23)",

"15+(A01)", "15+(A02)", "15+(A03)", "15+(A04)", "15+(A05)", "15+(A06)", "15+(A07)", "15+(A08)", "15+(A09)", "15+(A10)", "15+(A11)", "15+(A12)", "15+(B01)", "15+(B02)", "15+(B03)", "15+(B04)", "15+(B05)", "15+(B06)", "15+(B07)", "15+(B08)", "15+(B09)", "15+(B10)", "15+(B11)", "15+(B12)", "15+(C01)", "15+(C02)", "15+(C03)", "15+(C04)", "15+(C05)", "15+(C06)", "15+(C07)", "15+(C08)", "15+(C09)", "15+(C10)", "15+(C11)", "15+(C12)", "15+(C13)", "15+(C14)", "15+(C15)", "15+(C16)", "15+(C17)", "15+(C18)", "15+(C19)", "15+(C20)", "15+(C21)", "15+(C22)", "15+(C23)", "15+(C24)", "15+(C25)", "15+(C26)", "15+(C27)", "15+(C28)", "15+(C29)", "15+(C30)", "15+(C31)", "15+(C32)", "15+(C33)", "15+(C34)", "15+(C35)", "15+(C36)", "15+(C37)", "15+(C38)", "15+(C39)", "15+(C40)", "15+(C41)", "15+(C42)", "15+(C43)", "15+(C44)", "15+(C45)", "15+(C46)", "15+(C47)", "15+(C48)", "15+(D01)", "15+(D02)", "15+(D03)", "15+(D04)", "15+(D05)", "15+(E01)", "15+(E02)", "15+(E03)", "15+(E04)", "15+(E05)", "15+(F01)", "15+(F02)", "15+(F03)", "15+(G01)", "15+(G02)", "15+(G03)", "15+(G04)", "15+(G05)", "15+(G06)", "15+(G07)", "15+(G08)", "15+(G09)", "15+(G10)", "15+(G11)", "15+(G12)", "15+(G13)", "15+(H01)", "15+(H02)", "15+(H03)", "15+(H04)", "15+(H05)", "15+(H06)", "15+(H07)", "15+(H08)", "15+(H09)", "15+(H10)", "15+(H11)", "15+(H12)", "15+(H13)", "15+(H14)", "15+(H15)", "15+(H16)", "15+(H17)", "15+(H18)", "15+(H19)", "15+(H20)", "15+(H21)", "15+(H22)", "15+(H23)", "15+(H24)", "15+(H25)", "15+(H26)", "15+(H27)", "15+(H28)", "15+(H29)", "15+(H30)", "15+(H31)", "15+(H32)", "15+(H33)", "15+(H34)", "15+(H35)", "15+(H36)", "15+(H37)", "15+(H38)", "15+(H39)", "15+(H40)", "15+(H41)", "15+(H42)", "15+(H43)", "15+(H44)", "15+(H45)", "15+(H46)", "15+(H47)", "15+(H48)", "15+(H49)", "15+(H50)", "15+(I01)", "15+(I02)", "15+(I03)", "15+(I04)", "15+(I05)", "15+(I06)", "15+(I07)", "15+(I08)", "15+(I09)", "15+(I10)", "15+(J01)", "15+(J02)", "15+(J03)", "15+(J04)", "15+(J05)", "15+(J06)", "15+(K01)", "15+(K02)", "15+(K03)", "15+(K04)", "15+(K05)", "15+(K06)", "15+(K07)", "15+(K08)", "15+(K09)", "15+(K10)", "15+(K11)", "15+(K12)", "15+(K13)", "15+(K14)", "15+(L01)", "15+(L02)", "15+(L03)", "15+(L04)", "15+(L05)", "15+(L06)", "15+(L07)", "15+(L08)", "15+(L09)", "15+(L10)", "15+(L11)", "15+(L12)", "15+(L13)", "15+(L14)", "15+(L15)", "15+(L16)", "15+(L17)", "15+(L18)", "15+(L19)", "15+(L20)", "15+(L21)", "15+(L22)", "15+(L23)", "15+(L24)", "15+(L25)", "15+(L26)", "15+(L27)", "15+(L28)", "15+(L29)", "15+(L30)", "15+(L31)", "15+(L32)", "15+(L33)", "15+(L34)", "15+(M01)", "15+(M02)", "15+(M03)", "15+(M04)", "15+(M05)", "15+(M06)", "15+(M07)", "15+(M08)", "15+(M09)", "15+(M10)", "15+(M11)", "15+(M12)", "15+(M13)", "15+(M14)", "15+(M15)", "15+(M16)", "15+(M17)", "15+(M18)", "15+(M19)", "15+(M20)", "15+(M21)", "15+(M22)", "15+(M23)",

"16+(A01)", "16+(A02)", "16+(A03)", "16+(A04)", "16+(A05)", "16+(A06)", "16+(A07)", "16+(A08)", "16+(A09)", "16+(A10)", "16+(A11)", "16+(A12)", "16+(B01)", "16+(B02)", "16+(B03)", "16+(B04)", "16+(B05)", "16+(B06)", "16+(B07)", "16+(B08)", "16+(B09)", "16+(B10)", "16+(B11)", "16+(B12)", "16+(C01)", "16+(C02)", "16+(C03)", "16+(C04)", "16+(C05)", "16+(C06)", "16+(C07)", "16+(C08)", "16+(C09)", "16+(C10)", "16+(C11)", "16+(C12)", "16+(C13)", "16+(C14)", "16+(C15)", "16+(C16)", "16+(C17)", "16+(C18)", "16+(C19)", "16+(C20)", "16+(C21)", "16+(C22)", "16+(C23)", "16+(C24)", "16+(C25)", "16+(C26)", "16+(C27)", "16+(C28)", "16+(C29)", "16+(C30)", "16+(C31)", "16+(C32)", "16+(C33)", "16+(C34)", "16+(C35)", "16+(C36)", "16+(C37)", "16+(C38)", "16+(C39)", "16+(C40)", "16+(C41)", "16+(C42)", "16+(C43)", "16+(C44)", "16+(C45)", "16+(C46)", "16+(C47)", "16+(C48)", "16+(D01)", "16+(D02)", "16+(D03)", "16+(D04)", "16+(D05)", "16+(E01)", "16+(E02)", "16+(E03)", "16+(E04)", "16+(E05)", "16+(F01)", "16+(F02)", "16+(F03)", "16+(G01)", "16+(G02)", "16+(G03)", "16+(G04)", "16+(G05)", "16+(G06)", "16+(G07)", "16+(G08)", "16+(G09)", "16+(G10)", "16+(G11)", "16+(G12)", "16+(G13)", "16+(H01)", "16+(H02)", "16+(H03)", "16+(H04)", "16+(H05)", "16+(H06)", "16+(H07)", "16+(H08)", "16+(H09)", "16+(H10)", "16+(H11)", "16+(H12)", "16+(H13)", "16+(H14)", "16+(H15)", "16+(H16)", "16+(H17)", "16+(H18)", "16+(H19)", "16+(H20)", "16+(H21)", "16+(H22)", "16+(H23)", "16+(H24)", "16+(H25)", "16+(H26)", "16+(H27)", "16+(H28)", "16+(H29)", "16+(H30)", "16+(H31)", "16+(H32)", "16+(H33)", "16+(H34)", "16+(H35)", "16+(H36)", "16+(H37)", "16+(H38)", "16+(H39)", "16+(H40)", "16+(H41)", "16+(H42)", "16+(H43)", "16+(H44)", "16+(H45)", "16+(H46)", "16+(H47)", "16+(H48)", "16+(H49)", "16+(H50)", "16+(I01)", "16+(I02)", "16+(I03)", "16+(I04)", "16+(I05)", "16+(I06)", "16+(I07)", "16+(I08)", "16+(I09)", "16+(I10)", "16+(J01)", "16+(J02)", "16+(J03)", "16+(J04)", "16+(J05)", "16+(J06)", "16+(K01)", "16+(K02)", "16+(K03)", "16+(K04)", "16+(K05)", "16+(K06)", "16+(K07)", "16+(K08)", "16+(K09)", "16+(K10)", "16+(K11)", "16+(K12)", "16+(K13)", "16+(K14)", "16+(L01)", "16+(L02)", "16+(L03)", "16+(L04)", "16+(L05)", "16+(L06)", "16+(L07)", "16+(L08)", "16+(L09)", "16+(L10)", "16+(L11)", "16+(L12)", "16+(L13)", "16+(L14)", "16+(L15)", "16+(L16)", "16+(L17)", "16+(L18)", "16+(L19)", "16+(L20)", "16+(L21)", "16+(L22)", "16+(L23)", "16+(L24)", "16+(L25)", "16+(L26)", "16+(L27)", "16+(L28)", "16+(L29)", "16+(L30)", "16+(L31)", "16+(L32)", "16+(L33)", "16+(L34)", "16+(M01)",

"16+(M02)", "16+(M03)", "16+(M04)", "16+(M05)", "16+(M06)", "16+(M07)", "16+(M08)", "16+(M09)", "16+(M10)", "16+(M11)", "16+(M12)", "16+(M13)", "16+(M14)", "16+(M15)", "16+(M16)", "16+(M17)", "16+(M18)", "16+(M19)", "16+(M20)", "16+(M21)", "16+(M22)", "16+(M23)",

"17+(A01)", "17+(A02)", "17+(A03)", "17+(A04)", "17+(A05)", "17+(A06)", "17+(A07)", "17+(A08)", "17+(A09)", "17+(A10)", "17+(A11)", "17+(A12)", "17+(B01)", "17+(B02)", "17+(B03)", "17+(B04)", "17+(B05)", "17+(B06)", "17+(B07)", "17+(B08)", "17+(B09)", "17+(B10)", "17+(B11)", "17+(B12)", "17+(C01)", "17+(C02)", "17+(C03)", "17+(C04)", "17+(C05)", "17+(C06)", "17+(C07)", "17+(C08)", "17+(C09)", "17+(C10)", "17+(C11)", "17+(C12)", "17+(C13)", "17+(C14)", "17+(C15)", "17+(C16)", "17+(C17)", "17+(C18)", "17+(C19)", "17+(C20)", "17+(C21)", "17+(C22)", "17+(C23)", "17+(C24)", "17+(C25)", "17+(C26)", "17+(C27)", "17+(C28)", "17+(C29)", "17+(C30)", "17+(C31)", "17+(C32)", "17+(C33)", "17+(C34)", "17+(C35)", "17+(C36)", "17+(C37)", "17+(C38)", "17+(C39)", "17+(C40)", "17+(C41)", "17+(C42)", "17+(C43)", "17+(C44)", "17+(C45)", "17+(C46)", "17+(C47)", "17+(C48)", "17+(D01)", "17+(D02)", "17+(D03)", "17+(D04)", "17+(D05)", "17+(E01)", "17+(E02)", "17+(E03)", "17+(E04)", "17+(E05)", "17+(F01)", "17+(F02)", "17+(F03)", "17+(G01)", "17+(G02)", "17+(G03)", "17+(G04)", "17+(G05)", "17+(G06)", "17+(G07)", "17+(G08)", "17+(G09)", "17+(G10)", "17+(G11)", "17+(G12)", "17+(G13)", "17+(H01)", "17+(H02)", "17+(H03)", "17+(H04)", "17+(H05)", "17+(H06)", "17+(H07)", "17+(H08)", "17+(H09)", "17+(H10)", "17+(H11)", "17+(H12)", "17+(H13)", "17+(H14)", "17+(H15)", "17+(H16)", "17+(H17)", "17+(H18)", "17+(H19)", "17+(H20)", "17+(H21)", "17+(H22)", "17+(H23)", "17+(H24)", "17+(H25)", "17+(H26)", "17+(H27)", "17+(H28)", "17+(H29)", "17+(H30)", "17+(H31)", "17+(H32)", "17+(H33)", "17+(H34)", "17+(H35)", "17+(H36)", "17+(H37)", "17+(H38)", "17+(H39)", "17+(H40)", "17+(H41)", "17+(H42)", "17+(H43)", "17+(H44)", "17+(H45)", "17+(H46)", "17+(H47)", "17+(H48)", "17+(H49)", "17+(H50)", "17+(I01)", "17+(I02)", "17+(I03)", "17+(I04)", "17+(I05)", "17+(I06)", "17+(I07)", "17+(I08)", "17+(I09)", "17+(I10)", "17+(J01)", "17+(J02)", "17+(J03)", "17+(J04)", "17+(J05)", "17+(J06)", "17+(K01)", "17+(K02)", "17+(K03)", "17+(K04)", "17+(K05)", "17+(K06)", "17+(K07)", "17+(K08)", "17+(K09)", "17+(K10)", "17+(K11)", "17+(K12)", "17+(K13)", "17+(K14)", "17+(L01)", "17+(L02)", "17+(L03)", "17+(L04)", "17+(L05)", "17+(L06)", "17+(L07)", "17+(L08)", "17+(L09)", "17+(L10)", "17+(L11)", "17+(L12)", "17+(L13)", "17+(L14)", "17+(L15)", "17+(L16)", "17+(L17)", "17+(L18)", "17+(L19)", "17+(L20)", "17+(L21)", "17+(L22)", "17+(L23)", "17+(L24)", "17+(L25)", "17+(L26)", "17+(L27)", "17+(L28)", "17+(L29)", "17+(L30)", "17+(L31)", "17+(L32)", "17+(L33)", "17+(L34)", "17+(M01)", "17+(M02)", "17+(M03)", "17+(M04)", "17+(M05)", "17+(M06)", "17+(M07)", "17+(M08)", "17+(M09)", "17+(M10)", "17+(M11)", "17+(M12)", "17+(M13)", "17+(M14)", "17+(M15)", "17+(M16)", "17+(M17)", "17+(M18)", "17+(M19)", "17+(M20)", "17+(M21)", "17+(M22)", "17+(M23)",

"18+(A01)", "18+(A02)", "18+(A03)", "18+(A04)", "18+(A05)", "18+(A06)", "18+(A07)", "18+(A08)", "18+(A09)", "18+(A10)", "18+(A11)", "18+(A12)", "18+(B01)", "18+(B02)", "18+(B03)", "18+(B04)", "18+(B05)", "18+(B06)", "18+(B07)", "18+(B08)", "18+(B09)", "18+(B10)", "18+(B11)", "18+(B12)", "18+(C01)", "18+(C02)", "18+(C03)", "18+(C04)", "18+(C05)", "18+(C06)", "18+(C07)", "18+(C08)", "18+(C09)", "18+(C10)", "18+(C11)", "18+(C12)", "18+(C13)", "18+(C14)", "18+(C15)", "18+(C16)", "18+(C17)", "18+(C18)", "18+(C19)", "18+(C20)", "18+(C21)", "18+(C22)", "18+(C23)", "18+(C24)", "18+(C25)", "18+(C26)", "18+(C27)", "18+(C28)", "18+(C29)", "18+(C30)", "18+(C31)", "18+(C32)", "18+(C33)", "18+(C34)", "18+(C35)", "18+(C36)", "18+(C37)", "18+(C38)", "18+(C39)", "18+(C40)", "18+(C41)", "18+(C42)", "18+(C43)", "18+(C44)", "18+(C45)", "18+(C46)", "18+(C47)", "18+(C48)", "18+(D01)", "18+(D02)", "18+(D03)", "18+(D04)", "18+(D05)", "18+(E01)", "18+(E02)", "18+(E03)", "18+(E04)", "18+(E05)", "18+(F01)", "18+(F02)", "18+(F03)", "18+(G01)", "18+(G02)", "18+(G03)", "18+(G04)", "18+(G05)", "18+(G06)", "18+(G07)", "18+(G08)", "18+(G09)", "18+(G10)", "18+(G11)", "18+(G12)", "18+(G13)", "18+(H01)", "18+(H02)", "18+(H03)", "18+(H04)", "18+(H05)", "18+(H06)", "18+(H07)", "18+(H08)", "18+(H09)", "18+(H10)", "18+(H11)", "18+(H12)", "18+(H13)", "18+(H14)", "18+(H15)", "18+(H16)", "18+(H17)", "18+(H18)", "18+(H19)", "18+(H20)", "18+(H21)", "18+(H22)", "18+(H23)", "18+(H24)", "18+(H25)", "18+(H26)", "18+(H27)", "18+(H28)", "18+(H29)", "18+(H30)", "18+(H31)", "18+(H32)", "18+(H33)", "18+(H34)", "18+(H35)", "18+(H36)", "18+(H37)", "18+(H38)", "18+(H39)", "18+(H40)", "18+(H41)", "18+(H42)", "18+(H43)", "18+(H44)", "18+(H45)", "18+(H46)", "18+(H47)", "18+(H48)", "18+(H49)", "18+(H50)", "18+(I01)", "18+(I02)", "18+(I03)", "18+(I04)", "18+(I05)", "18+(I06)", "18+(I07)", "18+(I08)", "18+(I09)", "18+(I10)", "18+(J01)", "18+(J02)", "18+(J03)", "18+(J04)", "18+(J05)", "18+(J06)", "18+(K01)", "18+(K02)", "18+(K03)", "18+(K04)", "18+(K05)", "18+(K06)", "18+(K07)", "18+(K08)", "18+(K09)", "18+(K10)", "18+(K11)", "18+(K12)", "18+(K13)", "18+(K14)", "18+(L01)", "18+(L02)", "18+(L03)", "18+(L04)", "18+(L05)", "18+(L06)", "18+(L07)", "18+(L08)", "18+(L09)", "18+(L10)", "18+(L11)", "18+(L12)", "18+(L13)", "18+(L14)", "18+(L15)", "18+(L16)", "18+(L17)", "18+(L18)", "18+(L19)", "18+(L20)", "18+(L21)", "18+(L22)", "18+(L23)", "18+(L24)", "18+(L25)", "18+(L26)", "18+(L27)", "18+(L28)", "18+(L29)", "18+(L30)", "18+(L31)", "18+(L32)", "18+(L33)", "18+(L34)", "18+(M01)", "18+(M02)", "18+(M03)", "18+(M04)", "18+(M05)", "18+(M06)", "18+(M07)", "18+(M08)", "18+(M09)", "18+(M10)", "18+(M11)", "18+(M12)", "18+(M13)", "18+(M14)", "18+(M15)", "18+(M16)", "18+(M17)", "18+(M18)", "18+(M19)", "18+(M20)", "18+(M21)", "18+(M22)", "18+(M23)",

"19+(A01)", "19+(A02)", "19+(A03)", "19+(A04)", "19+(A05)", "19+(A06)", "19+(A07)", "19+(A08)", "19+(A09)", "19+(A10)", "19+(A11)", "19+(A12)", "19+(B01)", "19+(B02)", "19+(B03)", "19+(B04)", "19+(B05)", "19+(B06)", "19+(B07)", "19+(B08)", "19+(B09)", "19+(B10)", "19+(B11)", "19+(B12)", "19+(C01)", "19+(C02)", "19+(C03)", "19+(C04)", "19+(C05)", "19+(C06)", "19+(C07)", "19+(C08)", "19+(C09)", "19+(C10)", "19+(C11)", "19+(C12)", "19+(C13)", "19+(C14)", "19+(C15)", "19+(C16)", "19+(C17)", "19+(C18)", "19+(C19)", "19+(C20)", "19+(C21)", "19+(C22)", "19+(C23)", "19+(C24)", "19+(C25)", "19+(C26)", "19+(C27)", "19+(C28)", "19+(C29)", "19+(C30)", "19+(C31)", "19+(C32)", "19+(C33)", "19+(C34)", "19+(C35)", "19+(C36)", "19+(C37)", "19+(C38)", "19+(C39)", "19+(C40)", "19+(C41)", "19+(C42)", "19+(C43)", "19+(C44)", "19+(C45)", "19+(C46)", "19+

"(C47)", "19+(C48)", "19+(D01)", "19+(D02)", "19+(D03)", "19+(D04)", "19+(D05)", "19+(E01)", "19+(E02)", "19+(E03)", "19+(E04)", "19+(E05)", "19+(F01)", "19+(F02)", "19+(F03)", "19+(G01)", "19+(G02)", "19+(G03)", "19+(G04)", "19+(G05)", "19+(G06)", "19+(G07)", "19+(G08)", "19+(G09)", "19+(G10)", "19+(G11)", "19+(G12)", "19+(G13)", "19+(H01)", "19+(H02)", "19+(H03)", "19+(H04)", "19+(H05)", "19+(H06)", "19+(H07)", "19+(H08)", "19+(H09)", "19+(H10)", "19+(H11)", "19+(H12)", "19+(H13)", "19+(H14)", "19+(H15)", "19+(H16)", "19+(H17)", "19+(H18)", "19+(H19)", "19+(H20)", "19+(H21)", "19+(H22)", "19+(H23)", "19+(H24)", "19+(H25)", "19+(H26)", "19+(H27)", "19+(H28)", "19+(H29)", "19+(H30)", "19+(H31)", "19+(H32)", "19+(H33)", "19+(H34)", "19+(H35)", "19+(H36)", "19+(H37)", "19+(H38)", "19+(H39)", "19+(H40)", "19+(H41)", "19+(H42)", "19+(H43)", "19+(H44)", "19+(H45)", "19+(H46)", "19+(H47)", "19+(H48)", "19+(H49)", "19+(H50)", "19+(I01)", "19+(I02)", "19+(I03)", "19+(I04)", "19+(I05)", "19+(I06)", "19+(I07)", "19+(I08)", "19+(I09)", "19+(I10)", "19+(J01)", "19+(J02)", "19+(J03)", "19+(J04)", "19+(J05)", "19+(J06)", "19+(K01)", "19+(K02)", "19+(K03)", "19+(K04)", "19+(K05)", "19+(K06)", "19+(K07)", "19+(K08)", "19+(K09)", "19+(K10)", "19+(K11)", "19+(K12)", "19+(K13)", "19+(K14)", "19+(L01)", "19+(L02)", "19+(L03)", "19+(L04)", "19+(L05)", "19+(L06)", "19+(L07)", "19+(L08)", "19+(L09)", "19+(L10)", "19+(L11)", "19+(L12)", "19+(L13)", "19+(L14)", "19+(L15)", "19+(L15)", "19+(L16)", "19+(L17)", "19+(L18)", "19+(L19)", "19+(L20)", "19+(L21)", "19+(L22)", "19+(L23)", "19+(L24)", "19+(L25)", "19+(L26)", "19+(L27)", "19+(L28)", "19+(L29)", "19+(L30)", "19+(L31)", "19+(L32)", "19+(L33)", "19+(L34)", "19+(M01)", "19+(M02)", "19+(M03)", "19+(M04)", "19+(M05)", "19+(M06)", "19+(M07)", "19+(M08)", "19+(M09)", "19+(M10)", "19+(M11)", "19+(M12)", "19+(M13)", "19+(M14)", "19+(M15)", "19+(M16)", "19+(M17)", "19+(M18)", "19+(M19)", "19+(M20)", "19+(M21)", "19+(M22)", "19+(M23)",

"20+(A01)", "20+(A02)", "20+(A03)", "20+(A04)", "20+(A05)", "20+(A06)", "20+(A07)", "20+(A08)", "20+(A09)", "20+(A10)", "20+(A11)", "20+(A12)", "20+(B01)", "20+(B02)", "20+(B03)", "20+(B04)", "20+(B05)", "20+(B06)", "20+(B07)", "20+(B08)", "20+(B09)", "20+(B10)", "20+(B11)", "20+(B12)", "20+(C01)", "20+(C02)", "20+(C03)", "20+(C04)", "20+(C05)", "20+(C06)", "20+(C07)", "20+(C08)", "20+(C09)", "20+(C10)", "20+(C11)", "20+(C12)", "20+(C13)", "20+(C14)", "20+(C15)", "20+(C16)", "20+(C17)", "20+(C18)", "20+(C19)", "20+(C20)", "20+(C21)", "20+(C22)", "20+(C23)", "20+(C24)", "20+(C25)", "20+(C26)", "20+(C27)", "20+(C28)", "20+(C29)", "20+(C30)", "20+(C31)", "20+(C32)", "20+(C33)", "20+(C34)", "20+(C35)", "20+(C36)", "20+(C37)", "20+(C38)", "20+(C39)", "20+(C40)", "20+(C41)", "20+(C42)", "20+(C43)", "20+(C44)", "20+(C45)", "20+(C46)", "20+(C47)", "20+(C48)", "20+(D01)", "20+(D02)", "20+(D03)", "20+(D04)", "20+(D05)", "20+(E01)", "20+(E02)", "20+(E03)", "20+(E04)", "20+(E05)", "20+(F01)", "20+(F02)", "20+(F03)", "20+(G01)", "20+(G02)", "20+(G03)", "20+(G04)", "20+(G05)", "20+(G06)", "20+(G07)", "20+(G08)", "20+(G09)", "20+(G10)", "20+(G11)", "20+(G12)", "20+(G13)", "20+(H01)", "20+(H02)", "20+(H03)", "20+(H04)", "20+(H05)", "20+(H06)", "20+(H07)", "20+(H08)", "20+(H09)", "20+(H10)", "20+(H11)", "20+(H12)", "20+(H13)", "20+(H14)", "20+(H15)", "20+(H16)", "20+(H17)", "20+(H18)", "20+(H19)", "20+(H20)", "20+(H21)", "20+(H22)", "20+(H23)", "20+(H24)", "20+(H25)", "20+(H26)", "20+(H27)", "20+(H28)", "20+(H29)", "20+(H30)", "20+(H31)", "20+(H32)", "20+(H33)", "20+(H34)", "20+(H35)", "20+(H36)", "20+(H37)", "20+(H38)", "20+(H39)", "20+(H40)", "20+(H41)", "20+(H42)", "20+(H43)", "20+(H44)", "20+(H45)", "20+(H46)", "20+(H47)", "20+(H48)", "20+(H49)", "20+(H50)", "20+(I0)", "20+(I02)", "20+(I03)", "20+(I04)", "20+(I05)", "20+(I06)", "20+(I07)", "20+(I08)", "20+(I09)", "20+(I10)", "20+(J01)", "20+(J02)", "20+(J03)", "20+(J04)", "20+(J05)", "20+(J06)", "20+(K01)", "20+(K02)", "20+(K03)", "20+(K04)", "20+(K05)", "20+(K06)", "20+(K07)", "20+(K08)", "20+(K09)", "20+(K10)", "20+(K11)", "20+(K12)", "20+(K13)", "20+(K14)", "20+(L01)", "20+(L02)", "20+(L03)", "20+(L04)", "20+(L05)", "20+(L06)", "20+(L07)", "20+(L08)", "20+(L09)", "20+(L10)", "20+(L11)", "20+(L12)", "20+(L13)", "20+(L14)", "20+(L15)", "20+(L16)", "20+(L17)", "20+(L18)", "20+(L19)", "20+(L20)", "20+(L21)", "20+(L22)", "20+(L23)", "20+(L24)", "20+(L25)", "20+(L26)", "20+(L27)", "20+(L28)", "20+(L29)", "20+(L30)", "20+(L31)", "20+(L32)", "20+(L33)", "20+(L34)", "20+(M01)", "20+(M02)", "20+(M03)", "20+(M04)", "20+(M05)", "20+(M06)", "20+(M07)", "20+(M08)", "20+(M09)", "20+(M10)", "20+(M11)", "20+(M12)", "20+(M13)", "20+(M14)", "20+(M15)", "20+(M16)", "20+(M17)", "20+(M18)", "20+(M19)", "20+(M20)", "20+(M21)", "20+(M22)", "20+(M23)",

"21+(A01)", "21+(A02)", "21+(A03)", "21+(A04)", "21+(A05)", "21+(A06)", "21+(A07)", "21+(A08)", "21+(A09)", "21+(A10)", "21+(A11)", "21+(A12)", "21+(B01)", "21+(B02)", "21+(B03)", "21+(B04)", "21+(B05)", "21+(B06)", "21+(B07)", "21+(B08)", "21+(B09)", "21+(B10)", "21+(B11)", "21+(B12)", "21+(C01)", "21+(C02)", "21+(C03)", "21+(C04)", "21+(C05)", "21+(C06)", "21+(C07)", "21+(C08)", "21+(C09)", "21+(C10)", "21+(C11)", "21+(C12)", "21+(C13)", "21+(C14)", "21+(C15)", "21+(C16)", "21+(C17)", "21+(C18)", "21+(C19)", "21+(C20)", "21+(C21)", "21+(C22)", "21+(C23)", "21+(C24)", "21+(C25)", "21+(C26)", "21+(C27)", "21+(C28)", "21+(C29)", "21+(C30)", "21+(C31)", "21+(C32)", "21+(C33)", "21+(C34)", "21+(C35)", "21+(C36)", "21+(C37)", "21+(C38)", "21+(C39)", "21+(C40)", "21+(C41)", "21+(C42)", "21+(C43)", "21+(C44)", "21+(C45)", "21+(C46)", "21+(C47)", "21+(C48)", "21+(D01)", "21+(D02)", "21+(D03)", "21+(D04)", "21+(D05)", "21+(E01)", "21+(E02)", "21+(E03)", "21+(E04)", "21+(E05)", "21+(F01)", "21+(F02)", "21+(F03)", "21+(G01)", "21+(G02)", "21+(G03)", "21+(G04)", "21+(G05)", "21+(G06)", "21+(G07)", "21+(G08)", "21+(G09)", "21+(G10)", "21+(G11)", "21+(G12)", "21+(G13)", "21+(H01)", "21+(H02)", "21+(H03)", "21+(H04)", "21+(H05)", "21+(H06)", "21+(H07)", "21+(H08)", "21+(H09)", "21+(H10)", "21+(H11)", "21+(H12)", "21+(H13)", "21+(H14)", "21+(H15)", "21+(H16)", "21+(H17)", "21+(H18)", "21+(H19)", "21+(H20)", "21+(H21)", "21+(H22)", "21+(H23)", "21+(H24)", "21+(H25)", "21+(H26)", "21+(H27)", "21+(H28)", "21+(H29)", "21+(H30)", "21+(H31)", "21+(H32)", "21+(H33)", "21+(H34)", "21+(H35)", "21+(H36)", "21+(H37)", "21+(H38)", "21+(H39)", "21+(H40)", "21+(H41)", "21+(H42)", "21+(H43)", "21+(H44)", "21+(H45)", "21+(H46)", "21+(H47)", "21+(H48)", "21+(H49)", "21+(H50)", "21+(I01)", "21+(I02)", "21+(I03)", "21+(I04)", "21+(I05)", "21+(I06)", "21+(I07)", "21+

"21+(I08)", "21+(I09)", "21+(I10)", "21+(J01)", "21+(J02)", "21+(J03)", "21+(J04)", "21+(J05)", "21+(J06)", "21+(K01)", "21+(K02)", "21+(K03)", "21+(K04)", "21+(K05)", "21+(K06)", "21+(K07)", "21+(K08)", "21+(K09)", "21+(K10)", "21+(K11)", "21+(K12)", "21+(K13)", "21+(K14)", "21+(L01)", "21+(L02)", "21+(L03)", "21+(L04)", "21+(L05)", "21+(L06)", "21+(L07)", "21+(L08)", "21+(L09)", "21+(L10)", "21+(L11)", "21+(L12)", "21+(L13)", "21+(L14)", "21+(L15)", "21+(L16)", "21+(L17)", "21+(L18)", "21+(L19)", "21+(L20)", "21+(L21)", "21+(L22)", "21+(L23)", "21+(L24)", "21+(L25)", "21+(L26)", "21+(L27)", "21+(L28)", "21+(L29)", "21+(L30)", "21+(L31)", "21+(L32)", "21+(L33)", "21+(L34)", "21+(M01)", "21+(M02)", "21+(M03)", "21+(M04)", "21+(M05)", "21+(M06)", "21+(M07)", "21+(M08)", "21+(M09)", "21+(M10)", "21+(M11)", "21+(M12)", "21+(M13)", "21+(M14)", "21+(M15)", "21+(M16)", "21+(M17)", "21+(M18)", "21+(M19)", "21+(M20)", "21+(M21)", "21+(M22)", "3+(M23)",

"22+(A01)", "22+(A02)", "22+(A03)", "22+(A04)", "22+(A05)", "22+(A06)", "22+(A07)", "22+(A08)", "22+(A09)", "22+(A10)", "22+(A11)", "22+(A12)", "22+(B01)", "22+(B02)", "22+(B03)", "22+(B04)", "22+(B05)", "22+(B06)", "22+(B07)", "22+(B08)", "22+(B09)", "22+(B10)", "22+(B11)", "22+(B12)", "22+(C01)", "22+(C02)", "22+(C03)", "22+(C04)", "22+(C05)", "22+(C06)", "22+(C07)", "22+(C08)", "22+(C09)", "22+(C10)", "22+(C11)", "22+(C12)", "22+(C13)", "22+(C14)", "22+(C15)", "22+(C16)", "22+(C17)", "22+(C18)", "22+(C19)", "22+(C20)", "22+(C21)", "22+(C22)", "22+(C23)", "22+(C24)", "22+(C25)", "22+(C26)", "22+(C27)", "22+(C28)", "22+(C29)", "22+(C30)", "22+(C31)", "22+(C32)", "22+(C33)", "22+(C34)", "22+(C35)", "22+(C36)", "22+(C37)", "22+(C38)", "22+(C39)", "22+(C40)", "22+(C41)", "22+(C42)", "22+(C43)", "22+(C44)", "22+(C45)", "22+(C46)", "22+(C47)", "22+(C48)", "22+(D01)", "22+(D02)", "22+(D03)", "22+(D04)", "22+(D05)", "22+(E01)", "22+(E02)", "22+(E03)", "22+(E04)", "22+(E05)", "22+(F01)", "22+(F02)", "22+(F03)", "22+(G01)", "22+(G02)", "22+(G03)", "22+(G04)", "22+(G05)", "22+(G06)", "22+(G07)", "22+(G08)", "22+(G09)", "22+(C10)", "22+(G11)", "22+(G12)", "22+(G13)", "22+(H01)", "22+(H02)", "22+(H03)", "22+(H04)", "22+(H05)", "22+(H06)", "22+(H07)", "22+(H08)", "22+(H09)", "22+(H10)", "22+(H11)", "22+(H12)", "22+(H13)", "22+(H14)", "22+(H15)", "22+(H16)", "22+(H17)", "22+(H18)", "22+(H19)", "22+(H20)", "22+(H21)", "22+(H22)", "22+(H23)", "22+(H24)", "22+(H25)", "22+(H26)", "22+(H27)", "22+(H28)", "22+(H29)", "22+(H30)", "22+(H31)", "22+(H32)", "22+(H33)", "22+(H34)", "22+(H35)", "22+(H36)", "22+(H37)", "22+(H38)", "22+(H39)", "22+(H40)", "22+(H41)", "22+(H42)", "22+(H43)", "22+(H44)", "22+(H45)", "22+(H46)", "22+(H47)", "22+(H48)", "22+(H49)", "22+(H50)", "22+(I01)", "22+(I02)", "22+(I03)", "22+(I04)", "22+(I05)", "22+(I06)", "22+(I07)", "22+(I08)", "22+(I09)", "22+(I10)", "22+(J01)", "22+(J02)", "22+(J03)", "22+(J04)", "22+(J05)", "22+(J06)", "22+(K01)", "22+(K02)", "22+(K03)", "22+(K04)", "22+(K05)", "22+(K06)", "22+(K07)", "22+(K08)", "22+(K09)", "22+(K10)", "22+(K11)", "22+(K12)", "22+(K13)", "22+(K14)", "22+(L01)", "22+(L02)", "22+(L03)", "22+(L04)", "22+(L05)", "22+(L06)", "22+(L07)", "22+(L08)", "22+(L09)", "22+(L10)", "22+(L11)", "22+(L12)", "22+(L13)", "22+(L14)", "22+(L15)", "22+(L16)", "22+(L17)", "22+(L18)", "22+(L19)", "22+(L20)", "22+(L21)", "22+(L22)", "22+(L23)", "22+(L24)", "22+(L25)", "22+(L26)", "22+(L27)", "22+(L28)", "22+(L29)", "22+(L30)", "22+(L31)", "22+(L32)", "22+(L33)", "22+(L34)", "22+(M01)", "22+(M02)", "22+(M03)", "22+(M04)", "22+(M05)", "22+(M06)", "22+(M07)", "22+(M08)", "22+(M09)", "22+(M10)", "22+(M11)", "22+(M12)", "22+(M13)", "22+(M14)", "22+(M15)", "22+(M16)", "22+(M17)", "22+(M18)", "22+(M19)", "22+(M20)", "22+(M21)", "22+(M22)", "22+(M23)",

"23+(A01)", "23+(A02)", "23+(A03)", "23+(A04)", "23+(A05)", "23+(A06)", "23+(A07)", "23+(A08)", "23+(A09)", "23+(A10)", "23+(A11)", "23+(A12)", "23+(B01)", "23+(B02)", "23+(B03)", "23+(B04)", "23+(B05)", "23+(B06)", "23+(B07)", "23+(B08)", "23+(B09)", "23+(B10)", "23+(B11)", "23+(B12)", "23+(C01)", "23+(C02)", "23+(C03)", "23+(C04)", "23+(C05)", "23+(C06)", "23+(C07)", "23+(C08)", "23+(C09)", "23+(C10)", "23+(C11)", "23+(C12)", "23+(C13)", "23+(C14)", "23+(C15)", "23+(C16)", "23+(C17)", "23+(C18)", "23+(C19)", "23+(C20)", "23+(C21)", "23+(C22)", "23+(C23)", "23+(C24)", "23+(C25)", "23+(C26)", "23+(C27)", "23+(C28)", "23+(C29)", "23+(C30)", "23+(C31)", "23+(C32)", "23+(C33)", "23+(C34)", "23+(C35)", "23+(C36)", "23+(C37)", "23+(C38)", "23+(C39)", "23+(C40)", "23+(C41)", "23+(C42)", "23+(C43)", "23+(C44)", "23+(C45)", "23+(C46)", "23+(C47)", "23+(C48)", "23+(D01)", "23+(D02)", "23+(D03)", "23+(D04)", "23+(D05)", "23+(E01)", "23+(E02)", "23+(E03)", "23+(E04)", "23+(E05)", "23+(F01)", "23+(F02)", "23+(F03)", "23+(G01)", "23+(G02)", "23+(G03)", "23+(G04)", "23+(G05)", "23+(G06)", "23+(G07)", "23+(G08)", "23+(G09)", "23+(G10)", "23+(G11)", "23+(G12)", "23+(G13)", "23+(H01)", "23+(H02)", "23+(H03)", "23+(H04)", "23+(H05)", "23+(H06)", "23+(H07)", "23+(H08)", "23+(H09)", "23+(H10)", "23+(H11)", "23+(H12)", "23+(H13)", "23+(H14)", "23+(H15)", "23+(H16)", "23+(H17)", "23+(H18)", "23+(H19)", "23+(H20)", "23+(H21)", "23+(H22)", "23+(H23)", "23+(H24)", "23+(H25)", "23+(H26)", "23+(H27)", "23+(H28)", "23+(H29)", "23+(H30)", "23+(H31)", "23+(H32)", "23+(H33)", "23+(H34)", "23+(H35)", "23+(H36)", "23+(H37)", "23+(H38)", "23+(H39)", "23+(H40)", "23+(H41)", "23+(H42)", "23+(H43)", "23+(H44)", "23+(H45)", "23+(H46)", "23+(H47)", "23+(H48)", "23+(H49)", "23+(H50)", "23+(I01)", "23+(I02)", "23+(I03)", "23+(I04)", "23+(I05)", "23+(I06)", "23+(I07)", "23+(I08)", "23+(I09)", "23+(I10)", "23+(J01)", "23+(J02)", "23+(J03)", "23+(J04)", "23+(J05)", "23+(J06)", "23+(K01)", "23+(K02)", "23+(K03)", "23+(K04)", "23+(K05)", "23+(K06)", "23+(K07)", "23+(K08)", "23+(K09)", "23+(K10)", "23+(K11)", "23+(K12)", "23+(K13)", "23+(K14)", "23+(L01)", "23+(L02)", "23+(L03)", "23+(L04)", "23+(L05)", "23+(L06)", "23+(L07)", "23+(L08)", "23+(L09)", "23+(L10)", "23+(L11)", "23+(L12)", "23+(L13)", "23+(L14)", "23+(L15)", "23+(L16)", "23+(L17)", "23+(L18)", "23+(L19)", "23+(L20)", "23+(L21)", "23+(L22)", "23+(L23)", "23+(L24)", "23+(L25)", "23+(L26)", "23+(L27)", "23+(L28)", "23+(L29)", "23+(L30)", "23+(L31)", "23+(L32)", "23+(L33)", "23+(L34)", "23+(M01)", "23+(M02)", "23+(M03)", "23+(M04)", "23+(M05)", "23+(M06)", "23+(M07)", "23+(M08)", "23+(M09)", "23+(M10)", "23+(M11)", "23+(M12)", "23+(M13)", "23+(M14)", "23+(M15)", "23+(M16)", "23+(M17)", "23+(M18)", "23+(M19)", "23+(M20)", "23+(M21)", "23+(M22)", "23+(M23)",

"24+(A01)", "24+(A02)", "24+(A03)", "24+(A04)", "24+(A05)", "24+(A06)", "24+(A07)", "24+(A08)", "24+(A09)", "24+(A10)", "24+(A11)", "24+(A12)",

"24+(B01)", "24+(B02)", "24+(B03)", "24+(B04)", "24+(B05)", "24+(B06)", "24+(B07)", "24+(B08)", "24+(B09)", "24+(B10)", "24+(B11)", "24+(B12)", "24+(C01)", "24+(C02)", "24+(C03)", "24+(C04)", "24+(C05)", "24+(C06)", "24+(C07)", "24+(C08)", "24+(C09)", "24+(C10)", "24+(C11)", "24+(C12)", "24+(C13)", "24+(C14)", "24+(C15)", "24+(C16)", "24+(C17)", "24+(C18)", "24+(C19)", "24+(C20)", "24+(C21)", "24+(C22)", "24+(C23)", "24+(C24)", "24+(C25)", "24+(C26)", "24+(C27)", "24+(C28)", "24+(C29)", "24+(C30)", "24+(C31)", "24+(C32)", "24+(C33)", "24+(C34)", "24+(C35)", "24+(C36)", "24+(C37)", "24+(C38)", "24+(C39)", "24+(C40)", "24+(C41)", "24+(C42)", "24+(C43)", "24+(C44)", "24+(C45)", "24+(C46)", "24+(C47)", "24+(C48)", "24+(D01)", "24+(D02)", "24+(D03)", "24+(D04)", "24+(D05)", "24+(E01)", "24+(E02)", "24+(E03)", "24+(E04)", "24+(E05)", "24+(F01)", "24+(F02)", "24+(F03)", "24+(G01)", "24+(G02)", "24+(G03)", "24+(G04)", "24+(G05)", "24+(G06)", "24+(G07)", "24+(G08)", "24+(G09)", "24+(G10)", "24+(G11)", "24+(G12)", "24+(G13)", "24+(H01)", "24+(H02)", "24+(H03)", "24+(H04)", "24+(H05)", "24+(H06)", "24+(H07)", "24+(H08)", "24+(H09)", "24+(H10)", "24+(H11)", "24+(H12)", "24+(H13)", "24+(H14)", "24+(H15)", "24+(H16)", "24+(H17)", "24+(H18)", "24+(H19)", "24+(H20)", "24+(H21)", "24+(H22)", "24+(H23)", "24+(H24)", "24+(H25)", "24+(H26)", "24+(H27)", "24+(H28)", "24+(H29)", "24+(H30)", "24+(H31)", "24+(H32)", "24+(H33)", "24+(H34)", "24+(H35)", "24+(H36)", "24+(H37)", "24+(H38)", "24+(H39)", "24+(H40)", "24+(H41)", "24+(H42)", "24+(H43)", "24+(H44)", "24+(H45)", "24+(H46)", "24+(H47)", "24+(H48)", "24+(H49)", "24+(H50)", "24+(I01)", "24+(I02)", "24+(I03)", "24+(I04)", "24+(I05)", "24+(I06)", "24+(I07)", "24+(I08)", "24+(I09)", "24+(I10)", "24+(J01)", "24+(J02)", "24+(J03)", "24+(J04)", "24+(J05)", "24+(J06)", "24+(K01)", "24+(K02)", "24+(K03)", "24+(K04)", "24+(K05)", "24+(K06)", "24+(K07)", "24+(K08)", "24+(K09)", "24+(K10)", "24+(K11)", "24+(K12)", "24+(K13)", "24+(K14)", "24+(L01)", "24+(L02)", "24+(L03)", "24+(L04)", "24+(L05)", "24+(L06)", "24+(L07)", "24+(L08)", "24+(L09)", "24+(L10)", "24+(L11)", "24+(L12)", "24+(L13)", "24+(L14)", "24+(L15)", "24+(L16)", "24+(L17)", "24+(L18)", "24+(L19)", "24+(L20)", "24+(L21)", "24+(L22)", "24+(L23)", "24+(L24)", "24+(L25)", "24+(L26)", "24+(L27)", "24+(L28)", "24+(L29)", "24+(L30)", "24+(L31)", "24+(L32)", "24+(L33)", "24+(L34)", "24+(M01)", "24+(M02)", "24+(M03)", "24+(M04)", "24+(M05)", "24+(M06)", "24+(M07)", "24+(M08)", "24+(M09)", "24+(M10)", "24+(M11)", "24+(M12)", "24+(M13)", "24+(M14)", "24+(M15)", "24+(M16)", "24+(M17)", "24+(M18)", "24+(M19)", "24+(M20)", "24+(M21)", "24+(M22)", "24+(M23)",

"25+(A01)", "25+(A02)", "25+(A03)", "25+(A04)", "25+(A05)", "25+(A06)", "25+(A07)", "25+(A08)", "25+(A09)", "25+(A10)", "25+(A11)", "25+(A12)", "25+(B01)", "25+(B02)", "25+(B03)", "25+(B04)", "25+(B05)", "25+(B06)", "25+(B07)", "25+(B08)", "25+(B09)", "25+(B10)", "25+(B11)", "25+(B12)", "25+(C01)", "25+(C02)", "25+(C03)", "25+(C04)", "25+(C05)", "25+(C06)", "25+(C07)", "25+(C08)", "25+(C09)", "25+(C10)", "25+(C11)", "25+(C12)", "25+(C13)", "25+(C14)", "25+(C15)", "25+(C16)", "25+(C17)", "25+(C18)", "25+(C19)", "25+(C20)", "25+(C21)", "25+(C22)", "25+(C23)", "25+(C24)", "25+(C25)", "25+(C26)", "25+(C27)", "25+(C28)", "25+(C29)", "25+(C30)", "25+(C31)", "25+(C32)", "25+(C33)", "25+(C34)", "25+(C35)", "25+(C36)", "25+(C37)", "25+(C38)", "25+(C39)", "25+(C40)", "25+(C41)", "25+(C42)", "25+(C43)", "25+(C44)", "25+(C45)", "25+(C46)", "25+(C47)", "25+(C48)", "25+(D01)", "25+(D02)", "25+(D03)", "25+(D04)", "25+(D05)", "25+(E01)", "25+(E02)", "25+(E03)", "25+(E04)", "25+(E05)", "25+(F01)", "25+(F02)", "25+(F03)", "25+(G01)", "25+(G02)", "25+(G03)", "25+(G04)", "25+(G05)", "25+(G06)", "25+(G07)", "25+(G08)", "25+(G09)", "25+(G10)", "25+(G11)", "25+(G12)", "25+(G13)", "25+(H01)", "25+(H02)", "25+(H03)", "25+(H04)", "25+(H05)", "25+(H06)", "25+(H07)", "25+(H08)", "25+(H09)", "25+(H10)", "25+(H11)", "25+(H12)", "25+(H13)", "25+(H14)", "25+(H15)", "25+(H16)", "25+(H17)", "25+(H18)", "25+(H19)", "25+(H20)", "25+(H21)", "25+(H22)", "25+(H23)", "25+(H24)", "25+(H25)", "25+(H26)", "25+(H27)", "25+(H28)", "25+(H29)", "25+(H30)", "25+(H31)", "25+(H32)", "25+(H33)", "25+(H34)", "25+(H35)", "25+(H36)", "25+(H37)", "25+(H38)", "25+(H39)", "25+(H40)", "25+(H41)", "25+(H42)", "25+(H43)", "25+(H44)", "25+(H45)", "25+(H46)", "25+(H47)", "25+(H48)", "25+(H49)", "25+(H50)", "25+(I01)", "25+(I02)", "25+(I03)", "25+(I04)", "25+(I05)", "25+(I06)", "25+(I07)", "25+(I08)", "25+(I09)", "25+(I10)", "25+(J01)", "25+(J02)", "25+(J03)", "25+(J04)", "25+(J05)", "25+(J06)", "25+(K01)", "25+(K02)", "25+(K03)", "25+(K04)", "25+(K05)", "25+(K06)", "25+(K07)", "25+(K08)", "25+(K09)", "25+(K10)", "25+(K11)", "25+(K12)", "25+(K13)", "25+(K14)", "25+(L01)", "25+(L02)", "25+(L03)", "25+(L04)", "25+(L05)", "25+(L06)", "25+(L07)", "25+(L08)", "25+(L09)", "25+(L10)", "25+(L11)", "25+(L12)", "25+(L13)", "25+(L14)", "25+(L15)", "25+(L16)", "25+(L17)", "25+(L18)", "25+(L19)", "25+(L20)", "25+(L21)", "25+(L22)", "25+(L23)", "25+(L24)", "25+(L25)", "25+(L26)", "25+(L27)", "25+(L28)", "25+(L29)", "25+(L30)", "25+(L31)", "25+(L32)", "25+(L33)", "25+(L34)", "25+(M01)", "25+(M02)", "25+(M03)", "25+(M04)", "25+(M05)", "25+(M06)", "25+(M07)", "25+(M08)", "25+(M09)", "25+(M10)", "25+(M11)", "25+(M12)", "25+(M13)", "25+(M14)", "25+(M15)", "25+(M16)", "25+(M17)", "25+(M18)", "25+(M19)", "25+(M20)", "25+(M21)", "25+(M22)", "25+(M23)",

"26+(A01)", "26+(A02)", "26+(A03)", "26+(A04)", "26+(A05)", "26+(A06)", "26+(A07)", "26+(A08)", "26+(A09)", "26+(A10)", "26+(A11)", "26+(A12)", "26+(B01)", "26+(B02)", "26+(B03)", "26+(B04)", "26+(B05)", "26+(B06)", "26+(B07)", "26+(B08)", "26+(B09)", "26+(B10)", "26+(B11)", "26+(B12)", "26+(C01)", "26+(C02)", "26+(C03)", "26+(C04)", "26+(C05)", "26+(C06)", "26+(C07)", "26+(C08)", "26+(C09)", "26+(C10)", "26+(C11)", "26+(C12)", "26+(C13)", "26+(C14)", "26+(C15)", "26+(C16)", "26+(C17)", "26+(C18)", "26+(C19)", "26+(C20)", "26+(C21)", "26+(C22)", "26+(C23)", "26+(C24)", "26+(C25)", "26+(C26)", "26+(C27)", "26+(C28)", "26+(C29)", "26+(C30)", "26+(C31)", "26+(C32)", "26+(C33)", "26+(C34)", "26+(C35)", "26+(C36)", "26+(C37)", "26+(C38)", "26+(C39)", "26+(C40)", "26+(C41)", "26+(C42)", "26+(C43)", "26+(C44)", "26+(C45)", "26+(C46)", "26+(C47)", "26+(C48)", "26+(D01)", "26+(D02)", "26+(D03)", "26+(D04)", "26+(D05)", "26+(E01)", "26+(E02)", "26+(E03)", "26+(E04)", "26+(E05)", "26+(F01)", "26+(F02)", "26+(F03)", "26+(G01)", "26+(G02)", "26+(G03)", "26+(G04)", "26+(G05)", "26+(G06)", "26+(G07)", "26+(G08)", "26+(G09)", "26+(G10)", "26+(G11)", "26+(G12)", "26+(G13)", "26+(H01)", "26+(H02)", "26+(H03)", "26+(H04)", "26+(H05)", "26+(H06)", "26+(H07)", "26+(H08)", "26+(H09)", "26+

"26+(H10)", "26+(H11)", "26+(H12)", "26+(H13)", "26+(H14)", "26+(H15)", "26+(H16)", "26+(H17)", "26+(H18)", "26+(H19)", "26+(H20)", "26+(H21)", "26+(H22)", "26+(H23)", "26+(H24)", "26+(H25)", "26+(H26)", "26+(H27)", "26+(H28)", "26+(H29)", "26+(H30)", "26+(H31)", "26+(H32)", "26+(H33)", "26+(H34)", "26+(H35)", "26+(H36)", "26+(H37)", "26+(H38)", "26+(H39)", "26+(H40)", "26+(H41)", "26+(H42)", "26+(H43)", "26+(H44)", "26+(H45)", "26+(H46)", "26+(H47)", "26+(H48)", "26+(H49)", "26+(H50)", "26+(I01)", "26+(I02)", "26+(I03)", "26+(I04)", "26+(I05)", "26+(I06)", "26+(I07)", "26+(I08)", "26+(I09)", "26+(I10)", "26+(J01)", "26+(J02)", "26+(J03)", "26+(J04)", "26+(J05)", "26+(J06)", "26+(K01)", "26+(K02)", "26+(K03)", "26+(K04)", "26+(K05)", "26+(K06)", "26+(K07)", "26+(K08)", "26+(K09)", "26+(K10)", "26+(K11)", "26+(K12)", "26+(K13)", "26+(K14)", "26+(L01)", "26+(L02)", "26+(L03)", "26+(L04)", "26+(L05)", "26+(L06)", "26+(L07)", "26+(L08)", "26+(L09)", "26+(L10)", "26+(L11)", "26+(L12)", "26+(L13)", "26+(L14)", "26+(L15)", "26+(L16)", "26+(L17)", "26+(L18)", "26+(L19)", "26+(L20)", "26+(L21)", "26+(L22)", "26+(L23)", "26+(L24)", "26+(L25)", "26+(L26)", "26+(L27)", "26+(L28)", "26+(L29)", "26+(L30)", "26+(L31)", "26+(L32)", "26+(L33)", "26+(L34)", "26+(M01)", "26+(M02)", "26+(M03)", "26+(M04)", "26+(M05)", "26+(M06)", "26+(M07)", "26+(M08)", "26+(M09)", "26+(M10)", "26+(M11)", "26+(M12)", "26+(M13)", "26+(M14)", "26+(M15)", "26+(M16)", "26+(M17)", "26+(M18)", "26+(M19)", "26+(M20)", "26+(M21)", "26+(M22)", "26+(M23)",

"27+(A01)", "27+(A02)", "27+(A03)", "27+(A04)", "27+(A05)", "27+(A06)", "27+(A07)", "27+(A08)", "27+(A09)", "27+(A10)", "27+(A11)", "27+(A12)", "27+(B01)", "27+(B02)", "27+(B03)", "27+(B04)", "27+(B05)", "27+(B06)", "27+(B07)", "27+(B08)", "27+(B09)", "27+(B10)", "27+(B11)", "27+(B12)", "27+(C01)", "27+(C02)", "27+(C03)", "27+(C04)", "27+(C05)", "27+(C06)", "27+(C07)", "27+(C08)", "27+(C09)", "27+(C10)", "27+(C11)", "27+(C12)", "27+(C13)", "27+(C14)", "27+(C15)", "27+(C16)", "27+(C17)", "27+(C18)", "27+(C19)", "27+(C20)", "27+(C21)", "27+(C22)", "27+(C23)", "27+(C24)", "27+(C25)", "27+(C26)", "27+(C27)", "27+(C28)", "27+(C29)", "27+(C30)", "27+(C31)", "27+(C32)", "27+(C33)", "27+(C34)", "27+(C35)", "27+(C36)", "27+(C37)", "27+(C38)", "27+(C39)", "27+(C40)", "27+(C41)", "27+(C42)", "27+(C43)", "27+(C44)", "27+(C45)", "27+(C46)", "27+(C47)", "27+(C48)", "27+(D01)", "27+(D02)", "27+(D03)", "27+(D04)", "27+(D05)", "27+(E01)", "27+(E02)", "27+(E03)", "27+(E04)", "27+(E05)", "27+(F01)", "27+(F02)", "27+(F03)", "27+(G01)", "27+(G02)", "27+(G03)", "27+(G04)", "27+(G05)", "27+(G06)", "27+(G07)", "27+(G08)", "27+(G09)", "27+(G10)", "27+(G11)", "27+(G12)", "27+(G13)", "27+(H01)", "27+(H02)", "27+(H03)", "27+(H04)", "27+(H05)", "27+(H06)", "27+(H07)", "27+(H08)", "27+(H09)", "27+(H10)", "27+(H11)", "27+(H12)", "27+(H13)", "27+(H14)", "27+(H15)", "27+(H16)", "27+(H17)", "27+(H18)", "27+(H19)", "27+(H20)", "27+(H21)", "27+(H22)", "27+(H23)", "27+(H24)", "27+(H25)", "27+(H26)", "27+(H27)", "27+(H28)", "27+(H29)", "27+(H30)", "27+(H31)", "27+(H32)", "27+(H33)", "27+(H34)", "27+(H35)", "27+(H36)", "27+(H37)", "27+(H38)", "27+(H39)", "27+(H40)", "27+(H41)", "27+(H42)", "27+(H43)", "27+(H44)", "27+(H45)", "27+(H46)", "27+(H47)", "27+(H48)", "27+(H49)", "27+(H50)", "27+(I01)", "27+(I02)", "27+(I03)", "27+(I04)", "27+(I05)", "27+(I06)", "27+(I07)", "27+(I08)", "27+(I09)", "27+(I10)", "27+(J01)", "27+(J02)", "27+(J03)", "27+(J04)", "27+(J05)", "27+(J06)", "27+(K01)", "27+(K02)", "27+(K03)", "27+(K04)", "27+(K05)", "27+(K06)", "27+(K07)", "27+(K08)", "27+(K09)", "27+(K10)", "27+(K11)", "27+(K12)", "27+(K13)", "27+(K14)", "27+(L01)", "27+(L02)", "27+(L03)", "27+(L04)", "27+(L05)", "27+(L06)", "27+(L07)", "27+(L08)", "27+(L09)", "27+(L10)", "27+(L11)", "27+(L12)", "27+(L13)", "27+(L14)", "27+(L15)", "27+(L16)", "27+(L17)", "27+(L18)", "27+(L19)", "27+(L20)", "27+(L21)", "27+(L22)", "27+(L23)", "27+(L24)", "27+(L25)", "27+(L26)", "27+(L27)", "27+(L28)", "27+(L29)", "27+(L30)", "27+(L31)", "27+(L32)", "27+(L33)", "27+(L34)", "27+(M01)", "27+(M02)", "27+(M03)", "27+(M04)", "27+(M05)", "27+(M06)", "27+(M07)", "27+(M08)", "27+(M09)", "27+(M10)", "27+(M11)", "27+(M12)", "27+(M13)", "27+(M14)", "27+(M15)", "27+(M16)", "27+(M17)", "27+(M18)", "27+(M19)", "27+(M20)", "27+(M21)", "27+(M22)", "27+(M23)",

"28+(A01)", "28+(A02)", "28+(A03)", "28+(A04)", "28+(A05)", "28+(A06)", "28+(A07)", "28+(A08)", "28+(A09)", "28+(A10)", "28+(A11)", "28+(A12)", "28+(B01)", "28+(B02)", "28+(B03)", "28+(B04)", "28+(B05)", "28+(B06)", "28+(B07)", "28+(B08)", "28+(B09)", "28+(B10)", "28+(B11)", "28+(B12)", "28+(C01)", "28+(C02)", "28+(C03)", "28+(C04)", "28+(C05)", "28+(C06)", "28+(C07)", "28+(C08)", "28+(C09)", "28+(C10)", "28+(C11)", "28+(C12)", "28+(C13)", "28+(C14)", "28+(C15)", "28+(C16)", "28+(C17)", "28+(C18)", "28+(C19)", "28+(C20)", "28+(C21)", "28+(C22)", "28+(C23)", "28+(C24)", "28+(C25)", "28+(C26)", "28+(C27)", "28+(C28)", "28+(C29)", "28+(C30)", "28+(C31)", "28+(C32)", "28+(C33)", "28+(C34)", "28+(C35)", "28+(C36)", "28+(C37)", "28+(C38)", "28+(C39)", "28+(C40)", "28+(C41)", "28+(C42)", "28+(C43)", "28+(C44)", "28+(C45)", "28+(C46)", "28+(C47)", "28+(C48)", "28+(D01)", "28+(D02)", "28+(D03)", "28+(D04)", "28+(D05)", "28+(E01)", "28+(E02)", "28+(E03)", "28+(E04)", "28+(E05)", "28+(F01)", "28+(F02)", "28+(F03)", "28+(G01)", "28+(G02)", "28+(G03)", "28+(G04)", "28+(G05)", "28+(G06)", "28+(G07)", "28+(G08)", "28+(G09)", "28+(G10)", "28+(G11)", "28+(G12)", "28+(G13)", "28+(H01)", "28+(H02)", "28+(H03)", "28+(H04)", "28+(H05)", "28+(H06)", "28+(H07)", "28+(H08)", "28+(H09)", "28+(H10)", "28+(H11)", "28+(H12)", "28+(H13)", "28+(H14)", "28+(H15)", "28+(H16)", "28+(H17)", "28+(H18)", "28+(H19)", "28+(H20)", "28+(H21)", "28+(H22)", "28+(H23)", "28+(H24)", "28+(H25)", "28+(H26)", "28+(H27)", "28+(H28)", "28+(H29)", "28+(H30)", "28+(H31)", "28+(H32)", "28+(H33)", "28+(H34)", "28+(H35)", "28+(H36)", "28+(H37)", "28+(H38)", "28+(H39)", "28+(H40)", "28+(H41)", "28+(H42)", "28+(H43)", "28+(H44)", "28+(H45)", "28+(H46)", "28+(H47)", "28+(H48)", "28+(H49)", "28+(H50)", "28+(I01)", "28+(I02)", "28+(I03)", "28+(I04)", "28+(I05)", "28+(I06)", "28+(I07)", "28+(I08)", "28+(I09)", "28+(I10)", "28+(J01)", "28+(J02)", "28+(J03)", "28+(J04)", "28+(J05)", "28+(J06)", "28+(K01)", "28+(K02)", "28+(K03)", "28+(K04)", "28+(K05)", "28+(K06)", "28+(K07)", "28+(K08)", "28+(K09)", "28+(K10)", "28+(K11)", "28+(K12)", "28+(K13)", "28+(K14)", "28+(L01)", "28+(L02)", "28+(L03)", "28+(L04)", "28+(L05)", "28+(L06)", "28+(L07)", "28+(L08)", "28+(L09)", "28+(L10)", "28+(L11)", "28+(L12)", "28+(L13)", "28+(L14)", "28+(L15)", "28+(L16)", "28+(L17)", "28+(L18)", "28+(L19)", "28+(L20)",

"28+(L21)", "28+(L22)", "28+(L23)", "28+(L24)", "28+(L25)", "28+(L26)", "28+(L27)", "28+(L28)", "28+(L29)", "28+(L30)", "28+(L31)", "28+(L32)", "28+(L33)", "28+(L34)", "28+(M01)", "28+(M02)", "28+(M03)", "28+(M04)", "28+(M05)", "28+(M06)", "28+(M07)", "28+(M08)", "28+(M09)", "28+(M10)", "28+(M11)", "28+(M12)", "28+(M13)", "28+(M14)", "28+(M15)", "28+(M16)", "28+(M17)", "28+(M18)", "28+(M19)", "28+(M20)", "28+(M21)", "28+(M22)", "28+(M23)",

"29+(A01)", "29+(A02)", "29+(A03)", "29+(A04)", "29+(A05)", "29+(A06)", "29+(A07)", "29+(A08)", "29+(A09)", "29+(A10)", "29+(A11)", "29+(A12)", "29+(B01)", "29+(B02)", "29+(B03)", "29+(B04)", "29+(B05)", "29+(B06)", "29+(B07)", "29+(B08)", "29+(B09)", "29+(B10)", "29+(B11)", "29+(B12)", "29+(C01)", "29+(C02)", "29+(C03)", "29+(C04)", "29+(C05)", "29+(C06)", "29+(C07)", "29+(C08)", "29+(C09)", "29+(C10)", "29+(C11)", "29+(C12)", "29+(C13)", "29+(C14)", "29+(C15)", "29+(C16)", "29+(C17)", "29+(C18)", "29+(C19)", "29+(C20)", "29+(C21)", "29+(C22)", "29+(C23)", "29+(C24)", "29+(C25)", "29+(C26)", "29+(C27)", "29+(C28)", "29+(C29)", "29+(C30)", "29+(C31)", "29+(C32)", "29+(C33)", "29+(C34)", "29+(C35)", "29+(C36)", "29+(C37)", "29+(C38)", "29+(C39)", "29+(C40)", "29+(C41)", "29+(C42)", "29+(C43)", "29+(C44)", "29+(C45)", "29+(C46)", "29+(C47)", "29+(C48)", "29+(D01)", "29+(D02)", "29+(D03)", "29+(D04)", "29+(D05)", "29+(E01)", "29+(E02)", "29+(E03)", "29+(E04)", "29+(E05)", "29+(F01)", "29+(F02)", "29+(F03)", "29+(G01)", "29+(G02)", "29+(G03)", "29+(G04)", "29+(G05)", "29+(G06)", "29+(G07)", "29+(G08)", "29+(G09)", "29+(G10)", "29+(G11)", "29+(G12)", "29+(G13)", "29+(H01)", "29+(H02)", "29+(H03)", "29+(H04)", "29+(H05)", "29+(H06)", "29+(H07)", "29+(H08)", "29+(H09)", "29+(H10)", "29+(H11)", "29+(H12)", "29+(H13)", "29+(H14)", "29+(H15)", "29+(H16)", "29+(H17)", "29+(H18)", "29+(H19)", "29+(H20)", "29+(H21)", "29+(H22)", "29+(H23)", "29+(H24)", "29+(H25)", "29+(H26)", "29+(H27)", "29+(H28)", "29+(H29)", "29+(H30)", "29+(H31)", "29+(H32)", "29+(H33)", "29+(H34)", "29+(H35)", "29+(H36)", "29+(H37)", "29+(H38)", "29+(H39)", "29+(H40)", "29+(H41)", "29+(H42)", "29+(H43)", "29+(H44)", "29+(H45)", "29+(H46)", "29+(H47)", "29+(H48)", "29+(H49)", "29+(H50)", "29+(I01)", "29+(I02)", "29+(I03)", "29+(I04)", "29+(I05)", "29+(I06)", "29+(I07)", "29+(I08)", "29+(I09)", "29+(I10)", "29+(J01)", "29+(J02)", "29+(J03)", "29+(J04)", "29+(J05)", "29+(J06)", "29+(K01)", "29+(K02)", "29+(K03)", "29+(K04)", "29+(K05)", "29+(K06)", "29+(K07)", "29+(K08)", "29+(K09)", "29+(K10)", "29+(K11)", "29+(K12)", "29+(K13)", "29+(K14)", "29+(L01)", "29+(L02)", "29+(L03)", "29+(L04)", "29+(L05)", "29+(L06)", "29+(L07)", "29+(L08)", "29+(L09)", "29+(L10)", "29+(L11)", "29+(L12)", "29+(L13)", "29+(L14)", "29+(L15)", "29+(L16)", "29+(L17)", "29+(L18)", "29+(L19)", "29+(L20)", "29+(L21)", "29+(L22)", "29+(L23)", "29+(L24)", "29+(L25)", "29+(L26)", "29+(L27)", "29+(L28)", "29+(L29)", "29+(L30)", "29+(L31)", "29+(L32)", "29+(L33)", "29+(L34)", "29+(M01)", "29+(M02)", "29+(M03)", "29+(M04)", "29+(M05)", "29+(M06)", "29+(M07)", "29+(M08)", "29+(M09)", "29+(M10)", "29+(M11)", "29+(M12)", "29+(M13)", "29+(M14)", "29+(M15)", "29+(M16)", "29+(M17)", "29+(M18)", "29+(M19)", "29+(M20)", "29+(M21)", "29+(M22)", "29+(M23)",

"30+(A01)", "30+(A02)", "30+(A03)", "30+(A04)", "30+(A05)", "30+(A06)", "30+(A07)", "30+(A08)", "30+(A09)", "30+(A10)", "30+(A11)", "30+(A12)", "30+(B01)", "30+(B02)", "30+(B03)", "30+(B04)", "30+(B05)", "30+(B06)", "30+(B07)", "30+(B08)", "30+(B09)", "30+(B10)", "30+(B11)", "30+(B12)", "30+(C01)", "30+(C02)", "30+(C03)", "30+(C04)", "30+(C05)", "30+(C06)", "30+(C07)", "30+(C08)", "30+(C09)", "30+(C10)", "30+(C11)", "30+(C12)", "30+(C13)", "30+(C14)", "30+(C15)", "30+(C16)", "30+(C17)", "30+(C18)", "30+(C19)", "30+(C20)", "30+(C21)", "30+(C22)", "30+(C23)", "30+(C24)", "30+(C25)", "30+(C26)", "30+(C27)", "30+(C28)", "30+(C29)", "30+(C30)", "30+(C31)" "30+(C32)", "30+(C33)", "30+(C34)", "30+(C35)", "30+(C36)", "30+(C37)", "30+(C38)", "30+(C39)", "30+(C40)", "30+(C41)", "30+(C42)", "30+(C43)", "30+(C44)", "30+(C45)", "30+(C46)", "30+(C47)", "30+(C48)", "30+(D01)", "30+(D02)", "30+(D03)", "30+(D04)", "30+(D05)", "30+(E01)", "30+(E02)", "30+(E03)", "30+(E04)", "30+(E05)", "30+(F01)", "30+(F02)", "30+(F03)", "30+(G01)", "30+(G02)", "30+(G03)", "30+(G04)", "30+(G05)", "30+(G06)", "30+(G07)", "30+(G08)", "30+(G09)", "30+(G10)", "30+(G11)", "30+(G12)", "30+(G13)", "30+(H01)", "30+(H02)", "30+(H03)", "30+(H04)", "30+(H05)", "30+(H06)", "30+(H07)", "30+(H08)", "30+(H09)", "30+(H10)", "30+(H11)", "30+(H12)", "30+(H13)", "30+(H14)", "30+(H15)", "30+(H16)", "30+(H17)", "30+(H18)", "30+(H19)", "30+(H20)", "30+(H21)", "30+(H22)", "30+(H23)", "30+(H24)", "30+(H25)", "30+(H26)", "30+(H27)", "30+(H28)", "30+(H29)", "30+(H30)", "30+(H31)", "30+(H32)", "30+(H33)", "30+(H34)", "30+(H35)", "30+(H36)", "30+(H37)", "30+(H38)", "30+(H39)", "30+(H40)", "30+(H41)", "30+(H42)", "30+(H43)", "30+(H44)", "30+(H45)", "30+(H46)", "30+(H47)", "30+(H48)", "30+(H49)", "30+(H50)", "30+(I01)", "30+(I02)", "30+(I03)", "30+(I04)", "30+(I05)", "30+(I06)", "30+(I07)", "30+(I08)", "30+(I09)", "30+(I10)", "30+(J01)", "30+(J02)", "30+(J03)", "30+(J04)", "30+(J05)", "30+(J06)", "30+(K01)", "30+(K02)", "30+(K03)", "30+(K04)", "30+(K05)", "30+(K06)", "30+(K07)", "30+(K08)", "30+(K09)", "30+(K10)", "30+(K11)", "30+(K12)", "30+(K13)", "30+(K14)", "30+(L01)", "30+(L02)", "30+(L03)", "30+(L04)", "30+(L05)", "30+(L06)", "30+(L07)", "30+(L08)", "30+(L09)", "30+(L10)", "30+(L11)", "30+(L12)", "30+(L13)", "30+(L14)", "30+(L15)", "30+(L16)", "30+(L17)", "30+(L18)", "30+(L19)", "30+(L20)", "30+(L21)", "30+(L22)", "30+(L23)", "30+(L24)", "30+(L25)", "30+(L26)", "30+(L27)", "30+(L28)", "30+(L29)", "30+(L30)", "30+(L31)", "30+(L32)", "30+(L33)", "30+(L34)", "30+(M01)", "30+(M02)", "30+(M03)", "30+(M04)", "30+(M05)", "30+(M06)", "30+(M07)", "30+(M08)", "30+(M09)", "30+(M10)", "30+(M11)", "30+(M12)", "30+(M13)", "30+(M14)", "30+(M15)", "30+(M16)", "30+(M17)", "30+(M18)", "30+(M19)", "30+(M20)", "30+(M21)", "30+(M22)", "30+(M23)",

"31+(A01)", "31+(A02)", "31+(A03)", "31+(A04)", "31+(A05)", "31+(A06)", "31+(A07)", "31+(A08)", "31+(A09)", "31+(A10)", "31+(A11)", "31+(A12)", "31+(B01)", "31+(B02)", "31+(B03)", "31+(B04)", "31+(B05)", "31+(B06)", "31+(B07)", "31+(B08)", "31+(B09)", "31+(B10)", "31+(B11)", "31+(B12)", "31+(C01)", "31+(C02)", "31+(C03)", "31+(C04)", "31+(C05)", "31+(C06)", "31+(C07)", "31+(C08)", "31+(C09)", "31+(C10)", "31+(C11)", "31+(C12)", "31+(C13)", "31+(C14)", "31+(C15)", "31+(C16)", "31+(C17)", "31+(C18)", "31+(C19)", "31+(C20)", "31+(C21)", "31+(C22)", "31+(C23)", "31+(C24)", "31+(C25)", "31+(C26)", "31+(C27)", "31+(C28)", "31+(C29)", "31+(C30)", "31+(C31)", "31+(C32)", "31+(C33)",

"31+(C34)", "31+(C35)", "31+(C36)", "31+(C37)", "31+(C38)", "31+(C39)", "31+(C40)", "31+(C41)", "31+(C42)", "31+(C43)", "31+(C44)", "31+(C45)", "31+(C46)", "31+(C47)", "31+(C48)", "31+(D01)", "31+(D02)", "31+(D03)", "31+(D04)", "31+(D05)", "31+(E01)", "31+(E02)", "31+(E03)", "31+(E04)", "31+(E05)", "31+(F01)", "31+(F02)", "31+(F03)", "31+(G01)", "31+(G02)", "31+(G03)", "31+(G04)", "31+(G05)", "31+(G06)", "31+(G07)", "31+(G08)", "31+(G09)", "31+(G10)", "31+(G11)", "31+(G12)", "31+(G13)", "31+(H01)", "31+(H02)", "31+(H03)", "31+(H04)", "31+(H05)", "31+(H06)", "31+(H07)", "31+(H08)", "31+(H09)", "31+(H10)", "31+(H11)", "31+(H12)", "31+(H13)", "31+(H14)", "31+(H15)", "31+(H16)", "31+(H17)", "31+(H18)", "31+(H19)", "31+(H20)", "31+(H21)", "31+(H22)", "31+(H23)", "31+(H24)", "31+(H25)", "31+(H26)", "31+(H27)", "31+(H28)", "31+(H29)", "31+(H30)", "31+(H31)", "31+(H32)", "31+(H33)", "31+(H34)", "31+(H35)", "31+(H36)", "31+(H37)", "31+(H38)", "31+(H39)", "31+(H40)", "31+(H41)", "31+(H42)", "31+(H43)", "31+(H44)", "31+(H45)", "31+(H46)", "31+(H47)", "31+(H48)", "31+(H49)", "31+(H50)", "31+(I01)", "31+(I02)", "31+(I03)", "31+(I04)", "31+(I05)", "31+(I06)", "31+(I07)", "31+(I08)", "31+(I09)", "31+(I10)", "31+(J01)", "31+(J02)", "31+(J03)", "31+(J04)", "31+(J05)", "31+(J06)", "31+(K01)", "31+(K02)", "31+(K03)", "31+(K04)", "31+(K05)", "31+(K06)", "31+(K07)", "31+(K08)", "31+(K09)", "31+(K10)", "31+(K11)", "31+(K12)", "31+(K13)", "31+(K14)", "31+(L01)", "31+(L02)", "31+(L03)", "31+(L04)", "31+(L05)", "31+(L06)", "31+(L07)", "31+(L08)", "31+(L09)", "31+(L10)", "31+(L11)", "31+(L12)", "31+(L13)", "31+(L14)", "31+(L15)", "31+(L16)", "31+(L17)", "31+(L18)", "31+(L19)", "31+(L20)", "31+(L21)", "31+(L22)", "31+(L23)", "31+(L24)", "31+(L25)", "31+(L26)", "31+(L27)", "31+(L28)", "31+(L29)", "31+(L30)", "31+(L31)", "31+(L32)", "31+(L33)", "31+(L34)", "31+(M01)", "31+(M02)", "31+(M03)", "31+(M04)", "31+(M05)", "31+(M06)", "31+(M07)", "31+(M08)", "31+(M09)", "31+(M10)", "31+(M11)", "31+(M12)", "31+(M13)", "31+(M14)", "31+(M15)", "31+(M16)", "31+(M17)", "31+(M18)", "31+(M19)", "31+(M20)", "31+(M21)", "31+(M22)", "31+(M23)",

"32+(A01)", "32+(A02)", "32+(A03)", "32+(A04)", "32+(A05)", "32+(A06)", "32+(A07)", "32+(A08)", "32+(A09)", "32+(A10)", "32+(A11)", "32+(A12)", "32+(B01)", "32+(B02)", "32+(B03)", "32+(B04)", "32+(B05)", "32+(B06)", "32+(B07)", "32+(B08)", "32+(B09)", "32+(B10)", "32+(B11)", "32+(B12)", "32+(C01)", "32+(C02)", "32+(C03)", "32+(C04)", "32+(C05)", "32+(C06)", "32+(C07)", "32+(C08)", "32+(C09)", "32+(C10)", "32+(C11)", "32+(C12)", "32+(C13)", "32+(C14)", "32+(C15)", "32+(C16)", "32+(C17)", "32+(C18)", "32+(C19)", "32+(C20)", "32+(C21)", "32+(C22)", "32+(C23)", "32+(C24)", "32+(C25)", "32+(C26)", "32+(C27)", "32+(C28)", "32+(C29)", "32+(C30)", "32+(C31)", "32+(C32)", "32+(C33)", "32+(C34)", "32+(C35)", "32+(C36)", "32+(C37)", "32+(C38)", "32+(C39)", "32+(C40)", "32+(C41)", "32+(C42)", "32+(C43)", "32+(C44)", "32+(C45)", "32+(C46)", "32+(C47)", "32+(C48)", "32+(D01)", "32+(D02)", "32+(D03)", "32+(D04)", "32+(D05)", "32+(E01)", "32+(E02)", "32+(E03)", "32+(E04)", "32+(E05)", "32+(F01)", "32+(F02)", "32+(F03)", "32+(G01)", "32+(G02)", "32+(G03)", "32+(G04)", "32+(G05)", "32+(G06)", "32+(G07)", "32+(G08)", "32+(G09)", "32+(G10)", "32+(G11)", "32+(G12)", "32+(G13)", "32+(H01)", "32+(H02)", "32+(H03)", "32+(H04)", "32+(H05)", "32+(H06)", "32+(H07)", "32+(H08)", "32+(H09)", "32+(H10)", "32+(H11)", "32+(H12)", "32+(H13)", "32+(H14)", "32+(H15)", "32+(H16)", "32+(H17)", "32+(H18)", "32+(H19)", "32+(H20)", "32+(H21)", "32+(H22)", "32+(H23)", "32+(H24)", "32+(H25)", "32+(H26)", "32+(H27)", "32+(H28)", "32+(H29)", "32+(H30)", "32+(H31)", "32+(H32)", "32+(H33)", "32+(H34)", "32+(H35)", "32+(H36)", "32+(H37)", "32+(H38)", "32+(H39)", "32+(H40)", "32+(H41)", "32+(H42)", "32+(H43)", "32+(H44)", "32+(H45)", "32+(H46)", "32+(H47)", "32+(H48)", "32+(H49)", "32+(H50)", "32+(I01)", "32+(I02)", "32+(I03)", "32+(I04)", "32+(I05)", "32+(I06)", "32+(I07)", "32+(I08)", "32+(I09)", "32+(I10)", "32+(J01)", "32+(J02)", "32+(J03)", "32+(J04)", "32+(J05)", "32+(J06)", "32+(K01)", "32+(K02)", "32+(K03)", "32+(K04)", "32+(K05)", "32+(K06)", "32+(K07)", "32+(K08)", "32+(K09)", "32+(K10)", "32+(K11)", "32+(K12)", "32+(K13)", "32+(K14)", "32+(L01)", "32+(L02)", "32+(L03)", "32+(L04)", "32+(L05)", "32+(L06)", "32+(L07)", "32+(L08)", "32+(L09)", "32+(L10)", "32+(L11)", "32+(L12)", "32+(L13)", "32+(L14)", "32+(L15)", "32+(L16)", "32+(L17)", "32+(L18)", "32+(L19)", "32+(L20)", "32+(L21)", "32+(L22)", "32+(L23)", "32+(L24)", "32+(L25)", "32+(L26)", "32+(L27)", "32+(L28)", "32+(L29)", "32+(L30)", "32+(L31)", "32+(L32)", "32+(L33)", "32+(L34)", "32+(M01)", "32+(M02)", "32+(M03)", "32+(M04)", "32+(M05)", "32+(M06)", "32+(M07)", "32+(M08)", "32+(M09)", "32+(M10)", "32+(M11)", "32+(M12)", "32+(M13)", "32+(M14)", "32+(M15)", "32+(M16)", "32+(M17)", "32+(M18)", "32+(M19)", "32+(M20)", "32+(M21)", "32+(M22)", "32+(M23)",

"33+(A01)", "33+(A02)", "33+(A03)", "33+(A04)", "33+(A05)", "33+(A06)", "33+(A07)", "33+(A08)", "33+(A09)", "33+(A10)", "33+(A11)", "33+(A12)", "33+(B01)", "33+(B02)", "33+(B03)", "33+(B04)", "33+(B05)", "33+(B06)", "33+(B07)", "33+(B08)", "33+(B09)", "33+(B10)", "33+(B11)", "33+(B12)", "33+(C01)", "33+(C02)", "33+(C03)", "33+(C04)", "33+(C05)", "33+(C06)", "33+(C07)", "33+(C08)", "33+(C09)", "33+(C10)", "33+(C11)", "33+(C12)", "33+(C13)", "33+(C14)", "33+(C15)", "33+(C16)", "33+(C17)", "33+(C18)", "33+(C19)", "33+(C20)", "33+(C21)", "33+(C22)", "33+(C23)", "33+(C24)", "33+(C25)", "33+(C26)", "33+(C27)", "33+(C28)", "33+(C29)", "33+(C30)", "33+(C31)", "33+(C32)", "33+(C33)", "33+(C34)", "33+(C35)", "33+(C36)", "33+(C37)", "33+(C38)", "33+(C39)", "33+(C40)", "33+(C41)", "33+(C42)", "33+(C43)", "33+(C44)", "33+(C45)", "33+(C46)", "33+(C47)", "33+(C48)", "33+(D01)", "33+(D02)", "33+(D03)", "33+(D04)", "33+(D05)", "33+(E01)", "33+(E02)", "33+(E03)", "33+(E04)", "33+(E05)", "33+(F01)", "33+(F02)", "33+(F03)", "33+(G01)", "33+(G02)", "33+(G03)", "33+(G04)", "33+(G05)", "33+(G06)", "33+(G07)", "33+(G08)", "33+(G09)", "33+(G10)", "33+(G11)", "33+(G12)", "33+(G13)", "33+(H01)", "33+(H02)", "33+(H03)", "33+(H04)", "33+(H05)", "33+(H06)", "33+(H07)", "33+(H08)", "33+(H09)", "33+(H10)", "33+(H11)", "33+(H12)", "33+(H13)", "33+(H14)", "33+(H15)", "33+(H16)", "33+(H17)", "33+(H18)", "33+(H19)", "33+(H20)", "33+(H21)", "33+(H22)", "33+(H23)", "33+(H24)", "33+(H25)", "33+(H26)", "33+(H27)", "33+(H28)", "33+(H29)", "33+(H30)", "33+(H31)", "33+(H32)", "33+(H33)", "33+(H34)", "33+(H35)", "33+(H36)", "33+(H37)", "33+(H38)", "33+(H39)", "33+(H40)", "33+(H41)", "33+(H42)", "33+(H43)", "33+(H44)", "33+(H45)", "33+(H46)", "33+(H47)", "33+(H48)", "33+(H49)",

"33+(H50)", "33+(I01)", "33+(I02)", "33+(I03)", "33+(I04)", "33+(I05)", "33+(I06)", "33+(I07)", "33+(I08)", "33+(I09)", "33+(I10)", "33+(J01)", "33+(J02)", "33+(J03)", "33+(J04)", "33+(J05)", "33+(J06)", "33+(K01)", "33+(K02)", "33+(K03)", "33+(K04)", "33+(K05)", "33+(K06)", "33+(K07)", "33+(K08)", "33+(K09)", "33+(K10)", "33+(K11)", "33+(K12)", "33+(K13)", "33+(K14)", "33+(L01)", "33+(L02)", "33+(L03)", "33+(L04)", "33+(L05)", "33+(L06)", "33+(L07)", "33+(L08)", "33+(L09)", "33+(L10)", "33+(L11)", "33+(L12)", "33+(L13)", "33+(L14)", "33+(L15)", "33+(L16)", "33+(L17)", "33+(L18)", "33+(L19)", "33+(L20)", "33+(L21)", "33+(L22)", "33+(L23)", "33+(L24)", "33+(L25)", "33+(L26)", "33+(L27)", "33+(L28)", "33+(L29)", "33+(L30)", "33+(L31)", "33+(L32)", "33+(L33)", "33+(L34)", "33+(M01)", "33+(M02)", "33+(M03)", "33+(M04)", "33+(M05)", "33+(M06)", "33+(M07)", "33+(M08)", "33+(M09)", "33+(M10)", "33+(M11)", "33+(M12)", "33+(M13)", "33+(M14)", "33+(M15)", "33+(M16)", "33+(M17)", "33+(M18)", "33+(M19)", "33+(M20)", "33+(M21)", "33+(M22)", "33+(M23)",

"34+(A01)", "34+(A02)", "34+(A03)", "34+(A04)", "34+(A05)", "34+(A06)", "34+(A07)", "34+(A08)", "34+(A09)", "34+(A10)", "34+(A11)", "34+(A12)", "34+(B01)", "34+(B02)", "34+(B03)", "34+(B04)", "34+(B05)", "34+(B06)", "34+(B07)", "34+(B08)", "34+(B09)", "34+(B10)", "34+(B11)", "34+(B12)", "34+(C01)", "34+(C02)", "34+(C03)", "34+(C04)", "34+(C05)", "34+(C06)", "34+(C07)", "34+(C08)", "34+(C09)", "34+(C10)", "34+(C11)", "34+(C12)", "34+(C13)", "34+(C14)", "34+(C15)", "34+(C16)", "34+(C17)", "34+(C18)", "34+(C19)", "34+(C20)", "34+(C21)", "34+(C22)", "34+(C23)", "34+(C24)", "34+(C25)", "34+(C26)", "34+(C27)", "34+(C28)", "34+(C29)", "34+(C30)", "34+(C31)", "34+(C32)", "34+(C33)", "34+(C34)", "34+(C35)", "34+(C36)", "34+(C37)", "34+(C38)", "34+(C39)", "34+(C40)", "34+(C41)", "34+(C42)", "34+(C43)", "34+(C44)", "34+(C45)", "34+(C46)", "34+(C47)", "34+(C48)", "34+(D01)", "34+(D02)", "34+(D03)", "34+(D04)", "34+(D05)", "34+(E01)", "34+(E02)", "34+(E03)", "34+(E04)", "34+(E05)", "34+(F01)", "34+(F02)", "34+(F03)", "34+(G01)", "34+(G02)", "34+(G03)", "34+(G04)", "34+(G05)", "34+(G06)", "34+(G07)", "34+(G08)", "34+(G09)", "34+(G10)", "34+(G11)", "34+(G12)", "34+(G13)", "34+(H01)", "34+(H02)", "34+(H03)", "34+(H04)", "34+(H05)", "34+(H06)", "34+(H07)", "34+(H08)", "34+(H09)", "34+(H10)", "34+(H11)", "34+(H12)", "34+(H13)", "34+(H14)", "34+(H15)", "34+(H16)", "34+(H17)", "34+(H18)", "34+(H19)", "34+(H20)", "34+(H21)", "34+(H22)", "34+(H23)", "34+(H24)", "34+(H25)", "34+(H26)", "34+(H27)", "34+(H28)", "34+(H29)", "34+(H30)", "34+(H31)", "34+(H32)", "34+(H33)", "34+(H34)", "34+(H35)", "34+(H36)", "34+(H37)", "34+(H38)", "34+(H39)", "34+(H40)", "34+(H41)", "34+(H42)", "34+(H43)", "34+(H44)", "34+(H45)", "34+(H46)", "34+(H47)", "34+(H48)", "34+(H49)", "34+(H50)", "34+(I01)", "34+(I02)", "34+(I03)", "34+(I04)", "34+(I05)", "34+(I06)", "34+(I07)", "34+(I08)", "34+(I09)", "34+(I10)", "34+(J01)", "34+(J02)", "34+(J03)", "34+(J04)", "34+(J05)", "34+(J06)", "34+(K01)", "34+(K02)", "34+(K03)", "34+(K04)", "34+(K05)", "34+(K06)", "34+(K07)", "34+(K08)", "34+(K09)", "34+(K10)", "34+(K11)", "34+(K12)", "34+(K13)", "34+(K14)", "34+(L01)", "34+(L02)", "34+(L03)", "34+(L04)", "34+(L05)", "34+(L06)", "34+(L07)", "34+(L08)", "34+(L09)", "34+(L10)", "34+(L11)", "34+(L12)", "34+(L13)", "34+(L14)", "34+(L15)", "34+(L16)", "34+(L17)", "34+(L18)", "34+(L19)", "34+(L20)", "34+(L21)", "34+(L22)", "34+(L23)", "34+(L24)", "34+(L25)", "34+(L26)", "34+(L27)", "34+(L28)", "34+(L29)", "34+(L30)", "34+(L31)", "34+(L32)", "34+(L33)", "34+(L34)", "34+(M01)", "34+(M02)", "34+(M03)", "34+(M04)", "34+(M05)", "34+(M06)", "34+(M07)", "34+(M08)", "34+(M09)", "34+(M10)", "34+(M11)", "34+(M12)", "34+(M13)", "34+(M14)", "34+(M15)", "34+(M16)", "34+(M17)", "34+(M18)", "34+(M19)", "34+(M20)", "34+(M21)", "34+(M22)", "34+(M23)",

"35+(A01)", "35+(A02)", "35+(A03)", "35+(A04)", "35+(A05)", "35+(A06)", "35+(A07)", "35+(A08)", "35+(A09)", "35+(A10)", "35+(A11)", "35+(A12)", "35+(B01)", "35+(B02)", "35+(B03)", "35+(B04)", "35+(B05)", "35+(B06)", "35+(B07)", "35+(B08)", "35+(B09)", "35+(B10)", "35+(B11)", "35+(B12)", "35+(C01)", "35+(C02)", "35+(C03)", "35+(C04)", "35+(C05)", "35+(C06)", "35+(C07)", "35+(C08)", "35+(C09)", "35+(C10)", "35+(C11)", "35+(C12)", "35+(C13)", "35+(C14)", "35+(C15)", "35+(C16)", "35+(C17)", "35+(C18)", "35+(C19)", "35+(C20)", "35+(C21)", "35+(C22)", "35+(C23)", "35+(C24)", "35+(C25)", "35+(C26)", "35+(C27)", "35+(C28)", "35+(C29)", "35+(C30)", "35+(C31)", "35+(C32)", "35+(C33)", "35+(C34)", "35+(C35)", "35+(C36)", "35+(C37)", "35+(C38)", "35+(C39)", "35+(C40)", "35+(C41)", "35+(C42)", "35+(C43)", "35+(C44)", "35+(C45)", "35+(C46)", "35+(C47)", "35+(C48)", "35+(D01)", "35+(D02)", "35+(D03)", "35+(D04)", "35+(D05)", "35+(E01)", "35+(E02)", "35+(E03)", "35+(E04)", "35+(E05)", "35+(F01)", "35+(F02)", "35+(F03)", "35+(G01)", "35+(G02)", "35+(G03)", "35+(G04)", "35+(G05)", "35+(G06)", "35+(G07)", "35+(G08)", "35+(G09)", "35+(G10)", "35+(G11)", "35+(G12)", "35+(G13)", "35+(H01)", "35+(H02)", "35+(H03)", "35+(H04)", "35+(H05)", "35+(H06)", "35+(H07)", "35+(H08)", "35+(H09)", "35+(H10)", "35+(H11)", "35+(H12)", "35+(H13)", "35+(H14)", "35+(H15)", "35+(H16)", "35+(H17)", "35+(H18)", "35+(H19)", "35+(H20)", "35+(H21)", "35+(H22)", "35+(H23)", "35+(H24)", "35+(H25)", "35+(H26)", "35+(H27)", "35+(H28)", "35+(H29)", "35+(H30)", "35+(H31)", "35+(H32)", "35+(H33)", "35+(H34)", "35+(H35)", "35+(H36)", "35+(H37)", "35+(H38)", "35+(H39)", "35+(H40)", "35+(H41)", "35+(H42)", "35+(H43)", "35+(H44)", "35+(H45)", "35+(H46)", "35+(H47)", "35+(H48)", "35+(H49)", "35+(H50)", "35+(I01)", "35+(I02)", "35+(I03)", "35+(I04)", "35+(I05)", "35+(I06)", "35+(I07)", "35+(I08)", "35+(I09)", "35+(I10)", "35+(J01)", "35+(J02)", "35+(J03)", "35+(J04)", "35+(J05)", "35+(J06)", "35+(K01)", "35+(K02)", "35+(K03)", "35+(K04)", "35+(K05)", "35+(K06)", "35+(K07)", "35+(K08)", "35+(K09)", "35+(K10)", "35+(K11)", "35+(K12)", "35+(K13)", "35+(K14)", "35+(L01)", "35+(L02)", "35+(L03)", "35+(L04)", "35+(L05)", "35+(L06)", "35+(L07)", "35+(L08)", "35+(L09)", "35+(L10)", "35+(L11)", "35+(L12)", "35+(L13)", "35+(L14)", "35+(L15)", "35+(L16)", "35+(L17)", "35+(L18)", "35+(L19)", "35+(L20)", "35+(L21)", "35+(L22)", "35+(L23)", "35+(L24)", "35+(L25)", "35+(L26)", "35+(L27)", "35+(L28)", "35+(L29)", "35+(L30)", "35+(L31)", "35+(L32)", "35+(L33)", "35+(L34)", "35+(M01)", "35+(M02)", "35+(M03)", "35+(M04)", "35+(M05)", "35+(M06)", "35+(M07)", "35+(M08)", "35+(M09)", "35+(M10)", "35+(M11)", "35+(M12)", "35+(M13)", "35+(M14)", "35+(M15)", "35+(M16)", "35+(M17)", "35+(M18)", "35+(M19)", "35+(M20)", "35+(M21)", "35+(M22)", "35+(M23)",

"36+(A01)", "36+(A02)", "36+(A03)", "36+(A04)", "36+(A05)", "36+(A06)", "36+(A07)", "36+(A08)", "36+(A09)", "36+(A10)", "36+(A11)", "36+(A12)", "36+(B01)", "36+(B02)", "36+(B03)", "36+(B04)", "36+(B05)", "36+(B06)", "36+(B07)", "36+(B08)", "36+(B09)", "36+(B10)", "36+(B11)", "36+(B12)", "36+(C01)", "36+(C02)", "36+(C03)", "36+(C04)", "36+(C05)", "36+(C06)", "36+(C07)", "36+(C08)", "36+(C09)", "36+(C10)", "36+(C11)", "36+(C12)", "36+(C13)", "36+(C14)", "36+(C15)", "36+(C16)", "36+(C17)", "36+(C18)", "36+(C19)", "36+(C20)", "36+(C21)", "36+(C22)", "36+(C23)", "36+(C24)", "36+(C25)", "36+(C26)", "36+(C27)", "36+(C28)", "36+(C29)", "36+(C30)", "36+(C31)", "36+(C32)", "36+(C33)", "36+(C34)", "36+(C35)", "36+(C36)", "36+(C37)", "36+(C38)", "36+(C39)", "36+(C40)", "36+(C41)", "36+(C42)", "36+(C43)", "36+(C44)", "36+(C45)", "36+(C46)", "36+(C47)", "36+(C48)", "36+(D01)", "36+(D02)", "36+(D03)", "36+(D04)", "36+(D05)", "36+(E01)", "36+(E02)", "36+(E03)", "36+(E04)", "36+(E05)", "36+(F01)", "36+(F02)", "36+(F03)", "36+(G01)", "36+(G02)", "36+(G03)", "36+(G04)", "36+(G05)", "36+(G06)", "36+(G07)", "36+(G08)", "36+(G09)", "36+(G10)", "36+(G11)", "36+(G12)", "36+(C13)", "36+(H01)", "36+(H02)", "36+(H03)", "36+(H04)", "36+(H05)", "36+(H06)", "36+(H07)", "36+(H08)", "36+(H09)", "36+(H10)", "36+(H11)", "36+(H12)", "36+(H13)", "36+(H14)", "36+(H15)", "36+(H16)", "36+(H17)", "36+(H18)", "36+(H19)", "36+(H20)", "36+(H21)", "36+(H22)", "36+(H23)", "36+(H24)", "36+(H25)", "36+(H26)", "36+(H27)", "36+(H28)", "36+(H29)", "36+(H30)", "36+(H31)", "36+(H32)", "36+(H33)", "36+(H34)", "36+(H35)", "36+(H36)", "36+(H37)", "36+(H38)", "36+(H39)", "36+(H40)", "36+(H41)", "36+(H42)", "36+(H43)", "36+(H44)", "36+(H45)", "36+(H46)", "36+(H47)", "36+(H48)", "36+(H49)", "36+(H50)", "36+(I01)", "36+(I02)", "36+(I03)", "36+(I04)", "36+(I05)", "36+(I06)", "36+(I07)", "36+(I08)", "36+(I09)", "36+(I10)", "36+(J01)", "36+(J02)", "36+(J03)", "36+(J04)", "36+(J05)", "36+(J06)", "36+(K01)", "36+(K02)", "36+(K03)", "36+(K04)", "36+(K05)", "36+(K06)", "36+(K07)", "36+(K08)", "36+(K09)", "36+(K10)", "36+(K11)", "36+(K12)", "36+(K13)", "36+(K14)", "36+(L01)", "36+(L02)", "36+(L03)", "36+(L04)", "36+(L05)", "36+(L06)", "36+(L07)", "36+(L08)", "36+(L09)", "36+(L10)", "36+(L11)", "36+(L12)", "36+(L13)", "36+(L14)", "36+(L15)", "36+(L16)", "36+(L17)", "36+(L18)", "36+(L19)", "36+(L20)", "36+(L21)", "36+(L22)", "36+(L23)", "36+(L24)", "36+(L25)", "36+(L26)", "36+(L27)", "36+(L28)", "36+(L29)", "36+(L30)", "36+(L31)", "36+(L32)", "36+(L33)", "36+(L34)", "36+(M01)", "36+(M02)", "36+(M03)", "36+(M04)", "36+(M05)", "36+(M06)", "36+(M07)", "36+(M08)", "36+(M09)", "36+(M10)", "36+(M11)", "36+(M12)", "36+(M13)", "36+(M14)", "36+(M15)", "36+(M16)", "36+(M17)", "36+(M18)", "36+(M19)", "36+(M20)", "36+(M21)", "36+(M22)", "36+(M23)",

"37+(A01)", "37+(A02)", "37+(A03)", "37+(A04)", "37+(A05)", "37+(A06)", "37+(A07)", "37+(A08)", "37+(A09)", "37+(A10)", "37+(A11)", "37+(A12)", "37+(B01)", "37+(B02)", "37+(B03)", "37+(B04)", "37+(B05)", "37+(B06)", "37+(B07)", "37+(B08)", "37+(B09)", "37+(B10)", "37+(B11)", "37+(B12)", "37+(C01)", "37+(C02)", "37+(C03)", "37+(C04)", "37+(C05)", "37+(C06)", "37+(C07)", "37+(C08)", "37+(C09)", "37+(C10)", "37+(C11)", "37+(C12)", "37+(C13)", "37+(C14)", "37+(C15)", "37+(C16)", "37+(C17)", "37+(C18)", "37+(C19)", "37+(C20)", "37+(C21)", "37+(C22)", "37+(C23)", "37+(C24)", "37+(C25)", "37+(C26)", "37+(C27)", "37+(C28)", "37+(C29)", "37+(C30)", "37+(C31)", "37+(C32)", "37+(C33)", "37+(C34)", "37+(C35)", "37+(C36)", "37+(C37)", "37+(C38)", "37+(C39)", "37+(C40)", "37+(C41)", "37+(C42)", "37+(C43)", "37+(C44)", "37+(C45)", "37+(C46)", "37+(C47)", "37+(C48)", "37+(D01)", "37+(D02)", "37+(D03)", "37+(D04)", "37+(D05)", "37+(E01)", "37+(E02)", "37+(E03)", "37+(E04)", "37+(E05)", "37+(F01)", "37+(F02)", "37+(F03)", "37+(G01)", "37+(G02)", "37+(G03)", "37+(G04)", "37+(G05)", "37+(G06)", "37+(G07)", "37+(G08)", "37+(G09)", "37+(G10)", "37+(G11)", "37+(G12)", "37+(G13)", "37+(H01)", "37+(H02)", "37+(H03)", "37+(H04)", "37+(H05)", "37+(H06)", "37+(H07)", "37+(H08)", "37+(H09)", "37+(H10)", "37+(H11)", "37+(H12)", "37+(H13)", "37+(H14)", "37+(H15)", "37+(H16)", "37+(H17)", "37+(H18)", "37+(H19)", "37+(H20)", "37+(H21)", "37+(H22)", "37+(H23)", "37+(H24)", "37+(H25)", "37+(H26)", "37+(H27)", "37+(H28)", "37+(H29)", "37+(H30)", "37+(H31)", "37+(H32)", "37+(H33)", "37+(H34)", "37+(H35)", "37+(H36)", "37+(H37)", "37+(H38)", "37+(H39)", "37+(H40)", "37+(H41)", "37+(H42)", "37+(H43)", "37+(H44)", "37+(H45)", "37+(H46)", "37+(H47)", "37+(H48)", "37+(H49)", "37+(H50)", "37+(I01)", "37+(I02)", "37+(I03)", "37+(I04)", "37+(I05)", "37+(I06)", "37+(I07)", "37+(I08)", "37+(I09)", "37+(I10)", "37+(J01)", "37+(J02)", "37+(J03)", "37+(J04)", "37+(J05)", "37+(J06)", "37+(K01)", "37+(K02)", "37+(K03)", "37+(K04)", "37+(K05)", "37+(K06)", "37+(K07)", "37+(K08)", "37+(K09)", "37+(K10)", "37+(K11)", "37+(K12)", "37+(K13)", "37+(K14)", "37+(L01)", "37+(L02)", "37+(L03)", "37+(L04)", "37+(L05)", "37+(L06)", "37+(L07)", "37+(L08)", "37+(L09)", "37+(L10)", "37+(L11)", "37+(L12)", "37+(L13)", "37+(L14)", "37+(L15)", "37+(L16)", "37+(L17)", "37+(L18)", "37+(L19)", "37+(L20)", "37+(L21)", "37+(L22)", "37+(L23)", "37+(L24)", "37+(L25)", "37+(L26)", "37+(L27)", "37+(L28)", "37+(L29)", "37+(L30)", "37+(L31)", "37+(L32)", "37+(L33)", "37+(L34)", "37+(M01)", "37+(M02)", "37+(M03)", "37+(M04)", "37+(M05)", "37+(M06)", "37+(M07)", "37+(M08)", "37+(M09)", "37+(M10)", "37+(M11)", "37+(M12)", "37+(M13)", "37+(M14)", "37+(M15)", "37+(M16)", "37+(M17)", "37+(M18)", "37+(M19)", "37+(M20)", "37+(M21)", "37+(M22)", "37+(M23)".

In the composition of the present invention and in the method of the present invention, a suitable mixing ratio of [active ingredient A] selected from oxime-substituted amide compounds represented by the formula (I) and [active ingredient B] selected from known fungicidal or bactericidal compounds, is such that, relative to 1 part by weight of active ingredient A, active ingredient B is usually from 0.001 to 1,000 parts by weight, preferably from 0.01 to 100 parts by weight, more preferably from 0.1 to 10 parts by weight.

In the composition of the present invention and in the method of the present invention, a preferred amount of the active ingredient compound to be applied, may vary depending upon by e.g. the type of the target disease to be controlled, but is usually such that active ingredient A is from 0.1 to 1,000 g a.i./ha, and active ingredient B is from 0.1 to 1,000 g a.i./ha, and preferably active ingredient A is from 1 to 300 g a.i./ha, and active ingredient B is from 1 to 300 g a.i./ha.

In this specification, a "plant disease control agent" means a fungicide or bactericide to control target harmful pathogenic bacteria that infects plants.

In this specification, "plant" means cereal, fruits or vegetables which are cultivated as human food, feed crops for e.g. livestock and poultry, ornamental plants to appreciate their appearance and shapes, or vascular plants (Tracheophyta) planted in parks or streets. Specifically, the following plants may, for example, be mentioned, but the plant is not limited thereto.

Pinales belonging to the pine family (Pinaceae), such as Japanese Red Pine (*Pinus densiflora*), Scots Pine (*Pinus sylvestris*), Japanese Black Pine (*Pinus thunbergii*), etc.

*Magnolia* (magnoliids) belonging to pepper family (Piperaceae) such as Pepper (*Piper nigrum*), Lauraceae such as Avocado (*Persea americana*), etc., Monocots belonging to Araceae such as *Konjac* (*Amorphophallus konjac*), Eddoe (*Colocasia esculenta*), etc., Dioscoreaceae such as Chinese yam (*Dioscorea batatas*), Japanese yam (*Dioscorea japonica*), etc., green onion family (Alliaceae) such as Leek (*Allium ampeloprasum* var. *porrum*), Onion (*Allium cepa*), Rakkyo (*Allium chinense*), Welsh onion (*Allium fistulosum*), Garlic (*Allium sativum*), Chives (*Allium schoenoprasum*), Chive (*Allium schoenoprasum* var. *foliosum*), Oriental garlic (*Allium tuberosum*), Scallion (*Allium×wakegi*), etc., Asparagaceae such as *Asparagus* (*Asparagus officinalis*), etc., palm family (Arecaceae) Dypsis *lutescens* subfamily (Arecoideae) such as Coconut palm (*Cocos nucifera*), Oil palm (*Elaeis guineensis*), etc., palm family (Arecaceae) talipot subfamily (Coryphoideae) such as Date palm (*Phoenix dactylifera*), etc., pineapple family (Bromeliaceae) such as Pineapple (*Ananas comosus*), etc., Gramineae (Poaceae) Eruharuta subfamily (Ehrhartoideae) such as Rice (*Oryza sativa*), etc., Gramineae (Poaceae) bluegrass subfamily (Pooideae) such as Bent grass (*Agrostis* spp.), Blue grass (Poa spp.), Barley (*Hordeum vulgare*), Wheat (*Triticum aestivum, T. durum*), Rye (*Secale cereale*), etc., Gramineae (Poaceae) Higeshiba subfamily (Chloridoideae) such as Bermuda grass (*Cynodon dactylon*), Grass (*Zoysia* spp.), etc., Gramineae (Poaceae) millet subfamily (Panicoideae) such as Sugarcane (*Saccharum officinarum*), Sorgum (*Sorghum bicolor*), Corn (*Zea mays*), etc., Musaceae such as Banana (Musa spp.), etc., ginger family (Zingiberaceae) such as Myoga (*Zingiber mioga*), Ginger (*Zingiber officinale*).

Eudicots belonging to lotus family (Nelumbonaceae) such as Lotus root (*Nelumbo nucifera*), etc., leguminous (Fabaceae) such as Peanut (*Arachis hypogaea*), Chickpea (*Cicer arietinum*), Lentil (*Lens culinaris*), Pea (*Pisum sativum*), Broad bean (*Vicia faba*), Soybean (*Glycine max*), Common bean (*Phaseolus vulgaris*), Adzuki bean (*Vigna angularis*), Cowpea (*Vigna unguiculata*), etc., hemp family (Cannabaceae) such as Hop (*Humulus lupulus*), etc., mulberry family (Moraceae) such as Fig Tree (*Ficus carica*), Mulberry (*Morus* spp.), etc., buckthorn family (Rhamnaceae) such as Common jujube (*Ziziphus jujuba*), etc., rose family (Rosaceae) rose subfamily (Rosoideae) such as Strawberry (Fragaria), Rose (*Rosa* spp.), etc., rose family (Rosaceae) pear subfamily (Maloideae) such as Japanese loquat (*Eriobotrya japonica*), Apple (*Malus pumila*), European Pear (*Pyrus communis*), Nashi Pear (*Pyrus pyrifolia* var. *culta*), etc., rose family (Rosaceae) amygdaloideae (Prunoideae) such as Peach (*Amygdalus persica*), Apricot (*Prunus armeniaca*), Cherry (*Prunus avium*), Prune (*Prunus domestica*), Almond (*Prunus dulcis*), Japanese Apricot (*Prunus mume*), Japanese Plum (*Prunus salicina*), OOSHIMAZAKURA (*Cerasus speciosa*), Yoshino cherry tree (*Cerasus×yedoensis* 'Somei-yoshino'), etc., Cucurbitaceae such as Winter melon (*Benincasa hispida*), Watermelon (*Citrullus lanatus*), Bottle gourd (*Lagenaria siceraria* var. *hispida*), Luffa (*Luffa cylindrica*), Pumpkin (*Cucurbita* spp.), Zucchini (*Cucurbita pepo*), Bitter melon (*Momordica charantia* var. *pavel*), Muskmelon (*Cucumis melo*), Oriental pickling melon (*Cucumis melo* var. *conomon*), Oriental melon (*Cucumis melo* var. *makuwa*), Cucumber (*Cucumis sativus*), etc., beech family (Fagaceae) such as Japanese Chestnut (*Castanea crenata*), etc., walnut family (Juglandaceae) such as Walnut (*Juglans* spp.), etc., Anacardiaceae such as Cashew (*Anacardium occidentale*), Mango (*Mangifera indica*), Pistachio (*Pistacia vera*), etc., mandarin orange family (Rutaceae) rue subfamily (Rutoideae) such as Japanese pepper (*Zanthoxylum piperitum*), etc., mandarin orange family (Rutaceae) mandarin orange subfamily (Aurantioideae) such as Bitter orange (*Citrus aurantium*), Lime (*Citrus aurantifolia*), Hassaku orange (*Citrus hassaku*), Yuzu (*Citrus junos*), Lemon (*Citrus limon*), Natsumikan (*Citrus natsudaidai*), Grapefruit (*Citrus×paradisi*), Orange (*Citrus sinensis*), Kabosu (*Citrus sphaerocarpa*), Sudachi (*Citrus sudachi*), Mandarin Orange (*Citrus tangerina*), Satsuma (*Citrus unshiu*), Kumquat (*Fortunella* spp.), etc., cruciferous (Brassicaceae) such as Horseradish (*Armoracia rusticana*), Mustard (*Brassica juncea*), Takana (*Brassica juncea* var. *integrifolia*), Rapeseed (*Brassica napus*), Cauliflower (*Brassica oleracea* var. *botrytis*), Cabbage (*Brassica oleracea* var. *capitata*), Brussels sprout (*Brassica oleracea* var. *gemmifera*), Broccoli (*Brassica oleracea* var. *italica*), Green pak choi (*Brassica rapa* var. *chinensis*), Nozawana (*Brassica rapa* var. *hakabura*), Napa cabbage (*Brassica rapa* var. *nippooleifera*), Potherb Mustard (*Brassica rapa* var. *nipposinica*), Napa cabbage (*Brassica rapa* var. *pekinensis*), Turnip leaf (*Brassica rapa* var. *perviridis*), Turnip (*Brassica rapa* var. *rapa*), Garden rocket (*Eruca vesicaria*), Daikon (*Raphanus sativus* var. *longipinnatus*), Wasabi (*Wasabia japonica*), etc., papaya family (Caricaceae) such as Papaya (*Carica papaya*), etc., Malvaceae such as Okra (*Abelmoschus esculentus*), Cotton plant (*Gossypium* spp.), Cacao (*Theobroma cacao*), etc., grape family (Vitaceae) such as Grape (*Vitis* spp.), etc., Amaranthaceae such as Sugar beet (*Beta vulgaris* ssp. *vulgaris* var. *altissima*), Table beet (*Beta vulgaris* ssp. *vulgaris* var. *vulgaris*), Spinach (*Spinacia oleracea*), etc., Polygonaceae such as Buckweat (*Fagopyrum esculentum*), etc., Ebenaceae such as *Kaki* Persimmon (*Diospyros kaki*), etc., camellia family (Theaceae) such as Tea plant (*Camellia sinensis*), etc., *Actinidia* family (Actinidiaceae) such as Kiwifruit (*Actinidia deliciosa, A. chinensis*), etc., azalea family (Ericaceae) such as Blueberry (*Vaccinium* spp.), Cranberry (*Vaccinium* spp.), etc., madder family (Rubiaceae) such as Coffee plants (*Coffea* spp.), etc., Lamiaceae such as Lemon balm (*Melissa officinalis*), Mint (*Mentha* spp.), Basil (*Ocimum basilicum*), Shiso (*Perilla frutescens* var. *crispa*), perilla (*Perilla frutescens* var. *frutescens*), Common Sage (*Salvia officinalis*), Thyme (*Thymus* spp.), etc., sesame family (Pedaliaceae) such as Sesame (*Sesamum indicum*), etc., Oleaceae such as Olive (*Olea europaea*), etc., Convolvulaceae family (Convolvulaceae) such as Sweet potato (*Ipomoea batatas*), etc., Solanaceae such as Tomato (*Solanum lycopersicum*), Eggplant (*Solanum melongena*), Potato (*Solanum tuberosum*), Chili pepper (*Capsicum annuum*), Bell pepper (*Capsicum annuum* var. 'grossum'), Tobacco (*Nicotiana tabacum*), etc., Seri family (Apiaceae) such as Celery (*Apium graveolens* var. *dulce*), Coriander (*Coriandrum sativum*), Japanese honeywort (*Cryptotaenia Canadensis* subsp. *japonica*), Carrot (*Daucus carota* subsp. *sativus*), Parsley (*Petroselium crispum*), Italian parsley (*Petroselinum neapolitanum*), etc., Araliaceae such as Udo (*Aralia cordata*), *Aralia elata*, etc., Asteraceae thistle subfamily (Carduoideae) such as Artichoke (*Cynara scolymus*), etc., Asteraceae dandelion subfamily (Asteraceae) such as Chicory (*Cichorium intybus*), Lettuce (*Lactuca sativa*), etc., Asteraceae *Chrysanthemum* subfamily (Asteraceae) such as Florists' daisy (*Dendranthema grandiflorum*), Crown daisy (*Glebionis coronaria*), Sunflower (*Helianthus annuus*), Fuki (*Petasites japonicus*), Burdock (*Arctium lappa*), etc.

Further, the "plant" in this specification includes plants having resistance to HPPD inhibitors such as isoxaflutole, etc., ALS inhibitors such as imazethapyr, thifensulfuron-methyl, etc., EPSP synthetase inhibitors such as glyphosate, etc., glutamine synthetase inhibitors such as glufosinate, etc., acetyl-CoA carboxylase inhibitors such as sethoxydim, PPO inhibitors such as flumioxazin, etc., or herbicides such as bromoxynil, dicamba and 2,4-D, imparted by a classical breeding method or by a gene recombination technology.

As examples of "agricultural/horticultural plants" having such resistance imparted by a classical breeding method, there are rapeseed, wheat, sunflower, rice and corn which are resistant to imidazolinone type ALS inhibitory herbicides such as imazethapyr, etc., and they are already commercially available under the trade name "Clearfield" (registered trademark).

Similarly, there is soybean having resistance to sulfonylurea ALS inhibitory herbicides such as thifensulfuron-methyl, imparted by a classical breeding method, which is already commercially available under the trade name "STS soybean".

Similarly, SR corn, etc. are available as examples of agricultural/horticultural plants having resistance to acetyl CoA carboxylase inhibitors such as trione oxime type, aryloxy phenoxypropionic acid herbicides, imparted by a classical breeding method. Agricultural/horticultural plants having resistance to acetyl CoA carboxylase inhibitors imparted, are disclosed e.g. in Proceedings of the National Academy of Sciences of the United States of America (Proc. Natl. Acad. Sci. USA), Vol. 87, pp. 7175-7179 (1990). Further, mutant acetyl CoA carboxylase resistant to an acetyl CoA carboxylase inhibitor is reported in Weed Science, Vol. 53, pp. 728-746 (2005), etc., and by introducing such a mutant acetyl CoA carboxylase gene into a plant by a gene recombination technique, or by introducing a mutation to impart resistance into a crop acetyl CoA carboxylase, it is possible to produce a plant which is resistant to acetyl CoA carboxylase inhibitors. Further, as represented by the chimeric plasticine technology (Gura T. 1999. Repairing the Genome's Spelling Mistakes. Science 285: 316-318), base substitution mutation introducing nucleic acid is introduced into plant cells to induce a site-specific amino acid substitution mutation in the crop (acetyl-CoA carboxylase/herbicide target) gene, so that it is possible to produce a plant which is resistant to acetyl CoA carboxylase inhibitor/herbicide.

Examples of agricultural/horticultural plants having resistance imparted by gene recombination technology, include corn, soybean, cotton, rapeseed and sugar beet varieties resistant to glyphosate, and they are already commercially available under trade names "Roundup Ready" (registered trademark), "AgrisureGT" (registered trademark), etc. Similarly, there are corn, soybean, cotton and rape varieties having glufosinate-resistance imparted by gene recombination technology, and they are already commercially available under a trade name "LibertyLink" (registered trademark), etc. Similarly, cotton having bromoxynil resistance imparted by genetic engineering technology is already commercially available under a trade name "BXN".

The above "agricultural/horticultural plants" also include plants which became possible to synthesize selective toxins known e.g. in genus *Bacillus*, by using a genetic engineering technique.

Insecticidal toxins to be expressed in such genetically modified plants may, for example, be an insecticidal protein derived from *Bacillus cereus* or *Bacillus popilliae*; b-endotoxin such as Cry1Ab, Cry1Ac, Cry1F, Cry1Fa2, Cry2Ab, Cry3A, Cry3Bb1 or Cry9C derived from *Bacillus thuringiensis*, or an insecticidal protein such as VIP1, VIP2, VIP3 or VIP3A; an insecticidal protein derived from nematode; a scorpion toxin, a spider toxin, a bee toxin or a toxin produced by an animal, such as an insect-specific neurotoxin; a yarn fungal toxin; plant lectin; agglutinin; a trypsin inhibitor, a serine protease inhibitor, patatin, cystatin, a protease inhibitor such as a papain inhibitor; a ribosome inactivating protein (RIP) such as lysine, corn-RIP, abrin, saporin, bryodin, etc.; a steroid metabolism enzyme such as 3-hydroxy steroid oxidase, ecdysteroid-UDP-glucosyltransferase, cholesterol oxidase, etc.; an ecdysone inhibitor; HMG-CoA reductase; an ion channel inhibitor such as a sodium channel inhibitor, a calcium channel inhibitor, etc.; juvenile hormone esterase; diuretic hormone receptor; stilbene synthase; bibenzyl synthase; chitinase; glucanase; etc.

Further, toxins to be expressed in such genetically modified plants also include hybrid toxins, partially deficient toxins and modified toxins of 5-endotoxin protein, such as Cry1Ab, Cry1Ac, Cry1F, Cry1Fa2, Cry2Ab, Cry3A, Cry3Bb1 or Cry9C, or an insecticidal protein such as VIP1, VIP2, VIP3 or VIP3A. Hybrid toxins are produced by a new combination of different domains of such proteins by using recombinant techniques. As a partly deficient toxin, Cry1Ab with loss of a portion of the amino acid sequence is known. In a modified toxin, one or more amino acids of a naturally occurring toxin are substituted.

Examples of these toxins and recombinant plants capable of synthesizing these toxins are disclosed, for example, in patent documents such as EP-A-0374753, WO93/07278, WO95/34656, EP-A-0427529, EP-A-451878, WO03/052073. The toxins contained in such genetically modified plants will impart to the plants resistance, in particular, against Coleoptera pests, Diptera pests or lepidopteran pests.

Further, genetically modified plants that comprise one or more insecticidal pest-resistant genes, and express one or multiple toxins, are already known, and some of them are commercially available. Examples of such genetically engineered plants may, for example, be YieldGard <registered trademark> (a corn variety expressing Cry1Ab toxin), YieldGard Rootworm <registered trademark> (corn variety expressing Cry3Bb1 toxin), YieldGard Plus <registered trademark> (corn variety expressing Cry1Ab and Cry3Bb1 toxins), Herculex I<registered trademark> (corn variety expressing phosphinotricine N-acetyl transferase (PAT) for imparting resistance to Cry1 Fa2 toxin and glufosinate), NuCOTN33B <registered trademark> (cotton variety expressing Cry1Ac toxin), Bollgard I<registered trademark> (cotton variety expressing Cry1Ac toxin), Bollgard II<registered trademark> (cotton variety expressing Cry1Ac and Cry2Ab toxins), VIPCOT <registered trademark> (cotton variety expressing VIP toxin), NewLeaf <registered trademark> (potato variety expressing Cry3A toxin), NatureGuard Agrisure GT Advantage (NatureGard <registered trademark> Agrisure <registered trademark> GT Advantage) (GA21 glyphosate-resistant trait), Agrisure CB Advantage (Agrisure <registered trademark> CB Advantage) (Bt11 corn borer (CB) trait), Protecta <registered trademark>, etc.

The aforementioned plants include those which have ability to generate antipathogenic substances having selective actions, imparted by using gene recombination techniques.

Such antipathogenic substances may, for example, be PR proteins (PRPs, described in EP-A-0392225); ion channel inhibitors such as sodium channel inhibitors, calcium channel inhibitors (viruses produced KP1, KP4, KP6 toxins, etc. have been known), etc.; stilbene synthase; bibenzyl synthase; chitinase; glucanase; substances, etc. produced by microorganisms, such as peptide antibiotics, antibiotics having a heterocyclic ring, protein factors relating to plant disease resistance (so-called plant disease resistance genes, as described in WO03/000906); etc. Such antipathogenic substances and genetically engineered plants to produce them, are disclosed in e.g. EP-A-0392225, WO95/33818, EP-A-0353191, etc.

The aforementioned plants also include plants having useful traits such as traits to improve oil stuff ingredients or to reinforce amino acid content, imparted by using gene recombination technology. As an example, VISTIVE <registered trademark> (low linolenic soybean having reduced linolenic content) or high-lysine (hig hoil) corn (corn having a lysine or oil content increased), may be mentioned.

Further, with respect to the above-described classic herbicide traits or herbicide tolerance genes, insecticidal pest-resistant genes, anti-pathogenic substance producing genes, and useful traits such as traits to improve oil stuff ingredients or to reinforce amino acid content, stack varieties having a plurality of them combined, are also included.

The "pathogen" in this specification means a microorganism which is a pathogen of plant disease, and specifically, the following microorganisms may, for example, be mentioned, but the pathogen is not limited thereto.

Ascomycota fungi, such as *Taphrina* spp. (for example, *Taphrina deformans, T. pruni*, etc.), *Pneumocystis* spp., *Geotrichum* spp., *Candida* spp. (for example, *Candida albicans, C. sorbosa*, etc.), *Pichia* spp. (for example, *Pichia kluyveri*, etc.), *Capnodium* spp., *Fumago* spp., *Hypocapnodium* spp., *Cercospora* spp. (for example, *Cercospora apii, C. asparagi, C. beticola, C. capsici, C. carotae, C. kaki, C. kikuchii, C. zonata*, etc.), *Cercosporidium* spp., *Cladosporium* spp. (for example, *Cladosporium colocasiae, C. cucumerinum, C. variabile*, etc.), *Davidiella* spp., *Didymosporium* spp., *Heterosporium* spp. (for example, *Heterosporium allii*, etc.), *Mycosphaerella* spp. (for example, *Mycosphaerella arachidis, M. berkeleyi, M. cerasella, M. fijiensis, M. fragariae, M. graminicola, M. nawae, M. pinodes, M. pomi, M. zingiberis*, etc.), *Mycovellosiella* spp. (for example, *Mycovellosiella fulva, M. nattrassii*, etc.), *Paracercospora* spp. (for example, *Paracercospora egenula*, etc.), *Phaeoisariopsis* spp., *Phaeoramularia* spp., *Pseudocercospora* spp. (for example, *Pseudocercospora abelmoschi, P. fuligena, P. vitis*, etc.), *Pseudocercosporella* spp. (for example, *Pseudocercosporella capsellae*, etc.), *Ramichloridium* spp., *Ramularia* spp., *Septogloeum* spp., *Septoria* spp. (for example, *Septoria albopunctata, S. apiicola, S. chrysanthemella, S. helianthi, S. obesa*, etc.), *Sphaerulina* spp., *Aureobasidium* spp., *Kabatiella* spp., *Plowrightia* spp., *Stigmina* spp., *Elsinoe* spp. (for example, *Elsinoe ampelina, E. araliae, E. fawcettii*, etc.), *Sphaceloma* spp. (for example, *Sphaceloma caricae*, etc.), *Ascochyta* spp. (for example, *Ascochyta pisi*, etc.), *Corynespora* spp. (for example, *Corynespora cassiicola*, etc.), *Leptosphaeria* spp. (for example, *Leptosphaeria coniothyrium, L. maculans*, etc.), *Saccharicola* spp., *Phaeosphaeria* spp. (for example, *Phaeosphaeria nodorum*, etc.), *Ophiosphaerella* spp., *Setophoma* spp., *Helminthosporium* spp., *Alternaria* spp. (for example, *Alternaria alternata, A. brassicae, A. brassicicola, A. citri, A. dauci, A. helianthi, A. japonica, A. kikuchianaz, A. mali, A. panax, A. porri, A. radicina, A. solani*, etc.), *Bipolaris* spp. (for example, *Bipolaris sorghicola*, etc.), *Cochliobolus* spp. (for example, *Cochliobolus heterostrophus, C. lunatus, C. miyabeanus*, etc.), *Curvularia* spp. (for example, *Curvularia geniculata, C. verruculosa*, etc.), *Drechslera* spp., *Pleospora* spp. (for example, *Pleospora herbarum*, etc.), *Pyrenophora* spp. (for example, *Pyrenophora graminea, P. teres*, etc.), *Setosphaeria* spp. (for example, *Setosphaeria turcica*, etc.), *Stemphylium* spp. (for example, *Stemphylium botryosum, S. lycopersici, S. solani, S. vesicarium*, etc.), *Fusicladium* spp., *Venturia* spp. (for example, *Venturia carpophila, V. Inaequalis, V. nashicola, V. pirina*, etc.), *Didymella* spp. (for example, *Didymella bryoniae, D. fabae*, etc.), *Hendersonia* spp., *Phoma* spp. (for *example, Phoma erratica* var. *mikan, P. exigua* var. *exigua, P. wasabiae*, etc.), *Pyrenochaeta* spp. (for example, *Pyrenochaeta lycopersici*, etc.), *Stagonospora* spp. (for example, *Stagonospora sacchari*, etc.), *Botryosphaeria* spp. (for example, *Botryosphaeria berengeriana* f. sp. *piricola, B. dothidea*, etc.), *Dothiorella* spp., *Fusicoccum* spp., *Guignardia* spp., *Lasiodiplodia* spp. (for example, *Lasiodiplodia theobromae*, etc.), *Macrophoma* spp., *Macrophomina* spp., *Neofusicoccum* spp., *Phyllosticta* spp. (for example, *Phyllosticta zingiberis*, etc.), *Schizothyrium* spp. (for example, *Schizothyrium pomi*, etc.), *Acrospermum* spp., *Leptosphaerulina* spp., *Aspergillus* spp., *Penicillium* spp. (for example, *Penicillium digitatum, P. italicum, P. sclerotigenum*, etc.), *Microsporum* spp., *Trichophyton* spp. (for example, *Trichophyton mentagrophytes, T. rubrum*, etc.), *Histoplasma* spp., *Blumeria* spp. (for example, *Blumeria graminis* f. sp. *hordei*, B. g. f. sp. *tritici*, etc.), *Erysiphe* spp. (for example, *Erysiphe betae, E. cichoracearum, E. c.* var. *cichoracearum, E. heraclei, E. pisi*, etc.), *Golovinomyces* spp. (for example, *Golovinomyces cichoracearum* var. *latisporus*, etc.), *Leveillula* spp. (for example, *Leveillula taurica*, etc.), *Microsphaera* spp., *Oidium* spp. (for example, *Oidium neolycopersici*, etc.), *Phyllactinia* spp. (for example, *Phyllactinia kakicola, P. mali, P. moricola*, etc.), *Podosphaera* spp. (for example, *Podosphaera fusca, P. leucotricha, P. pannosa, P. tridactyla* var. *tridactyla, P. xanthii*, etc.), *Sphaerotheca* spp. (for example, *Sphaerotheca aphanis* var. *aphanis, S. fuliginea*, etc.), *Uncinula* spp. for example, *Uncinula necator*, U. n. var. *necator*, etc.), *Uncinuliella* spp. (for example, *Uncinuliella simulans* var. *simulans*, U. s. var. *tandae*, etc.), *Blumeriella* spp. (for example, *Blumeriella jaapii*, etc.), *Cylindrosporium* spp., *Diplocarpon* spp. (for example, *Diplocarpon mali, D. mespili, D. rosae*, etc.), *Gloeosporium* spp. (for example, *Gloeosporium minus*, etc.), *Marssonina* spp., *Tapesia* spp. (for example, *Tapesia acuformis, T. yallundae*, etc.), *Lachnum* spp., *Scleromitrula* spp., *Botryotinia* spp. (for example, *Botryotinia fuckeliana*, etc.), *Botrytis* spp. (for example, *Botrytis allii, B. byssoidea, B. cinerea, B. elliptica, B. fabae, B. squamosa*, etc.), *Ciborinia* spp., *Grovesinia* spp., *Monilia mumecola, Monilinia* spp. (for example, *Monilinia fructicola, M. fructigena, M. laxa, M. mali, M. vaccinii-corymbosi*, etc.), *Sclerotinia* spp. (for example, *Sclerotinia borealis, S. homoeocarpa, S. minor, S. sclerotiorum*, etc.), *Valdensia* spp. (for example, *Valdensia heterodoxa*, etc.), *Claviceps* spp. (for example, *Claviceps sorghi, C. sorghicola*, etc.), *Epichloe* spp., *Ephelis japonica, Villosiclava virens, Hypomyces* spp. (for example, *Hypomyces solani* f. sp. *mori*, H. s. f. sp. *pisi*, etc.), *Trichoderma* spp. (for example *Trichoderma viride*, etc.), *Calonectria* spp. (for example, *Calonectria ilicicola*, etc.), *Candelospora* spp., *Cylindro-*

*carpon* spp., *Cylindrocladium* spp., *Fusarium* spp. (for example, *Fusarium arthrosporioides*, *F. crookwellense*, *F. culmorum*, *F. cuneirostrum*, *F. oxysporum*, F. o. f. sp. *adzukicola*, F. o. f. sp. *allii*, F. o. f. sp. *asparagi*, F. o. f. sp. *batatas*, F. o. f. sp. *cepae*, F. o. f. sp. *colocasiae*, F. o. f. sp. *conglutinans*, F. o. f. sp. *cubense*, F. o. f. sp. *cucumerinum*, F. o. f. sp. *fabae*, F. o. f. sp. *fragariae*, F. o. f. sp. *lactucae*, F. o. f. sp. *lagenariae*, F. o. f. sp. *lycopersici*, F. o. f. sp. *melongenae*, F. o. f. sp. *melonis*, F. o. f. sp. *nelumbinicola*, F. o. f. sp. *niveum*, F. o. f. sp. *radicis-lycopersici*, F. o. f. sp. *raphani*, F. o. f. sp. *spinaciae*, *F. sporotrichioides*, *F. solani*, F. s. f. sp. *cucurbitae*, F. s. f. sp. *eumartii*, F. s. f. sp. *glycines*, F. s. f. sp. *pisi*, F. s. f. sp. *Radicicola*, *F. virguliforme*, etc.), *Gibberella* spp. (for example, *Gibberella avenacea*, *G. baccata*, *G. fujikuroi*, *G. zeae*, etc.), *Haematonectria* spp., *Nectria* spp., *Ophionectria* spp., *Caldariomyces* spp., *Myrothecium* spp., *Trichothecium* spp., *Verticillium* spp. (for example, *Verticillium albo-atrum*, *V. dahliae*, *V. longisporum*, etc.), *Ceratocystis* spp. (for example, *Ceratocystis ficicola*, *C. fimbriata*, etc.), *Thielaviopsis* spp. (for example, *Thielaviopsis basicola*, etc.), *Adisciso* spp., *Monochaetia* spp., *Pestalotia* spp. (for example, *Pestalotia eriobotrifolia*, etc.), *Pestalotiopsis* spp. (for example, *Pestalotiopsis funerea*, *P. longiseta*, *P. neglecta*, *P. theae*, etc.), *Physalospora* spp., *Nemania* spp., *Nodulisporium* spp., *Rosellinia* spp. (for example, *Rosellinia necatrix*, etc.), *Monographella* spp. (for example, *Monographella nivalis*, etc.), *Ophiostoma* spp., *Cryphonectria* spp. (for example, *Cryphonectria parasitica*, etc.), *Diaporthe* spp. (for example, *Diaporthe citri*, *D. kyushuensis*, *D. nomurai*, *D. tanakae*, etc.), *Diaporthopsis* spp., *Phomopsis* spp. (for example, *Phomopsis asparagi*, *P. fukushii*, *P. obscurans*, *P. vexans*, etc.), *Cryptosporella* spp., *Discula* spp. (for example, *Discula theae-sinensis*, etc.), *Gnomonia* spp., *Coniella* spp., *Coryneum* spp., *Greeneria* spp., *Melanconis* spp., *Cytospora* spp., *Leucostoma* spp., *Valsa* spp. (for example, *Valsa ceratosperma*, etc.), *Tubakia* spp., *Monosporascus* spp., *Clasterosporium* spp., *Gaeumannomyces* spp. (for example, *Gaeumannomyces graminis*, etc.), *Magnaporthe* spp. (for example, *Magnaporthe grisea*, etc.), *Pyricularia* spp. (for example, *Pyricularia zingiberis*, etc.), *Monilochaetes infuscans*, *Colletotrichum* spp. (for example, *Colletotrichum acutatum*, *C. capsici*, *C. cereale*, *C. destructivum*, *C. fragariae*, *C. lindemuthianum*, *C. nigrum*, *C. orbiculare*, *C. spinaciae*, etc.), *Glomerella* spp. (for example, *Glomerella cingulata*, etc.), *Khuskia oryzae*, *Phyllachora* spp. (for example, *Phyllachora pomigena*, etc.), *Ellisembia* spp., *Briosia* spp., *Cephalosporium* spp. (for example, *Cephalosporium gramineum*, etc.), *Epicoccum* spp., *Gloeocercospora sorghi*, *Mycocentrospora* spp., *Peltaster* spp. (for example, *Peltaster fructicola*, etc.), *Phaeocytostroma* spp., *Phialophora* spp. (for example, *Phialophora gregata*, etc.), *Pseudophloeosporella dioscoreae*, *Pseudoseptoria* spp., *Rhynchosporium* spp. (for example, *Rhynchosporium secalis*, etc.), *Sarocladium* spp., *Coleophoma* spp., *Helicoceras oryzae*, etc.

Basidiomycota fungi, such as *Septobasidium* spp. (for example, *Septobasidium bogoriense*, *S. tanakae*, etc.), *Helicobasidium* spp. (for example, *Helicobasidium longisporum*, etc.), *Coleosporium* spp. (for example, *Coleosporium plectranthi*, etc.), *Cronartium* spp., *Phakopsora* spp. (for example, *Phakopsora artemisiae*, *P. nishidana*, *P. pachyrhizi*, etc.), *Physopella* spp. (for example, *Physopella ampelopsidis*, etc.), *Kuehneola* spp. (for example, *Kuehneola japonica*, etc.), *Phragmidium* spp. (for example, *Phragmidium fusiforme*, *P. mucronatum*, *P. rosae-multiflorae*, etc.), *Gymnosporangium* spp. (for example, *Gymnosporangium asiaticum*, *G. yamadae*, etc.), *Puccinia* spp. (for example, *Puccinia allii*, *P. brachypodii* var. *poae-nemoralis*, *P. coronata*, P. c. var. *coronata*, *P. cynodontis*, *P. graminis*, P. g. subsp. *graminicola*, *P. hordei*, *P. horiana*, *P. kuehnii*, *P. melanocephala*, *P. recondita*, *P. striiformis* var. *striiformis*, *P. tanaceti* var. *tanaceti*, *P. tokyensis*, *P. zoysiae*, etc.), *Uromyces* spp. (for example, *Uromyces phaseoli* var. *azukicola*, U. p. var. *phaseoli*, *Uromyces viciae-fabae* var. *viciae-fabae*, etc.), *Naohidemyces vaccinii*, *Nyssopsora* spp., *Leucotelium* spp., *Tranzschelia* spp. (for example, *Tranzschelia discolor*, etc.), *Aecidium* spp., *Blastospora* spp. (for example, *Blastospora smilacis*, etc.), *Uredo* spp., *Sphacelotheca* spp., *Urocystis* spp., *Sporisorium* spp. (for example, *Sporisorium scitamineum*, etc.), *Ustilago* spp. (for example, *Ustilago maydis*, *U. nuda*, etc.), *Entyloma* spp., *Exobasidium* spp. (for example, *Exobasidium reticulatum*, *E. vexans*, etc.), *Microstroma* spp., *Tilletia* spp. (for example, *Tilletia caries*, *T. controversa*, *T. laevis*, etc.), *Itersonilia* spp. (for example, *Itersonilia perplexans*, etc.), *Cryptococcus* spp., *Bovista* spp. (for example, *Bovista dermoxantha*, etc.), *Lycoperdon* spp. (for example, *Lycoperdon curtisii*, *L. perlatum*, etc.), *Conocybe* spp. (for example, *Conocybe apala*, etc.), *Marasmius* spp. (for example, *Marasmius oreades*, etc.), *Armillaria* spp., *Helotium* spp., *Lepista* spp. (for example, *Lepista subnuda*, etc.), *Sclerotium* spp. (for example, *Sclerotium cepivorum*, etc.), *Typhula* spp. (for example, *Typhula incarnata*, *T. ishikariensis* var. *ishikariensis*, etc.), *Athelia* spp. (for example, *Athelia rolfsii*, etc.), *Ceratobasidium* spp. (for example, *Ceratobasidium cornigerum*, etc.), *Ceratorhiza* spp., *Rhizoctonia* spp. (for example, *Rhizoctonia solani*, etc.), *Thanatephorus* spp. (for example, *Thanatephorus cucumeris*, etc.), *Laetisaria* spp., *Waitea* spp., *Fomitiporia* spp., *Ganoderma* spp., *Chondrostereum purpureum*, *Phanerochaete* spp., etc.

Chitridiomycota fungi, such as *Olpidium* spp., etc.

Blastocladiomycota fungi, such as *Physoderma* spp., etc.

Mucoromycotina fungi, such as *Choanephora* spp., *Choanephoroidea cucurbitae*, *Mucor* spp. (for example, *Mucor fragilis*, etc.), *Rhizopus* spp. (for example, *Rhizopus arrhizus*, *R. chinensis*, *R. oryzae*, *R. stolonifer* var. *stolonifer*, etc.), etc.

Cercozoa protists, such as *Plasmodiophora* spp. (for example, *Plasmodiophora brassicae*, etc.), *Spongospora subterranea* f. sp. *subterranea*, etc.

Heterokontophyta Oomycetes, such as *Aphanomyces* spp. (for example, *Aphanomyces cochlioides*, *A. raphani*, etc.), *Albugo* spp. (for example, *Albugo macrospora*, *A. wasabiae*, etc.), *Bremia* spp. (for example, *Bremia lactucae*, etc.), *Hyaloperonospora* spp., *Peronosclerospora* spp., *Peronospora* spp. (for example, *Peronospora alliariae-wasabi*, *P. chrysanthemi-coronarii*, *P. destructor*, *P. farinosa* f. sp. *spinaciae*, *P. manshurica*, *P. parasitica*, *P. sparsa*, etc.), *Plasmopara* spp. (for example, *Plasmopara halstedii*, *P. nivea*, *P. viticola*, etc.), *Pseudoperonospora* spp. (for example, *Pseudoperonospora cubensis*, etc.), *Sclerophthora* spp., *Phytophthora* spp. (for example, *Phytophthora cactorum*, *P. capsici*, *P. citricola*, *P. citrophthora*, *P. cryptogea*, *P. fragariae*, *P. infestans*, *P. melonis*, *P. nicotianae*, *P. palmivora*, *P. porri*, *P. sojae*, *P. syringae*, *P. vignae* f. sp. *adzukicola*, etc.), *Pythium* spp. (for example, *Pythium afertile*, *P. aphanidermatum*, *P. apleroticum*, *P. aristosporum*, *P. arrhenomanes*, *P. buismaniae*, *P. debaryanum*, *P. graminicola*, *P. horinouchiense*, *P. irregulare*, *P. iwayamai*, *P. myriotylum*, *P. okanoganense*, *P. paddicum*, *P. paroecandrum*, *P. periplocum*, *P. spinosum*, *P. sulcatum*, *P. sylvaticum*, *P. ultimum* var. *ultimum*, *P. vanterpoolii*, *P. vexans*, *P. volutum*, etc.), etc.

Actinobacteria gram-positive fungi, such as *Clavibacter* spp. (for example, *Clavibacter michiganensis* subsp. *michiganensis*, etc.), *Curtobacterium* spp., *Leifsonia* spp. (for example, *Leifsonia xyli* subsp. *xyli*, etc.), *Streptomyces* spp. (for example, *Streptomyces ipomoeae*, etc.), etc.

Firmicutes gram-positive fungi, such as *Clostridium* sp., etc.

Tenericutes gram-positive fungi, such as *Phytoplasma*, etc.

Proteobacteria gram-negative fungi, such as *Rhizobium* spp. (for example, *Rhizobium radiobacter*, etc.), *Acetobacter* spp., *Burkholderia* spp. (for example, *Burkholderia andropogonis, B. cepacia, B. gladioli, B. glumae, B. plantarii*, etc.), *Acidovorax* spp. (for example, *Acidovorax avenae* subsp. *avenae*, A. a. subsp. *citrulli, A. konjaci*, etc.), *Herbaspirillum* spp., *Ralstonia* spp. (for example, *Ralstonia solanacearum*, etc.), *Xanthomonas* spp. (for example, *Xanthomonas albilineans, X. arboricola* pv. *pruni, X. axonopodis* pv. *vitians, X. campestris* pv. *campestris*, X. c. pv. *cucurbitae*, X. c. pv. *glycines*, X. c. pv. *mangiferaeindicae*, X. c. pv. *nigromaculans*, X. c. pv. *vesicatoria, X. citri* subsp. *citri, X. oryzae* pv. *oryzae*, etc.), *Pseudomonas* spp. (for example, *Pseudomonas cichorii, P. fluorescens, P. marginalis*, P. m. pv. *marginalis, P. savastanoi* pv. *glycinea, P. syringae*, P. s. pv. *actinidiae*, P. s. pv. *eriobotryae*, P. s. pv. *helianthi*, P. s. pv. *lachrymans*, P. s. pv. *maculicola*, P. s. pv. *mori*, P. s. pv. *morsprunorum*, P. s. pv. *spinaciae*, P. s. pv. *syringae*, P. s. pv. *theae, P. viridiflava*, etc.), *Rhizobacter* spp., *Brenneria* spp. (for example, *Brenneria nigrifluens*, etc.), *Dickeya* spp. (for example, *Dickeya dianthicola, D. zeae*, etc.), *Erwinia* spp. (for example, *Erwinia amylovora, E. rhapontici*, etc.), *Pantoea* spp., *Pectobacterium* spp. (for example, *Pectobacterium atrosepticum, P. carotovorum, P. wasabiae*, etc.), etc.

As specific examples of plant diseases to be caused by infection and proliferation of these pathogens, the following plant diseases may, for example be mentioned, but the plant diseases are not limited thereto.

Leaf curl (*Taphrina deformans*), Plum pockets (*Taphrina pruni*), Leaf spot (*Cercospora asparagi*), Cercospora leaf spot (*Cercospora beticola*), Frogeye leaf spot (*Cercospora capsici*), Angular leaf spot (*Cercospora kaki*), Purple stain (*Cercospora kikuchii*), Brown Leaf spot (*Mycosphaerella arachidis*), Cylindrosporium leaf spot (*Mycosphaerella cerasella, Blumeriella jaapii*), Black sigatoka (*Mycosphaerella fijiensis*), Speckled leaf blotch (*Mycosphaerella graminicola*), Circular leaf spot (*Mycosphaerella nawae*), *Mycosphaerella* blight (*Mycosphaerella pinodes*), Leaf spot (*Mycosphaerella zingiberis*), Leaf mold (*Mycovellosiella fulva*), Leaf mold (*Mycovellosiella nattrassii*), Cercospora leaf mold (*Pseudocercospora fuligena*), Isariopsis leaf spot (*Pseudocercospora vitis*), Leaf spot (*Pseudocercosporella capsellae*), Leaf spot (*Septoria chrysanthemella*), Leaf blight (*Septoria obesa*), Anthracnose (*Elsinoe ampelina*), Spot anthracnose (*Elsinoe araliae*), Scab (*Elsinoe fawcettii*), Leaf spot (*Ascochyta pisi*), Corynespora leaf spot (*Corynespora cassiicola*), Stem canker (*Leptosphaeria coniothyrium*), Glume blotch (*Leptosphaeria nodorum*), Leaf spot (*Alternaria alternata*), *Alternaria* leaf spot (*Alternaria brassicae*), Leaf blight (*Alternaria dauci*), Black spot (*Alternaria kikuchiana*), *Alternaria* blotch (*Alternaria mali*), *Alternaria* leaf spot (*Alternaria porri*), Target spot (*Bipolaris sorghicola*), Southern leaf blight (*Cochliobolus heterostrophus*), Brown spot (*Cochliobolus miyabeanus*), Tip blight (*Pleospora herbarum*), Stripe (*Pyrenophora graminea*), Net blotch (*Pyrenophora teres*), Leaf blight (*Setosphaeria turcica*), Northern leaf blight (*Setosphaeria turcica*), Leaf spot (*Stemphylium botryosum*), Scab (*Venturia carpophila*), Scab (*Venturia Inaequalis*), Scab (*Venturia nashicola*), Gummy stem blight (*Didymella bryoniae*), Leaf spot (*Phoma exigua* var. *exigua*), Streak (*Phoma wasabiae*), Ring rot (*Botryosphaeria berengeriana* f. sp. *piricola*), Soft rot (*Botryosphaeria dothidea, Lasiodiplodia theobromae, Diaporthe* sp.), Common green mold (*Penicillium digitatum*), Blue mold (*Penicillium italicum*), Powdery mildew (*Blumeria graminis* f. sp. *hordei*), Powdery mildew (*Blumeria graminis* f. sp. *tritici*), Powdery mildew (*Erysiphe betae, Leveillula taurica, Oidium* sp., *Podosphaera xanthii*), Powdery mildew (*Erysiphe cichoracearum, Leveillula taurica, Sphaerotheca fuliginea*), Powdery mildew (*Erysiphe heraclei*), Powdery mildew (*Erysiphe pisi*), Powdery mildew (*Leveillula taurica, Oidium neolycopersici, Oidium* sp.), Powdery mildew (*Leveillula taurica*), Powdery mildew (*Oidium* sp., *Podosphaera xanthii*), Powdery mildew (*Oidium* sp.), Powdery mildew (*Phyllactinia kakicola*), Powdery mildew (*Podosphaera fusca*), Powdery mildew (*Podosphaera leucotricha*), Powdery mildew (*Podosphaera pannosa, Uncinuliella simulans* var. *simulans*, U. s. var. *tandae*), Powdery mildew (*Podosphaera xanthii*), Powdery mildew (*Sphaerotheca aphanis* var. *aphanis*), Powdery mildew (*Sphaerotheca fuliginea*), Powdery mildew (*Uncinula necator*, U. n. var. *necator*), Blotch (*Diplocarpon mali*), Black spot (*Diplocarpon rosae*), Gray mold neck rot (*Botrytis allii*), Gray mold, *Botrytis* blight (*Botrytis cinerea*), Leaf blight (*Botrytis cinerea, B. byssoidea, B. squamosa*), Chocolate spot (*Botrytis cinerea, B. elliptica, B. fabae*), Brown rot (*Monilinia fructicola, M. fructigena, M. laxa*), Blossom blight (*Monilinia mali*), Dollar spot (*Sclerotinia homoeocarpa*), Cottony rot, *Sclerotinia* rot, Stem rot (*Sclerotinia sclerotiorum*), False smut (*Villosiclava virens*), Root necrosis (*Calonectria ilicicola*), *Fusarium* blight (*Fusarium crookwellense, F. culmorum, Gibberella avenacea, G. zeae, Monographella nivalis*), *Fusarium* blight (*Fusarium culmorum, Gibberella avenacea, G. zeae*), Dry rot (*Fusarium oxysporum, F. solani* f. sp. *radicicola*), Brown rot (*Fusarium oxysporum, F. solani* f. sp. *pisi*, F. s. f. sp. *radicicola*), *Fusarium* wilt (*Fusarium oxysporum* f. sp. *adzukicola*), *Fusarium* basal rot (*Fusarium oxysporum* f. sp. *allii, F. solani* f. sp. *radicicola*), Stem rot (*Fusarium oxysporum* f. sp. *batatas, F. solani*), Dry rot (*Fusarium oxysporum* f. sp. *colocasiae*), Yellows (*Fusarium oxysporum* f. sp. *conglutinans*), Panama disease (*Fusarium oxysporum* f. sp. *cubense*), *Fusarium* wilt (*Fusarium oxysporum* f. sp. *fragariae*), Root rot (*Fusarium oxysporum* f. sp. *lactucae*), *Fusarium* wilt (*Fusarium oxysporum* f. sp. *lagenariae*, F. o. f. sp. *niveum*), *Fusarium* wilt (*Fusarium oxysporum* f. sp. *lycopersici*), *Fusarium* wilt (*Fusarium oxysporum* f. sp. *melonis*), Yellows (*Fusarium oxysporum* f. sp. *raphani*), *Fusarium* wilt (*Fusarium oxysporum* f. sp. *spinaciae*), Soybean Sudden Death Syndrome (*Fusarium solani* f. sp. *glycines, Fusarium virguliforme*), "Bakanae" disease (*Gibberella fujikuroi*), *Verticillium* black spot (*Verticillium albo-atrum, V. dahliae*), *Verticillium* wilt (*Verticillium dahliae*), *Ceratocystis* canker (*Ceratocystis ficicola*), Black rot (*Ceratocystis fimbriata*), Gray blight (*Pestalotiopsis longiseta, P. theae*), Endothia canker (*Cryphonectria parasitica*), Melanose (*Diaporthe citri*), Stem blight (*Phomopsis asparagi*), *Phomopsis* canker (*Phomopsis fukushii*), Brown spot (*Phomopsis vexans*), Anthracnose (*Discula theae-sinensis*), *Valsa* canker (*Valsa ceratosperma*), Blast (*Magnaporthe grisea*), Crown rot (*Colletotrichum acutatum, C. fragariae, Glomerella cingulata*), Bitter rot (*Colletotrichum acutatum, Glomerella cingulata*), Anthracnose (*Colletotrichum acutatum, Glomerella cingulata*), Anthracnose (*Colletotrichum acutatum*), Ripe rot (*Colletotrichum* acutatum, Glomerella cingulata), Anthracnose (Colletotrichum acutatum), Anthracnose (Colletotrichum lindemuthianum), Anthracnose (Colletotrichum orbiculare), Anthracnose (Glomerella cingulata), Anthracnose (Glomerella cingulata), Anthracnose (Glomerella cingulata), Brown stem rot (Phialophora gregata), Leaf spot (Pseudophloeosporella dioscoreae), Scald (Rhynchosporium secalis), Rust (Phakopsora nishidana), Rust (Phakopsora pachyrhizi), Rust (Kuehneola japonica, Phragmidium fusiforme, P. mucronatum, P. rosae-multiflorae), Rust (Gymnosporangium asiaticum), Rust (Gymnosporangium yamadae), Rust (Puccinia allii), Rust (Puccinia horiana), Brown rust (Puccinia recondita), Rust (Puccinia tanaceti var. tanaceti), Rust (Uromyces viciae-fabae var. viciae-fabae), Smut (Sporisorium scitamineum), Smut (Ustilago maydis), Loose smut (Ustilago nuda), Net blister blight (Exobasidium reticulatum), Blister blight (Exobasidium vexans), Stem rot, Southern blight (Athelia rolfsii), Root and stem rot (Ceratobasidium cornigerum, Rhizoctonia solani), ginger crest blight (Rhizoctonia solani), Damping-off (Rhizoctonia solani), Damping-off (Rhizoctonia solani), Bottom rot (Rhizoctonia solani), Brown patch, Large patch (Rhizoctonia solani), Sheath blight (Thanatephorus cucumeris), Root rot Leaf blight (Thanatephorus cucumeris), Rhizopus rot (Rhizopus stolonifer var. stolonifer), Clubroot (Plasmodiophora brassicae), Aphanomyces root rot (Aphanomyces cochlioides), White rust (Albugo macrospora), Downy mildew (Bremia lactucae), Downy mildew (Peronospora chrysanthemi-coronarii), Downy mildew (Peronospora destructor), Downy mildew (Peronospora farinosa f. sp. spinaciae), Downy mildew (Peronospora manshurica), Downy mildew (Peronospora parasitica), Downy mildew (Peronospora sparsa), Downy mildew (Plasmopara halstedii), Downy mildew (Plasmopara nivea), Downy mildew (Plasmopara viticola), Downy mildew (Pseudoperonospora cubensis), Phytophthora root rot (Phytophthora cactorum), Brown rot (Phytophthora capsici), Phytophthora rot (Phytophthora capsici), Phytophthora blight (Phytophthora capsici), Phytophthora rot (Phytophthora cryptogea), Late blight (Phytophthora infestans), White powdery rot (Phytophthora palmivora), Leaf blight (Phytophthora porri), Phytophthora root and stem rot (Phytophthora sojae), Phytophthora stem rot (Phytophthora vignae f. sp. adzukicola), Damping-off (Pythium aphanidermatum, P. myriotylum, P. paroecandrum, P. ultimum var. ultimum), Root rot (Pythium aristosporum), Browning root rot (Pythium arrhenomanes, P. graminicola), Damping-off (Pythium buismaniae, P. myriotylum), Root rot (Pythium myriotylum), Root rot (Pythium myriotylum, P. ultimum var. ultimum), Brown blotted root rot (Pythium sulcatum), Bacterial canker (Clavibacter michiganensis subsp. michiganensis), Scab (Streptomyces spp.), Crown gall (Rhizobium radiobacter), Bacterial stripe (Burkholderia andropogonis), Soft rot (Burkholderia cepacia, Pseudomonas marginalis pv. marginalis, Erwinia rhapontici), Bacterial grain rot (Burkholderia gladioli, B. glumae), Bacterial fruit blotch (Acidovorax avenae subsp. citrulli), Bacterial leaf blight (Acidovorax konjaci), Bacterial wilt (Ralstonia solanacearum), Bacterial shot hole (Xanthomonas arboricola pv. pruni, Pseudomonas syringae pv. syringae, Brenneria nigrifluens), Bacterial leaf spot (Xanthomonas arboricola pv. pruni), Bacterial spot (Xanthomonas axonopodis pv. vitians), Black rot (Xanthomonas campestris pv. campestris), Bacterial pustule (Xanthomonas campestris pv. glycines), Bacterial spot (Xanthomonas campestris pv. nigromaculans), Bacterial spot (Xanthomonas campestris pv. vesicatoria), Citrus canker (Xanthomonas citri subsp. citri), garlic spring rot (Pseudomonas cichorii, P. marginalis pv. marginalis, Erwinia sp.), Bacterial rot (Pseudomonas cichorii, P. marginalis pv. marginalis, P. viridiflava), Bacterial blossom blight (Pseudomonas marginalis pv. marginalis, P. syringae pv. syringae, P. viridiflava), Bacterial canker (Pseudomonas syringae pv. actinidiae), Canker (Pseudomonas syringae pv. eriobotryae), Bacterial spot (Pseudomonas syringae pv. lachrymans), Bacterial black spot (Pseudomonas syringae pv. maculicola), Bacterial canker (Pseudomonas syringae pv. morsprunorum, Erwinia sp.), Bacterial shoot blight (Pseudomonas syringae pv. theae), Bacterial soft rot (Dickeya sp., Pectobacterium carotovorum), Fire blight (Erwinia amylovora), Soft rot (Pectobacterium carotovorum), Bacterial soft rot (Pectobacterium carotovorum).

The "useful insects" in this specification means insects useful in that products which they produce, may be utilized for human life, or they may contribute to efficiency of agricultural operations as they may be used for pollination of fruits or vegetables. Specifically, for example, Japanese honeybee (Apis cerana japonica), Western honey bee (Apis mellifera), Bumblebee (Bombus consobrinus wittenburgi, B. diversus diversus, B. hypocrita, B. ignitus, B. terrestris), Hornfaced bee (Osmia cornifrons) and Silkworm (Bombyx mori), may be mentioned, but the useful insects are not limited to these.

The "natural enemies" in this specification means organisms which, by predation and parasitism, will kill or inhibit growth of a specific species of organism, especially a specific species of organism that harm crops. Specifically, the following organisms may, for example, be mentioned, but specific examples of natural enemies are not limited thereto.

Parasitic wasps belonging to Braconidae such as Dacnusa sasakawai, Dacnusa sibirica, Aphidius colemani, Apanteles glomeratus, etc., Aphelinidae such as Aphelinus albipodus, Aphelinus asychis, Aphelinus gossypii, Aphelinus maculatus, Aphelinus varipes, Encarsia formosa, Eretmocerus eremicus, Eretmocerus mundus, etc., and Eulophidae such as Chrysocharis pentheus, Neochrysocharis formosa, Diglyphus isaea, Hemiptarsenus varicornis), etc.; Aphidophagous gall midge (Aphidoletes aphidimyza); Seven-spot ladybird (Coccinella septempunctata); Asian lady beetle (Harmonia axyridis); Predatory beetle (Propylea japonica); Anthocorid predatory bugs belonging to Anthocoridae such as Orius minutus, Orius nagaii, Orius sauteri, Minute pirate bug (Orius strigicollis); Predatory mirid belonging to Miridae such as Pilophorus typicus, Nesidiocoris tenuis, etc.; Predatory thrips belonging to Aeolothripidae such as Franklinothrips vespiformis; Green lacewing belonging to Chrysopidae such as Dichochrysa formosanus, Chrysoperla nipponensis, etc.; Predatory mite belonging to Phytoseiidae such as Neoseiulus californicus, Amblyseius cucumeris, Amblyseius degenerans, Amblyseius swirskii, Phytoseiulus persimilis, etc.; Wolf spider (Pardosa pseudoannulata); Crab spider (Misumenops tricuspidatus).

The composition of the present invention can effectively control many plant diseases that occur in vascular plants (Tracheophyta) such as Pinales, magnoliids, monocots, eudicots, etc.

Pathogens may, for example, be Ascomycota fungi, Basidiomycota fungi, Chitridiomycota fungi, Blastocladiomycota fungi, Mucoromycotina fungi, Cercozoa protists, Heterokontophyta Oomycetes, Actinobacteria Gram-positive fungi, Tenericutes Gram-positive fungi and Proteobacteria Gram-negative fungi, etc.

The composition of the present invention exhibits excellent control effects at a low concentration, especially against plant pathogenic fungi belonging to Ascomycota and Basidiomycota, among such pathogens.

The composition of the present invention may be used in the form of a mixture obtained simply by mixing active ingredient A selected from oxime-substituted amide compounds of the formula (I) and active ingredient B selected from known fungicidal or bactericidal active compounds, but may usually be practically used as formulated into an optional formulation such as a soluble concentrate, an emulsifiable concentrate, a wettable powder, a water soluble powder, a water dispersible granule, a water soluble granule, a suspension concentrate, a concentrated emulsion, a suspoemulsion, a microemulsion, a dustable powder, a granule, a tablet or an emulsifiable gel, by mixing with a suitable solid carrier or liquid carrier, and further optionally by adding surfactants, penetrating agents, spreading agents, thickeners, antifreeze agents, binders, anti-caking agents, disintegrants, defoamers, preservatives, stabilizing agents, etc. From the viewpoint of laborsaving and safety improvement, the above optional formulation may be supplied as sealed in a water soluble capsule or a water-soluble package such as a bag made of a water-soluble film.

Solid carriers may, for example, be natural minerals, such as quartz, calcite, meerschaum, dolomite, chalk, kaolinite, pyrophyllite, sericite, halloysite, metahalloysite, kibushi clay, frog eyes clay, pottery stone, zeeklite, allophane, whitebait, Kira, talc, bentonite, activated clay, acid clay, pumice, attapulgite, zeolite, diatomaceous earth, etc.; baked products of natural minerals, such as calcined clay, perlite, Shirasu balloon, vermiculite, Ata Pal gas clay, calcined diatomaceous earth, etc.; inorganic salts, such as magnesium carbonate, calcium carbonate, sodium carbonate, sodium hydrogen carbonate, ammonium sulfate, sodium sulfate, magnesium sulfate, diammonium hydrogen phosphate, ammonium dihydrogen phosphate, potassium chloride, etc.; sugars such as glucose, fructose, sucrose, lactose, etc.; polysaccharides, such as starch, powdered cellulose, dextrin, etc.; organic materials, such as urea, urea derivatives, benzoic acid, a salt of benzoic acid, etc.; plants, such as wood flour, cork powder, corn cobs, walnut shell, tobacco stems, etc.; fly ash, white carbon (for example, hydrous synthetic silica, anhydrous synthetic silica, hydrous synthetic silicate, etc.), a fertilizer; etc.

The liquid carriers may, for example, be aromatic hydrocarbons, such as xylene, alkyl (e.g. $C_9$ or $C_{10}$) benzene, phenylxylylethane and alkyl (e.g. $C_1$ or $C_3$) naphthalene, etc.; aliphatic hydrocarbons, such as machine oil, normal paraffin, isoparaffin, naphthene, etc.; mixtures of aromatic hydrocarbons and aliphatic hydrocarbons, such as kerosene, etc.; alcohols, such as ethanol, isopropanol, cyclohexanol, phenoxyethanol, benzyl alcohol, etc.; polyhydric alcohols, such as ethylene glycol, propylene glycol, diethylene glycol, hexylene glycol, polyethylene glycol, polypropylene glycol, etc.; ethers, such as propyl cellosolve, butyl cellosolve, phenyl cellosolve, propylene glycol monomethyl ether, propylene glycol monoethyl ether, propylene glycol monopropyl ether, propylene glycol monobutyl ether, propylene glycol monophenyl ether, etc.; ketones, such as acetophenone, cyclohexanone, γ-butyrolactone, etc.;

esters, such as fatty acid methyl esters, succinic acid dialkyl esters, glutamic acid dialkyl esters, adipic acid dialkyl esters, phthalic acid dialkyl esters, etc.; acid amides, such as N-alkyl ($C_1$, $C_8$, $C_{12}$, etc.) pyrrolidone, etc.; oils, such as soybean oil, linseed oil, rapeseed oil, coconut oil, cottonseed oil, castor oil, etc.; dimethylsulfoxide, water; etc.

These solid and liquid carriers may be used alone or in combination of two or more of them.

The surfactants may, for example, be nonionic surfactants such as polyoxyethylene alkyl ethers, polyoxyethylene alkyl (mono- or di-)phenyl ethers, polyoxyethylene (mono-, di- or tri-)styrylphenyl ethers, polyoxyethylene polyoxypropylene block copolymers, polyoxyethylene fatty acid (mono- or di-)esters, sorbitan fatty acid esters, polyoxyethylene sorbitan fatty acid esters, castor oil ethylene oxide adducts, acetylene glycol, acetylene alcohol, ethylene oxide adducts of acetylene glycol, ethylene oxide adducts of acetylene alcohol, alkyl glycosides, etc.; anionic surfactants, such as alkyl sulfates, alkylbenzene sulfonates, lignin sulfonates, alkyl sulfosuccinates, naphthalene sulfonates, alkylnaphthalene sulfonates, salts of formalin condensate of naphthalenesulfonic acid, salts of formalin condensate of alkylnaphthalene sulfonic acid, polyoxyethylene alkyl ether sulfuric acid or phosphoric acid ester salts, polyoxyethylene (mono- or di-)alkylphenyl ether sulfate or phosphate ester salts, polyoxyethylene (mono-, di- or tri)styrylphenyl ether sulfuric or phosphoric ester salts, polycarboxylates (for example, polyacrylic acid salts, polymaleic acid salts, a copolymer of maleic acid and olefin, etc.), polystyrene sulfonate, etc.; cationic surfactants, such as alkyl amine salts, alkyl quaternary ammonium salts, etc.; amphoteric surfactants of amino acid type, betaine type, etc.; silicone surfactants, fluorine surfactants; etc.

The content of such surfactant(s) is not particularly limited, but is usually in the range of preferably from 0.05 to 20 parts by weight, more preferably from 0.1 to 15 parts by weight, relative to 100 parts by weight of the formulation of the composition of the present invention. These surfactants may be used alone or in combination of two or more of them.

The application amount of the composition of the present invention may vary depending upon the application scene, application time, application method, cultivated plants, etc., but usually, as the amount of active ingredient, is preferably from 0.005 to 50 kg, more preferably from 0.01 to 2 kg, per hectare (ha).

Now, examples of formulations in the case of using the composition of the present invention, will be presented. However, formulations of the present invention are not limited thereto.

In the following Formulation Examples, "parts" means parts by weight, and "active ingredient compound" is a general term for active ingredient A selected from oxime-substituted amide compounds of the formula (I), and for active ingredient B selected from known fungicidal or bactericidal active compounds.

[Wettable Powder]

| | |
|---|---|
| Active ingredient compound | 0.1 to 80 parts |
| Solid carrier | 5 to 98.9 parts |
| Surfactant | 1 to 10 parts |
| Others | 0 to 5 parts |

Others may, for example, be an anti-caking agent, a stabilizing agent, etc.

[Emulsion]

| | |
|---|---|
| Active ingredient compound | 0.1 to 30 parts |
| Organic solvent | 45 to 95 parts |
| Surfactant | 4.9 to 30 parts |

-continued

| Water | 0 to 50 parts |
|---|---|
| Others | 0 to 10 parts |

Others may, for example, be a spreading agent, a stabilizing agent, etc.

[Suspension]

| Active ingredient compound | 0.1 to 70 parts |
|---|---|
| Liquid carrier | 15 to 98.89 parts |
| Surfactant | 1 to 12 parts |
| Others | 0.01 to 30 parts |

Others may, for example, be an anti-freezing agent, a thickener, etc.

[Water Dispersible Granules]

| Active ingredient compound | 0.1 to 90 parts |
|---|---|
| Solid carrier | 0 to 98.9 parts |
| Surfactant | 1 to 20 parts |
| Others | 0 to 10 parts |

Others may, for example, be a binder, a stabilizing agent, etc.

[Solution]

| Active ingredient compound | 0.01 to 70 parts |
|---|---|
| Liquid carrier | 20 to 99.99 parts |
| Others | 0 to 10 parts |

Others may, for example, be an anti-freezing agent, a spreading agent, etc.

[Granules]

| Active ingredient compound | 0.01 to 80 parts |
|---|---|
| Solid carrier | 10 to 99.99 parts |
| Others | 0 to 10 parts |

Others may, for example, be a binding agent, a stabilizing agent, etc.

[Powder]

| Active ingredient compound | 0.01 to 30 parts |
|---|---|
| Solid carrier | 65 to 99.99 parts |
| Others | 0 to 5 parts |

Others may, for example, be a drift preventing agent, a stabilizing agent, etc.

Now, Formulation Examples wherein the composition of the present invention using active ingredients, is more specifically shown, will be presented, but the present invention is not limited thereto.

In the following Formulation Examples, "parts" means parts by weight.

[Formulation Example 1] Wettable Powder

| Compound No. 20 | 10 parts |
|---|---|
| Compound No. H35 | 10 parts |
| Pyrophyllite | 74 parts |
| Sorpol 5039 | 4 parts |
| (trade name, mixture of nonionic surfactant and anionic surfactant: manufactured by Toho Chemical Industry Co., Ltd.) | |
| CARPLEX #80D | 2 parts |
| (trade name, synthetic hydrous silicic acid: manufactured by Shionogi & Co., Ltd.) | |

The above components are uniformly mixed and pulverized to obtain a wettable powder.

[Formulation Example 2] Emulsifiable Concentrate

| Compound No. 11 | 3 parts |
|---|---|
| Compound No. C17 | 2 parts |
| Xylene | 75 parts |
| N-Mechiripiroridon | 15 parts |
| Sorpol 2680 | 15 parts |
| (trade name, mixture of nonionic surfactant and anionic surfactant: manufactured by Toho Chemical Industry Co., Ltd.) | |

The above components are uniformly mixed to obtain an emulsifiable concentrate.

[Formulation Example 3] Emulsifiable Concentrate

| Compound No. 24 | 2 parts |
|---|---|
| Compound No. C18 | 2 parts |
| DBE | 36 parts |
| (trade name, a mixture of dimethyl adipate, dimethyl glutarate and dimethyl succinate; manufactured by INVISTA Co., Ltd.) | |
| Isobutyl adipate | 30 parts |
| N-methylpyrrolidone | 10 parts |
| Soprophor BSU | 14 parts |
| (trade name, nonionic surfactant; manufactured by Rhodia (Rhodia) Co., Ltd.) | |
| Rhodacal 70BC | 6 parts |
| (trade name, anionic surfactant; manufactured by Rhodia Co., Ltd.) | |

The above components are uniformly mixed to obtain an emulsifiable concentrate.

[Formulation Example 4] Emulsifiable Concentrate

| Compound No. 27 | 2 parts |
|---|---|
| Compound No. H10 | 2 parts |
| DBE | 11 parts |
| (trade name, a mixture of dimethyl adipate, dimethyl glutarate and dimethyl succinate; manufactured by INVISTA Inc.) | |
| Isobutyl adipate | 30 parts |
| N-methylpyrrolidone | 5 parts |
| Soprophor BSU | 14 parts |
| (trade name, nonionic surfactant; manufactured by Rhodia Co., Ltd.) | |
| Rhodacal 70BC | 6 parts |
| (trade name, anionic surfactant; manufactured by Rhodia Co., Ltd.) | |
| Propylene glycol | 10 parts |
| Water | 20 parts |

The above components are uniformly mixed to obtain an emulsifiable concentrate.

[Formulation Example 5] Suspension Concentrate

| | |
|---|---|
| Compound No. 25 | 15 parts |
| Compound No. H31 | 10 parts |
| Agrisol S-710 | 10 parts |
| (trade name, nonionic surfactant; manufactured by Kao Corporation) | |
| Lennox 1000C | 0.5 parts |
| (trade name, anionic surfactant: manufactured by Toho Chemical Industry Co., Ltd.) | |
| Xanthan gum | 0.2 parts |
| Water | 64.3 parts |

The above components are uniformly mixed, followed by wet pulverization to obtain a suspension concentrate.

[Formulation Example 6] Water Dispersible Granule

| | |
|---|---|
| Compound No. 4 | 40 parts |
| Compound No. E04 | 35 parts |
| High tenor NE-15 | 5 parts |
| (trade name, anionic surfactant; manufactured by Dai-ichi Kogyo Seiyaku Co., Ltd.) | |
| VANILLEX N | 10 parts |
| (trade name, anionic surfactant; manufactured by Nippon Paper Industries Co., Ltd.) | |
| CARPLEX #80D | 10 parts |
| (trade name, synthetic hydrous silicic acid; manufactured by Shionogi & Co., Ltd.) | |

The above components are uniformly mixed and pulverized, then after addition of a small amount of water, stirred and mixed, and granulated by an extrusion granulator, followed by drying to obtain a water dispersible granule.

[Formulation Example 7] Granule

| | |
|---|---|
| Compound No. 8 | 3 parts |
| Compound No. F01 | 2 parts |
| Bentonite | 50 parts |
| Talc | 45 parts |

The above components are uniformly mixed and pulverized, then after adding a small amount of water, stirred and mixed, and granulated by an extrusion granulator, followed by drying to obtain granules.

[Formulation Example 8] Dustable Powder

| | |
|---|---|
| Compound No. 9 | 2 parts |
| Compound No. D02 | 1 part |
| CARPLEX #80D | 0.5 part |
| (trade name, synthetic hydrous silicic acid; manufactured by Shionogi & Co., Ltd.) | |
| Kaolinite | 95 parts |
| Diisopropyl phosphate | 1.5 parts |

The above components are uniformly mixed and pulverized to obtain a dustable powder.

In use, the above respective formulations will be diluted from 1 to 20,000 times with water, and will be applied so that the active ingredient would be from 0.005 to 50 kg per hectare (ha).

In the present invention, it is possible to formulate and use, as mentioned above, a composition comprising one or more compounds of active ingredient A and one or more compounds selected from B-I group to B-XII group of active ingredients B, but it is also possible that an agent containing active ingredient A and an agent containing active ingredient B, are separately prepared, and these agents are used for treatment or application at the same time or in close temporal proximity, whereby it is possible to obtain synergistic excellent controlling effects. Here, when they are to be applied in temporal proximity, it is desirable to perform the subsequent application after the agent initially applied is sufficiently dried, although such may depend also on the controlling means, the target disease to be controlled, etc.

Here, the ratio of using the separate agents which contain active ingredient A and active ingredient B, respectively, as active ingredients, is the same including the preferred embodiments, as the content ratio of active ingredient A and active ingredient B in the composition comprising both active ingredients A and active ingredient B.

Further, from the viewpoint of efficiency of the work, etc., it is preferred to use the composition comprising both active ingredient A and active ingredient B, as active ingredients.

EXAMPLES

Now, in order to specifically demonstrate the usefulness of the present invention, Test Examples will be given below, but the present invention is by no means limited by these Examples.

[Test Example 1] Preventive Test Against Gray Mold

Using the following compound listed in Table 2 (the active ingredient A) and the compound listed in Table 5 through Table 15 (active ingredient B), an agent was prepared in accordance with the above Formulation Example. This agent was diluted with water to a predetermined concentration to obtain a test solution. Then, cucumber (variety: Sagami-hanjiro) was planted in a plastic pot of 90 $cm^3$, and in the cotyledon stage, 5 ml of the obtained test solution, was sprayed by a spray gun and air-dried. Thereafter, the treated leaf was cut off and placed in a plastic container which filled approximately 0.5 cm in depth water. A suspension of conidia of cucumber gray mold fungus (*Botrytis cinerea*) and a dissolved PDA culture medium were mixed at a ratio of 1:1 (mass ratio), and the mixture was dropped to inoculate the treated leaf with 30 μl. After the inoculation, the plastic container was sealed and left at 20° C. for 3 days, the ratio of the formed lesion occupying the inoculated leaf was measured, and the preventive value was calculated in accordance with the following calculation formula. The results are shown in Table 17 through Table 26.

Preventive value=[1−(treated plot lesion area ratio/ untreated plot lesion area ratio)]×100

Further, from the preventive value at each agent concentration, synergy was calculated by using the Colby method (Colby S. R. 1976, Weeds 15, 20-22). The calculation method is as follows.

$E = X + Y - XY/100$

X: preventive value of A agent at x concentration
Y: preventive value of B agent at y concentration
E: theoretical value expected by treatment of the mixture of A agent and B agent.

The obtained result is analyzed to be synergy if the observed value is larger than the expected value, to be antagonism if the expected value is larger than the observed value, and to be an additive effect if the observed value and the expected value are the same.

TABLE 17

| Compound No. | Concentration (ppm) | Preventive value |
|---|---|---|
| 4 | 3 | 75 |
| 9 | 1 | 75 |
| 14 | 3 | 75 |
| 18 | 3 | 88 |
| 20 | 3 | 63 |
| 28 | 3 | 75 |
| 35 | 3 | 88 |
| 36 | 3 | 75 |

TABLE 18

| Compound No. | Concentration (ppm) | Preventive value |
|---|---|---|
| C18 | 3 | 30 |
| C28 | 10 | 45 |
| C40 | 100 | 0 |
| C03 | 3 | 60 |
| C17 | 50 | 20 |
| H35 | 20 | 45 |
| H10 | 10 | 60 |
| H49 | 25 | 30 |
| B01 | 3 | 50 |
| E04 | 3 | 60 |
| F01 | 35 | 50 |
| D02 | 8 | 55 |
| L25 | 50 | 50 |
| H13 | 50 | 63 |

TABLE 19

| Compound No. [concentration (ppm)] | Preventive value | Theoretical value |
|---|---|---|
| 4(3) + C18(3) | 94 | 83 |
| 4(3) + C28(10) | 100 | 86 |
| 4(3) + C40(100) | 75 | 75 |
| 4(3) + C03(3) | 94 | 90 |
| 4(3) + C17(50) | 88 | 80 |
| 4(3) + H35(20) | 100 | 86 |
| 4(3) + H10(10) | 88 | 90 |
| 4(3) + H49(25) | 94 | 83 |
| 4(3) + B01(3) | 94 | 88 |
| 4(3) + E04(3) | 88 | 90 |
| 4(3) + F01(35) | 94 | 88 |
| 4(3) + D02(8) | 94 | 89 |
| 4(3) + L25(50) | 94 | 88 |
| 4(3) + H13(50) | 100 | 91 |

TABLE 20

| Compound No. [concentration (ppm)] | Preventive value | Theoretical value |
|---|---|---|
| 18(3) + C18(3) | 94 | 91 |
| 18(3) + C28(10) | 100 | 93 |
| 18(3) + C40(100) | 88 | 88 |
| 18(3) + C03(3) | 100 | 95 |
| 18(3) + C17(50) | 94 | 90 |
| 18(3) + H35(20) | 94 | 93 |
| 18(3) + H10(10) | 94 | 95 |
| 18(3) + H49(25) | 100 | 92 |
| 18(3) + B01(3) | 94 | 94 |
| 18(3) + E04(3) | 94 | 95 |
| 18(3) + F01(35) | 94 | 94 |

TABLE 20-continued

| Compound No. [concentration (ppm)] | Preventive value | Theoretical value |
|---|---|---|
| 18(3) + D02(8) | 94 | 95 |
| 18(3) + L25(50) | 94 | 94 |
| 18(3) + H13(50) | 94 | 95 |

TABLE 21

| Compound No. [concentration (ppm)] | Preventive value | Theoretical value |
|---|---|---|
| 28(3) + C18(3) | 100 | 83 |
| 28(3) + C28(10) | 100 | 86 |
| 28(3) + C40(100) | 88 | 75 |
| 28(3) + C03(3) | 94 | 90 |
| 28(3) + C17(50) | 94 | 80 |
| 28(3) + H35(20) | 94 | 86 |
| 28(3) + H10(10) | 94 | 90 |
| 28(3) + H49(25) | 94 | 83 |
| 28(3) + B01(3) | 94 | 88 |
| 28(3) + E04(3) | 94 | 90 |
| 28(3) + F01(35) | 94 | 88 |
| 28(3) + D02(8) | 94 | 89 |
| 28(3) + L25(50) | 88 | 88 |
| 28(3) + H13(50) | 100 | 91 |

TABLE 22

| Compound No. [concentration (ppm)] | Preventive value | Theoretical value |
|---|---|---|
| 20(3) + C18(3) | 100 | 74 |
| 20(3) + C28(10) | 100 | 80 |
| 20(3) + C40(100) | 75 | 63 |
| 20(3) + C03(3) | 94 | 85 |
| 20(3) + C17(50) | 94 | 70 |
| 20(3) + H35(20) | 94 | 79 |
| 20(3) + H10(10) | 81 | 85 |
| 20(3) + H49(25) | 94 | 74 |
| 20(3) + B01(3) | 94 | 81 |
| 20(3) + E04(3) | 81 | 85 |
| 20(3) + F01(35) | 94 | 81 |
| 20(3) + D02(8) | 88 | 83 |
| 20(3) + L25(50) | 81 | 81 |
| 20(3) + H13(50) | 94 | 86 |

TABLE 23

| Compound No. [concentration (ppm)] | Preventive value | Theoretical value |
|---|---|---|
| 14(3) + C18(3) | 94 | 83 |
| 14(3) + C28(10) | 100 | 86 |
| 14(3) + C40(100) | 88 | 75 |
| 14(3) + C03(3) | 94 | 90 |
| 14(3) + C17(50) | 88 | 80 |
| 14(3) + H35(20) | 94 | 86 |
| 14(3) + H10(10) | 94 | 90 |
| 14(3) + H49(25) | 94 | 83 |
| 14(3) + B01(3) | 94 | 88 |
| 14(3) + E04(3) | 94 | 90 |
| 14(3) + F01(35) | 94 | 88 |
| 14(3) + D02(8) | 94 | 89 |
| 14(3) + L25(50) | 100 | 88 |
| 14(3) + H13(50) | 100 | 91 |

TABLE 24

| Compound No. [concentration (ppm)] | Preventive value | Theoretical value |
|---|---|---|
| 9(3) + C18(3) | 94 | 83 |
| 9(3) + C28(10) | 94 | 86 |
| 9(3) + C40(100) | 75 | 75 |
| 9(3) + C03(3) | 88 | 90 |
| 9(3) + C17(50) | 94 | 80 |
| 9(3) + H35(20) | 100 | 86 |
| 9(3) + H10(10) | 88 | 90 |
| 9(3) + H49(25) | 100 | 83 |
| 9(3) + B01(3) | 88 | 88 |
| 9(3) + E04(3) | 94 | 90 |
| 9(3) + F01(35) | 94 | 88 |
| 9(3) + D02(8) | 88 | 89 |
| 9(3) + L25(50) | 100 | 88 |
| 9(3) + H13(50) | 100 | 91 |

TABLE 25

| Compound No. [concentration (ppm)] | Preventive value | Theoretical value |
|---|---|---|
| 35(3) + C18(3) | 100 | 91 |
| 35(3) + C28(10) | 100 | 93 |
| 35(3) + C40(100) | 88 | 88 |
| 35(3) + C03(3) | 94 | 95 |
| 35(3) + C17(50) | 94 | 90 |
| 35(3) + H35(20) | 94 | 93 |
| 35(3) + H10(10) | 94 | 95 |
| 35(3) + H49(25) | 100 | 92 |
| 35(3) + B01(3) | 100 | 94 |
| 35(3) + E04(3) | 94 | 95 |
| 35(3) + F01(35) | 94 | 94 |
| 35(3) + D02(8) | 94 | 95 |
| 35(3) + L25(50) | 100 | 94 |
| 35(3) + H13(50) | 94 | 95 |

TABLE 26

| Compound No. [concentration (ppm)] | Preventive value | Theoretical value |
|---|---|---|
| 36(3) + C18(3) | 90 | 83 |
| 36(3)) + C28(10) | 90 | 86 |
| 36(3) + C40(100) | 86 | 75 |
| 36(3) + C03(3) | 92 | 90 |
| 36(3) + C17(50) | 85 | 80 |
| 36(3) + H35(20) | 94 | 86 |
| 36(3) + H10(10) | 96 | 90 |
| 36(3) + H49(25) | 92 | 83 |
| 36(3) + B01(3) | 90 | 88 |
| 36(3) + E04(3) | 94 | 90 |
| 36(3) + F01(35) | 94 | 88 |
| 36(3) + D02(8) | 94 | 89 |
| 36(3) + L25(50) | 90 | 88 |
| 36(3) + H 13(50) | 100 | 91 |

[Test Example 2] Preventive Test Against Gray Mold

Using the following compound listed in Table 2 (active ingredient A) and the following compound listed in Table 5 through Table 15 (active ingredient B) as active ingredients, a preventive test against gray mold was conducted in accordance with the method described in Test Example 1. The results are shown in Table 27 through Table 33.

TABLE 27

| Compound No. | Concentration (ppm) | Preventive value |
|---|---|---|
| 25 | 1 | 63 |
| 27 | 3 | 50 |
| 32 | 1 | 94 |
| 33 | 3 | 45 |
| 34 | 1 | 63 |

TABLE 28

| Compound No. | Concentration (ppm) | Preventive value |
|---|---|---|
| C18 | 3 | 28 |
| C28 | 10 | 56 |
| C40 | 100 | 0 |
| C03 | 3 | 58 |
| C17 | 50 | 25 |
| H35 | 20 | 50 |
| H10 | 10 | 50 |
| H49 | 25 | 25 |
| B01 | 3 | 45 |
| E04 | 3 | 58 |
| F01 | 35 | 48 |
| D02 | 8 | 56 |
| L25 | 50 | 55 |
| H13 | 50 | 60 |

TABLE 29

| Compound No. [concentration (ppm)] | Preventive value | Theoretical value |
|---|---|---|
| 25(1) + C18(3) | 88 | 73 |
| 25(1) + C28(10) | 94 | 84 |
| 25(1) + C40(100) | 75 | 63 |
| 25(1) + C03(3) | 94 | 84 |
| 25(1) + C17(50) | 75 | 72 |
| 25(1) + H35(20) | 63 | 82 |
| 25(1) + H10(10) | 81 | 82 |
| 25(1) + H49(25) | 94 | 72 |
| 25(1) + B01(3) | 88 | 80 |
| 25(1) + E04(3) | 85 | 84 |
| 25(1) + F01(35) | 82 | 81 |
| 25(1) + D02(8) | 85 | 84 |
| 25(1) + L25(50) | 90 | 83 |
| 25(1) + H13(50) | 94 | 85 |

TABLE 30

| Compound No. [concentration (ppm)] | Preventive value | Theoretical value |
|---|---|---|
| 27(3) + C18(3) | 75 | 65 |
| 27(3) + C28(10) | 80 | 73 |
| 27(3) + C40(100) | 55 | 50 |
| 27(3) + C03(3) | 84 | 80 |
| 27(3) + C17(50) | 65 | 60 |
| 27(3) + H35(20) | 80 | 73 |
| 27(3) + H10(10) | 85 | 80 |
| 27(3) + H49(25) | 94 | 65 |
| 27(3) + B01(3) | 100 | 75 |
| 27(3) + E04(3) | 85 | 80 |
| 27(3) + F01(35) | 75 | 75 |
| 27(3) + D02(8) | 80 | 78 |
| 27(3) + L25(50) | 80 | 75 |
| 27(3) + H13(50) | 94 | 81 |

TABLE 31

| Compound No. [concentration (ppm)] | Preventive value | Theoretical value |
|---|---|---|
| 32(1) + C18(3) | 96 | 96 |
| 32(1) + C28(10) | 98 | 97 |
| 32(1) + C40(100) | 96 | 94 |
| 32(1) + C03(3) | 98 | 97 |
| 32(1) + C17(50) | 97 | 96 |
| 32(1) + H35(20) | 100 | 97 |
| 32(1) + H10(10) | 100 | 97 |
| 32(1) + H49(25) | 100 | 96 |
| 32(1) + B01(3) | 100 | 97 |
| 32(1) + E04(3) | 100 | 97 |
| 32(1) + F01(35) | 100 | 97 |
| 32(1) + D02(8) | 100 | 97 |
| 32(1) + L25(50) | 100 | 97 |
| 32(1) + H13(50) | 100 | 98 |

TABLE 32

| Compound No. [concentration (ppm)] | Preventive value | Theoretical value |
|---|---|---|
| 33(3) + C18(3) | 65 | 60 |
| 33(3)) + C28(10) | 80 | 76 |
| 33(3) + C40(100) | 50 | 45 |
| 33(3) + C03(3) | 78 | 77 |
| 33(3) + C17(50) | 60 | 59 |
| 33(3) + H35(20) | 75 | 73 |
| 33(3) + H10(10) | 75 | 73 |
| 33(3) + H49(25) | 88 | 59 |
| 33(3) + B01(3) | 75 | 70 |
| 33(3) + E04(3) | 75 | 77 |
| 33(3) + F01(35) | 75 | 71 |
| 33(3) + D02(8) | 78 | 76 |
| 33(3) + L25(50) | 80 | 75 |
| 33(3) + H13(50) | 83 | 78 |

TABLE 33

| Compound No. [concentration (ppm)] | Preventive value | Theoretical value |
|---|---|---|
| 34(1) + C18(3) | 75 | 73 |
| 34(1) + C28(10) | 86 | 84 |
| 34(1) + C40(100) | 69 | 63 |
| 34(1) + C03(3) | 88 | 84 |
| 34(1) + C17(50) | 75 | 72 |
| 34(1) + H35(20) | 82 | 82 |
| 34(1) + H10(10) | 90 | 82 |
| 34(1) + H49(25) | 94 | 72 |
| 34(1) + B01(3) | 75 | 80 |
| 34(1) + E04(3) | 90 | 84 |
| 34(1) + F01(35) | 90 | 81 |
| 34(1) + D02(8) | 85 | 84 |
| 34(1) + L25(50) | 85 | 83 |
| 34(1) + H13(50) | 88 | 85 |

[Test Example 3] Preventive Test Against Gray Mold

Using the following compound listed in Table 2 (active ingredient A) and the following compound listed in Table 5 or Table 6 (active ingredient B) as active ingredients, a preventive test against gray mold was conducted in accordance with the method described in Test Example 1. The results are shown in Table 34 through Table 48.

TABLE 34

| Compound No. | Concentration (ppm) | Preventive value |
|---|---|---|
| 4 | 3 | 70 |
| 9 | 1 | 70 |
| 14 | 3 | 75 |
| 18 | 3 | 85 |
| 20 | 3 | 65 |
| 25 | 1 | 75 |
| 27 | 3 | 55 |
| 28 | 3 | 77 |
| 32 | 1 | 90 |
| 33 | 3 | 45 |
| 34 | 1 | 70 |
| 35 | 3 | 90 |
| 36 | 3 | 80 |

TABLE 35

| Compound No. | Concentration (ppm) | Preventive value |
|---|---|---|
| B05 | 10 | 60 |
| B06 | 50 | 45 |
| C01 | 5 | 60 |
| C02 | 50 | 70 |
| C06 | 5 | 63 |
| C07 | 100 | 50 |
| C08 | 1 | 65 |
| C09 | 100 | 55 |
| C10 | 5 | 45 |
| C12 | 10 | 60 |
| C14 | 100 | 65 |
| C15 | 5 | 60 |
| C16 | 10 | 50 |

TABLE 36

| Compound No. [concentration (ppm)] | Preventive value | Theoretical value |
|---|---|---|
| 4(3) + B05(10) | 90 | 88 |
| 4(3) + B06(50) | 84 | 84 |
| 4(3) + C01(5) | 88 | 88 |
| 4(3) + C02(50) | 95 | 91 |
| 4(3) + C06(5) | 90 | 89 |
| 4(3) + C07(100) | 90 | 85 |
| 4(3) + C08(1) | 95 | 90 |
| 4(3) + C09(100) | 90 | 87 |
| 4(3) + C10(5) | 90 | 84 |
| 4(3) + C12(10) | 90 | 88 |
| 4(3) + C14(100) | 92 | 90 |
| 4(3) + C15(5) | 94 | 88 |
| 4(3) + C16(10) | 90 | 85 |

TABLE 37

| Compound No. [concentration (ppm)] | Preventive value | Theoretical value |
|---|---|---|
| 9(1) + B05(10) | 92 | 88 |
| 9(1) + B06(50) | 84 | 84 |
| 9(1) + C01(5) | 90 | 88 |
| 9(1) + C02(50) | 95 | 91 |
| 9(1) + C06(5) | 92 | 89 |
| 9(1) + C07(100) | 92 | 85 |
| 9(1) + C08(1) | 93 | 90 |
| 9(1) + C09(100) | 88 | 87 |
| 9(1) + C10(5) | 92 | 84 |
| 9(1) + C12(10) | 95 | 88 |
| 9(1) + C14(100) | 94 | 90 |
| 9(1) + C15(5) | 90 | 88 |
| 9(1) + C16(10) | 92 | 85 |

TABLE 38

| Compound No. [concentration (ppm)] | Preventive value | Theoretical value |
| --- | --- | --- |
| 14(3) + B05(10) | 90 | 90 |
| 14(3) + B06(50) | 88 | 86 |
| 14(3) + C01(5) | 90 | 90 |
| 14(3) + C02(50) | 95 | 93 |
| 14(3) + C06(5) | 90 | 91 |
| 14(3) + C07(100) | 88 | 88 |
| 14(3) + C08(1) | 93 | 91 |
| 14(3) + C09(100) | 92 | 89 |
| 14(3) + C10(5) | 90 | 86 |
| 14(3) + C12(10) | 90 | 90 |
| 14(3) + C14(100) | 92 | 91 |
| 14(3) + C15(5) | 93 | 90 |
| 14(3) + C16(10) | 86 | 88 |

TABLE 39

| Compound No. [concentration (ppm)] | Preventive value | Theoretical value |
| --- | --- | --- |
| 18(3) + B05(10) | 95 | 94 |
| 18(3) + B06(50) | 94 | 92 |
| 18(3) + C01(5) | 95 | 94 |
| 18(3) + C02(50) | 95 | 96 |
| 18(3) + C06(5) | 95 | 94 |
| 18(3) + C07(100) | 90 | 93 |
| 18(3) + C08(1) | 95 | 95 |
| 18(3) + C09(100) | 95 | 93 |
| 18(3) + C10(5) | 95 | 92 |
| 18(3) + C12(10) | 95 | 94 |
| 18(3) + C14(100) | 95 | 95 |
| 18(3) + C15(5) | 95 | 94 |
| 18(3) + C16(10) | 90 | 93 |

TABLE 40

| Compound No. [concentration (ppm)] | Preventive value | Theoretical value |
| --- | --- | --- |
| 20(3) + B05(10) | 92 | 86 |
| 20(3) + B06(50) | 85 | 84 |
| 20(3) + C01(5) | 88 | 88 |
| 20(3) + C02(50) | 92 | 91 |
| 20(3) + C06(5) | 90 | 89 |
| 20(3) + C07(100) | 92 | 85 |
| 20(3) + C08(1) | 95 | 90 |
| 20(3) + C09(100) | 90 | 87 |
| 20(3) + C10(5) | 90 | 84 |
| 20(3) + C12(10) | 95 | 88 |
| 20(3) + C14(100) | 92 | 90 |
| 20(3) + C15(5) | 95 | 88 |
| 20(3) + C16(10) | 92 | 85 |

TABLE 41

| Compound No. [concentration (ppm)] | Preventive value | Theoretical value |
| --- | --- | --- |
| 25(1) + B05(10) | 92 | 90 |
| 25(1) + B06(50) | 90 | 86 |
| 25(1) + C01(5) | 92 | 90 |
| 25(1) + C02(50) | 95 | 93 |
| 25(1) + C06(5) | 95 | 91 |
| 25(1) + C07(100) | 92 | 88 |
| 25(1) + C08(1) | 95 | 91 |
| 25(1) + C09(100) | 95 | 89 |
| 25(1) + C10(5) | 90 | 86 |
| 25(1) + C12(10) | 95 | 90 |
| 25(1) + C14(100) | 96 | 91 |
| 25(1) + C15(5) | 95 | 90 |
| 25(1) + C16(10) | 95 | 88 |

TABLE 42

| Compound No. [concentration (ppm)] | Preventive value | Theoretical value |
| --- | --- | --- |
| 27(3) + B05(10) | 88 | 82 |
| 27(3) + B06(50) | 80 | 75 |
| 27(3) + C01(5) | 88 | 82 |
| 27(3) + C02(50) | 95 | 87 |
| 27(3) + C06(5) | 90 | 83 |
| 27(3) + C07(100) | 85 | 78 |
| 27(3) + C08(1) | 90 | 84 |
| 27(3) + C09(100) | 85 | 80 |
| 27(3) + C10(5) | 80 | 75 |
| 27(3) + C12(10) | 90 | 82 |
| 27(3) + C14(100) | 84 | 84 |
| 27(3) + C15(5) | 90 | 82 |
| 27(3) + C16(10) | 85 | 78 |

TABLE 43

| Compound No. [concentration (ppm)] | Preventive value | Theoretical value |
| --- | --- | --- |
| 28(3) + B05(10) | 92 | 91 |
| 28(3) + B06(50) | 90 | 87 |
| 28(3) + C01(5) | 95 | 91 |
| 28(3) + C02(50) | 95 | 93 |
| 28(3) + C06(5) | 93 | 91 |
| 28(3) + C07(100) | 95 | 89 |
| 28(3) + C08(1) | 95 | 92 |
| 28(3) + C09(100) | 90 | 90 |
| 28(3) + C10(5) | 90 | 87 |
| 28(3) + C12(10) | 91 | 91 |
| 28(3) + C14(100) | 95 | 92 |
| 28(3) + C15(5) | 95 | 91 |
| 28(3) + C16(10) | 90 | 89 |

TABLE 44

| Compound No. [concentration (ppm)] | Preventive value | Theoretical value |
| --- | --- | --- |
| 32(1) + B05(10) | 100 | 96 |
| 32(1) + B06(50) | 98 | 95 |
| 32(1) + C01(5) | 100 | 96 |
| 32(1) + C02(50) | 100 | 97 |
| 32(1) + C06(5) | 100 | 96 |
| 32(1) + C07(100) | 100 | 95 |
| 32(1) + C08(1) | 100 | 97 |
| 32(1) + C09(100) | 100 | 96 |
| 32(1) + C10(5) | 100 | 95 |
| 32(1) + C12(10) | 98 | 96 |
| 32(1) + C14(100) | 100 | 97 |
| 32(1) + C15(5) | 100 | 96 |
| 32(1) + C16(10) | 100 | 95 |

TABLE 45

| Compound No. [concentration (ppm)] | Preventive value | Theoretical value |
|---|---|---|
| 33(3) + B05(10) | 80 | 78 |
| 33(3) + B06(50) | 80 | 70 |
| 33(3) + C01(5) | 80 | 78 |
| 33(3) + C02(50) | 90 | 84 |
| 33(3) + C06(5) | 85 | 80 |
| 33(3) + C07(100) | 80 | 73 |
| 33(3) + C08(1) | 85 | 81 |
| 33(3) + C09(100) | 80 | 75 |
| 33(3) + C10(5) | 80 | 70 |
| 33(3) + C12(10) | 80 | 78 |
| 33(3) + C14(100) | 85 | 81 |
| 33(3) + C15(5) | 80 | 78 |
| 33(3) + C16(10) | 80 | 73 |

TABLE 46

| Compound No. [concentration (ppm)] | Preventive value | Theoretical value |
|---|---|---|
| 34(1) + B05(10) | 95 | 88 |
| 34(1) + B06(50) | 86 | 84 |
| 34(1) + C01(5) | 90 | 88 |
| 34(1) + C02(50) | 92 | 91 |
| 34(1) + C06(5) | 90 | 89 |
| 34(1) + C07(100) | 90 | 85 |
| 34(1) + C08(1) | 92 | 90 |
| 34(1) + C09(100) | 90 | 87 |
| 34(1) + C10(5) | 90 | 84 |
| 34(1) + C12(10) | 90 | 88 |
| 34(1) + C14(100) | 92 | 90 |
| 34(1) + C15(5) | 90 | 88 |
| 34(1) + C16(10) | 90 | 85 |

TABLE 47

| Compound No. [concentration (ppm)] | Preventive value | Theoretical value |
|---|---|---|
| 35(3) + B05(10) | 95 | 96 |
| 35(3) + B06(50) | 96 | 95 |
| 35(3) + C01(5) | 100 | 96 |
| 35(3) + C02(50) | 96 | 97 |
| 35(3) + C06(5) | 98 | 96 |
| 35(3) + C07(100) | 93 | 95 |
| 35(3) + C08(1) | 98 | 97 |
| 35(3) + C09(100) | 98 | 96 |
| 35(3) + C10(5) | 95 | 95 |
| 35(3) + C12(10) | 96 | 96 |
| 35(3) + C14(100) | 95 | 97 |
| 35(3) + C15(5) | 95 | 96 |
| 35(3) + C16(10) | 97 | 95 |

TABLE 48

| Compound No. [concentration (ppm)] | Preventive value | Theoretical value |
|---|---|---|
| 36(3) + B05(10) | 95 | 92 |
| 36(3) + B06(50) | 90 | 89 |
| 36(3) + C01(5) | 95 | 92 |
| 36(3) + C02(50) | 95 | 94 |
| 36(3) + C06(5) | 95 | 93 |
| 36(3) + C07(100) | 92 | 90 |
| 36(3) + C08(1) | 95 | 93 |
| 36(3) + C09(100) | 95 | 91 |
| 36(3) + C10(5) | 90 | 89 |
| 36(3) + C12(10) | 94 | 92 |
| 36(3) + C14(100) | 95 | 93 |
| 36(3) + C15(5) | 96 | 92 |
| 36(3) + C16(10) | 95 | 90 |

[Test Example 4] Preventive Test Against Gray Mold

Using the following compound listed in Table 2 (active ingredient A) and the following compound listed in Table 6 through Table 16 (active ingredient B) as active ingredients, a preventive test against gray mold was conducted in accordance with the method described in Test Example 1. The results are shown in Table 49 through Table 63.

TABLE 49

| Compound No. | Concentration (ppm) | Preventive value |
|---|---|---|
| 4 | 3 | 60 |
| 9 | 1 | 72 |
| 14 | 3 | 65 |
| 18 | 3 | 75 |
| 20 | 3 | 65 |
| 25 | 1 | 75 |
| 27 | 3 | 45 |
| 28 | 3 | 75 |
| 32 | 1 | 80 |
| 33 | 3 | 50 |
| 34 | 1 | 50 |
| 35 | 3 | 88 |
| 36 | 3 | 80 |

TABLE 50

| Compound No. | Concentration (ppm) | Preventive value |
|---|---|---|
| C23 | 100 | 35 |
| C29 | 10 | 45 |
| C31 | 50 | 40 |
| C32 | 10 | 30 |
| C33 | 10 | 50 |
| C36 | 10 | 60 |
| C39 | 10 | 40 |
| C43 | 50 | 45 |
| D01 | 50 | 50 |
| E02 | 100 | 5 |
| F02 | 10 | 55 |
| G06 | 100 | 35 |
| H05 | 10 | 45 |
| H07 | 10 | 50 |
| H12 | 10 | 55 |
| H15 | 10 | 55 |
| H16 | 10 | 50 |
| H17 | 10 | 45 |
| H23 | 10 | 60 |
| H24 | 10 | 60 |
| H28 | 10 | 45 |
| H29 | 10 | 50 |
| H31 | 10 | 50 |
| H36 | 10 | 55 |
| H44 | 100 | 35 |
| H45 | 100 | 10 |
| L16 | 100 | 45 |
| L24 | 100 | 45 |
| M01 | 100 | 15 |
| M09 | 100 | 5 |

TABLE 51

| Compound No. [concentration (ppm)] | Preventive value | Theoretical value |
|---|---|---|
| 4(3) + C23(100) | 75 | 74 |
| 4(3) + C29(10) | 80 | 78 |
| 4(3) + C31(50) | 80 | 76 |
| 4(3) + C32(10) | 75 | 72 |
| 4(3) + C33(10) | 85 | 80 |
| 4(3) + C36(10) | 85 | 84 |
| 4(3) + C39(10) | 80 | 76 |
| 4(3) + C43(50) | 80 | 78 |
| 4(3) + D01(50) | 80 | 80 |
| 4(3) + E02(100) | 65 | 62 |
| 4(3) + F02(10) | 85 | 82 |
| 4(3) + G06(100) | 75 | 74 |
| 4(3) + H05(100) | 80 | 78 |
| 4(3) + H07(10) | 80 | 80 |
| 4(3) + H12(10) | 80 | 82 |
| 4(3) + H15(10) | 85 | 82 |
| 4(3) + H16(10) | 80 | 80 |
| 4(3) + H17(10) | 80 | 78 |
| 4(3) + H23(10) | 85 | 84 |
| 4(3) + H24(10) | 85 | 84 |
| 4(3) + H28(10) | 80 | 78 |
| 4(3) + H29(10) | 85 | 80 |
| 4(3) + H31(10) | 90 | 80 |
| 4(3) + H36(10) | 85 | 82 |
| 4(3) + H44(100) | 80 | 74 |
| 4(3) + H45(100) | 70 | 64 |
| 4(3) + L16(100) | 80 | 78 |
| 4(3) + L24(100) | 85 | 78 |
| 4(3) + M01(100) | 70 | 66 |
| 4(3) + M09(100) | 70 | 62 |

TABLE 52

| Compound No. [concentration (ppm)] | Preventive value | Theoretical value |
|---|---|---|
| 9(1) + C23(100) | 85 | 82 |
| 9(1) + C29(10) | 90 | 85 |
| 9(1) + C31(50) | 85 | 83 |
| 9(1) + C32(10) | 85 | 80 |
| 9(1) + C33(10) | 85 | 86 |
| 9(1) + C36(10) | 90 | 89 |
| 9(1) + C39(10) | 85 | 83 |
| 9(1) + C43(50) | 85 | 85 |
| 9(1) + D01(50) | 90 | 86 |
| 9(1) + E02(100) | 75 | 73 |
| 9(1) + F02(10) | 90 | 87 |
| 9(1) + G06(100) | 85 | 82 |
| 9(1) + H05(100) | 90 | 85 |
| 9(1) + H07(10) | 90 | 86 |
| 9(1) + H12(10) | 85 | 87 |
| 9(1) + H15(10) | 90 | 87 |
| 9(1) + H16(10) | 90 | 86 |
| 9(1) + H17(10) | 85 | 85 |
| 9(1) + H23(10) | 90 | 89 |
| 9(1) + H24(10) | 90 | 89 |
| 9(1) + H28(10) | 90 | 85 |
| 9(1) + H29(10) | 90 | 86 |
| 9(1) + H31(10) | 90 | 86 |
| 9(1) + H36(10) | 90 | 87 |
| 9(1) + H44(100) | 85 | 82 |
| 9(1) + H45(100) | 80 | 75 |
| 9(1) + L16(100) | 85 | 85 |
| 9(1) + L24(100) | 85 | 85 |
| 9(1) + M01(100) | 80 | 76 |
| 9(1) + M09(100) | 85 | 73 |

TABLE 53

| Compound No. [concentration (ppm)] | Preventive value | Theoretical value |
|---|---|---|
| 14(3) + C23(100) | 85 | 77 |
| 14(3) + C29(10) | 90 | 81 |
| 14(3) + C31(50) | 95 | 79 |
| 14(3) + C32(10) | 90 | 76 |
| 14(3) + C33(10) | 90 | 83 |
| 14(3) + C36(10) | 95 | 86 |
| 14(3) + C39(10) | 90 | 79 |
| 14(3) + C43(50) | 90 | 81 |
| 14(3) + D01(50) | 90 | 83 |
| 14(3) + E02(100) | 80 | 67 |
| 14(3) + F02(10) | 95 | 84 |
| 14(3) + G06(100) | 90 | 77 |
| 14(3) + H05(100) | 90 | 81 |
| 14(3) + H07(10) | 95 | 83 |
| 14(3) + H12(10) | 95 | 84 |
| 14(3) + H15(10) | 95 | 84 |
| 14(3) + H16(10) | 95 | 83 |
| 14(3) + H17(10) | 95 | 81 |
| 14(3) + H23(10) | 95 | 86 |
| 14(3) + H24(10) | 95 | 86 |
| 14(3) + H28(10) | 90 | 81 |
| 14(3) + H29(10) | 95 | 83 |
| 14(3) + H31(10) | 90 | 83 |
| 14(3) + H36(10) | 95 | 84 |
| 14(3) + H44(100) | 90 | 77 |
| 14(3) + H45(100) | 85 | 69 |
| 14(3) + L16(100) | 90 | 81 |
| 14(3) + L24(100) | 90 | 81 |
| 14(3) + M01(100) | 85 | 70 |
| 14(3) + M09(100) | 85 | 67 |

TABLE 54

| Compound No. [concentration (ppm)] | Preventive value | Theoretical value |
|---|---|---|
| 18(3) + C23(100) | 85 | 84 |
| 18(3) + C29(10) | 90 | 86 |
| 18(3) + C31(50) | 87 | 85 |
| 18(3) + C32(10) | 85 | 83 |
| 18(3) + C33(10) | 90 | 88 |
| 18(3) + C36(10) | 83 | 90 |
| 18(3) + C39(10) | 88 | 85 |
| 18(3) + C43(50) | 90 | 86 |
| 18(3) + D01(50) | 92 | 88 |
| 18(3) + E02(100) | 80 | 76 |
| 18(3) + F02(10) | 90 | 89 |
| 18(3) + G06(100) | 85 | 84 |
| 18(3) + H05(100) | 85 | 86 |
| 18(3) + H07(10) | 90 | 88 |
| 18(3) + H12(10) | 95 | 89 |
| 18(3) + H15(10) | 90 | 89 |
| 18(3) + H16(10) | 95 | 88 |
| 18(3) + H17(10) | 90 | 86 |
| 18(3) + H23(10) | 95 | 90 |
| 18(3) + H24(10) | 92 | 90 |
| 18(3) + H28(10) | 90 | 86 |
| 18(3) + H29(10) | 90 | 88 |
| 18(3) + H31(10) | 92 | 88 |
| 18(3) + H36(10) | 95 | 89 |
| 18(3) + H44(100) | 90 | 84 |
| 18(3) + H45(100) | 80 | 78 |
| 18(3) + L16(100) | 90 | 86 |
| 18(3) + L24(100) | 90 | 86 |
| 18(3) + M01(100) | 80 | 79 |
| 18(3) + M09(100) | 80 | 76 |

TABLE 55

| Compound No. [concentration (ppm)] | Preventive value | Theoretical value |
| --- | --- | --- |
| 20(3) + C23(100) | 90 | 77 |
| 20(3) + C29(10) | 85 | 81 |
| 20(3) + C31(50) | 85 | 79 |
| 20(3) + C32(10) | 80 | 76 |
| 20(3) + C33(10) | 90 | 88 |
| 20(3) + C36(10) | 90 | 86 |
| 20(3) + C39(10) | 85 | 79 |
| 20(3) + C43(50) | 75 | 81 |
| 20(3) + D01(50) | 85 | 83 |
| 20(3) + E02(100) | 85 | 67 |
| 20(3) + F02(10) | 90 | 84 |
| 20(3) + G06(100) | 88 | 77 |
| 20(3) + H05(100) | 90 | 81 |
| 20(3) + H07(10) | 85 | 83 |
| 20(3) + H12(10) | 90 | 84 |
| 20(3) + H15(10) | 90 | 84 |
| 20(3) + H16(10) | 85 | 83 |
| 20(3) + H17(10) | 85 | 81 |
| 20(3) + H23(10) | 85 | 86 |
| 20(3) + H24(10) | 90 | 86 |
| 20(3) + H28(10) | 90 | 81 |
| 20(3) + H29(10) | 85 | 83 |
| 20(3) + H31(10) | 85 | 83 |
| 20(3) + H36(10) | 85 | 84 |
| 20(3) + H44(100) | 80 | 77 |
| 20(3) + H45(100) | 75 | 69 |
| 20(3) + L16(100) | 90 | 81 |
| 20(3) + L24(100) | 90 | 81 |
| 20(3) + M01(100) | 80 | 70 |
| 20(3) + M09(100) | 75 | 67 |

TABLE 56

| Compound No. [concentration (ppm)] | Preventive value | Theoretical value |
| --- | --- | --- |
| 25(1) + C23(100) | 85 | 84 |
| 25(1) + C29(10) | 90 | 86 |
| 25(1) + C31(50) | 90 | 85 |
| 25(1) + C32(10) | 85 | 83 |
| 25(1) + C33(10) | 90 | 88 |
| 25(1) + C36(10) | 90 | 90 |
| 25(1) + C39(10) | 90 | 85 |
| 25(1) + C43(50) | 90 | 86 |
| 25(1) + D01(50) | 90 | 88 |
| 25(1) + E02(100) | 80 | 76 |
| 25(1) + F02(10) | 90 | 89 |
| 25(1) + G06(100) | 85 | 84 |
| 25(1) + H05(100) | 90 | 86 |
| 25(1) + H07(10) | 90 | 88 |
| 25(1) + H12(10) | 90 | 89 |
| 25(1) + H15(10) | 90 | 89 |
| 25(1) + H16(10) | 90 | 88 |
| 25(1) + H17(10) | 90 | 86 |
| 25(1) + H23(10) | 95 | 90 |
| 25(1) + H24(10) | 94 | 90 |
| 25(1) + H28(10) | 86 | 86 |
| 25(1) + H29(10) | 90 | 88 |
| 25(1) + H31(10) | 92 | 88 |
| 25(1) + H36(10) | 90 | 89 |
| 25(1) + H44(100) | 85 | 84 |
| 25(1) + H45(100) | 80 | 78 |
| 25(1) + L16(100) | 88 | 86 |
| 25(1) + L24(100) | 86 | 86 |
| 25(1) + M01(100) | 80 | 79 |
| 25(1) + M09(100) | 80 | 76 |

TABLE 57

| Compound No. [concentration (ppm)] | Preventive value | Theoretical value |
| --- | --- | --- |
| 27(3) + C23(100) | 70 | 64 |
| 27(3) + C29(10) | 76 | 70 |
| 27(3) + C31(50) | 75 | 67 |
| 27(3) + C32(10) | 70 | 62 |
| 27(3) + C33(10) | 80 | 73 |
| 27(3) + C36(10) | 80 | 78 |
| 27(3) + C39(10) | 70 | 67 |
| 27(3) + C43(50) | 85 | 70 |
| 27(3) + D01(50) | 80 | 73 |
| 27(3) + E02(100) | 75 | 48 |
| 27(3) + F02(10) | 90 | 75 |
| 27(3) + G06(100) | 70 | 64 |
| 27(3) + H05(100) | 75 | 70 |
| 27(3) + H07(10) | 80 | 73 |
| 27(3) + H12(10) | 80 | 75 |
| 27(3) + H15(10) | 85 | 75 |
| 27(3) + H16(10) | 80 | 73 |
| 27(3) + H17(10) | 77 | 70 |
| 27(3) + H23(10) | 82 | 78 |
| 27(3) + H24(10) | 80 | 78 |
| 27(3) + H28(10) | 78 | 70 |
| 27(3) + H29(10) | 87 | 73 |
| 27(3) + H31(10) | 85 | 73 |
| 27(3) + H36(10) | 80 | 75 |
| 27(3) + H44(100) | 85 | 64 |
| 27(3) + H45(100) | 70 | 51 |
| 27(3) + L16(100) | 88 | 70 |
| 27(3) + L24(100) | 85 | 70 |
| 27(3) + M01(100) | 70 | 53 |
| 27(3) + M09(100) | 50 | 48 |

TABLE 58

| Compound No.] [concentration (ppm)] | Preventive value | Theoretical value |
| --- | --- | --- |
| 28(3) + C23(100) | 85 | 84 |
| 28(3) + C29(10) | 90 | 86 |
| 28(3) + C31(50) | 86 | 85 |
| 28(3) + C32(10) | 86 | 83 |
| 28(3) + C33(10) | 90 | 88 |
| 28(3) + C36(10) | 90 | 90 |
| 28(3) + C39(10) | 88 | 85 |
| 28(3) + C43(50) | 90 | 86 |
| 28(3) + D01(50) | 85 | 88 |
| 28(3) + E02(100) | 75 | 76 |
| 28(3) + F02(10) | 90 | 89 |
| 28(3) + G06(100) | 85 | 84 |
| 28(3) + H05(100) | 95 | 86 |
| 28(3) + H07(10) | 90 | 88 |
| 28(3) + H12(10) | 90 | 89 |
| 28(3) + H15(10) | 85 | 89 |
| 28(3) + H16(10) | 90 | 88 |
| 28(3) + H17(10) | 90 | 86 |
| 28(3) + H23(10) | 95 | 90 |
| 28(3) + H24(10) | 92 | 90 |
| 28(3) + H28(10) | 90 | 86 |
| 28(3) + H29(10) | 90 | 88 |
| 28(3) + H31(10) | 90 | 88 |
| 28(3) + H36(10) | 90 | 89 |
| 28(3) + H44(100) | 85 | 84 |
| 28(3) + H45(100) | 80 | 78 |
| 28(3) + L16(100) | 90 | 86 |
| 28(3) + L24(100) | 90 | 86 |
| 28(3) + M01(100) | 80 | 79 |
| 28(3) + M09(100) | 80 | 76 |

TABLE 59

| Compound No. [concentration (ppm)] | Preventive value | Theoretical value |
| --- | --- | --- |
| 32(1) + C23(100) | 85 | 87 |
| 32(1) + C29(10) | 90 | 89 |
| 32(1) + C31(50) | 90 | 88 |
| 32(1) + C32(10) | 85 | 86 |
| 32(1) + C33(10) | 92 | 90 |
| 32(1) + C36(10) | 90 | 92 |
| 32(1) + C39(10) | 90 | 88 |
| 32(1) + C43(50) | 90 | 89 |
| 32(1) + D01(50) | 90 | 90 |
| 32(1) + E02(100) | 85 | 81 |
| 32(1) + F02(10) | 90 | 91 |
| 32(1) + G06(100) | 90 | 87 |
| 32(1) + H05(100) | 92 | 89 |
| 32(1) + H07(10) | 94 | 90 |
| 32(1) + H12(10) | 95 | 91 |
| 32(1) + H15(10) | 95 | 91 |
| 32(1) + H16(10) | 92 | 90 |
| 32(1) + H17(10) | 90 | 89 |
| 32(1) + H23(10) | 95 | 92 |
| 32(1) + H24(10) | 94 | 92 |
| 32(1) + H28(10) | 92 | 89 |
| 32(1) + H29(10) | 90 | 90 |
| 32(1) + H31(10) | 92 | 90 |
| 32(1) + H36(10) | 90 | 91 |
| 32(1) + H44(100) | 88 | 87 |
| 32(1) + H45(100) | 85 | 82 |
| 32(1) + L16(100) | 92 | 89 |
| 32(1) + L24(100) | 92 | 89 |
| 32(1) + M01(100) | 85 | 83 |
| 32(1) + M09(100) | 84 | 81 |

TABLE 60

| Compound No. [concentration (ppm)] | Preventive value | Theoretical value |
| --- | --- | --- |
| 33(3) + C23(100) | 70 | 68 |
| 33(3) + C29(10) | 75 | 73 |
| 33(3) + C31(50) | 75 | 70 |
| 33(3) + C32(10) | 70 | 65 |
| 33(3) + C33(10) | 85 | 75 |
| 33(3) + C36(10) | 85 | 80 |
| 33(3) + C39(10) | 75 | 70 |
| 33(3) + C43(50) | 80 | 73 |
| 33(3) + D01(50) | 78 | 75 |
| 33(3) + E02(100) | 65 | 53 |
| 33(3) + F02(10) | 83 | 78 |
| 33(3) + G06(100) | 75 | 68 |
| 33(3) + H05(100) | 80 | 73 |
| 33(3) + H07(10) | 80 | 75 |
| 33(3) + H12(10) | 85 | 78 |
| 33(3) + H15(10) | 82 | 78 |
| 33(3) + H16(10) | 85 | 75 |
| 33(3) + H17(10) | 85 | 73 |
| 33(3) + H23(10) | 85 | 80 |
| 33(3) + H24(10) | 95 | 80 |
| 33(3) + H28(10) | 80 | 73 |
| 33(3) + H29(10) | 85 | 75 |
| 33(3) + H31(10) | 85 | 75 |
| 33(3) + H36(10) | 85 | 78 |
| 33(3) + H44(100) | 75 | 68 |
| 33(3) + H45(100) | 70 | 55 |
| 33(3) + L16(100) | 80 | 73 |
| 33(3) + L24(100) | 86 | 73 |
| 33(3) + M01(100) | 75 | 58 |
| 33(3) + M09(100) | 65 | 53 |

TABLE 61

| Compound No. [concentration (ppm)] | Preventive value | Theoretical value |
| --- | --- | --- |
| 34(1) + C23(100) | 72 | 68 |
| 34(1) + C29(10) | 80 | 73 |
| 34(1) + C31(50) | 75 | 70 |
| 34(1) + C32(10) | 70 | 65 |
| 34(1) + C33(10) | 80 | 75 |
| 34(1) + C36(10) | 85 | 80 |
| 34(1) + C39(10) | 92 | 70 |
| 34(1) + C43(50) | 80 | 73 |
| 34(1) + D01(50) | 80 | 75 |
| 34(1) + E02(100) | 60 | 53 |
| 34(1) + F02(10) | 80 | 78 |
| 34(1) + G06(100) | 75 | 68 |
| 34(1) + H05(100) | 80 | 73 |
| 34(1) + H07(10) | 77 | 75 |
| 34(1) + H12(10) | 80 | 78 |
| 34(1) + H15(10) | 82 | 78 |
| 34(1) + H16(10) | 77 | 75 |
| 34(1) + H17(10) | 80 | 73 |
| 34(1) + H23(10) | 82 | 80 |
| 34(1) + H24(10) | 85 | 80 |
| 34(1) + H28(10) | 70 | 73 |
| 34(1) + H29(10) | 85 | 75 |
| 34(1) + H31(10) | 80 | 75 |
| 34(1) + H36(10) | 80 | 78 |
| 34(1) + H44(100) | 72 | 68 |
| 34(1) + H45(100) | 72 | 55 |
| 34(1) + L16(100) | 80 | 73 |
| 34(1) + L24(100) | 80 | 73 |
| 34(1) + M01(100) | 66 | 58 |
| 34(1) + M09(100) | 65 | 53 |

TABLE 62

| Compound No. [concentration (ppm)] | Preventive value | Theoretical value |
| --- | --- | --- |
| 35(3) + C23(100) | 85 | 92 |
| 35(3) + C29(10) | 90 | 93 |
| 35(3) + C31(50) | 95 | 93 |
| 35(3) + C32(10) | 94 | 92 |
| 35(3) + C33(10) | 96 | 94 |
| 35(3) + C36(10) | 98 | 95 |
| 35(3) + C39(10) | 95 | 93 |
| 35(3) + C43(50) | 95 | 93 |
| 35(3) + D01(50) | 96 | 94 |
| 35(3) + E02(100) | 90 | 89 |
| 35(3) + F02(10) | 96 | 95 |
| 35(3) + G06(100) | 94 | 92 |
| 35(3) + H05(100) | 95 | 93 |
| 35(3) + H07(10) | 95 | 94 |
| 35(3) + H12(10) | 95 | 95 |
| 35(3) + H15(10) | 95 | 95 |
| 35(3) + H16(10) | 95 | 94 |
| 35(3) + H17(10) | 95 | 93 |
| 35(3) + H23(10) | 95 | 95 |
| 35(3) + H24(10) | 96 | 95 |
| 35(3) + H28(10) | 95 | 93 |
| 35(3) + H29(10) | 98 | 94 |
| 35(3) + H31(10) | 96 | 94 |
| 35(3) + H36(10) | 96 | 95 |
| 35(3) + H44(100) | 94 | 92 |
| 35(3) + H45(100) | 90 | 89 |
| 35(3) + L16(100) | 95 | 93 |
| 35(3) + L24(100) | 95 | 93 |
| 35(3) + M01(100) | 95 | 90 |
| 35(3) + M09(100) | 90 | 89 |

TABLE 63

| Compound No. [concentration (ppm)] | Preventive value | Theoretical value |
|---|---|---|
| 36(3) + C23(100) | 90 | 87 |
| 36(3) + C29(10) | 90 | 89 |
| 36(3) + C31(50) | 88 | 88 |
| 36(3) + C32(10) | 90 | 86 |
| 36(3) + C33(10) | 92 | 90 |
| 36(3) + C36(10) | 92 | 92 |
| 36(3) + C39(10) | 90 | 88 |
| 36(3) + C43(50) | 90 | 89 |
| 36(3) + D01(50) | 90 | 90 |
| 36(3) + E02(100) | 80 | 81 |
| 36(3) + F02(10) | 92 | 91 |
| 36(3) + G06(100) | 90 | 87 |
| 36(3) + H05(100) | 92 | 89 |
| 36(3) + H07(10) | 95 | 90 |
| 36(3) + H12(10) | 95 | 91 |
| 36(3) + H15(10) | 90 | 91 |
| 36(3) + H16(10) | 90 | 90 |
| 36(3) + H17(10) | 90 | 89 |
| 36(3) + H23(10) | 94 | 92 |
| 36(3) + H24(10) | 90 | 92 |
| 36(3) + H28(10) | 90 | 89 |
| 36(3) + H29(10) | 90 | 90 |
| 36(3) + H31(10) | 94 | 90 |
| 36(3) + H36(10) | 95 | 91 |
| 36(3) + H44(100) | 90 | 87 |
| 36(3) + H45(100) | 85 | 82 |
| 36(3) + L16(100) | 95 | 89 |
| 36(3) + L24(100) | 90 | 89 |
| 36(3) + M01(100) | 85 | 83 |
| 36(3) + M09(100) | 85 | 81 |

[Test Example 5] Efficacy Test on Rice Sheath Blight (Spray Treatment and Prevention Test)

An agent comprising the following compound listed in Table 2 (active ingredient A) and the compound listed in Table 6 (C17: active ingredient B) as active ingredients, was prepared in accordance with the above Formulation Example. The agent was diluted with water to a predetermined concentration to obtain a test solution. Then, in a plastic pot of 90 cm³, rice (Nipponbare) was seeded by 5 grains in one place, and to the grown seedlings in 4 seedling phase, the test solution was applied by a spray gun in an amount of 5 ml per pot, for treatment.

One day after the treatment, 1 g of mycelium flora of rice sheath blight fungus (*Rhizoctonia solani*) cultured in bran medium, was put by 5 g to a close-to-ground part of seedlings, and the pot was placed in a moist chamber set in temperature of 25° C. and humidity more than 95% RH for eight days. The height of the lesions which appeared in the highest position from the close-to-ground part (lesion height) was investigated, and the preventive value was calculated in accordance with the following formula.

Preventive value=[1−(treated plot lesion height/untreated plot lesion height)]×100

Further, from the preventive value for each agent concentration, synergy was calculated by using the Colby method (Colby S. R. 1976, Weeds 15, 20-22). The results are shown in Table 64 and Table 65.

TABLE 64

| Compound No. | Concentration (ppm) | Preventive value |
|---|---|---|
| 4 | 250 | 7 |
| 18 | 250 | 8 |
| 28 | 250 | 9 |
| 20 | 250 | 0 |
| 14 | 250 | 6 |
| 36 | 250 | 0 |
| C17 | 5 | 69 |

TABLE 65

| Compound No. [concentration (ppm)] | Preventive value | Theoretical value |
|---|---|---|
| 4(250) + C17(5) | 81 | 71 |
| 18(250) + C17(5) | 88 | 71 |
| 28(250) + C17(5) | 89 | 72 |
| 20(250) + C17(5) | 75 | 69 |
| 14(250) + C17(5) | 79 | 69 |
| 36(250) + C17(5) | 75 | 69 |

[Test Example 6] Efficacy Test on Rice Sheath Blight (Spray Treatment and Prevention Test)

Using the following compound listed in Table 2 (active ingredient A) and the compound listed in Table 6 (C17: active ingredient B) as active ingredients, a preventive test on rice sheath blight was conducted in accordance with the above Test Example 5. The results are shown in Table 66 and Table 67.

TABLE 66

| Compound No. | Concentration (ppm) | Preventive value |
|---|---|---|
| 9 | 250 | 10 |
| 25 | 250 | 8 |
| 27 | 250 | 8 |
| 32 | 250 | 6 |
| 33 | 250 | 4 |
| 34 | 250 | 5 |
| 35 | 250 | 5 |
| C17 | 5 | 75 |

TABLE 67

| Compound No. [concentration (ppm)] | Preventive value | Theoretical value |
|---|---|---|
| 9(250) + C17(5) | 80 | 78 |
| 25(250) + C17(5) | 80 | 77 |
| 27(250) + C17(5) | 82 | 77 |
| 32(250) + C17(5) | 79 | 77 |
| 33(250) + C17(5) | 80 | 76 |
| 34(250) + C17(5) | 78 | 76 |
| 35(250) + C17(5) | 80 | 76 |

[Test Example 7] Efficacy Test on Cucumber Downy Mildew (Spray Treatment and Prevention Test)

An agent comprising the following compound listed in Table 2 (active ingredient A) and the compound listed in Table 6 (C40: active ingredient B) as active ingredients, was prepared in accordance with the above Formulation Example. This agent was diluted with water to a predetermined concentration to obtain a test solution. Then, to seedlings of cucumber (variety: Sagami-hanjiro) at 1.5-leaf stage grown in a pot with a diameter of 7 cm, the test solution was applied by a spray gun in an amount of 10 ml per pot, for treatment. One day after the treatment, a spore suspension (2×100,000 cfu/ml) of cucumber downy mildew (*Pseudoperenospora cubensis*), was spray-inoculated, and the pot was placed in a moist chamber set in temperature of 20° C. and humidity more than 95% RH for 24 hours. After placing the pot in a glass greenhouse for 6 days, the ratio of the formed lesion area occupying the inoculated leaves was measured, and the preventive value was calculated in accordance with the following formula.

Preventive value=[1−(treated plot lesion area ratio/untreated plot lesion area ratio)]×100

Further, from the preventive value for each agent concentration, synergy was calculated by using the Colby method (Colby S. R. 1976, Weeds 15, 20-22). The results are shown in Table 68 and Table 69.

TABLE 68

| Compound No. | Concentration (ppm) | Preventive value |
| --- | --- | --- |
| 4 | 250 | 0 |
| 9 | 250 | 0 |
| 14 | 250 | 0 |
| 18 | 250 | 0 |
| 20 | 250 | 5 |
| 25 | 250 | 5 |
| 27 | 250 | 0 |
| 28 | 250 | 5 |
| 32 | 250 | 0 |
| 33 | 250 | 0 |
| 34 | 250 | 5 |
| 35 | 250 | 0 |
| 36 | 250 | 0 |
| C40 | 0.5 | 75 |

TABLE 69

| Compound No. [concentration (ppm)] | Preventive value | Theoretical value |
| --- | --- | --- |
| 4(250) + C40(0.5) | 80 | 75 |
| 9(250) + C40(0.5) | 80 | 75 |
| 14(250) + C40(0.5) | 80 | 75 |
| 18(250) + C40(0.5) | 80 | 75 |
| 20(250) + C40(0.5) | 80 | 76 |
| 25(250) + C40(0.5) | 85 | 76 |
| 27(250) + C40(0.5) | 75 | 75 |
| 28(250) + C40(0.5) | 75 | 76 |
| 32(250) + C40(0.5) | 80 | 75 |
| 33(250) + C40(0.5) | 80 | 75 |
| 34(250) + C40(0.5) | 70 | 76 |
| 35(250) + C40(0.5) | 82 | 75 |
| 36(250) + C40(0.5) | 85 | 75 |

[Test Example 8] Efficacy Test on Wheat Glume Blotch (Spray Treatment and Prevention Test)

An agent comprising the following compound listed in Table 2 (active ingredient A) and the following compound listed in Table 6, Table 11 or Table 15 (active ingredient B) as active ingredients, was prepared in accordance with the above Formulation Example. This agent was diluted with water to a predetermined concentration to obtain a test solution. Then, to seedlings of wheat (variety: Haruyutaka) at the 1-leaf stage, seeded in a pot with a diameter of 7 cm, with 5 seeds per pot, and grown for 7 days, the test solution was applied by a spray gun in an amount of 5 ml per pot, for treatment. One day after the treatment, a spore suspension (1×100,000 cfu/ml) of wheat glume blotch (*Leptosphaeria nodorum*) was spray-inoculated, and the pot was placed in a moist chamber set in temperature of 20° C. and humidity more than 95% RH for 48 hours. After placing the pot in a glass greenhouse for 7 days, the ratio of the formed lesion area occupying the inoculated leaves was measured, and the preventive value was calculated in accordance with the following formula.

Preventive value=[1−(treated plot lesion area ratio/untreated plot lesion area ratio)]×100

Further, from the preventive value for each agent concentration, synergy was calculated by using the Colby method (Colby S. R. 1976, Weeds 15, 20-22). The results are shown in Table 70 through Table 84.

TABLE 70

| Compound No. | Concentration (ppm) | Preventive value |
| --- | --- | --- |
| 4 | 10 | 65 |
| 4 | 3 | 40 |
| 9 | 10 | 75 |
| 9 | 3 | 60 |
| 14 | 10 | 80 |
| 14 | 3 | 75 |
| 18 | 10 | 65 |
| 18 | 3 | 50 |
| 20 | 10 | 85 |
| 20 | 3 | 80 |
| 25 | 10 | 85 |
| 25 | 3 | 75 |
| 27 | 10 | 85 |
| 27 | 3 | 75 |
| 28 | 10 | 85 |
| 28 | 3 | 60 |
| 32 | 10 | 85 |
| 32 | 3 | 60 |
| 33 | 10 | 45 |
| 33 | 3 | 20 |
| 34 | 10 | 85 |
| 34 | 3 | 80 |
| 35 | 10 | 70 |
| 35 | 3 | 50 |
| 36 | 10 | 70 |
| 36 | 3 | 55 |

TABLE 71

| Compound No. | Concentration (ppm) | Preventive value |
| --- | --- | --- |
| C18 | 1 | 65 |
| C28 | 5 | 45 |
| C29 | 10 | 50 |
| C32 | 1 | 50 |
| C33 | 1 | 65 |
| C36 | 25 | 45 |
| C39 | 50 | 70 |
| H35 | 5 | 45 |
| H10 | 1 | 50 |
| H13 | 25 | 50 |
| H23 | 5 | 45 |
| H24 | 100 | 70 |
| H29 | 50 | 45 |
| H31 | 50 | 30 |
| L25 | 50 | 50 |

TABLE 72

| Compound No. [concentration (ppm)] | Preventive value | Theoretical value |
| --- | --- | --- |
| 4(10) + C18(1) | 90 | 88 |
| 4(3) + C18(1) | 85 | 79 |
| 4(10) + C28(5) | 85 | 81 |

TABLE 72-continued

| Compound No. [concentration (ppm)] | Preventive value | Theoretical value |
|---|---|---|
| 4(3) + C28(5) | 70 | 67 |
| 4(10) + C29(10) | 80 | 83 |
| 4(3) + C29(10) | 75 | 70 |
| 4(10) + C32(1) | 85 | 83 |
| 4(3) + C32(1) | 70 | 70 |
| 4(10) + C33(1) | 90 | 88 |
| 4(3) + C33(1) | 80 | 79 |
| 4(10) + C36(25) | 85 | 81 |
| 4(3) + C36(25) | 70 | 67 |
| 4(10) + C39(50) | 90 | 90 |
| 4(3) + C39(50) | 80 | 82 |
| 4(10) + H35(5) | 80 | 81 |
| 4(3) + H35(5) | 70 | 67 |
| 4(10) + H10(1) | 85 | 83 |
| 4(3) + H10(1) | 75 | 70 |
| 4(10) + H13(25) | 85 | 83 |
| 4(3) + H13(25) | 70 | 70 |
| 4(10) + H23(5) | 80 | 81 |
| 4(3) + H23(5) | 70 | 67 |
| 4(10) + H24(100) | 90 | 90 |
| 4(3) + H24(100) | 85 | 82 |
| 4(10) + H29(50) | 80 | 81 |
| 4(3) + H29(50) | 70 | 67 |
| 4(10) + H31(50) | 80 | 76 |
| 4(3) + H31(50) | 60 | 58 |
| 4(10) + L25(50) | 85 | 83 |
| 4(3) + L25(50) | 75 | 70 |

TABLE 73

| Compound No. [concentration (ppm)] | Preventive value | Theoretical value |
|---|---|---|
| 9(10) + C18(1) | 93 | 91 |
| 9(3) + C18(1) | 90 | 86 |
| 9(10) + C28(5) | 90 | 86 |
| 9(3) + C28(5) | 80 | 78 |
| 9(10) + C29(10) | 85 | 88 |
| 9(3) + C29(10) | 80 | 80 |
| 9(10) + C32(1) | 90 | 88 |
| 9(3) + C32(1) | 75 | 80 |
| 9(10) + C33(1) | 95 | 91 |
| 9(3) + C33(1) | 95 | 86 |
| 9(10) + C36(25) | 90 | 86 |
| 9(3) + C36(25) | 80 | 78 |
| 9(10) + C39(50) | 95 | 93 |
| 9(3) + C39(50) | 90 | 88 |
| 9(10) + H35(5) | 90 | 86 |
| 9(3) + H35(5) | 80 | 78 |
| 9(10) + H10(1) | 90 | 88 |
| 9(3) + H10(1) | 85 | 80 |
| 9(10) + H13(25) | 90 | 88 |
| 9(3) + H13(25) | 85 | 80 |
| 9(10) + H23(5) | 90 | 86 |
| 9(3) + H23(5) | 80 | 78 |
| 9(10) + H24(100) | 95 | 93 |
| 9(3) + H24(100) | 90 | 88 |
| 9(10) + H29(50) | 90 | 86 |
| 9(3) + H29(50) | 70 | 78 |
| 9(10) + H31(50) | 80 | 83 |
| 9(3) + H31(50) | 75 | 72 |
| 9(10) + L25(50) | 85 | 88 |
| 9(3) + L25(50) | 75 | 80 |

TABLE 74

| Compound No. [concentration (ppm)] | Preventive value | Theoretical value |
|---|---|---|
| 14(10) + C18(1) | 95 | 93 |
| 14(3) + C18(1) | 90 | 91 |
| 14(10) + C28(5) | 90 | 89 |

TABLE 74-continued

| Compound No. [concentration (ppm)] | Preventive value | Theoretical value |
|---|---|---|
| 14(3) + C28(5) | 85 | 86 |
| 14(10) + C29(10) | 90 | 90 |
| 14(3) + C29(10) | 85 | 88 |
| 14(10) + C32(1) | 98 | 90 |
| 14(3) + C32(1) | 90 | 88 |
| 14(10) + C33(1) | 95 | 93 |
| 14(3) + C33(1) | 90 | 91 |
| 14(10) + C36(25) | 90 | 89 |
| 14(3) + C36(25) | 85 | 86 |
| 14(10) + C39(50) | 95 | 94 |
| 14(3) + C39(50) | 90 | 93 |
| 14(10) + H35(5) | 95 | 89 |
| 14(3) + H35(5) | 90 | 86 |
| 14(10) + H10(1) | 95 | 90 |
| 14(3) + H10(1) | 90 | 88 |
| 14(10) + H13(25) | 95 | 90 |
| 14(3) + H13(25) | 90 | 88 |
| 14(10) + H23(5) | 90 | 89 |
| 14(3) + H23(5) | 90 | 86 |
| 14(10) + H24(100) | 95 | 94 |
| 14(3) + H24(100) | 85 | 93 |
| 14(10) + H29(50) | 95 | 89 |
| 14(3) + H29(50) | 85 | 86 |
| 14(10) + H31(50) | 90 | 86 |
| 14(3) + H31(50) | 95 | 83 |
| 14(10) + L25(50) | 95 | 90 |
| 14(3) + L25(50) | 90 | 88 |

TABLE 75

| Compound No. [concentration (ppm)] | Preventive value | Theoretical value |
|---|---|---|
| 18(10) + C18(1) | 90 | 88 |
| 18(3) + C18(1) | 85 | 83 |
| 18(10) + C28(5) | 85 | 81 |
| 18(3) + C28(5) | 85 | 73 |
| 18(10) + C29(10) | 90 | 83 |
| 18(3) + C29(10) | 80 | 75 |
| 18(10) + C32(1) | 95 | 83 |
| 18(3) + C32(1) | 85 | 75 |
| 18(10) + C33(1) | 95 | 88 |
| 18(3) + C33(1) | 90 | 83 |
| 18(10) + C36(25) | 85 | 81 |
| 18(3) + C36(25) | 80 | 73 |
| 18(10) + C39(50) | 95 | 90 |
| 18(3) + C39(50) | 95 | 85 |
| 18(10) + H35(5) | 90 | 81 |
| 18(3) + H35(5) | 80 | 73 |
| 18(10) + H10(1) | 90 | 83 |
| 18(3) + H10(1) | 85 | 75 |
| 18(10) + H13(25) | 95 | 83 |
| 18(3) + H13(25) | 80 | 75 |
| 18(10) + H23(5) | 90 | 81 |
| 18(3) + H23(5) | 80 | 73 |
| 18(10) + H24(100) | 98 | 90 |
| 18(3) + H24(100) | 90 | 85 |
| 18(10) + H29(50) | 98 | 81 |
| 18(3) + H29(50) | 85 | 73 |
| 18(10) + H31(50) | 80 | 76 |
| 18(3) + H31(50) | 75 | 65 |
| 18(10) + L25(50) | 93 | 83 |
| 18(3) + L25(50) | 80 | 75 |

TABLE 76

| Compound No. [concentration (ppm)] | Preventive value | Theoretical value |
|---|---|---|
| 20(10) + C18(1) | 98 | 95 |
| 20(3) + C18(1) | 90 | 93 |
| 20(10) + C28(5) | 95 | 92 |

TABLE 76-continued

| Compound No. [concentration (ppm)] | Preventive value | Theoretical value |
|---|---|---|
| 20(3) + C28(5) | 90 | 89 |
| 20(10) + C29(10) | 95 | 93 |
| 20(3) + C29(10) | 90 | 90 |
| 20(10) + C32(1) | 95 | 93 |
| 20(3) + C32(1) | 93 | 90 |
| 20(10) + C33(1) | 95 | 95 |
| 20(3) + C33(1) | 95 | 93 |
| 20(10) + C36(25) | 95 | 92 |
| 20(3) + C36(25) | 90 | 89 |
| 20(10) + C39(50) | 98 | 96 |
| 20(3) + C39(50) | 98 | 94 |
| 20(10) + H35(5) | 95 | 92 |
| 20(3) + H35(5) | 90 | 89 |
| 20(10) + H10(1) | 95 | 93 |
| 20(3) + H10(1) | 90 | 90 |
| 20(10) + H13(25) | 95 | 93 |
| 20(3) + H13(25) | 85 | 90 |
| 20(10) + H23(5) | 90 | 92 |
| 20(3) + H23(5) | 90 | 89 |
| 20(10) + H24(100) | 98 | 96 |
| 20(3) + H24(100) | 95 | 94 |
| 20(10) + H29(50) | 95 | 92 |
| 20(3) + H29(50) | 85 | 89 |
| 20(10) + H31(50) | 90 | 90 |
| 20(3) + H31(50) | 85 | 86 |
| 20(10) + L25(50) | 95 | 93 |
| 20(3) + L25(50) | 93 | 90 |

TABLE 77

| Compound No. [concentration (ppm)] | Preventive value | Theoretical value |
|---|---|---|
| 25(10) + C18(1) | 98 | 95 |
| 25(3) + C18(1) | 85 | 91 |
| 25(10) + C28(5) | 93 | 92 |
| 25(3) + C28(5) | 90 | 86 |
| 25(10) + C29(10) | 95 | 93 |
| 25(3) + C29(10) | 90 | 88 |
| 25(10) + C32(1) | 95 | 93 |
| 25(3) + C32(1) | 95 | 88 |
| 25(10) + C33(1) | 95 | 95 |
| 25(3) + C33(1) | 93 | 91 |
| 25(10) + C36(25) | 98 | 92 |
| 25(3) + C36(25) | 90 | 86 |
| 25(10) + C39(50) | 98 | 96 |
| 25(3) + C39(50) | 98 | 93 |
| 25(10) + H35(5) | 95 | 92 |
| 25(3) + H35(5) | 90 | 86 |
| 25(10) + H10(1) | 95 | 93 |
| 25(3) + H10(1) | 88 | 88 |
| 25(10) + H13(25) | 98 | 93 |
| 25(3) + H13(25) | 90 | 88 |
| 25(10) + H23(5) | 93 | 92 |
| 25(3) + H23(5) | 85 | 86 |
| 25(10) + H24(100) | 98 | 96 |
| 25(3) + H24(100) | 98 | 93 |
| 25(10) + H29(50) | 98 | 92 |
| 25(3) + H29(50) | 90 | 86 |
| 25(10) + H31(50) | 98 | 90 |
| 25(3) + H31(50) | 90 | 83 |
| 25(10) + L25(50) | 95 | 93 |
| 25(3) + L25(50) | 93 | 88 |

TABLE 78

| Compound No. [concentration (ppm)] | Preventive value | Theoretical value |
|---|---|---|
| 27(10) + C18(1) | 98 | 95 |
| 27(3) + C18(1) | 85 | 91 |
| 27(10) + C28(5) | 93 | 92 |

TABLE 78-continued

| Compound No. [concentration (ppm)] | Preventive value | Theoretical value |
|---|---|---|
| 27(3) + C28(5) | 90 | 86 |
| 27(10) + C29(10) | 95 | 93 |
| 27(3) + C29(10) | 90 | 88 |
| 27(10) + C32(1) | 95 | 93 |
| 27(3) + C32(1) | 95 | 88 |
| 27(10) + C33(1) | 95 | 95 |
| 27(3) + C33(1) | 93 | 91 |
| 27(10) + C36(25) | 98 | 92 |
| 27(3) + C36(25) | 90 | 86 |
| 27(10) + C39(50) | 98 | 96 |
| 27(3) + C39(50) | 98 | 93 |
| 27(10) + H35(5) | 95 | 92 |
| 27(3) + H35(5) | 90 | 86 |
| 27(10) + H10(1) | 95 | 93 |
| 27(3) + H10(1) | 88 | 88 |
| 27(10) + H13(25) | 98 | 93 |
| 27(3) + H13(25) | 90 | 88 |
| 27(10) + H23(5) | 93 | 92 |
| 27(3) + H23(5) | 85 | 86 |
| 27(10) + H24(100) | 98 | 96 |
| 27(3) + H24(100) | 95 | 93 |
| 27(10) + H29(50) | 98 | 92 |
| 27(3) + H29(50) | 90 | 86 |
| 27(10) + H31(50) | 93 | 90 |
| 27(3) + H31(50) | 85 | 83 |
| 27(10) + L25(50) | 95 | 93 |
| 27(3) + L25(50) | 93 | 88 |

TABLE 79

| Compound No. [concentration (ppm)] | Preventive value | Theoretical value |
|---|---|---|
| 28(10) + C18(1) | 98 | 95 |
| 28(3) + C18(1) | 95 | 86 |
| 28(10) + C28(5) | 95 | 92 |
| 28(3) + C28(5) | 90 | 78 |
| 28(10) + C29(10) | 95 | 93 |
| 28(3) + C29(10) | 85 | 80 |
| 28(10) + C32(1) | 95 | 93 |
| 28(3) + C32(1) | 90 | 80 |
| 28(10) + C33(1) | 98 | 95 |
| 28(3) + C33(1) | 90 | 86 |
| 28(10) + C36(25) | 98 | 92 |
| 28(3) + C36(25) | 90 | 78 |
| 28(10) + C39(50) | 98 | 96 |
| 28(3) + C39(50) | 95 | 88 |
| 28(10) + H35(5) | 95 | 92 |
| 28(3) + H35(5) | 90 | 78 |
| 28(10) + H10(1) | 98 | 93 |
| 28(3) + H10(1) | 90 | 80 |
| 28(10) + H13(25) | 98 | 93 |
| 28(3) + H13(25) | 95 | 80 |
| 28(10) + H23(5) | 95 | 92 |
| 28(3) + H23(5) | 85 | 78 |
| 28(10) + H24(100) | 98 | 96 |
| 28(3) + H24(100) | 95 | 88 |
| 28(10) + H29(50) | 98 | 92 |
| 28(3) + H29(50) | 90 | 78 |
| 28(10) + H31(50) | 95 | 90 |
| 28(3) + H31(50) | 80 | 72 |
| 28(10) + L25(50) | 98 | 93 |
| 28(3) + L25(50) | 90 | 80 |

TABLE 80

| Compound No. [concentration (ppm)] | Preventive value | Theoretical value |
|---|---|---|
| 32(10) + C18(1) | 98 | 95 |
| 32(3) + C18(1) | 95 | 86 |
| 32(10) + C28(5) | 95 | 92 |

TABLE 80-continued

| Compound No. [concentration (ppm)] | Preventive value | Theoretical value |
|---|---|---|
| 32(3) + C28(5) | 90 | 78 |
| 32(10) + C29(10) | 95 | 93 |
| 32(3) + C29(10) | 85 | 80 |
| 32(10) + C32(1) | 95 | 93 |
| 32(3) + C32(1) | 90 | 80 |
| 32(10) + C33(1) | 98 | 95 |
| 32(3) + C33(1) | 90 | 86 |
| 32(10) + C36(25) | 98 | 92 |
| 32(3) + C36(25) | 90 | 78 |
| 32(10) + C39(50) | 98 | 96 |
| 32(3) + C39(50) | 95 | 88 |
| 32(10) + H35(5) | 95 | 92 |
| 32(3) + H35(5) | 90 | 78 |
| 32(10) + H10(1) | 98 | 93 |
| 32(3) + H10(1) | 90 | 80 |
| 32(10) + H13(25) | 98 | 93 |
| 32(3) + H13(25) | 95 | 80 |
| 32(10) + H23(5) | 95 | 92 |
| 32(3) + H23(5) | 85 | 78 |
| 32(10) + H24(100) | 98 | 96 |
| 32(3) + H24(100) | 95 | 88 |
| 32(10) + H29(50) | 98 | 92 |
| 32(3) + H29(50) | 90 | 78 |
| 32(10) + H31(50) | 95 | 90 |
| 32(3) + H31(50) | 80 | 72 |
| 32(10) + L25(50) | 98 | 93 |
| 32(3) + L25(50) | 90 | 80 |

TABLE 81

| Compound No. [concentration (ppm)] | Preventive value | Theoretical value |
|---|---|---|
| 33(10) + C18(1) | 85 | 81 |
| 33(3) + C18(1) | 75 | 72 |
| 33(10) + C28(5) | 75 | 70 |
| 33(3) + C28(5) | 60 | 56 |
| 33(10) + C29(10) | 75 | 73 |
| 33(3) + C29(10) | 65 | 60 |
| 33(10) + C32(1) | 75 | 73 |
| 33(3) + C32(1) | 70 | 60 |
| 33(10) + C33(1) | 80 | 81 |
| 33(3) + C33(1) | 75 | 72 |
| 33(10) + C36(25) | 75 | 70 |
| 33(3) + C36(25) | 60 | 56 |
| 33(10) + C39(50) | 90 | 84 |
| 33(3) + C39(50) | 80 | 76 |
| 33(10) + H35(5) | 70 | 70 |
| 33(3) + H35(5) | 50 | 56 |
| 33(10) + H10(1) | 75 | 73 |
| 33(3) + H10(1) | 60 | 60 |
| 33(10) + H13(25) | 80 | 73 |
| 33(3) + H13(25) | 65 | 60 |
| 33(10) + H23(5) | 75 | 70 |
| 33(3) + H23(5) | 60 | 56 |
| 33(10) + H24(100) | 80 | 84 |
| 33(3) + H24(100) | 80 | 76 |
| 33(10) + H29(50) | 75 | 70 |
| 33(3) + H29(50) | 60 | 56 |
| 33(10) + H31(50) | 65 | 62 |
| 33(3) + H31(50) | 50 | 44 |
| 33(10) + L25(50) | 75 | 73 |
| 33(3) + L25(50) | 55 | 60 |

TABLE 82

| Compound No. [concentration (ppm)] | Preventive value | Theoretical value |
|---|---|---|
| 34(10) + C18(1) | 98 | 95 |
| 34(3) + C18(1) | 98 | 93 |
| 34(10) + C28(5) | 95 | 92 |

TABLE 82-continued

| Compound No. [concentration (ppm)] | Preventive value | Theoretical value |
|---|---|---|
| 34(3) + C28(5) | 90 | 89 |
| 34(10) + C29(10) | 95 | 93 |
| 34(3) + C29(10) | 95 | 90 |
| 34(10) + C32(1) | 95 | 93 |
| 34(3) + C32(1) | 98 | 90 |
| 34(10) + C33(1) | 98 | 95 |
| 34(3) + C33(1) | 98 | 93 |
| 34(10) + C36(25) | 98 | 92 |
| 34(3) + C36(25) | 95 | 89 |
| 34(10) + C39(50) | 98 | 96 |
| 34(3) + C39(50) | 98 | 94 |
| 34(10) + H35(5) | 95 | 92 |
| 34(3) + H35(5) | 90 | 89 |
| 34(10) + H10(1) | 95 | 93 |
| 34(3) + H10(1) | 95 | 90 |
| 34(10) + H13(25) | 95 | 93 |
| 34(3) + H13(25) | 95 | 90 |
| 34(10) + H23(5) | 95 | 92 |
| 34(3) + H23(5) | 90 | 89 |
| 34(10) + H24(100) | 95 | 96 |
| 34(3) + H24(100) | 98 | 94 |
| 34(10) + H29(50) | 95 | 92 |
| 34(3) + H29(50) | 90 | 89 |
| 34(10) + H31(50) | 95 | 90 |
| 34(3) + H31(50) | 90 | 86 |
| 34(10) + L25(50) | 95 | 93 |
| 34(3) + L25(50) | 90 | 90 |

TABLE 83

| Compound No. [concentration (ppm)] | Preventive value | Theoretical value |
|---|---|---|
| 35(10) + C18(1) | 95 | 90 |
| 35(3) + C18(1) | 90 | 83 |
| 35(10) + C28(5) | 85 | 84 |
| 35(3) + C28(5) | 80 | 73 |
| 35(10) + C29(10) | 90 | 85 |
| 35(3) + C29(10) | 80 | 75 |
| 35(10) + C32(1) | 98 | 85 |
| 35(3) + C32(1) | 90 | 75 |
| 35(10) + C33(1) | 95 | 90 |
| 35(3) + C33(1) | 90 | 83 |
| 35(10) + C36(25) | 95 | 84 |
| 35(3) + C36(25) | 80 | 73 |
| 35(10) + C39(50) | 95 | 91 |
| 35(3) + C39(50) | 90 | 85 |
| 35(10) + H35(5) | 90 | 84 |
| 35(3) + H35(5) | 85 | 73 |
| 35(10) + H10(1) | 90 | 85 |
| 35(3) + H10(1) | 90 | 75 |
| 35(10) + H13(25) | 90 | 85 |
| 35(3) + H13(25) | 90 | 75 |
| 35(10) + H23(5) | 90 | 84 |
| 35(3) + H23(5) | 80 | 73 |
| 35(10) + H24(100) | 95 | 91 |
| 35(3) + H24(100) | 90 | 85 |
| 35(10) + H29(50) | 90 | 84 |
| 35(3) + H29(50) | 85 | 73 |
| 35(10) + H31(50) | 85 | 79 |
| 35(3) + H31(50) | 80 | 65 |
| 35(10) + L25(50) | 90 | 85 |
| 35(3) + L25(50) | 85 | 75 |

TABLE 84

| Compound No. [concentration (ppm)] | Preventive value | Theoretical value |
|---|---|---|
| 36(10) + C18(1) | 93 | 90 |
| 36(3) + C18(1) | 85 | 84 |
| 35(10) + C28(5) | 90 | 84 |

TABLE 84-continued

| Compound No. [concentration (ppm)] | Preventive value | Theoretical value |
|---|---|---|
| 35(3) + C28(5) | 88 | 75 |
| 35(10) + C29(10) | 93 | 85 |
| 35(3) + C29(10) | 85 | 78 |
| 35(10) + C32(1) | 98 | 85 |
| 35(3) + C32(1) | 80 | 78 |
| 35(10) + C33(1) | 90 | 90 |
| 35(3) + C33(1) | 88 | 84 |
| 35(10) + C36(25) | 90 | 84 |
| 35(3) + C36(25) | 80 | 75 |
| 35(10) + C39(50) | 98 | 91 |
| 35(3) + C39(50) | 95 | 87 |
| 35(10) + H35(5) | 90 | 84 |
| 35(3) + H35(5) | 85 | 75 |
| 35(10) + H10(1) | 93 | 85 |
| 35(3) + H10(1) | 90 | 78 |
| 35(10) + H13(25) | 90 | 85 |
| 35(3) + H13(25) | 85 | 78 |
| 35(10) + H23(5) | 90 | 84 |
| 35(3) + H23(5) | 85 | 75 |
| 35(10) + H24(100) | 95 | 91 |
| 35(3) + H24(100) | 90 | 87 |
| 35(10) + H29(50) | 90 | 84 |
| 35(3) + H29(50) | 80 | 75 |
| 35(10) + H31(50) | 85 | 79 |
| 35(3) + H31(50) | 80 | 69 |
| 35(10) + L25(50) | 93 | 85 |
| 35(3) + L25(50) | 80 | 78 |

[Test Example 9] Efficacy Test on Wheat Glume Blotch (Seed Treatment)

An agent comprising the following compound listed in Table 2 (active ingredient A) and the compound listed in Table 11 (H35: active ingredient B) as active ingredients, was prepared in accordance with the above Formulation Example. This agent was diluted with water to a predetermined concentration to obtain a test solution. A predetermined amount of the test solution was put in a glass bottle of 5 ml, and 0.5 g (approximately 15 grains) of wheat seeds (variety: Haruyutaka) were added, stirred and air-dried. In each pot with a diameter of 7 cm having soil put therein, 3 grains were seeded and grown for 14 days. To seedlings of the wheat (variety: Haruyutaka) grown to a 1-leaf stage, a spore suspension (100,000 cfu/ml) of wheat glume blotch (*Leptosphaeria nodorum*) was spray-inoculated, and the pot was placed in a moist chamber set in temperature of 20° C. and humidity more than 95% RH for 48 hours. After placing the pot for 7 days in a glass greenhouse, the ratio of the formed lesion area occupying the inoculated leaves was measured, and the preventive value was calculated in accordance with the following formula.

Preventive value=[1−(treated plot lesion area ratio/untreated plot lesion area ratio)]×100

Further, from the preventive value at each agent concentration, synergy was calculated by using the Colby method (Colby S. R. 1976, Weeds 15, 20-22).

The results are shown in Table 85 and Table 86.

TABLE 85

| Compound No. | Processing amount (mg/1 g seed) | Preventive value |
|---|---|---|
| 4 | 10 | 75 |
| 4 | 5 | 70 |
| 9 | 10 | 77 |
| 9 | 5 | 75 |

TABLE 85-continued

| Compound No. | Processing amount (mg/1 g seed) | Preventive value |
|---|---|---|
| 14 | 10 | 82 |
| 14 | 5 | 41 |
| 20 | 10 | 99 |
| 20 | 5 | 90 |
| 25 | 10 | 95 |
| 25 | 5 | 83 |
| 28 | 10 | 88 |
| 28 | 5 | 77 |
| H35 | 5 | 75 |
| H35 | 1 | 60 |

TABLE 86

| Compound No. [processing amount (mg/1 g seed)] | Preventive value | Theoretical value |
|---|---|---|
| 4(10) + H35(5) | 95 | 94 |
| 4(5) + H35(1) | 90 | 88 |
| 9(10) + H35(5) | 95 | 94 |
| 9(5) + H35(1) | 92 | 90 |
| 14(10) + H35(5) | 100 | 95 |
| 14(5) + H35(1) | 84 | 76 |
| 20(10) + H35(5) | 100 | 100 |
| 20(5) + H35(1) | 100 | 96 |
| 25(10) + H35(5) | 100 | 99 |
| 25(5) + H35(1) | 95 | 93 |
| 28(10) + H35(5) | 100 | 97 |
| 28(5) + H35(1) | 85 | 91 |

[Test Example 10] Efficacy Test on Wheat Powdery Mildew (Seed Treatment)

An agent comprising the following compound listed in Table 2 (active ingredient A) and the compound listed in Table 11 (H35: active ingredient B) as active ingredients, was prepared in accordance with the above Formulation Example. This agent was diluted with water to a predetermined concentration to obtain a test solution. A predetermined amount of test solution was put in a glass bottle of 5 ml, and 0.5 g (approximately 15 grains) of wheat seeds (variety: Norin 61) were added, stirred and air-dried. In each pot with a diameter of 7 cm and having soil put therein, 3 grains were seeded and grown for 14 days. To the wheat seedlings grown to the 1-leaf stage, a spore suspension (100,000 cfu/ml) of wheat powdery mildew (*Blumeria graminis*) was spray-inoculated. After placing the pot in a glass greenhouse for 10 days, the ratio of the formed lesion area occupying the inoculated leaves was measured, and the preventive value was calculated in accordance with the following formula.

Preventive value=[1−(treated plot lesion area ratio/untreated plot lesion area ratio)]×100

Further, from the preventive value at each agent concentration, synergy was calculated by using the Colby method (Colby S. R. 1976, Weeds 15, 20-22).

The results are shown in Table 87 and Table 88.

TABLE 87

| Compound No. | Processing amount (mg/1 g seed) | Preventive value |
|---|---|---|
| 4 | 10 | 99 |
| 4 | 5 | 97 |
| 9 | 10 | 100 |
| 9 | 5 | 100 |

TABLE 87-continued

| Compound No. | Processing amount (mg/1 g seed) | Preventive value |
|---|---|---|
| 14 | 10 | 100 |
| 14 | 5 | 97 |
| 18 | 10 | 98 |
| 18 | 5 | 62 |
| 20 | 10 | 100 |
| 20 | 5 | 100 |
| 25 | 10 | 100 |
| 25 | 5 | 100 |
| 27 | 10 | 90 |
| 27 | 5 | 85 |
| 28 | 10 | 100 |
| 28 | 5 | 100 |
| 33 | 10 | 61 |
| 33 | 5 | 20 |
| 34 | 10 | 85 |
| 34 | 5 | 20 |
| 35 | 10 | 61 |
| 35 | 5 | 20 |
| 36 | 10 | 100 |
| 36 | 5 | 99 |
| H35 | 0.1 | 95 |
| H35 | 0.025 | 80 |

TABLE 88

| Compound No. [processing amount (mg/1 g seed)] | Preventive value | Theoretical value |
|---|---|---|
| 4(10) + H35(0.5) | 100 | 100 |
| 4(5) + H35(0.1) | 100 | 99 |
| 9(10) + H35(0.5) | 100 | 100 |
| 9(5) + H35(0.1) | 100 | 100 |
| 14(10) + H35(0.5) | 100 | 100 |
| 14(5) + H35(0.1) | 100 | 99 |
| 18(10) + H35(0.5) | 100 | 100 |
| 18(5) + H35(0.1) | 100 | 92 |
| 20(10) + H35(0.5) | 100 | 100 |
| 20(5) + H35(0.1) | 100 | 100 |
| 25(10) + H35(0.5) | 100 | 100 |
| 25(5) + H35(0.1) | 100 | 100 |
| 27(10) + H35(0.5) | 100 | 100 |
| 27(5) + H35(0.1) | 100 | 97 |
| 28(10) + H35(0.5) | 100 | 100 |
| 28(5) + H35(0.1) | 100 | 100 |
| 32(10) + H35(0.5) | 100 | 98 |
| 32(5) + H35(0.1) | 95 | 84 |
| 33(10) + H35(0.5) | 100 | 99 |
| 33(5) + H35(0.1) | 95 | 84 |
| 34(10) + H35(0.5) | 100 | 98 |
| 34(5) + H35(0.1) | 90 | 84 |
| 35(10) + H35(0.5) | 100 | 100 |
| 35(5) + H35(0.1) | 100 | 100 |

[Test Example 11] Efficacy Test on Cucumber Powdery Mildew (Irrigation Treatment)

An agent comprising the following compound listed in Table 2 (active ingredient A) and the compound listed in Table 6 (C18: active ingredient B), was prepared in accordance with the above Formulation Example. This agent was diluted with water to a predetermined concentration to obtain a test solution. 5 ml of the test solution was irrigated by a pipette to the close-to-ground part of cucumber seedlings at the 1 leaf stage (variety: Sagami-hanjiro), grown in a styrol cup with a diameter of 10 cm, and next day, the seedlings were transplanted to the to 4 cun pots. Then, after cultivation for 7 days in a glass greenhouse, to the first true leaf of the cucumber, a spore suspension (100,000 cfu/ml) of cucumber powdery mildew (*Sphaerotheca cucurbitae*) was inoculated by spraying. After 10 days in a glass greenhouse, the ratio of the formed lesion area occupying the inoculated leaves was measured, and the preventive value was calculated in accordance with the following formula.

Preventive value=[1−(treated plot lesion area ratio/untreated plot lesion area ratio)]×100

Further, from the preventive value at each agent concentration, synergy was calculated by using the Colby method (Colby S. R. 1976, Weeds 15, 20-22). The results are shown in Table 89 and Table 90.

TABLE 89

| Compound No. | Concentration (ppm) | Preventive value |
|---|---|---|
| 4 | 500 | 60 |
| 9 | 500 | 95 |
| 14 | 500 | 22.5 |
| 18 | 500 | 35 |
| 20 | 500 | 100 |
| 25 | 500 | 100 |
| 27 | 500 | 60 |
| 28 | 500 | 75 |
| 32 | 500 | 30 |
| 33 | 500 | 15 |
| 34 | 500 | 60 |
| 35 | 500 | 30 |
| 36 | 500 | 35 |
| C18 | 6.3 | 50 |

TABLE 90

| Compound No. [concentration (ppm)] | Preventive value | Theoretical value |
|---|---|---|
| 4(500) + C18(6.3) | 90 | 80 |
| 9(500) + C18(6.3) | 100 | 98 |
| 14(500) + C18(6.3) | 85 | 61 |
| 18(500) + C18(6.3) | 90 | 68 |
| 20(500) + C18(6.3) | 100 | 100 |
| 25(500) + C18(6.3) | 100 | 100 |
| 27(500) + C18(6.3) | 95 | 80 |
| 28(500) + C18(6.3) | 100 | 88 |
| 32(500) + C18(6.3) | 85 | 65 |
| 33(500) + C18(6.3) | 85 | 58 |
| 34(500) + C18(6.3) | 95 | 80 |
| 35(500) + C18(6.3) | 80 | 65 |
| 36(500) + C18(6.3) | 80 | 68 |

INDUSTRIAL APPLICABILITY

The composition of the present invention and the method of the present invention exhibit synergistic excellent controlling effects against pathogens that cause various diseases and can be utilized in a wide range of fields in the agricultural/horticultural fields.

The entire disclosure of Japanese Patent Application No. 2014-022529 filed on Feb. 7, 2014 including specification, claims and summary is incorporated herein by reference in its entirety.

The invention claimed is:

1. A composition, comprising:
an active ingredient A and an active ingredient B,
wherein the active ingredient A comprises at least one oxime-substituted amide compound represented by the formula (I), or an N-oxide or a salt thereof, (I)
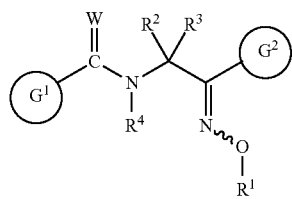
where G¹ represents a structure of G¹-1, G¹-2, G¹-3, G¹-7, G¹-8, G¹-9, G¹-11, G¹-12, G¹-13, G¹-16, G¹-27, G¹-32, G¹-33 or G¹-50,
G¹-1
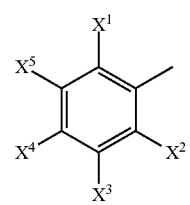
G¹-2
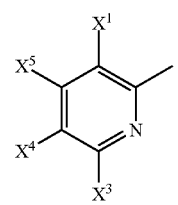
G¹-3
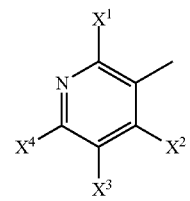
G¹-7
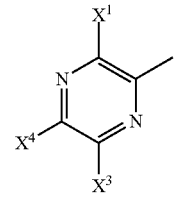
G¹-8
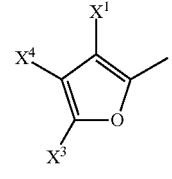
G¹-9
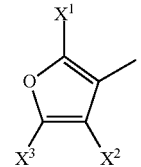
-continued
G¹-11
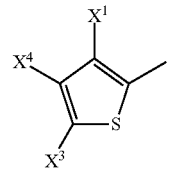
G¹-12
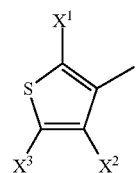
G¹-13
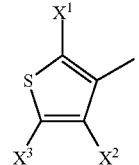
G¹-16
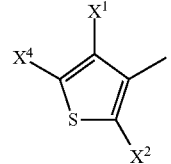
G¹-27
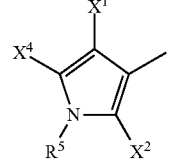
G¹-32
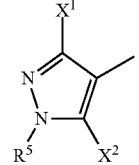
G¹-33
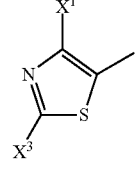

-continued

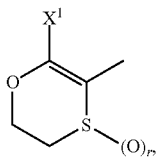
G¹-50

G² represents a structure of G²-1, G²-2, G²-6 or G²-9,

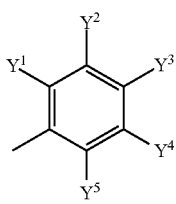
G²-1

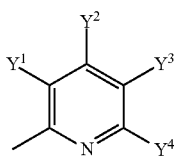
G²-2

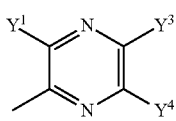
G²-6

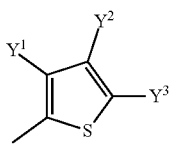
G²-9

W represents an oxygen atom or a sulfur atom,
$X^1$ represents a halogen atom, nitro, methyl, difluoromethyl or trifluoromethyl,
$X^2$ represents a hydrogen atom, or optionally, when $G^1$ represents a structure of $G^1$-27 and $X^1$ represents trifluoromethyl, $X^2$ represents a halogen atom,
$X^3$ represents a hydrogen atom or methyl,
$X^4$ represents a hydrogen atom or a halogen atom,
$X^5$ represents a hydrogen atom,
$Y^1$ represents a hydrogen atom, a halogen atom, methyl, trifluoromethyl or methoxy,
$Y^2$ represents a hydrogen atom, a halogen atom, cyano, methoxy, methylthio, methylsulfinyl or methylsulfonyl,
$Y^3$ represents a hydrogen atom, a halogen atom, cyano, $C_1$-$C_4$ alkyl, trifluoromethyl, $C_2$-$C_4$ alkenyl, $C_2$-$C_6$ alkynyl, ($C_2$-$C_6$) alkynyl optionally substituted by $R^6$, —$OR^7$, $C_1$-$C_4$ alkylthio, —$C(R^8)$=$NOR^9$, phenyl, D-3 or D-7,
$Y^4$ represents a hydrogen atom or a halogen atom,
$Y^5$ represents a hydrogen atom,
r is 0, 1 or 2,
$R^1$ represents $C_1$-$C_6$ alkyl, $C_1$-$C_4$ haloalkyl, ($C_1$-$C_4$) alkyl substituted by $R^{10}$, $C_3$-$C_6$ cycloalkyl, $C_3$-$C_6$ alkenyl, $C_3$-$C_4$ haloalkenyl, $C_3$-$C_6$ alkynyl or phenyl,
$R^2$ represents a hydrogen atom, methyl or ethyl, provided that $R^2$ represents methyl or ethyl when $G^1$ represents a structure of $G^1$-1, $X^1$ represents a chlorine atom, $X^2$, $X^3$ and $X^5$ each represents a hydrogen atom, $X^4$ represents a hydrogen atom or a chlorine atom, and $G^2$ represents a structure of $G^2$-1, $Y^3$ represents a chlorine atom, $Y^1$, $Y^2$, $Y^4$ and $Y^5$ each represents a hydrogen atom,
$R^3$ represents a hydrogen atom or methyl, or optionally $R^2$ and $R^3$ together form a cyclopropyl ring,
$R^4$ represents a hydrogen atom, $C_1$-$C_4$ haloalkylthio, $C_1$-$C_4$ alkylcarbonyl or $C_1$-$C_4$ alkoxycarbonyl,
$R^5$ represents methyl,
$R^6$ represents a halogen atom, $C_3$-$C_6$ cycloalkyl, hydroxy ($C_3$-$C_6$)cycloalkyl, $C_5$-$C_6$ cycloalkenyl, —OH, —$OR^7$, alkylcarbonyloxy, $C_1$-$C_4$ alkylsulfonyloxy, $C_1$-$C_4$ alkylthio, trimethylsilyl, —$C(R^8)$=$NOR^9$, phenyl, phenyl substituted by $(Z)_m$ or D-32,
Z represents a halogen atom, cyano, nitro, $C_1$-$C_4$ alkyl, trifluoromethyl, methoxy, trifluoromethoxy, trifluoromethylthio or phenyl, and when m or n represents 2 or more, each Z is identical with or different from one another, and when there are two neighboring Z's, the two neighboring Z's optionally form —CH=CH—CH=CH— to form a 6-membered ring together with the carbon atoms attached to the two Z's,
$R^7$ represents $C_1$-$C_4$ alkyl, $C_1$-$C_4$ haloalkyl, $C_1$-$C_4$ alkoxy ($C_1$-$C_2$)alkyl, E-14, $C_3$-$C_4$ alkynyl or phenyl substituted by $(Z)_m$,
$R^8$ represents a hydrogen atom or methyl,
$R^9$ represents methyl or ethyl,
$R^{10}$ represents cyano, $C_3$-$C_6$ cycloalkyl, E-5, E-9, $C_1$-$C_4$ alkoxy, $C_1$-$C_4$ alkylthio, trimethylsilyl, —$C(R^{11})$=$NOR^{12}$, phenyl, phenyl substituted by $(Z)_m$, D-10 or D-32,
D-3, D-7, D-10 and D-32, respectively, represent aromatic heterocyclic rings of formulae

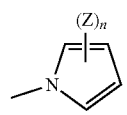
D-3

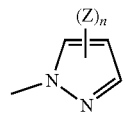
D-7

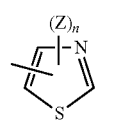
D-10

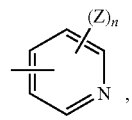
D-32

E-5, E-9 and E-14, respectively, represent saturated heterocyclic rings of formulae

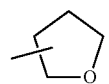
E-5

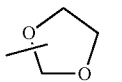

E-9

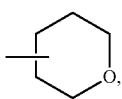

E-14

$R^{11}$ represents methyl,
$R^{12}$ represents methyl or ethyl,
m represents an integer of 1, 2 or 3, and
n represents an integer of 0, 1 or 2,
the active ingredient B comprises at least one compound selected from the group consisting of
benalaxyl, benalaxyl-M, furalaxyl, metalaxyl, metalaxyl-M, ofurace, oxadixyl, bupirimate, ethirimol, hymexazol, octhilinone, oxolinic acid,
benomyl, carbendazim, fuberidazole, thiabendazole, thiophanate-methyl, diethofencarb, ethaboxam, zoxamide, pencycuron, fluopicolide, diflumetorim, benodanil,
benzovindiflupyr, bixafen, boscalid, carboxin, fenfuram, fluopyram, flutolanil, fluxapyroxad, furametpyr, isofetamid, isopyrazam, mepronil, oxycarboxin, penflufen, penthiopyrad, sedaxane, thifluzamide, azoxystrobin, coumoxystrobin, dimoxystrobin, enestrobin, enoxastrobin, famoxadone, fenamidone, fenaminstrobin, flufenoxystrobin, fluoxastrobin, kresoxim-methyl, mandestrobin, metominostrobin, orysastrobin, picoxystrobin, pyraclostrobin, pyrametostrobin, pyraoxystrobin, pyribencarb-methyl, pyriminostrobin, triclopyricab, trifloxystrobin, amisulbrom, cyazofamid, dinocap, fluazinam, meptyldinocap, fentin, tributyltin oxide, silthiofam, ametoctradin,
cyprodinil, mepanipyrim, pyrimethanil, blasticidin-S, kasugamycin, streptomycin, oxytetracycline,
proquinazid, quinoxyfen, fenpiclonil, fludioxonil, chlozolinate,
iprodione, procymidone, vinclozolin,
edifenphos, iprobenfos, isoprothiolane, pyrazophos, biphenyl, chloroneb, dicloran, etridiazole, quintozene, tecnazene, tolclofos-methyl, propamocarb hydrochloride, Bacillus subtilis,
azaconazole, bitertanol, bromuconazole, climbazole, cyproconazole, diclobutrazol, difenoconazole, diniconazole, diniconazole-M, epoxiconazole, etaconazole, fenarimol, fenbuconazole, fluotrimazole, fluquinconazole, flusilazole, flutriafol, furconazole, hexaconazole, imazalil, imibenconazole, ipconazole, metconazole, myclobutanil, nuarimol, oxpoconazole fumarate, pefurazoate, penconazole, prochloraz, propiconazole, prothioconazole, pyrifenox, pyrisoxazole, simeconazole, tebuconazole, tetraconazole, triadimefon, triadimenol, triflumizole, triforine, triticonazole, aldimorph, dodemorph acetate, fenpropidin, fenpropimorph, piperalin, spiroxamine, tridemorph, fenhexamid, fenpyrazamine,
validamycin, polyoxins, polyoxorim, benthiavalicarb-isopropyl, dimethomorph, flumorph, iprovalicarb, mandipropamid, pyrimorph, valifenalate,
phthalide, pyroquilon, tricyclazole, carpropamid, diclocymet, fenoxanil,
acibenzolar-S-methyl, probenazole, isotianil, tiadinil,
laminarin, bordeaux mixture, cheshunt mixture, copper carbonate basic, copper hydroxide, copper naphthenate, copper oleate, copper oxychloride, copper sulfate, basic copper sulfate, oxine copper, calcium polysulfide, sulfur, amobam, ferbam, mancozeb, maneb, metiram, polycarbamate, propineb, thiram, ziram, captan, folpet, chlorothalonil, dichlofluanid, tolylfluanid, guazatine, iminoctadine-albesilate, iminoctadine-triacetate, anilazine, dithianon, chinomethionat, fluoroimide,
cyflufenamid, cymoxanil, diclomezine, dodine, ferimzone, flusulfamide, flutianil, fosetyl-aluminium, metrafenone, oxathiapiprolin, pyriofenone, tebufloquin, tolprocarb, triazoxide, potassium hydrogen carbonate, sodium hydrogen carbonate, shiitake mycelium extract, shiitake fruiting body extract, BCF-082, and NNF-0721.

2. The composition of claim 1,
wherein, in the formula (I),
$G^1$ represents a structure of $G^1$-1 $G^1$-2 $G^1$-3, $G^1$-7, $G^1$-11, $G^1$-12, $G^1$-16, $G^1$-27 or $G^1$-33,
$G^2$ represents a structure of $G^2$-1, $G^2$-2 or $G^2$-9,
W represents an oxygen atom,
$X^1$ represents a halogen atom, methyl, difluoromethyl or trifluoromethyl,
$X^2$ represents a hydrogen atom,
$X^3$ represents a hydrogen atom or methyl,
$X^4$ represents a hydrogen atom,
$X^5$ represents a hydrogen atom,
$Y^1$ represents a halogen atom,
$Y^2$ represents a hydrogen atom, a halogen atom, methoxy, methylthio or methylsulfonyl,
$Y^3$ represents a halogen atom, trifluoromethyl, $C_2$-$C_4$ alkenyl, $C_2$-$C_6$ alkynyl, ($C_2$-$C_6$) alkynyl optionally substituted by $R^6$, $C_1$-$C_4$ haloalkoxy or —C($R^8$)=$NOR^9$,
$Y^4$ represents a hydrogen atom or a halogen atom,
$Y^5$ represents a hydrogen atom,
$R^1$ represents $C_1$-$C_6$ alkyl, $C_1$-$C_4$ haloalkyl, ($C_1$-$C_4$) alkyl substituted by $R^{10}$, $C_3$-$C_6$ cycloalkyl, $C_3$-$C_6$ alkenyl, $C_3$-$C_4$ haloalkenyl or $C_3$-$C_6$ alkynyl,
$R^2$ represents a hydrogen atom or methyl, provided that when $G^2$ is a structure represented by $G^2$-1, $R^2$ represents methyl,
$R^3$ represents a hydrogen atom,
$R^4$ represents a hydrogen atom,
$R^5$ represents methyl,
$R^6$ represents a halogen atom, $C_3$-$C_6$ cycloalkyl, —$OR^7$, trimethylsilyl, —C($R^8$)=$NOR^9$ or phenyl,
$R^7$ represents $C_1$-$C_4$ alkyl or $C_1$-$C_4$ alkoxymethyl,
$R^{10}$ represents $C_3$-$C_6$ cycloalkyl, trimethylsilyl, phenyl, phenyl substituted by $(Z)_m$, or D-32,
Z represents a halogen atom or cyano, and when m represents 2 or more, each Z is identical with or different from one another, and
n represents an integer of 1.

3. The composition of claim 1,
wherein, in the formula (I),
$G^1$ represents a structure of $G^1$-1, $G^1$-3, $G^1$-27 or $G^1$-33,
$G^2$ represents a structure of $G^2$-2,
$X^1$ represents a chlorine atom, an iodine atom, difluoromethyl or trifluoromethyl,
$X^2$ represents a hydrogen atom,
$X^3$ represents a hydrogen atom or methyl,
$X^4$ represents a hydrogen atom,
$X^5$ represents a hydrogen atom,
$Y^1$ represents a chlorine atom or a bromine atom,
$Y^2$ represents a hydrogen atom, a chlorine atom or methoxy, Y³ represents a chlorine atom, a bromine atom, trifluoromethyl, $C_2$-$C_6$ alkynyl, or ($C_2$-$C_6$) alkynyl optionally substituted by $R^6$, Y⁴ represents a hydrogen atom, R¹ represents $C_1$-$C_4$ alkyl, $C_1$-$C_4$ haloalkyl or cyclopropylmethyl, R² represents a hydrogen atom or methyl, R³ represents a hydrogen atom, R⁴ represents a hydrogen atom, R⁵ represents methyl, and R⁶ represents a halogen atom, cyclopropyl or $C_1$-$C_4$ alkoxy.

4. The composition of claim 1,
wherein, in the formula (I),
G¹ represents a structure of G¹-1,
X¹ represents an iodine atom or trifluoromethyl, and
X², X³, X⁴ and X⁵ each represents a hydrogen atom.

5. The composition of claim 1,
wherein, in the formula (I),
G¹ represents a structure of G¹-3,
X¹ represents a chlorine atom or difluoromethyl, and
X², X³ and X⁴ each represents a hydrogen atom.

6. The composition of claim 1,
wherein, in the formula (I),
G¹ represents a structure of G¹-27,
X¹ represents difluoromethyl,
X² represents a hydrogen atom, and
R⁵ represents methyl.

7. The composition of claim 1,
wherein, in the formula (I),
G¹ represents a structure of G¹-33,
X¹ represents difluoromethyl, and
X³ represents methyl.

8. The composition of claim 1, wherein the active ingredient B comprises at least one compound selected from the group consisting of benalaxyl, benalaxyl-M, furalaxyl, metalaxyl, metalaxyl-M, ofurace, oxadixyl, bupirimate, ethirimol, hymexazol, octhilinone, and oxolinic acid.

9. The composition of claim 1, wherein the active ingredient B comprises at least one compound selected from the group consisting of benomyl, carbendazim, fuberidazole, thiabendazole, thiophanate-methyl, diethofencarb, ethaboxam, zoxamide, pencycuron, fluopicolide, diflumetorim, and benodanil.

10. The composition of claim 1, wherein the active ingredient B comprises at least one compound selected from the group consisting of benzovindiflupyr, bixafen, boscalid, carboxin, fenfuram, fluopyram, flutolanil, fluxapyroxad, furametpyr, isofetamid, isopyrazam, mepronil, oxycarboxin, penflufen, penthiopyrad, sedaxane, thifluzamide, azoxystrobin, coumoxystrobin, dimoxystrobin, enestrobin, enoxastrobin, famoxadone, fenamidone, fenaminstrobin, flufenoxystrobin, fluoxastrobin, kresoxim-methyl, mandestrobin, metominostrobin, orysastrobin, picoxystrobin, pyraclostrobin, pyrametostrobin, pyraoxystrobin, pyribencarb-methyl, pyriminostrobin, triclopyricab, trifloxystrobin, amisulbrom, cyazofamid, dinocap, fluazinam, meptyldinocap, fentin, tributyltin oxide, silthiofam, and ametoctradin.

11. The composition of claim 1, wherein the active ingredient B comprises at least one compound selected from the group consisting of cyprodinil, mepanipyrim, pyrimethanil, blasticidin-S, kasugamycin, streptomycin, and oxytetracycline.

12. The composition of claim 1, wherein the active ingredient B comprises at least one compound selected from the group consisting of proquinazid, quinoxyfen, fenpiclonil, fludioxonil, chlozolinate, iprodione, procymidone, and vinclozolin.

13. The composition of claim 1, wherein the active ingredient B comprises at least one compound selected from the group consisting of edifenphos, iprobenfos, isoprothiolane, pyrazophos, biphenyl, chloroneb, dicloran, etridiazole, quintozene, tecnazene, tolclofos-methyl, propamocarb hydrochloride, and *Bacillus subtilis*.

14. The composition of claim 1, wherein the active ingredient B comprises at least one compound selected from the group consisting of azaconazole, bitertanol, bromuconazole, climbazole, cyproconazole, diclobutrazol, difenoconazole, diniconazole, diniconazole-M, epoxiconazole, etaconazole, fenarimol, fenbuconazole, fluotrimazole, fluquinconazole, flusilazole, flutriafol, furconazole, hexaconazole, imazalil, imibenconazole, ipconazole, metconazole, myclobutanil, nuarimol, oxpoconazole fumarate, pefurazoate, penconazole, prochloraz, propiconazole, prothioconazole, pyrifenox, pyrisoxazole, simeconazole, tebuconazole, tetraconazole, triadimefon, triadimenol, triflumizole, triforine, triticonazole, aldimorph, dodemorph acetate, fenpropidin, fenpropimorph, piperalin, spiroxamine, tridemorph, fenhexamid, and fenpyrazamine.

15. The composition of claim 1, wherein the active ingredient B comprises at least one compound selected from the group consisting of validamycin, polyoxins, polyoxorim, benthiavalicarb-isopropyl, dimethomorph, flumorph, iprovalicarb, mandipropamid, pyrimorph, and valifenalate.

16. The composition of claim 1, wherein the active ingredient B comprises at least one compound selected from the group consisting of phthalide, pyroquilon, tricyclazole, carpropamid, diclocymet, and fenoxanil.

17. The composition of claim 1, wherein the active ingredient B comprises at least one compound selected from the group consisting of acibenzolar-S-methyl, probenazole, isotianil, and tiadinil.

18. The composition of claim 1, wherein the active ingredient B comprises at least one compound selected from the group consisting of laminarin, bordeaux mixture, cheshunt mixture, copper carbonate basic, copper hydroxide, copper naphthenate, copper oleate, copper oxychloride, copper sulfate, basic copper sulfate, oxine copper, calcium polysulfide, sulfur, amobam, ferbam, mancozeb, maneb, metiram, polycarbamate, propineb, thiram, ziram, captan, folpet, chlorothalonil, dichlofluanid, tolylfluanid, guazatine, iminoctadine-albesilate, iminoctadine-triacetate, anilazine, dithianon, chinomethionat, and fluoroimide.

19. The composition of claim 1, wherein the active ingredient B comprises at least one compound selected from the group consisting of cyflufenamid, cymoxanil, diclomezine, dodine, ferimzone, flusulfamide, flutianil, fosetyl-aluminium, metrafenone, oxathiapiprolin, pyriofenone, tebufloquin, tolprocarb, triazoxide, potassium hydrogen carbonate, sodium hydrogen carbonate, shiitake mycelium extract, shiitake fruiting body extract, BCF-082, and NNF-0721.

20. A method for controlling noxious insects, nematodes or bacteria, comprising:
treating at the same time a subject with an active ingredient A and an active ingredient B, wherein the active ingredient A comprises at least one oxime-substituted amide compound represented by the formula (I), or an N-oxide or a salt thereof,

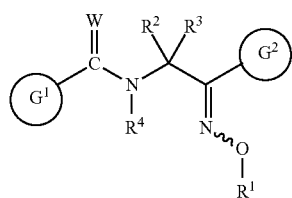 (I)
where G¹ represents a structure of G¹-1, G¹-2, G¹-3, G¹-7, G¹-8, G¹-9, G¹-11, G¹-12, G¹-13, G¹-16, G¹-27, G¹-32, G¹-33 or G¹-50,
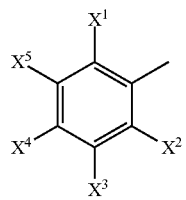 G¹-1
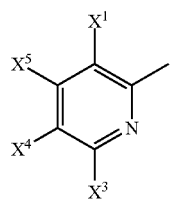 G¹-2
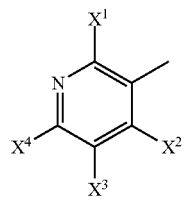 G¹-3
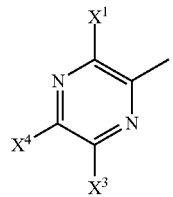 G¹-7
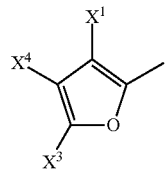 G¹-8
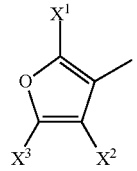 G¹-9
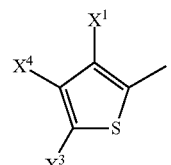 G¹-11
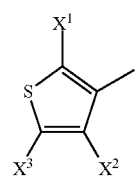 G¹-12
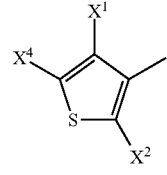 G¹-13
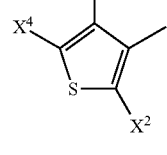 G¹-16
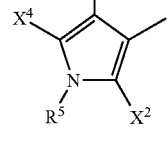 G¹-27
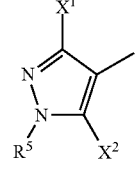 G¹-32
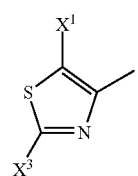 G¹-33
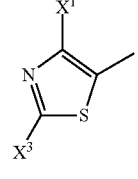 G¹-50
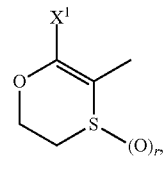

$G^2$ represents a structure of $G^2$-1, $G^2$-2, $G^2$-6 or $G^2$-9,

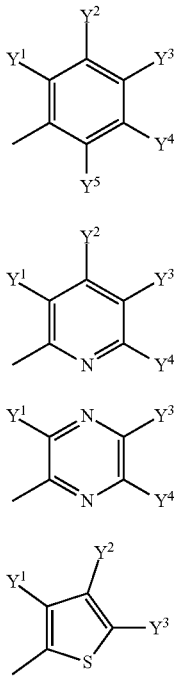

W represents an oxygen atom or a sulfur atom,
$X^1$ represents a halogen atom, nitro, methyl, difluoromethyl or trifluoromethyl,
$X^2$ represents a hydrogen atom, or optionally, when $G^1$ represents a structure of $G^1$-27 and $X^1$ represents trifluoromethyl, $X^2$ represents a halogen atom,
$X^3$ represents a hydrogen atom or methyl,
$X^4$ represents a hydrogen atom or a halogen atom,
$X^5$ represents a hydrogen atom,
$Y^1$ represents a hydrogen atom, a halogen atom, methyl, trifluoromethyl or methoxy,
$Y^2$ represents a hydrogen atom, a halogen atom, cyano, methoxy, methylthio, methylsulfinyl or methylsulfonyl,
$Y^3$ represents a hydrogen atom, a halogen atom, cyano, $C_1$-$C_4$ alkyl, trifluoromethyl, $C_2$-$C_4$ alkenyl, $C_2$-$C_6$ alkynyl, ($C_2$-$C_6$) alkynyl optionally substituted by $R^6$, —$OR^7$, $C_1$-$C_4$ alkylthio, —$C(R^8)$=$NOR^9$, phenyl, D-3 or D-7,
$Y^4$ represents a hydrogen atom or a halogen atom,
$Y^5$ represents a hydrogen atom,
r is 0, 1 or 2,
$R^1$ represents $C_1$-$C_6$ alkyl, $C_1$-$C_4$ haloalkyl, ($C_1$-$C_4$) alkyl substituted by $R^{10}$, $C_3$-$C_6$ cycloalkyl, $C_3$-$C_6$ alkenyl, $C_3$-$C_4$ haloalkenyl, $C_3$-$C_6$ alkynyl or phenyl,
$R^2$ represents a hydrogen atom, methyl or ethyl, provided that $R^2$ represents methyl or ethyl when $G^1$ represents a structure of $G^1$-1, $X^1$ represents a chlorine atom, $X^2$, $X^3$ and $X^5$ each represents a hydrogen atom, $X^4$ represents a hydrogen atom or a chlorine atom, and $G^2$ represents a structure of $G^2$-1, $Y^3$ represents a chlorine atom, $Y^1$, $Y^2$, $Y^4$ and $Y^5$ each represents a hydrogen atom,
$R^3$ represents a hydrogen atom or methyl, or optionally $R^2$ and $R^3$ together form a cyclopropyl ring,
$R^4$ represents a hydrogen atom, $C_1$-$C_4$ haloalkylthio, $C_1$-$C_4$ alkylcarbonyl or $C_1$-$C_4$ alkoxycarbonyl, $R^5$ represents methyl,
$R^6$ represents a halogen atom, $C_3$-$C_6$ cycloalkyl, hydroxy ($C_3$-$C_6$)cycloalkyl, $C_5$-$C_6$ cycloalkenyl, —OH, —$OR^7$, $C_1$-$C_4$ alkylcarbonyloxy, $C_1$-$C_4$ alkylsulfonyloxy, $C_1$-$C_4$ alkylthio, trimethylsilyl, —$C(R^8)$=$NOR^9$, phenyl, phenyl substituted by $(Z)_m$ or D-32,
Z represents a halogen atom, cyano, nitro, $C_1$-$C_4$ alkyl, trifluoromethyl, methoxy, trifluoromethoxy, trifluoromethylthio or phenyl, and when m or n represents 2 or more, each Z is identical with or different from one another, and when there are two neighboring Z's, the two neighboring Z's optionally form —CH=CH—CH=CH— to form a 6-membered ring together with the carbon atoms attached to the two Z's,
$R^7$ represents $C_1$-$C_4$ alkyl, $C_1$-$C_4$ haloalkyl, $C_1$-$C_4$ alkoxy ($C_1$-$C_2$)alkyl, E-14, $C_3$-$C_4$ alkynyl or phenyl substituted by $(Z)_m$,
$R^8$ represents a hydrogen atom or methyl,
$R^9$ represents methyl or ethyl,
$R^{10}$ represents cyano, $C_3$-$C_6$ cycloalkyl, E-5, E-9, $C_1$-$C_4$ alkoxy, $C_1$-$C_4$ alkylthio, trimethylsilyl, —$C(R^{11})$=$NOR^{12}$, phenyl, phenyl substituted by $(Z)_m$, D-10 or D-32,
D-3, D-7, D-10 and D-32, respectively, represent aromatic heterocyclic rings of formulae

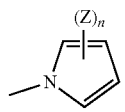

D-3

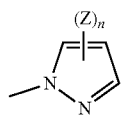

D-7

D-10

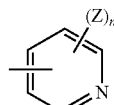

D-32

E-5, E-9 and E-14, respectively, represent saturated heterocyclic rings of formulae

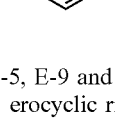

E-5

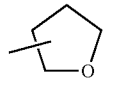

E-9

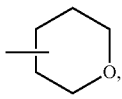 E-14

$R^{11}$ represents methyl,
$R^{12}$ represents methyl or ethyl,
m represents an integer of 1, 2 or 3, and
n represents an integer of 0, 1 or 2,
the active ingredient B comprises at least one compound selected from the group consisting of benalaxyl, benalaxyl-M, furalaxyl, metalaxyl, metalaxyl-M, ofurace, oxadixyl, bupirimate, ethirimol, hymexazol, octhilinone, oxolinic acid, benomyl, carbendazim, fuberidazole, thiabendazole, thiophanate-methyl, diethofencarb, ethaboxam, zoxamide, pencycuron, fluopicolide, diflumetorim, benodanil, benzovindiflupyr, bixafen, boscalid, carboxin, fenfuram, fluopyram, flutolanil, fluxapyroxad, furametpyr, isofetamid, isopyrazam, mepronil, oxycarboxin, penflufen, penthiopyrad, sedaxane, thifluzamide, azoxystrobin, coumoxystrobin, dimoxystrobin, enestrobin, enoxastrobin, famoxadone, fenamidone, fenaminstrobin, flufenoxystrobin, fluoxastrobin, kresoxim-methyl, mandestrobin, metominostrobin, orysastrobin, picoxystrobin, pyraclostrobin, pyrametostrobin, pyraoxystrobin, pyribencarb-methyl, pyriminostrobin, triclopyricab, trifloxystrobin, amisulbrom, cyazofamid, dinocap, fluazinam, meptyldinocap, fentin, tributyltin oxide, silthiofam, ametoctradin, cyprodinil, mepanipyrim, pyrimethanil, blasticidin-S, kasugamycin, streptomycin, oxytetracycline, proquinazid, quinoxyfen, fenpiclonil, fludioxonil, chlozolinate, iprodione, procymidone, vinclozolin, edifenphos, iprobenfos, isoprothiolane, pyrazophos, biphenyl, chloroneb, dicloran, etridiazole, quintozene, tecnazene, tolclofos-methyl, propamocarb hydrochloride, *Bacillus subtilis*, azaconazole, bitertanol, bromuconazole, climbazole, cyproconazole, diclobutrazol, difenoconazole, diniconazole, diniconazole-M, epoxiconazole, etaconazole, fenarimol, fenbuconazole, fluotrimazole, fluquinconazole, flusilazole, flutriafol, furconazole, hexaconazole, imazalil, imibenconazole, ipconazole, metconazole, myclobutanil, nuarimol, oxpoconazole fumarate, pefurazoate, penconazole, prochloraz, propiconazole, prothioconazole, pyrifenox, pyrisoxazole, simeconazole, tebuconazole, tetraconazole, triadimefon, triadimenol triflumizole, triforine, triticonazole, aldimorph, dodemorph acetate, fenpropidin, fenpropimorph, piperalin, spiroxamine, tridemorph, fenhexamid, fenpyrazamine, validamycin, polyoxins, polyoxorim, benthiavalicarb-isopropyl, dimethomorph, flumorph, iprovalicarb, mandipropamid, pyrimorph, valifenalate, phthalide, pyroquilon, tricyclazole, carpropamid, diclocymet, fenoxanil, acibenzolar-S-methyl, probenazole, isotianil, tiadinil, laminarin, bordeaux mixture, cheshunt mixture, copper carbonate basic, copper hydroxide, copper naphthenate, copper oleate, copper oxychloride, copper sulfate, basic copper sulfate, oxine copper, calcium polysulfide, sulfur, amobam, ferbam, mancozeb, maneb, metiram, polycarbamate, propineb, thiram, ziram, captan, folpet, chlorothalonil, dichlofluanid, tolylfluanid, guazatine, iminoctadine-albesilate, iminoctadine-triacetate, anilazine, dithianon, chinomethionat, fluoroimide, cyflufenamid, cymoxanil, diclomezine, dodine, ferimzone, flusulfamide, flutianil, fosetyl-aluminium, metrafenone, oxathiapiprolin, pyriofenone, tebufloquin, tolprocarb, triazoxide, potassium hydrogen carbonate, sodium hydrogen carbonate, shiitake mycelium extract, shiitake fruiting body extract, BCF-082, and NNF-0721.

21. The method of claim 20, wherein an application rate of each of the active ingredient A and the active ingredient B is from 0.1 to 1,000 g a.i./ha.

22. The method of claim 20, wherein an application dosage, as an amount of the active ingredient A and the active ingredient B, is from 0.005 to 50 kg/ha.

* * * * *